US006063599A

United States Patent [19]
Tang et al.

[11] Patent Number: 6,063,599
[45] Date of Patent: *May 16, 2000

[54] DIROFILARIA AND BRUGIA ANKYRIN PROTEINS, NUCLEIC ACID MOLECULES, AND USES THEREOF

[75] Inventors: Liang Tang; E. Scot Blehm, both of Fort Collins, Colo.

[73] Assignee: Heska Corporation, Fort Collins, Colo.

[ * ] Notice: This patent is subject to a terminal disclaimer.

[21] Appl. No.: 09/065,474

[22] Filed: Apr. 24, 1998

Related U.S. Application Data

[63] Continuation-in-part of application No. 08/847,429, Apr. 24, 1997, Pat. No. 5,827,692.

[51] Int. Cl.[7] .......................... C12P 21/06; C07H 17/00; C07K 14/00
[52] U.S. Cl. .................... 435/69.1; 435/320.1; 435/325; 435/253.2; 536/231; 530/350
[58] Field of Search ......................... 536/23.1; 435/69.1, 435/325, 252.3, 320.1; 530/350

[56] References Cited

U.S. PATENT DOCUMENTS 5,561,054 10/1996 Kron et al. .............................. 435/69.1
5,827,692 10/1999 Tang et al. .............................. 435/69.1

FOREIGN PATENT DOCUMENTS

WO 96/40884 12/1996 WIPO .

OTHER PUBLICATIONS

Meinkoth, et al., 1984, *Analytical Biochemistry*, vol. 138, pp. 267–284.
Bargmann, et al., 1991, *Science*, 251, pp. 1243–1246.
Bennett, 1992, *The Journal of Biological Chemistry*, 267:13, pp. 8703–8706.
Davis, et al., 1994, *The Journal of Biological Chemistry*, 269:44, pp. 27163–27166.
Erttmann, et al., 1996, *Tropical Medicine and International Health*, 1:5, pp. 558–574.
Erttmann, et al., 1996, *The Journal of Biological Chemistry*, 271:3, pp. 1645–1650.
Erttmann, et al., 1996, *FEBS Letters* 390, pp. 21–24.
Kordeli, et al., 1995, *The Journal of Biological Chemistry*, 270:5, pp. 2352–2359.
Kunimoto, et al., 1991, *The Journal of Cell Biology*, 115:5, pp. 1319–1331.
Lambert, et al., 1993, *The Journal of Neuroscience*, 13:9, pp. 3725–3735.
Otsuka, et al., 1995, *The Journal of Cell Biology*, 129:4, pp. 1081–1092.
Smith, et al., 1991, *Proc. Natl. Acad. Sci. USA*, 88, pp. 6971–6975.
Srinivasan, et al., 1988, *Nature*, 333, pp. 177–180.
Feng, et al., 1985, *J. Mol. Evol. 21*, pp. 112–125.
Johnson, et al., 1993, *J. Mol. Biol. 233*, pp. 716–738.
Meinkoth, et al., 1984, *Analytical Biochemistry 138*, pp. 267–284.

*Primary Examiner*—Karen Cochrane Carlson
*Attorney, Agent, or Firm*—Heska Corporation

[57] ABSTRACT

The present invention relates to Dirofilaria ankyrin proteins and to Brugia ankyrin proteins; to Dirofilaria ankyrin nucleic acid molecules and to Brugia ankyrin nucleic acid molecules, including those that encode such ankyrin proteins; to antibodies raised against such ankyrin proteins; and to compounds that inhibit Dirofilaria or Brugia ankyrin function. The present invention also includes methods to identify and obtain such proteins, nucleic acid molecules, antibodies, and inhibitory compounds. Also included in the present invention are therapeutic compositions comprising such proteins, nucleic acid molecules, antibodies and/or inhibitory compounds as well as the use of such therapeutic compositions to protect animals from diseases caused by parasitic helminths.

19 Claims, No Drawings

DIROFILARIA AND BRUGIA ANKYRIN PROTEINS, NUCLEIC ACID MOLECULES, AND USES THEREOF

CROSS-REFERENCE TO RELATED APPLICATIONS

This application is a continuation-in-part of U.S. patent application Ser. No. 08/847,429, filed Apr. 24, 1997, now U.S. Pat. No. 5,827,692. The patent application referred to in this section is incorporated by reference herein in its entirety.

FIELD OF THE INVENTION

The present invention relates to Dirofilaria and Brugia ankyrin nucleic acid molecules, proteins encoded by such nucleic acid molecules, antibodies raised against such proteins, compounds capable of inhibiting the function of such proteins and methods to identify such inhibitors. The present invention also includes therapeutic compositions comprising such nucleic acid molecules, proteins, antibodies, and/or inhibitors, as well as their use to protect animals from diseases caused by parasitic helminths, such as heartworm disease, elephantiasis, and hydrocele.

BACKGROUND OF THE INVENTION

Parasitic helminth infections in animals, including humans, are typically treated by chemical drugs. One disadvantage with chemical drugs is that they must be administered often. For example, dogs susceptible to heartworm are typically treated monthly. Repeated administration of drugs, however, often leads to the development of resistant helminth strains that no longer respond to treatment. Furthermore, many of the chemical drugs cause harmful side effects in the animals being treated, and as larger doses become required due to the build up of resistance, the side effects become even greater. Moreover, a number of drugs only treat symptoms of a parasitic disease but are unable to prevent infection by the parasitic helminth.

An alternative method to prevent parasitic helminth infection includes administering a vaccine against a parasitic helminth. Although many investigators have tried to develop vaccines based on specific antigens, it is well understood that the ability of an antigen to stimulate antibody production does not necessarily correlate with the ability of the antigen to stimulate an immune response capable of protecting an animal from infection, particularly in the case of parasitic helminths. Although a number of prominent antigens have been identified in several parasitic helminths, including in Dirofilaria and Brugia species, there is yet to be a commercially available vaccine developed for any parasitic helminth.

As an example of the complexity of parasitic helminths, the life cycle of D. immitis, the helminth that causes heartworm, includes a variety of life forms, each of which presents different targets, and challenges, for immunization. In a mosquito, D. immitis microfilariae go through two larval stages (L1 and L2) and become mature third stage larvae (L3), which can then be transmitted back to the dog when the mosquito takes a blood meal. In a dog, the L3 molt to the fourth larval stage (L4), and subsequently to the fifth stage, or immature adults. The immature adults migrate to the heart and pulmonary arteries, where they mature to adult heartworms. Adult heartworms are quite large and preferentially inhabit the heart and pulmonary arteries of an animal. Sexually mature adults, after mating, produce microfilariae which traverse capillary beds and circulate in the vascular system of the dog. In particular, heartworm is a major problem in dogs, which typically do not develop immunity upon infection (i.e., dogs can become reinfected even after being cured by chemotherapy). In addition, heartworm infection has been reported in cats, ferrets, and humans.

As such, there remains a need to identify efficacious compositions that protect animals against diseases caused by parasitic helminths such as D. immitis and B. malayi. Such compositions would preferably also protect animals from infection by such helminths.

The mechanisms and regulatory pathways involved in D. immitis migration and development are not clear. From infective L3 to mature adult, the nematode has to migrate and develop, with two molts, within its definitive host. It has been shown in the free living nematode, Caenorhabditis elegans (C. elegans), that the development of the larvae is regulated by environmental signals through chemosensory neurons. Blockage of signal transmission affects the development of the nematode (Bargmann, et al., 1991, Science, 251, 1243–1246). Many neuron-related genes have been identified in C. elegans. Mutations of the genes which control normal neuron function in C. elegans will not only affect the behavior of the nematode, but will also affect the development of the larvae and egg laying of mutated female worms. In parasitic nematodes, very little is known about mechanisms involved in the signal transmission and the developmental regulation of the parasites. However, host and tissue specificities in parasite infections suggest that parasitic nematodes might also need correct environmental signals for development.

Ankyrins are peripheral membrane proteins which have been found in erythrocyte, kidney and neuronal cells of mammals. Genes coding for three different mammalian ankyrins (ankyrin$_R$, ankyrin$_B$ and ankyrin$_G$) have been cloned. Ankyrin$_R$ was originally identified as part of the erythrocyte membrane skeleton, and was recently also localized to the plasma membrane of a subpopulation of post mitotic neurons in rat brain (Lambert, et al., 1993, J. Neurosci., 13, 3725–3735). Ankyrin$_B$ is a developmentally regulated human brain protein which has two alternatively spliced isoforms with molecular masses of 220 kilodaltons (kD) and 440 kD (Kunimoto, et al., 1991, J. Cell Biology, 115, 1319–1331). Ankyrin$_G$ is a more recently isolated human gene that encodes two neural-specific ankyrin variants (480 kD and 270 kD), which have been localized to the axonal initial segment and node of Ranvier (Kordeli, et al., 1995, J. Biol. Chem., 270, 2352–2359). Studies on mammalian ankyrins indicate that ankyrins bind a variety of proteins which have functions involved with the anion exchanger (Drenckhahn, et al., 1988, Science, 230, 1287–1289), Na+/K+-ATPase, amiloride-sensitive sodium channel in kidney (Smith, et al., 1991, Proc. Natl. Acad. Sci. U.S.A., 88, 6971–6975), voltage dependent sodium channel of the brain and the neuromuscularjunction (Srinivasan, et al., 1988, Nature, 333, 177–180), and nervous system cell adhesion molecules (Davis, et al., 1994, J. Biol. Chem., 269, 27163–27166).

Analyses of mammalian ankyrins have revealed that these large proteins are divided into three functional domains. These include an N-terminal membrane-binding domain of about 89–95 kD, a spectrin-binding domain of about 62 kD, and a C-terminal regulatory domain of about 50–55 kD. The membrane-binding domain is primarily comprised of tandem repeats of about 33 amino acids each. This domain usually has about 22–24 copies of these repeats. The repeat units appear to function in binding to membrane proteins such as anion exchangers, sodium channels, and certain adhesion molecules. The spectrin-binding domain, as the name implies, functions in binding to the spectrin-based cytoskeleton of cells positioned inside the plasma membrane. Finally, the regulatory domain, which is the most variant domain among the different ankyrins that have been studied, appears to function in as a repressor and/or an activator of the protein-binding activities of the other two domains. Some of the variability seen in this domain among different ankyrin species appears to be the result of alternative splicing of nascent transcripts. For a review of ankyrin structure and function, see, for example, Bennett, 1992, *J. Biol. Chem.*, 267, 8703–8706. Bennett, ibid., is herein incorporated by reference in its entirety.

An ankyrin gene (UNC-44) has also been identified in the free living nematode, *C. elegans*. Mutation of UNC-44 affects the development and function of the nervous system (Otsuka et al., 1995, *J. Cell Biology*, 129, 1081–1092). More recently, a cDNA encoding a 90-kilodalton (kD) neuronal protein, E1, which is reported to be an ankyrin-related protein, has been cloned from the filariid nematode, *Onchocerca volvulus* (*O. volvulus*), a human parasite. The cDNA was identified by using immuno-screening with antisera collected from putatively immune individuals from an endemic area of onchocerciasis. Localization studies by immunohistochemical assay indicated that the *O. volvulus* E1 native protein was localized to the nerve ring, the neuronal cell bodies, and the basal labyrinth within the extracellular clefts of the hypodermis in the adult nematode (Erttmann et al., 1996a, *J. Biol. Chem.*, 271, 1645–1650). This 462-amino acid *O. volvulus* protein is reported to be full length.

SUMMARY OF THE INVENTION

The present invention relates to a novel product and a process to protect animals against parasitic helminth infection (e.g., prevent and/or treat such an infection). According to the present invention there are provided Dirofilaria and Brugia ankyrin proteins and mimetopes thereof; Dirofilaria and Brugia ankyrin nucleic acid molecules, including those that encode such proteins; antibodies raised against such ankyrin proteins (i.e., anti-Dirofilaria and anti-Brugia ankyrin antibodies); and compounds that inhibit the function of parasitic helminth ankyrins (i.e, inhibitory compounds).

The present invention also includes methods to obtain and/or identify such proteins, nucleic acid molecules, antibodies and inhibitory compounds. Also included in the present invention are therapeutic compositions comprising such proteins, nucleic acid molecules, antibodies, and/or inhibitory compounds, as well as use of such therapeutic compositions to protect animals from diseases caused by parasitic helminths.

One embodiment of the present invention is an isolated nucleic acid molecule that includes either a Dirofilaria ankyrin nucleic acid molecule, preferably a *Dirofilaria immitis* (*D. immitis*) ankyrin nucleic acid molecule, or a Brugia ankyrin nucleic acid molecule, preferably a *Brugia malayi* (*B. malayi*) ankyrin nucleic acid molecule. Such nucleic acid molecules are referred to as ankyrin nucleic acid molecules. A *D. immitis* ankyrin nucleic acid molecule preferably includes nucleic acid sequence SEQ ID NO:1, SEQ ID NO:3, SEQ ID NO:4, SEQ ID NO:5, SEQ ID NO:6, SEQ ID NO:8, SEQ ID NO:9, SEQ ID NO:10, SEQ ID NO:11, SEQ ID NO:13, SEQ ID NO:14, SEQ ID NO:16, SEQ ID NO:17, SEQ ID NO:18, SEQ ID NO:19, SEQ ID NO:21, SEQ ID NO:22, SEQ ID NO:24, SEQ ID NO:25, SEQ ID NO:26, SEQ ID NO:27, SEQ ID NO:29, SEQ ID NO:30, SEQ ID NO:31, SEQ ID NO:32, SEQ ID NO:34, SEQ ID NO:35, SEQ ID NO:36, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:130, SEQ ID NO:132, SEQ ID NO:134, SEQ ID NO:136; SEQ ID NO:138, SEQ ID NO:140, SEQ ID NO:141, SEQ ID NO:143, SEQ ID NO:144, and/or SEQ ID NO:146, and a *B. malayi* ankyrin nucleic acid molecule preferably includes nucleic acid sequence SEQ ID NO:37, SEQ ID NO:38, SEQ ID NO:40, and/or SEQ ID NO:41.

In one embodiment, a preferred *D. immitis* or *B. malayi* ankyrin nucleic acid molecule comprises a coding region of at least about 1500 nucleotides, preferably at least about 3000 nucleotides, even more preferably at least about 4500 nucleotides, which is capable of encoding an ankyrin protein of at least about 500 amino acids in length, preferably at least about 1000 amino acids in length, even more preferably at least about 1500 amino acids in length. In another embodiment, a preferred *D. immitis* or *B. malayi* ankyrin nucleic acid molecule comprises a full-length coding region which encodes a full-length ankyrin protein.

The present invention also relates to recombinant molecules, recombinant viruses and recombinant cells that include an isolated ankyrin nucleic acid molecule of the present invention. Also included are methods to produce such nucleic acid molecules, recombinant molecules, recombinant viruses and recombinant cells.

Another embodiment of the present invention includes either a Dirofilaria or a Brugia ankyrin protein, or a protein that includes a Dirofilaria or a Brugia ankyrin protein. Preferred ankyrin proteins include *D. immitis* ankyrin proteins or *B. malayi* ankyrin proteins. A preferred *D. immitis* ankyrin protein comprises amino acid sequence SEQ ID NO:2, SEQ ID NO:7, SEQ ID NO:12, SEQ ID NO:15, SEQ ID NO:20, SEQ ID NO:23, SEQ ID NO:28, SEQ ID NO:33, SEQ ID NO:139, SEQ ID NO:142, SEQ ID NO:145, SEQ ID NO:161, SEQ ID NO:162, SEQ ID NO:163, SEQ ID NO:165, SEQ ID NO:166, SEQ ID NO:167, SEQ ID NO:168, SEQ ID NO:169, SEQ ID NO:170, and/or SEQ ID NO:171, and a preferred *B. malayi* ankyrin protein comprises amino acid sequence SEQ ID NO:38.

In one embodiment, a preferred *D. immitis* or *B. malayi* ankyrin protein comprises an amino acid sequence of at least about in length, preferably at least about 1000 amino acids in length, even more preferably at least about 1500 amino acids in length. In another embodiment, a preferred *D. immitis* or *B. malayi* ankyrin protein comprises a full-length protein, i.e., a protein encoded by a full-length coding region.

The present invention also relates to: mimetopes of either Dirofilaria or Brugia ankyrin proteins, preferably to mimetopes of either *D. immitis* and *B. malayi* ankyrin proteins; isolated antibodies that selectively bind to either Dirofilaria or Brugia ankyrin proteins or mimetopes thereof; and inhibitors of Dirofilaria or Brugia ankyrin protein function. Also included are methods, including recombinant methods, to produce proteins, mimetopes, antibodies, and inhibitors of the present invention.

Yet another embodiment of the present invention is a therapeutic composition that is capable of protecting an animal from disease caused by a parasitic helminth. Such a therapeutic composition includes one or more of the following protective compounds: a Dirofilaria or a Brugia ankyrin protein or a mimetope thereof; an isolated Dirofilaria or Brugia ankyrin nucleic acid molecule; an isolated antibody that selectively binds to a Dirofilaria or a Brugia ankyrin protein; and/or a compound capable of inhibiting ankyrin function identified by its ability to inhibit either Dirofilaria or a Brugia ankyrin function. A preferred therapeutic composition of the present invention also includes an excipient, an adjuvant and/or a carrier. Preferred ankyrin nucleic acid molecule therapeutic compositions of the present invention include genetic vaccines, recombinant virus vaccines and recombinant cell vaccines. Also included in the present invention is a method to protect an animal from disease caused by a parasitic helminth, comprising the step of administering to the animal a therapeutic composition of the present invention.

DETAILED DESCRIPTION OF THE INVENTION

The present invention provides for isolated Dirofilaria and Brugia ankyrin proteins, isolated Dirofilaria and Brugia ankyrin nucleic acid molecules, antibodies directed against Dirofilaria and Brugia ankyrin proteins, and compounds able to inhibit parasitic helminth ankyrin function (i.e., inhibitory compounds). As used herein, the terms isolated Dirofilaria ankyrin proteins, isolated Brugia ankyrin proteins, isolated Dirofilaria ankyrin nucleic acid molecules, and isolated Brugia ankyrin nucleic acid molecules refers to ankyrin proteins and ankyrin nucleic acid molecules derived from parasitic helminths of the genera Dirofilaria and Brugia and, as such, can be obtained from their natural source, or can be produced using, for example, recombinant nucleic acid technology or chemical synthesis. Also included in the present invention is the use of these proteins, nucleic acid molecules, antibodies, and inhibitory compounds as therapeutic compositions to protect animals from parasitic helminth diseases as well as in other applications, such as those disclosed below.

The biological functions of ankyrin-related proteins in filariid nematodes are not known. However, inhibiting normal functions of the nervous system in parasitic nematodes might cause neurons to become insensitive to exogenous signals and lead to defects in the development of the parasite. While not being bound by theory, the possible link between neuronal proteins and the development of parasitic nematodes indicates that neuronal proteins, such as ankyrins, could be potential candidates for the development of a vaccine against parasitic nematode infections.

Dirofilaria and Brugia ankyrin proteins and nucleic acid molecules of the present invention have utility because they represent novel targets for anti-parasite vaccines and drugs. The products and processes of the present invention are advantageous because they enable the inhibition of parasite developmental and migratory pathways that involve ankyrin. While not being bound by theory, it is believed that nematode ankyrin-like proteins might affect the development and function of the nematode nervous system, rendering neurons insensitive to exogenous signals involved in migration and development.

Isolation of D. immitis and B. malayi ankyrin nucleic acid molecules and proteins of the present invention was surprising even in view of the reported O. volvulus E1 nucleic acid molecule and protein disclosed by Erttmann, et al., 1996a, ibid., and the reported C. elegans UNC-44 nucleic acid molecule and protein disclosed by Otsuka, et al., ibid. As described in more detail in the Examples, it was very difficult to isolate D. immitis ankyrin nucleic acid molecules, despite the knowledge of these reported O. volvulus and C. elegans nucleic acid sequences. Moreover, Erttmann, et al., 1996b, Trop. Med. Int. Health, 1, 558–574, teaches away from a D. immitis analog of the O. volvulus E1 protein, in that the reference discloses that affinity-purified rabbit antibodies raised against the O. volvulus E1 protein do not react with D. immitis by immunohistochemical analysis (see Erttmann, et al., 1996b, ibid., Table 2).

Furthermore, isolated D. immitis and B. malayi ankyrin nucleic acid molecules and proteins of the present invention, and particularly D. immitis and B. malayi ankyrin nucleic acid molecules containing full-length coding regions and full-length D. immitis and B. malayi ankyrin proteins, are distinct from the O. volvulus E1 nucleic acid molecule and protein disclosed by Erttmann, et al., 1996a, ibid. For example, the inventors disclose herein a D. immitis ankyrin cDNA molecule of about 5503 nucleotides that encodes a full-length protein of about 1745 amino acids, and has a predicted size of about 191.7 kD. This nucleic acid molecule and protein are in dramatic contrast to the reported O. volvulus full-length E1 protein of 462 amino acids (the O. volvulus full-length E1 protein is only about 26% the size of the D. immitis full-length protein), and to the reported O. volvulus E1 full-length cDNA molecule of 2043 nucleotides encoding that protein (i.e. the O. volvulus full-length cDNA is only about 37% the size of the D. immitis full-length nucleic acid molecule). The B. malayi ankyrin nucleic acid molecule disclosed herein, encoding a non-full-length ankyrin protein, spans a region of the B. malayi ankyrin gene that has no similarity to the O. volvulus E1 nucleic acid molecule and protein, i.e., the B. malayi nucleic acid molecule disclosed herein is in a region 5' to the region that would correspond to the O. volvulus E1 nucleic acid molecule and protein.

One embodiment of the present invention is an isolated protein that includes a Dirofilaria ankyrin protein or a Brugia ankyrin protein. It is to be noted that the term "a" or "an" entity refers to one or more of that entity; for example, a protein refers to one or more proteins or at least one protein. As such, the terms "a" (or "an"), "one or more" and "at least one" can be used interchangeably herein. It is also to be noted that the terms "comprising", "including", and "having" can be used interchangeably. According to the present invention, an isolated, or biologically pure, protein, is a protein that has been removed from its natural milieu. As such, "isolated" and "biologically pure" do not necessarily reflect the extent to which the protein has been purified. An isolated protein of the present invention can be obtained from its natural source, can be produced using recombinant DNA technology, or can be produced by chemical synthesis.

As used herein, an isolated ankyrin protein of the present invention (i.e., a Dirofilaria ankyrin protein or a Brugia ankyrin protein) can be a full-length protein or any homolog of such a protein. An isolated protein of the present invention, including a homolog, can be identified in a straight-forward manner by the protein's ability to elicit an immune response against a Dirofilaria ankyrin protein or a Brugia ankyrin protein. Examples of Dirofilaria and Brugia ankyrin homologs include Dirofilaria and Brugia ankyrin proteins in which amino acids have been deleted (e.g., a truncated version of the protein, such as a peptide), inserted, inverted, substituted and/or derivatized (e.g., by glycosylation, phosphorylation, acetylation, myristoylation, prenylation, palmitoylation, amidation and/or addition of glycerophosphatidyl inositol) such that the homolog includes at least one epitope capable of eliciting an immune response against a Dirofilaria or Brugia ankyrin protein, and/or of binding to an antibody directed against a Dirofilaria or Brugia ankyrin protein. That is, when the homolog is administered to an animal as an immunogen, using techniques known to those skilled in the art, the animal will produce an immune response against at least one epitope of a natural Dirofilaria or Brugia ankyrin protein. The ability of a protein to effect an immune response can be measured using techniques known to those skilled in the art. As used herein, the term "epitope" refers to the smallest portion of a protein or other antigen capable of selectively binding to the antigen binding site of an antibody or a T-cell receptor. It is well accepted by those skilled in the art that the minimal size of a protein epitope is about six to seven amino acids.

Dirofilaria and Brugia ankyrin protein homologs can be the result of natural allelic variation or natural mutation. Dirofilaria and Brugia ankyrin protein homologs of the present invention can also be produced using techniques known in the art including, but not limited to, direct modifications to the protein or modifications to the gene encoding the protein using, for example, classic or recombinant DNA techniques to effect random or targeted mutagenesis.

Ankyrin proteins of the present invention are encoded by Dirofilaria ankyrin nucleic acid molecules or Brugia ankyrin nucleic acid molecules. As used herein, a Dirofilaria or Brugia ankyrin nucleic acid molecule includes nucleic acid sequences related to a natural Dirofilaria or Brugia ankyrin gene, and preferably, to a *D. immitis* or a *B. malayi* ankyrin gene. As used herein, a Dirofilaria or Brugia ankyrin gene includes all regions such as regulatory regions that control production of the Dirofilaria or Brugia ankyrin protein encoded by the gene (such as, but not limited to, transcription, translation or post-translation control regions) as well as the coding region itself, and any introns or non-translated coding regions. As used herein, a gene that "includes" or "comprises" a sequence may include that sequence in one contiguous array, or may include the sequence as fragmented exons. As used herein, the term "coding region" refers to a continuous linear array of nucleotides that translates into a protein. A full-length coding region is that coding region that is translated into a full-length, i.e., a complete protein as would be initially translated in its natural millieu, prior to any post-translational modifications. In one embodiment, a *D. immitis* ankyrin gene of the present invention includes the nucleic acid sequence SEQ ID NO:32, as well as the complement of SEQ ID NO:32. Nucleic acid sequence SEQ ID NO:32 represents the deduced sequence of the coding strand of a cDNA (complementary DNA) denoted herein as *D. immitis* ankyrin nucleic acid molecule nDiAnk$_{5503}$, the production of which is disclosed in the Examples. Nucleic acid molecule nDiAnk$_{5503}$ comprises an apparently full-length coding region. The complement of SEQ ID NO:32 (represented herein by SEQ ID NO:34) refers to the nucleic acid sequence of the strand complementary to the strand having SEQ ID NO:32, which can easily be determined by those skilled in the art. Likewise, a nucleic acid sequence complement of any nucleic acid sequence of the present invention refers to the nucleic acid sequence of the nucleic acid strand that is complementary to (i.e., can form a double helix with) the strand for which the sequence is cited. It should be noted that since nucleic acid sequencing technology is not entirely error-free, SEQ ID NO:32 (as well as other nucleic acid and protein sequences presented herein) represents an apparent nucleic acid sequence of the nucleic acid molecule encoding a *D. immitis* ankyrin protein of the present invention.

In another embodiment, a *D. immitis* ankyrin gene or nucleic acid molecule can be an allelic variant that includes a similar but not identical sequence to SEQ ID NO:32, SEQ ID NO:34, or any other *D. immitis* nucleic acid sequence cited herein. An allelic variant of a *D. immitis* ankyrin gene including SEQ ID NO:32 and SEQ ID NO:34, is a gene that occurs at essentially the same locus (or loci) in the genome as the gene including SEQ ID NO:32 and SEQ ID NO:34, but which, due to natural variations caused by, for example, mutation or recombination, has a similar but not identical sequence. Because natural selection typically selects against alterations that affect function, allelic variants usually encode proteins having similar activity to that of the protein encoded by the gene to which they are being compared. Allelic variants of genes or nucleic acid molecules can also comprise alterations in the 5' or 3' untranslated regions of the gene (e.g., in regulatory control regions), or can involve alternative splicing of a nascent transcript, thereby bringing alternative exons into juxtaposition. Similarly, a *B. malayi* ankyrin gene or nucleic acid molecule can be an allelic variant that includes a similar but not identical sequence to SEQ ID NO:37 and SEQ ID NO:39. Allelic variants are well known to those skilled in the art and would be expected to be found within a given parasitic helminth such as Dirofilaria or Brugia, since the respective genomes are diploid, and sexual reproduction will result in the reassortment of alleles.

The minimal size of an ankyrin protein homolog of the present invention is a size sufficient to be encoded by a nucleic acid molecule capable of forming a stable hybrid (i.e., hybridize under stringent hybridization conditions) with the complementary sequence of a nucleic acid molecule encoding the corresponding natural protein. As used herein, "stringent hybridization conditions" refer to those experimental conditions under which nucleic acid molecules having similar nucleic acid sequences will anneal to each other. Stringent hybridization conditions typically permit the hybridization of nucleic acid molecules having at least about 70% nucleic acid sequence identity with the nucleic acid molecule being used as a probe in the hybridization reaction. Formulae to calculate the appropriate hybridization and wash conditions to achieve hybridization permitting 30% or less mis-match between two nucleic acid molecules are disclosed, for example, in Meinkoth et al., 1984, *Anal. Biochem* 138, 267–284. Meinkoth et al., ibid, is by reference herein in its entirety.

Briefly, at page 269, column 1, Meinkoth et al. teach the following: "The formation of nucleic acid hybrids is a reversible process and an understanding of the parameters which affect their stability enable one to derive the optimal conditions for discriminating between perfect and imperfect hybrids. The melting temperature ($T_m$) is affected by ionic strength (M, in mol/liter), base composition (% G +C), the length of the shortest chain in the duplex (n), and the concentration of helix destabilizing agents such as formamide. . . . The following equation has been derived from analyzing the influence of these factors on hybrid stability:

$$T_m = 81.5° C. + 16.6 \log M + 0.41(\% \, G+C) - 500/n - 0.61(\% \, \text{formamide}).$$

This equation pertains to probes longer than approximately 50 nucleotides. Hybrids between oligonucleotides (14–20 bp) and immobilized DNA show decreased stability . . . and an empirical formula has been determined to define the optimal conditions for their hybridization. . . . The temperature at which 50% of these short duplexes dissociate ($T_d$) when the hybridization is performed under standard conditions (e.g., 0.9 M NaCl) is:

$$T_d(°C.)=4(G+C)+2(A+T)$$

where G, C, A, and T indicate the number of the corresponding nucleotides in the oligomer. A temperature 5° below the $T_d$ is used to detect hybridization between perfectly matched molecules. . . .

The stability of duplexes formed between strands with mismatched bases is decreased according to the number and location of the mismatches and is especially pronounced for short (e.g., 14 bp) oligonucleotides. For hybrids longer than 150 bp, the $T_m$ of a DNA duplex decreases by 1° C. with every 1% of base pairs which are mismatched. . . . For hybrids shorter than 20 bp, the $T_m$ decreases by approximately 5° C. for every mismatched base pair. . . . In order to minimize the hybridization of probe to related but nonidentical sequences, hybridization reactions must be performed under the most stringent conditions possible. From the discussion above, hybridization stringency can be altered by adjusting the salt and/or formamide concentrations and/or by changing the temperature. The stringency can be adjusted either during the hybridization step, or in the posthybridization washes. . . . It is often convenient to perform the hybridization at low stringencies and wash at increasing stringencies, analyzing the results after each wash. This enables the detection of related sequences and the monitoring of the effectiveness of the washes in removing these sequences. This strategy also enables one to obtain an estimate of sequence relatedness. . . . As such, the size of the nucleic acid molecule encoding such a protein homolog is dependent on nucleic acid composition and percent homology between the nucleic acid molecule and complementary sequence. It should also be noted that the extent of homology required to form a stable hybrid can vary depending on whether the homologous sequences are interspersed throughout the nucleic acid molecules or are clustered (i.e., localized) in distinct regions on the nucleic acid molecules. The minimal size of such nucleic acid molecules is typically at least about 12 to about 15 nucleotides in length if the nucleic acid molecules are GC-rich and at least about 15 to about 17 bases in length if they are AT-rich. As such, the minimal size of a nucleic acid molecule used to encode an ankyrin protein homolog of the present invention is from about 12 to about 18 nucleotides in length. Thus, the minimal size of an ankyrin protein homolog of the present invention is from about 4 to about 6 amino acids in length. There is no limit, other than a practical limit, on the maximal size of such a nucleic acid molecule in that the nucleic acid molecule can include a portion of a gene, an entire gene, or multiple genes, or portions thereof. The preferred size of a protein encoded by a nucleic acid molecule of the present invention depends on whether a full-length, fusion, multivalent, or functional portion of such a protein is desired.

A preferred Dirofilaria or Brugia ankyrin protein of the present invention is a compound that when administered to an animal in an effective manner, is capable of protecting that animal from disease caused by a parasitic helminth. In accordance with the present invention, the ability of an ankyrin protein of the present invention to protect an animal from disease by a parasitic helminth refers to the ability of that protein to, for example, treat, ameliorate and/or prevent disease caused by parasitic helminths. In one embodiment, a Dirofilaria or Brugia ankyrin protein of the present invention can elicit an immune response (including a humoral and/or cellular immune response) against a parasitic helminth.

Suitable parasites to target include any parasite that is essentially incapable of causing disease in an animal administered a Dirofilaria or Brugia ankyrin protein of the present invention. As such, parasites to target includes any parasite that produces a protein having one or more epitopes that can be targeted by a humoral and/or cellular immune response against a Dirofilaria or Brugia ankyrin protein of the present invention and/or that can be targeted by an inhibitory compound that otherwise inhibits ankyrin function (e.g., a compound that binds to ankyrin thereby blocking parasite development and/or migration regulatory pathways), thereby resulting in the decreased ability of the parasite to cause disease in an animal. Preferred parasitic helminths to target include nematodes, cestodes, and trematodes, with nematodes being preferred. Preferred nematodes to target include filariid, ascarid, capillarid, strongylid, strongyloides, trichostrongyle, and trichurid nematodes. Particularly preferred nematodes are those of the genera Acanthocheilonema, Aelurostrongylus, Ancylostoma, Angiostrongylus, Ascaris, Brugia, Bunostomum, Capillaria, Chabertia, Cooperia, Crenosoma, Dictyocaulus, Dioctophyme, Dipetalonema, Diphyllobothrium, Diplydium, Dirofilaria, Dracunculus, Enterobius, Filaroides, Haemonchus, Lagochilascaris, Loa, Mansonella, Muellerius, Nanophyetus, Necator, Nematodirus, Oesophagostomum, Onchocerca, Opisthorchis, Ostertagia, Parafilaria, Paragonimus, Parascaris, Physaloptera, Protostrongylus, Setaria, Spirocerca, Spirometra, Stephanofilaria, Strongyloides, Strongylus, Thelazia, Toxascaris, Toxocara, Trichinella, Trichostrongylus, Trichuris, Uncinaria, and Wuchereria. Preferred filariid nematodes include Dirofilaria, Onchocerca, Acanthocheilonema, Brugia, Dipetalonema, Loa, Parafilaria, Setaria, Stephanofilaria and Wuchereria filariid nematodes, with *D. immitis* and *B. malayi* being even more preferred.

The present invention also includes mimetopes of Dirofilaria and Brugia ankyrin proteins of the present invention. As used herein, a mimetope of a Dirofilaria or Brugia ankyrin protein of the present invention refers to any compound that is able to mimic the activity of such an ankyrin protein, often because the mimetope has a structure that mimics the particular ankyrin protein. Mimetopes can be, but are not limited to: peptides that have been modified to decrease their susceptibility to degradation such as all-D retro peptides; anti-idiotypic and/or catalytic antibodies, or fragments thereof; non-proteinaceous immunogenic portions of an isolated protein (e.g., carbohydrate structures); and synthetic or natural organic molecules, including nucleic acids. Such mimetopes can be designed using computer-generated structures of proteins of the present invention. Mimetopes can also be obtained by generating random samples of molecules, such as oligonucleotides, peptides or other organic molecules, and screening such samples by affinity chromatography techniques using the corresponding binding partner.

One embodiment of a Dirofilaria or Brugia ankyrin protein of the present invention is a fusion protein that includes a Dirofilaria or Brugia ankyrin protein-containing domain attached to one or more fusion segments. Suitable fusion segments for use with the present invention include, but are not limited to, segments that can: enhance a protein's stability; act as an immunopotentiator to enhance an immune response against a Dirofilaria or Brugia ankyrin protein;

and/or assist in purification of a Dirofilaria or Brugia ankyrin protein (e.g., by affinity chromatography). A suitable fusion segment can be a domain of any size that has the desired function (e.g., imparts increased stability, imparts increased immunogenicity to a protein, and/or simplifies purification of a protein). Fusion segments can be joined to amino and/or carboxyl termini of the Dirofilaria or Brugia ankyrin-containing domain of the protein and can be susceptible to cleavage in order to enable straight-forward recovery of a Dirofilaria or Brugia ankyrin protein. Fusion proteins are preferably produced by culturing a recombinant cell transformed with a fusion nucleic acid molecule that encodes a protein including the fusion segment attached to either the carboxyl and/or amino terminal end of a ankyrin-containing domain. Preferred fusion segments include a metal binding domain (e.g., a poly-histidine segment); an immunoglobulin binding domain (e.g., Protein A; Protein G; T cell; B cell; Fc receptor or complement protein antibody-binding domains); a sugar binding domain (e.g., a maltose binding domain); and/or a "tag" domain (e.g., at least a portion of β-galactosidase, a strep tag peptide, a T7 tag peptide, a Flag™ peptide, or other domains that can be purified using compounds that bind to the domain, such as monoclonal antibodies). More preferred fusion segments include metal binding domains, such as a poly-histidine segment; a maltose binding domain; a strep tag peptide, such as that available from Biometra in Tampa, Fla.; and an S10 peptide. Examples of particularly preferred fusion proteins of the present invention include PHIS-PDiAnk$_{352}$, PHIS-PDiAnk$_{422}$, PHIS-PDiAnk$_{288}$, PHIS-PDiAnk$_{864}$, PHISDiANK$_{352}$, PHISDiANK$_{422}$, and PHISDiANK$_{288}$ production of which is disclosed herein.

In another embodiment, a Dirofilaria or Brugia ankyrin protein of the present invention also includes at least one additional protein segment that is capable of protecting an animal from one or more diseases. Such a multivalent protective protein can be produced by culturing a cell transformed with a nucleic acid molecule comprising two or more nucleic acid domains joined together in such a manner that the resulting nucleic acid molecule is expressed as a multivalent protective compound containing at least two protective compounds capable of protecting an animal from diseases caused, for example, by at least one infectious agent.

Examples of multivalent protective compounds include, but are not limited to, a Dirofilaria or Brugia ankyrin protein of the present invention attached to one or more compounds protective against one or more other infectious agents, particularly an agent that infects humans, cats, dogs, cattle and/or horses, such as, but not limited to: viruses (e.g., adenoviruses, caliciviruses, coronaviruses, distemper viruses, hepatitis viruses, herpesviruses, immunodeficiency viruses, infectious peritonitis viruses, leukemia viruses, oncogenic viruses, panleukopenia viruses, papilloma viruses, parainfluenza viruses, parvoviruses, rabies viruses, and reoviruses, as well as other cancer-causing or cancer-related viruses); bacteria (e.g., Actinomyces, Bacillus, Bacteroides, Bordetella, Bartonella, Borrelia, Brucella, Campylobacter, Capnocytophaga, Clostridium, Corynebacterium, Coxiella, Dermatophilus, Enterococcus, Ehrlichia, Escherichia, Francisella, Fusobacterium, Haemobartonella, Helicobacter, Klebsiella, L-form bacteria, Leptospira, Listeria, Mycobacteria, Mycoplasma, Neorickettsia, Nocardia, Pasteurella, Peptococcus, Peptostreptococcus, Proteus, Pseudomonas, Rickettsia, Rochalimaea, Salmonella, Shigella, Staphylococcus, Streptococcus, and Yersinia; fungi and fungal-related micro-organisms (e.g., Absidia, Acremonium, Alternaria, Aspergillus, Basidiobolus, Bipolaris, Blastomyces, Candida, Chlamydia, Coccidioides, Conidiobolus, Cryptococcus, Curvalaria, Epidermophyton, Exophiala, Geotrichum, Histoplasma, Madurella, Malassezia, Microsporum, Moniliella, Mortierella, Mucor, Paecilomyces, Penicillium, Phialemonium, Phialophora, Prototheca, Pseudallescheria, Pseudomicrodochium, Pythium, Rhinosporidium, Rhizopus, Scolecobasidium, Sporothrix, Stemphylium, Trichophyton, Trichosporon, and Xylohypha; and other parasites (e.g., Babesia, Balantidium, Besnoitia, Cryptosporidium, Eimeria, Encephalitozoon, Entamoeba, Giardia, Hammondia, Hepatozoon, Isospora, Leishmania, Microsporidia, Neospora, Nosema, Pentatrichomonas, Plasmodium, Pneumocystis, Sarcocystis, Schistosoma, Theileria, Toxoplasma, and Trypanosoma, as well as helminth parasites, such as those disclosed herein). In one embodiment, a Dirofilaria or Brugia ankyrin protein of the present invention is attached to one or more additional compounds protective against heartworm disease, elephantiasis, or hydrocele. In another embodiment, one or more protective compounds, such as those listed above, can be included in a multivalent vaccine comprising a Dirofilaria or Brugia ankyrin protein of the present invention and one or more other protective molecules as separate compounds.

A preferred isolated protein of the present invention is a protein encoded by at least one of the following nucleic acid molecules: nDiAnk$_{937}$, nDiAnk$_{936}$, nDiAnk$_{1029}$, nDiAnk$_{810}$, nDiAnk$_{600}$, nDiAnk$_{1228}$, nDiAnk$_{1227}$, nDiAnk$_{573}$, nDiAnk$_{911}$, nDiAnk$_{909}$, nDiAnk$_{1096}$, nDiAnk$_{1044}$, nDiAnk$_{5503}$, nDiAnk$_{5235}$, nDiAnk$_{1056}$, nDiAnk$_{1266}$, nDiAnk$_{864}$, nBmAnk$_{908}$, and nBmAnk$_{906}$, or allelic variants of any of these nucleic acid molecules. Another preferred isolated protein is encoded by a nucleic acid molecule the having nucleic acid sequence SEQ ID NO:1, SEQ ID NO:4, SEQ ID NO:6, SEQ ID NO:9, SEQ ID NO:11, SEQ ID NO:14, SEQ ID NO:17, SEQ ID NO:19, SEQ ID NO:22, SEQ ID NO:25, SEQ ID NO:27, SEQ ID NO:30, SEQ ID NO:32, SEQ ID NO:35, SEQ ID NO:38, SEQ ID NO:40, SEQ ID NO:86, SEQ ID NO:88, SEQ ID NO:90, SEQ ID NO:92, SEQ ID NO:93, SEQ ID NO:94, SEQ ID NO:96, SEQ ID NO:98, SEQ ID NO:100, SEQ ID NO:102, SEQ ID NO:104, SEQ ID NO:106, SEQ ID NO:138, SEQ ID NO:141, and/or SEQ ID NO:144; or an allelic variant of such a nucleic acid molecule.

Translation of SEQ ID NO:1, the coding strand of nDiAnk$_{937}$, yields a protein of about 312 amino acids, denoted herein as PDiAnk$_{312}$, the amino acid sequence of which is presented in SEQ ID NO:2, assuming a first in-frame codon extending from nucleotide 1 to nucleotide 3 of SEQ ID NO:1. The coding region encoding PDiAnk$_{312}$ is presented herein as nDiAnk$_{936}$, which has the nucleotide sequence SEQ ID NO:4 (the coding strand) and SEQ ID NO:5 (the complementary strand).

Translation of SEQ ID NO:6, the coding strand of nDiAnk$_{1029}$, yields a protein of about 270 amino acids, denoted herein as PDiAnk$_{270}$, the amino acid sequence of which is presented in SEQ ID NO:7, assuming a first in-frame codon extending from nucleotide 2 to nucleotide 4 of SEQ ID NO:6, and a termination codon extending from nucleotide 812 to nucleotide 814 of SEQ ID NO:6. The coding region encoding PDiAnk$_{270}$, not including the termination codon, is presented herein as nDiAnk$_{810}$, which has the nucleotide sequence SEQ ID NO:9 (the coding strand) and SEQ ID NO:10 (the complementary strand). The 147 amino acid residues on the C-terminal end of PDiAnk$_{312}$ lined up with 100% identity to the 147 amino acid residues on the N-terminal end of PDiAnk$_{270}$. PDiAnk$_{270}$ thus represents approximately 123 amino acids of new *D. immitis* ankyrin amino acid sequence. The presence of a termination codon and a poly-A tail on nDiAnk$_{1029}$ indicates that nDiAnk$_{1029}$ represents the authentic 3' end of the *D. immitis* ankyrin messenger RNA that was reverse-transcribed into cDNA.

Translation of SEQ ID NO:11, the coding strand of nDiAnk$_{600}$, yields a protein of about 200 amino acids, denoted herein as PDiAnk$_{200}$, the amino acid sequence of which is presented in SEQ ID NO:12, assuming a first in-frame codon extending from nucleotide 1 to nucleotide 3 of SEQ ID NO:11. The 14 amino acid residues on the C-terminal end of PDiAnk$_{200}$ lined up with 100% identity to the 14 amino acid residues on the N-terminal end of PDi-Ank$_{312}$. PDiAnk$_{200}$ thus represents approximately 186 amino acids of new *D. immitis* ankyrin amino acid sequence.

Translation of SEQ ID NO:14, the coding strand of nDiAnk$_{1228}$, yields a protein of about 409 amino acids, denoted herein as PDiAnk$_{409}$, the amino acid sequence of which is presented in SEQ ID NO:15, assuming a first in-frame codon extending from nucleotide 1 to nucleotide 3 of SEQ ID NO:14. The coding region encoding PDiAnk$_{409}$ is presented herein as nDiAnk$_{1227}$, which has the nucleotide sequence SEQ ID NO:17 (the coding strand) and SEQ ID NO:18 (the complementary strand). The 32 amino acid residues on the C-terminal end of PDiAnk$_{409}$ lined up with 100% identity to the 32 amino acid residues on the N-terminal end of PDiAnk$_{200}$. PDiAnk$_{409}$ thus represents about 377 amino acids of new *D. immitis* ankyrin amino acid sequence.

Translation of SEQ ID NO:19, the coding strand of nDiAnk$_{573}$, yields a protein of about 191 amino acids, denoted herein as PDiAnk$_{191}$, the amino acid sequence of which is presented in SEQ ID NO:20, assuming a first in-frame codon extending from nucleotide 1 to nucleotide 3 of SEQ ID NO:19. The 32 amino acid residues on the C-terminal end of PDiAnk$_{191}$ lined up with 100% identity to the 32 amino acid residues on the N-terminal end of PDi-Ank$_{409}$. PDiAnk$_{191}$ thus represents approximately 159 amino acids of new *D. immitis* ankyrin amino acid sequence.

Translation of SEQ ID NO:22, the coding strand of nDiAnk$_{911}$, yields a protein of about 303 amino acids, denoted herein as PDiAnk$_{303}$, the amino acid sequence of which is presented in SEQ ID NO:23, assuming a first in-frame codon extending from nucleotide 1 to nucleotide 3 of SEQ ID NO:22. The coding region encoding PDiAnk$_{303}$ is presented herein as nDiAnk$_{909}$, which has the nucleotide sequence SEQ ID NO:25 (the coding strand) and SEQ ID NO:26 (the complementary strand). The 54 amino acid residues on the C-terminal end of PDiAnk$_{303}$ lined up with 100% identity to the 54 amino acid residues on the N-terminal end of the PDiAnk$_{409}$. PDiAnk$_{303}$ thus represents approximately 249 amino acids of new *D. immitis* ankyrin amino acid sequence.

Translation of SEQ ID NO:27, the coding strand of nDiAnk$_{1096}$, yields a protein of about 348 amino acids, denoted herein as PDiAnk$_{348}$, the amino acid sequence of which is presented in SEQ ID NO:28, assuming a start codon extending from nucleotide 51 to nucleotide 53 of SEQ ID NO:27. The nucleic acid molecule representing the coding region encoding PDiAnk$_{348}$, denoted herein as nDiAnk$_{1044}$, is presented herein as SEQ ID NO:30 (the coding strand) and SEQ ID NO:31 (the complementary strand). The about 9 amino acid residues on the C-terminal end of PDiAnk$_{348}$ lined up with about 100% identity to the about 9 amino acid residues on the N-terminal end of the PDiAnk$_{303}$. PDiAnk$_{348}$ thus represents approximately 339 amino acids of new *D. immitis* ankyrin amino acid sequence.

Translation of SEQ ID NO:32, the coding strand of nDiAnk$_{5503}$, yields a full-length polypeptide of about 1745 amino acids, denoted PDiAnk$_{1745}$, assuming a start codon extending from nucleotide 51 through nucleotide 53 of SEQ ID NO:32, and a stop codon extending from nucleotide 5286 through nucleotide 5285 of SEQ ID NO:32. The resulting amino acid sequence is presented as SEQ ID NO:33. The coding region encoding PDiAnk$_{1745}$, not including the termination codon, is denoted herein as nDiANK$_{5235}$, and has the nucleotide sequence SEQ ID NO:35 (the coding strand) and SEQ ID NO:36 (the complementary strand). SEQ ID NO:35 is predicted to encode a protein with a molecular mass of about 191.7 kD and with a predicted pI of about 5.76, as calculated by the DNAsis program (available from Hitachi Software, San Bruno, Calif.).

A homology search of a non-redundant protein database was performed with SEQ ID NO:33, using the blastp program available through the BLAST™ network of the National Center for Biotechnology Information (NCBI) (National Library of Medicine, National Institutes of Health, Baltimore, Md.), available on the World Wide Web. This database includes SwissProt+PIR+SPupdate+GenPept+GPUpdate+PDB databases. The highest scoring match of the homology search at amino acid level was GenBank™ accession number gi|1208874, a *C. elegans* ankyrin-like protein, to which SEQ ID NO:33 showed about 69% identity, spanning from about amino acid 1 through about amino acid 1745 of SEQ ID NO:33. The second highest highest scoring match of the homology search at amino acid level was GenBank™ accession number gi|406288, a human brain ankyrin protein (variant I, Ankyrin$_B$), to which SEQ ID NO:33 showed about 51% identity, spanning from about amino acid 1 through about amino acid 1745.

SEQ ID NO:33 was also compared with the protein sequence of the *O. volvulus* E1 protein as disclosed by Erttmann, et al., 1996a, ibid. A region of SEQ ID NO:33 spanning from about amino acid 1282 to about amino acid 1745 showed about 78% identity to the 462-amino acid *O. volvulus* E1 protein. At the nucleotide level, the cDNA encoding SEQ ID NO:33 (i.e., SEQ ID NO:32) was compared to the cDNA encoding the *O. volvulus* E1 protein. A region of SEQ ID NO:32 spanning from about nucleotide 3423 to about nucleotide 5474 showed about 88% nucleic acid identity to the cDNA encoding the *O. volvulus* E1 protein.

Translation of SEQ ID NO:37, the coding strand of nBmAnk$_{908}$, yields a non-full-length polypeptide of about 302 amino acids, denoted PBmAnk$_{302}$, assuming a first in-frame codon extending from nucleotide 1 through nucleotide 3 of SEQ ID NO:37. The resulting amino acid sequence is presented as SEQ ID NO:38. The coding region encoding PBmAnk$_{302}$ is denoted herein as nBmANK$_{906}$, and has the nucleotide sequence SEQ ID NO:40 (the coding strand) and SEQ ID NO:41 (the complementary strand).

A homology search of a non-redundant protein database was performed on SEQ ID NO:38 using the BLAST network. The homology spans from about amino acid 1 through amino acid 302 of SEQ ID NO:38. The highest scoring match of the homology search at amino acid level was GenBank accession number A57282, a *C. elegans* ankyrin-like protein, which was about 86% identical to SEQ ID NO:38 through a region extending from about amino acid 353 through about amino acid 654 of A57282.

The amino acid sequence of SEQ ID NO:38 was also compared to *D. immitis* ankyrin protein PDiAnk$_{1745}$ (i.e.

SEQ ID NO:33 of the present invention). PBmAnk$_{302}$ had 95% identity to the region of SEQ ID NO:33 spanning from about amino acid 341 through about amino acid 642.

Preferred ankyrin proteins of the present invention include proteins that are at least about 75%, preferably at least about 80%, more preferably at least about 85%, even more preferably at least about 90%, and even more preferably at least about 95% identical, and even more preferably at least about 98% identical to PdiAnk$_{1745}$, PDiANK$_{352}$, PDiANK$_{422}$, or PDiANK$_{288}$; or are at least about 90%, and preferably at least about 95%, identical to PBmAnk$_{302}$. More preferred are ankyrin proteins comprising PDiAnk$_{312}$, PDiAnk$_{270}$, PDiAnk$_{200}$, PDiAnk$_{409}$, PDiAnk$_{191}$, PDiAnk$_{303}$, PDiAnk$_{348}$, PDiAnk$_{1745}$, PDiANK$_{352}$, PdiANK$_{422}$, PDiANK$_{288}$ or PBmAnk$_{302}$; and proteins encoded by allelic variants of a nucleic acid molecules encoding these proteins.

A preferred ankyrin protein of the present invention includes a protein having an amino acid sequence that are at least about 75%, preferably at least about 80%, more preferably at least about 85%, even more preferably at least about 90%, and even more preferably at least about 95%, and even more preferably at least about 98% identical to SEQ ID NO:33, SEQ ID NO:138, SEQ ID NO:141, SEQ ID NO:144; or a protein having amino acid sequences that is at least about 90%, and preferably at least about 95% identical to SEQ ID NO:38. Another preferred ankyrin protein of the present invention includes a protein having an amino acid sequence that is at least about 75% identical to SEQ ID NO:33, an amino acid sequence that is at least about 90% identical to SEQ ID NO:38 an amino acid sequence that is at least about 85% identical to SEQ ID NO:139, an amino acid sequence that is at least about 95% identical to SEQ ID NO:142, an amino acid sequence that is at least about 75% identical to SEQ ID NO:145, an amino acid sequence that is at least about 75% identical to SEQ ID NO:161, an amino acid sequence that is at least about 85% identical to SEQ ID NO:162, an amino acid sequence that is at least about 85% identical to SEQ ID NO:163, an amino acid sequence that is at least about 90% identical to SEQ ID NO:165, an amino acid sequence that is at least about 75% identical to SEQ ID NO:166, an amino acid sequence that is at least about 90% identical to SEQ ID NO:167, an amino acid sequence that is at least about 80% identical to SEQ ID NO:168, an amino acid sequence that is at least about 95% identical to SEQ ID NO:169, an amino acid sequence that is at least about 7 5% identical to SEQ ID NO:170, or an amino acid sequence that is at least about 95% identical to SEQ ID NO:171. A more preferred are ankyrin protein comprises amino acid sequence SEQ ID NO:2, SEQ ID NO:7, SEQ ID NO:12, SEQ ID NO:15, SEQ ID NO:20, SEQ ID NO:23, SEQ ID NO:28, SEQ ID NO:33, SEQ ID NO:38, SEQ ID NO:139, SEQ ID NO:142, SEQ ID NO:145, SEQ ID NO:161, SEQ ID NO:162, SEQ ID NO:163, SEQ ID NO:165, SEQ ID NO:166, SEQ ID NO:167, SEQ ID NO:168, SEQ ID NO:169, SEQ ID NO:170, and/or SEQ ID NO:171; and an ankyrin protein encoded by an allelic variant of a nucleic acid molecule encoding an ankyrin protein having any one of these amino acid sequences.

Particularly preferred Dirofilaria ankyrin proteins of the present invention comprise amino acid sequence SEQ ID NO:33 (including, but not limited to, the proteins consisting of amino acid sequence SEQ ID NO:33, fusion proteins and multivalent proteins), and proteins encoded by allelic variants of nucleic acid molecules encoding proteins having amino acid sequence SEQ ID NO:33; and particularly preferred Brugia ankyrin proteins of the present invention comprise amino acid sequence SEQ ID NO:38 (including, but not limited to, the proteins consisting of SEQ ID NO:38, fusion proteins and multivalent proteins), and proteins encoded by allelic variants of nucleic acid molecules encoding proteins having amino acid sequence SEQ ID NO:38.

In one embodiment, a preferred D. immitis or B. malayi ankyrin protein of the present invention comprises an amino acid sequence of at least about 500 amino acids, preferably at least about 1000 amino acids, and even more preferably at least about 1500 amino acids. Within this embodiment, a preferred D. immitis ankyrin protein of the present invention has an amino acid sequence comprising at least a portion of SEQ ID NO:33. In another embodiment, a preferred D. immitis or B. malayi ankyrin protein comprises a full-length protein, i.e., a protein encoded by a full-length coding region. A particularly preferred apparently full-length ankyrin protein is PDiAnk$_{1745}$.

Additional preferred ankyrin proteins of the present invention include proteins encoded by nucleic acid molecules comprising at least a portion of nDiAnk$_{937}$, nDiAnk$_{936}$, nDiAnk$_{1029}$, nDiAnk$_{810}$, nDiAnk$_{600}$, nDiAnk$_{1228}$, nDiAnk$_{1227}$, nDiAnk$_{573}$, nDiAnk$_{911}$, nDiAnk$_{909}$, nDiAnk$_{1096}$, nDiAnk$_{1044}$, nDiAnk$_{5503}$, nDiAnk$_{5235}$, nBmAnk$_{908}$, nDiAnk$_{1056}$, nDiAnk$_{1266}$, nDiAnk$_{864}$, and/or nBmAnk$_{906}$, as well as ankyrin proteins encoded by allelic variants of these nucleic acid molecules.

Also preferred are ankyrin proteins encoded by nucleic acid molecules having nucleic acid sequences comprising at least a portion of SEQ ID NO:1, SEQ ID NO:4, SEQ ID NO:6, SEQ ID NO:9, SEQ ID NO:11, SEQ ID NO:14, SEQ ID NO:17, SEQ ID NO:19, SEQ ID NO:22, SEQ ID NO:25, SEQ ID NO:27, SEQ ID NO:30, SEQ ID NO:32, SEQ ID NO:35, SEQ ID NO:37, SEQ ID NO:40, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:138, SEQ ID NO:141, and/or SEQ ID NO:144 as well as allelic variants of these nucleic acid molecules.

In another embodiment, a preferred Dirofilaria or Brugia ankyrin protein of the present invention is encoded by a nucleic acid molecule comprising at least about 1500 nucleotides, preferably at least about 3000 nucleotides and more preferably at least about 4500 nucleotides. Within this embodiment is an ankyrin protein encoded by at least a portion nDiAnk$_{5503}$ or by an allelic variant of this nucleic acid molecule. In yet another embodiment, a preferred Dirofilaria or Brugia ankyrin protein of the present invention is encoded by a nucleic acid molecule comprising an apparently full-length ankyrin coding region, i.e., a nucleic acid molecule encoding an apparently full-length ankyrin protein.

Another embodiment of the present invention is an isolated nucleic acid molecule comprising either a Dirofilaria ankyrin nucleic acid molecule or a Brugia ankyrin nucleic acid molecule. The identifying characteristics of such nucleic acid molecules is heretofore described. A nucleic acid molecule of the present invention can include an isolated natural Dirofilaria or Brugia ankyrin gene or a homolog thereof, the latter of which is described in more detail below. A nucleic acid molecule of the present invention can include one or more regulatory regions, full-length or partial coding regions, or combinations thereof. The minimal size of a nucleic acid molecule of the present invention is a size sufficient to allow the formation of a stable hybrid (i.e., hybridization under stringent hybridization conditions) with the complementary sequence of another nucleic acid molecule. As such, the minimal size of an ankyrin nucleic acid molecule of the present invention is from about 12 to about 18 nucleotides in length. Preferred ankyrin nucleic acid molecules include *D. immitis* ankyrin nucleic acid molecules and *B. malayi* ankyrin nucleic acid molecules.

In accordance with the present invention, an isolated nucleic acid molecule is a nucleic acid molecule that has been removed from its natural milieu (i.e., that has been subjected to human manipulation) and can include DNA, RNA, or derivatives of either DNA or RNA. As such, "isolated" does not reflect the extent to which the nucleic acid molecule has been purified. An isolated Dirofilaria or Brugia ankyrin nucleic acid molecule of the present invention can be isolated from its natural source or produced using recombinant DNA technology (e.g., polymerase chain reaction (PCR) amplification or cloning) or chemical synthesis. Isolated Dirofilaria or Brugia ankyrin nucleic acid molecules can include, for example, natural allelic variants and nucleic acid molecules modified by nucleotide insertions, deletions, substitutions, and/or inversions in a manner such that the modifications do not substantially interfere with the nucleic acid molecule's ability to encode an ankyrin protein of the present invention.

A Dirofilaria or Brugia ankyrin nucleic acid molecule homolog can be produced using a number of methods known to those skilled in the art, see, for example, Sambrook et al., 1989, *Molecular Cloning: A Laboratory Manual,* Cold Spring Harbor Labs Press; Sambrook et al., ibid., is herein incorporated by reference in its entirety. For example, nucleic acid molecules can be modified using a variety of techniques including, but not limited to, classic mutagenesis and recombinant DNA techniques such as site-directed mutagenesis, chemical treatment, restriction enzyme cleavage, ligation of nucleic acid fragments, PCR amplification, synthesis of oligonucleotide mixtures and ligation of mixture groups to "build" a mixture of nucleic acid molecules, and combinations thereof. Nucleic acid molecule homologs can be selected by hybridization with a Dirofilaria or Brugia ankyrin nucleic acid molecule or by screening the function of a protein encoded by the nucleic acid molecule (e.g., ability to elicit an immune response against at least one epitope of a Dirofilaria or Brugia ankyrin protein).

An isolated nucleic acid molecule of the present invention can include a nucleic acid sequence that encodes at least one Dirofilaria or Brugia ankyrin protein of the present invention, examples of such proteins being disclosed herein. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a Dirofilaria or Brugia ankyrin protein.

A preferred nucleic acid molecule of the present invention, when administered to an animal, is capable of protecting that animal from disease caused by a parasitic helminth. As will be disclosed in more detail below, such a nucleic acid molecule can be, or encode, an antisense RNA, a molecule capable of triple helix formation, a ribozyme, or other nucleic acid-based drug compound. In additional embodiments, a nucleic acid molecule of the present invention can encode a protective protein (e.g., an ankyrin protein of the present invention), the nucleic acid molecule being delivered to the animal, for example, by direct injection (i.e, as a genetic vaccine) or in a vehicle such as a recombinant virus vaccine or a recombinant cell vaccine.

One embodiment of the present invention is an ankyrin nucleic acid molecule comprising all or part of nucleic acid molecules $nDiAnk_{937}$, $nDiAnk_{936}$, $nDiAnk_{1029}$, $nDiAnk_{810}$, $nDiAnk_{600}$, $nDiAnk_{1228}$, $nDiAnk_{1227}$, $nDiAnk_{573}$, $nDiAnk_{911}$, $nDiAnk_{909}$, $nDiAnk_{1096}$, $nDiAnk_{1044}$, $nDiAnk_{5503}$, $nDiAnk_{5235}$, $nDiAnk_{1056}$, $nDiAnk_{1266}$, $nDiAnk_{864}$, $nBmAnk_{908}$, or $nBmAnk_{906}$, or allelic variants of these nucleic acid molecules. Another preferred nucleic acid molecule of the present invention includes at least a portion of nucleic acid sequence SEQ ID NO:1, SEQ ID NO:3, SEQ ID NO:4, SEQ ID NO:5, SEQ ID NO:6, SEQ ID NO:8, SEQ ID NO:9, SEQ ID NO:10, SEQ ID NO:11, SEQ ID NO:13, SEQ ID NO:14, SEQ ID NO:16, SEQ ID NO:17, SEQ ID NO:18, SEQ ID NO:19, SEQ ID NO:21, SEQ ID NO:22, SEQ ID NO:24, SEQ ID NO:25, SEQ ID NO:26, SEQ ID NO:27, SEQ ID NO:29, SEQ ID NO:30, SEQ ID NO:31, SEQ ID NO:32, SEQ ID NO:34, SEQ ID NO:35, SEQ ID NO:36, SEQ ID NO:37, SEQ ID NO:39, SEQ ID NO:40, SEQ ID NO:41, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:138, SEQ ID NO:141, and/or SEQ ID NO:144, as well as allelic variants of nucleic acid molecules having these nucleic acid sequences. Such nucleic acid molecules can include nucleotides in addition to those included in the SEQ ID NOs, such as, but not limited to, a full-length gene, a full-length coding region, a nucleic acid molecule encoding a fusion protein, or a nucleic acid molecule encoding a multivalent protective compound.

In one embodiment, an ankyrin nucleic acid molecule of the present invention encodes a protein that is at least about 75%, preferably at least about 80%, more preferably at least about 85%, even more preferably at least about 90%, and even more preferably at least about 95% identical to $PDiAnk_{1745}$; or is at least about 90%, and preferably at least about 95%, identical to $PBmAnk_{302}$. Even more preferred is a nucleic acid molecule encoding $PDiAnk_{312}$, $PDiAnk_{270}$, $PDiAnk_{200}$, $PDiAnk_{409}$, $PDiAnk_{191}$, $PDiAnk_{303}$, $PDiAnk_{348}$, $PDiAnk_{1745}$, $PBmAnk_{302}$, and/or an allelic variant of such a nucleic acid molecule.

In another embodiment, an ankyrin nucleic acid molecule of the present invention encodes a protein having an amino acid sequence that is at least about 75%, preferably at least about 80%, more preferably at least about 85%, even more preferably at least about 90%, and even more preferably at least about 95% identical to SEQ ID NO:33; or is at least about 90%, and preferably at least about 95%, identical to SEQ ID NO:38. The present invention also includes an ankyrin nucleic acid molecule encoding a protein having at least a portion of SEQ ID NO:2, SEQ ID NO:7, SEQ ID NO:12, SEQ ID NO:15, SEQ ID NO:20, SEQ ID NO:23, SEQ ID NO:28, SEQ ID NO:33 SEQ ID NO:38, SEQ ID NO:139, SEQ ID NO:142, SEQ ID NO:145, SEQ ID NO:161, SEQ ID NO:162, SEQ ID NO:163, SEQ ID NO:165, SEQ ID NO:166, SEQ ID NO:167, SEQ ID NO:168, SEQ ID NO:169, SEQ ID NO:170, and/or SEQ ID NO:171, as well as allelic variants of an ankyrin nucleic acid molecule encoding a protein having these sequences, including nucleic acid molecules that have been modified to accommodate codon usage properties of the cells in which such nucleic acid molecules are to be expressed.

In another embodiment, a preferred Dirofilaria or Brugia ankyrin nucleic acid molecule encodes an ankyrin protein comprising at least about 500 amino acids, preferably at least about 1000 amino acids, and more preferably at least about 1500 amino acids; i.e., an ankyrin nucleic acid molecule that comprises a contiguous ankyrin coding region of at least about 1500 nucleotides, preferably at least about 3000 nucleotides, and more preferably at least about 4500 nucleotides.

In yet another embodiment, a preferred Dirofilaria or Brugia ankyrin nucleic acid molecule of the present invention comprises an apparently full-length ankyrin coding region, i.e., the preferred nucleic acid molecule encodes an apparently full-length ankyrin protein.

Knowing the nucleic acid sequences of certain Dirofilaria or Brugia ankyrin nucleic acid molecules of the present invention allows one skilled in the art to, for example, (a) make copies of those nucleic acid molecules, (b) obtain nucleic acid molecules including at least a portion of such nucleic acid molecules (e.g., nucleic acid molecules including full-length genes, full-length coding regions, regulatory control sequences, truncated coding regions), and (c) obtain other Dirofilaria or Brugia ankyrin nucleic acid molecules. Such nucleic acid molecules can be obtained in a variety of ways including screening appropriate expression libraries with antibodies of the present invention, or amplifying genomic DNA; traditional cloning techniques using oligonucleotide probes of the present invention to screen appropriate libraries; and PCR amplification of appropriate libraries or DNA using oligonucleotide primers of the present invention. Preferred libraries to screen or from which to amplify nucleic acid molecules include Dirofilaria or Brugia L3, L4 or adult cDNA libraries as well as genomic DNA libraries. Similarly, preferred DNA sources from which to amplify nucleic acid molecules include Dirofilaria or Brugia L3, L4 or adult cDNA and genomic DNA. Techniques to clone and amplify genes are disclosed, for example, in Sambrook et al., ibid.

The present invention also includes nucleic acid molecules that are oligonucleotides capable of hybridizing, under stringent hybridization conditions, with complementary regions of other, preferably longer, nucleic acid molecules of the present invention such as those comprising Dirofilaria or Brugia ankyrin nucleic acid molecules or other parasitic helminth ankyrin nucleic acid molecules. Oligonucleotides of the present invention can be RNA, DNA, or derivatives of either. The minimum size of such oligonucleotides is the size required for formation of a stable hybrid between an oligonucleotide and a complementary sequence on a nucleic acid molecule of the present invention. A preferred oligonucleotide of the present invention has a maximum size of about 100 nucleotides. The present invention includes oligonucleotides that can be used as, for example, probes to identify nucleic acid molecules, primers to produce nucleic acid molecules, or therapeutic reagents to inhibit Dirofilaria or Brugia ankyrin protein production or activity (e.g., as antisense-, triplex formation-, ribozyme- and/or RNA drug-based reagents). The present invention also includes the use of such oligonucleotides to protect animals from disease using one or more of such technologies. Appropriate oligonucleotide-containing therapeutic compositions can be administered to an animal using techniques known to those skilled in the art.

One embodiment of the present invention includes a recombinant vector, which includes at least one isolated nucleic acid molecule of the present invention, inserted into any vector capable of delivering the nucleic acid molecule into a host cell. Such a vector contains heterologous nucleic acid sequences, that is nucleic acid sequences that are not naturally found adjacent to nucleic acid molecules of the present invention and that preferably are derived from a species other than the species from which the nucleic acid molecule(s) are derived. The vector can be either RNA or DNA, either prokaryotic or eukaryotic, and typically is a virus or a plasmid. Recombinant vectors can be used in the cloning, sequencing, and/or otherwise manipulating of Dirofilaria and Brugia ankyrin nucleic acid molecules of the present invention.

One type of recombinant vector, referred to herein as a recombinant molecule, comprises a nucleic acid molecule of the present invention operatively linked to an expression vector. The phrase operatively linked refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, parasite, insect, other animal, and plant cells. Preferred expression vectors of the present invention can direct gene expression in bacterial, yeast, helminth or other parasite, insect and mammalian cells, and more preferably in the cell types disclosed herein.

In particular, expression vectors of the present invention contain regulatory sequences such as transcription control sequences, translation control sequences, origins of replication, and other regulatory sequences that are compatible with the recombinant cell and that control the expression of nucleic acid molecules of the present invention. In particular, recombinant molecules of the present invention include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, helminth or other endoparasite, or insect and mammalian cells, such as, but not limited to, tac, lac, trp, trc, oxy-pro, omp/lpp, rrnB, bacteriophage lambda (such as lambda $p_L$ and lambda $p_R$ and fusions that include such promoters), bacteriophage T7, T7lac, bacteriophage T3, bacteriophage SP6, bacteriophage SP01, metallothionein, alpha-mating factor, Pichia alcohol oxidase, alphavirus subgenomic promoter, antibiotic resistance gene, baculovirus, *Heliothis zea* insect virus, vaccinia virus, herpesvirus, raccoon poxvirus, other poxvirus, adenovirus, cytomegalovirus (such as immediate early promoter), simian virus 40, retrovirus, actin, retroviral long terminal repeat, Rous sarcoma virus, heat shock, phosphate and nitrate transcription control sequences as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukins). Transcription control sequences of the present invention can also include naturally occurring transcription control sequences naturally associated with parasitic helminths, such as *D immitis* or *B. malayi* transcription control sequences.

Suitable and preferred nucleic acid molecules to include in recombinant vectors of the present invention are as disclosed herein. Preferred nucleic acid molecules to include in recombinant vectors, and particularly in recombinant molecules, include $nDiAnk_{937}$, $nDiAnk_{936}$, $nDiAnk_{1029}$, $nDiAnk_{810}$, $nDiAnk_{600}$, $nDiAnk_{1228}$, $nDiAnk_{1227}$, $nDiAnk_{573}$, $nDiAnk_{911}$, $nDiAnk_{909}$, $nDiAnk_{1096}$, $nDiAnk_{1044}$, $nDiAnk_{5503}$, $nDiAnk_{5235}$, $nDiAnk_{1056}$, $nDiAnk_{1266}$, $nDiAnk_{864}$, $nBmAnk_{908}$, and $nBmAnk_{906}$. Particularly preferred recombinant molecules of the present invention include $pTrc-nDiAnk_{1866}$, $pTrc-nDiAnk_{1056}$, $pTrc-nDiAnk_{1266}$, $pTrc-nDiAnk_{864}$, $pTrc-nDiAnk_{1056}$, $pTrc-nDiAnk_{1266}$, and $pTrc-nDiAnk_{864}$, the production of which are described in the Examples section.

Recombinant molecules of the present invention may also (a) contain secretory signals (i.e., signal segment nucleic acid sequences) to enable an expressed parasitic helminth protein of the present invention to be secreted from the cell that produces the protein and/or (b) contain fusion sequences which lead to the expression of nucleic acid molecules of the present invention as fusion proteins. Examples of suitable signal segments include any signal segment capable of directing the secretion of a protein of the present invention. Preferred signal segments include, but are not limited to, tissue plasminogen activator (t-PA), interferon, interleukin, growth hormone, histocompatibility and viral envelope glycoprotein signal segments. Suitable fusion segments encoded by fusion segment nucleic acids are disclosed herein. In addition, a nucleic acid molecule of the present invention can be joined to a fusion segment that directs the encoded protein to the proteosome, such as a ubiquitin fusion segment. Eukaryotic recombinant molecules may also include intervening and/or untranslated sequences surrounding and/or within the nucleic acid sequences of nucleic acid molecules of the present invention.

Another embodiment of the present invention includes a recombinant cell comprising a host cell transformed with one or more recombinant molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained. Preferred nucleic acid molecules with which to transform a cell include Dirofilaria and Brugia ankyrin nucleic acid molecules disclosed herein. Particularly preferred nucleic acid molecules with which to transform a cell include $nDiAnk_{937}$, $nDiAnk_{936}$, $nDiAnk_{1029}$, $nDiAnk_{810}$, $nDiAnk_{600}$, $nDiAnk_{1228}$, $nDiAnk_{1227}$, $nDiAnk_{573}$, $nDiAnk_{911}$, $nDiAnk_{909}$, $nDiAnk_{1096}$, $nDiAnk_{1044}$, $nDiAnk_{5503}$, $nDiAnk_{5235}$, $nDiAnk_{1056}$, $nDiAnk_{1266}$, $nDiAnk_{864}$, $nBmAnk_{908}$, and $nBmAnk_{906}$.

Suitable host cells to transform include any cell that can be transformed with a nucleic acid molecule of the present invention. Host cells can be either untransformed cells or cells that are already transformed with at least one nucleic acid molecule (e.g., nucleic acid molecules encoding one or more proteins of the present invention and/or other proteins useful in the production of multivalent vaccines). Host cells of the present invention either can be endogenously (i.e., naturally) capable of producing Dirofilaria or Brugia ankyrin proteins of the present invention or can be capable of producing such proteins after being transformed with at least one nucleic acid molecule of the present invention. Host cells of the present invention can be any cell capable of producing at least one protein of the present invention, and include bacterial, fungal (including yeast), parasite (including helminth, protozoa and ectoparasite), other insect, other animal and plant cells. Preferred host cells include bacterial, mycobacterial, yeast, helminth, insect and mammalian cells. More preferred host cells include Salmonella, Escherichia, Bacillus, Listeria, Saccharomyces, Spodoptera, Mycobacteria, Trichoplusia, BHK (baby hamster kidney) cells, MDCK cells (Madin-Darby canine kidney cell line), CRFK cells (Crandell feline kidney cell line), CV-1 cells (African monkey kidney cell line used, for example, to culture raccoon poxvirus), COS (e.g., COS-7) cells, and Vero cells. Particularly preferred host cells are *Escherichia coli*, including *E. coli* K-12 derivatives; *Salmonella typhi*; *Salmonella typhimurium*, including attenuated strains such as UK-1 χ3987 and SR-11 χ4072; *Spodoptera frugiperda*; *Trichoplusia ni*; BHK cells; MDCK cells; CRFK cells; CV-1 cells; COS cells; Vero cells; and non-tumorigenic mouse myoblast G8 cells (e.g., ATCC CRL 1246). Additional appropriate mammalian cell hosts include other kidney cell lines, other fibroblast cell lines (e.g., human, murine or chicken embryo fibroblast cell lines), myeloma cell lines, Chinese hamster ovary cells, mouse NIH/3T3 cells, $LMTK^{31}$ cells and/or HeLa cells. In one embodiment, the proteins may be expressed as heterologous proteins in myeloma cell lines employing immunoglobulin promoters.

A recombinant cell is preferably produced by transforming a host cell with one or more recombinant molecules, each comprising one or more nucleic acid molecules of the present invention operatively linked to an expression vector containing one or more transcription control sequences, examples of which are disclosed herein. Particularly preferred recombinant molecules include $pTrc-nDiAnk_{1866}$, $pTrc-nDiAnk_{1056}$, $pTrc-nDiAnk_{1266}$, $pTrc-nDiAnk_{864}$, $pTrc-nDiAnk_{1056}$, $pTrc-nDiAnk_{1266}$, and $pTrc-nDiAnk_{864}$.

A recombinant cell of the present invention includes any cell transformed with at least one of any nucleic acid molecule of the present invention. Suitable and preferred nucleic acid molecules as well as suitable and preferred recombinant molecules with which to transfer cells are disclosed herein. Particularly preferred recombinant cells include *E. coli*:$pTrc-nDiAnk_{1866}$, *E. coli*:$pTrc-nDiAnk_{1056}$, *E. coli*:$pTrc-nDiAnk_{1266}$, *E. coli*:$pTrc-nDiAnk_{864}$, *E. coli*:$pTrc-nDiAnk_{1056}$, *E. coli*:$pTrc-nDiAnk_{1266}$, *E. coli*:$pTrc-nDiAnk_{864}$. Details regarding the production of these recombinant cells are disclosed herein.

Recombinant cells of the present invention can also be co-transformed with one or more recombinant molecules including Dirofilaria or Brugia ankyrin nucleic acid molecules encoding one or more proteins of the present invention and one or more other nucleic acid molecules encoding other protective compounds, as disclosed herein (e.g., to produce multivalent vaccines).

Recombinant DNA technologies can be used to improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, deletion of sequences that destabilize transcripts, and use of control signals that temporally separate recombinant cell growth from recombinant enzyme production during fermentation. The activity of an expressed recombinant protein of the present invention may be improved by fragmenting, modifying, or derivatizing nucleic acid molecules encoding such a protein.

Isolated Dirofilaria or Brugia ankyrin proteins of the present invention can be produced in a variety of ways, including production and recovery of natural proteins, production and recovery of recombinant proteins, and chemical synthesis of the proteins. In one embodiment, an isolated protein of the present invention is produced by culturing a cell capable of expressing the protein under conditions effective to produce the protein, and recovering the protein. A preferred cell to culture is a recombinant cell of the present invention. Effective culture conditions include, but are not limited to, effective media, bioreactor, temperature, pH and oxygen conditions that permit protein production. An effective, medium refers to any medium in which a cell is cultured to produce a Dirofilaria or Brugia ankyrin protein of the present invention. Such medium typically comprises an aqueous medium having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art. Examples of suitable conditions are included in the Examples section.

Depending on the vector and host system used for production, resultant proteins of the present invention may either remain within the recombinant cell; be secreted into the fermentation medium; be secreted into a space between two cellular membranes, such as the periplasmic space in *E. coli*; or be retained on the outer surface of a cell or viral membrane.

The phrase "recovering the protein", as well as similar phrases, refers to collecting the whole fermentation medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization. Proteins of the present invention are preferably retrieved in "substantially pure" form. As used herein, "substantially pure" refers to a purity that allows for the effective use of the protein as a therapeutic composition or diagnostic. A therapeutic composition for animals, for example, should exhibit no substantial toxicity and preferably should be capable of stimulating the production of antibodies in a treated animal.

The present invention also includes isolated (i.e., removed from their natural milieu) antibodies that selectively bind to a Dirofilaria or Brugia ankyrin protein of the present invention or a mimetope thereof (e.g., anti-Dirofilaria ankyrin antibodies or anti-Brugia ankyrin antibodies). As used herein, the term "selectively binds to" an ankyrin protein refers to the ability of antibodies of the present invention to preferentially bind to specified proteins and mimetopes thereof of the present invention. Binding can be measured using a variety of methods standard in the art including enzyme immunoassays (e.g., ELISA), immunoblot assays, etc.; see, for example, Sambrook et al., ibid., and Harlow, et al., 1988, *Antibodies, a Laboratory Manual*, Cold Spring Harbor Labs Press; Harlow et al., ibid., is herein incorporated by reference in its entirety. An anti-ankyrin antibody of the present invention preferably selectively binds to a Dirofilaria or Brugia ankyrin protein in such a way as to inhibit the function of that protein.

Isolated antibodies of the present invention can include antibodies in serum, or antibodies that have been purified to varying degrees. Antibodies of the present invention can be polyclonal or monoclonal, or can be functional equivalents such as antibody fragments and genetically-engineered antibodies, including single chain antibodies or chimeric antibodies that can bind to one or more epitopes.

A preferred method to produce antibodies of the present invention includes (a) administering to an animal an effective amount of a protein, peptide or mimetope thereof of the present invention to produce the antibodies and (b) recovering the antibodies. In another method, antibodies of the present invention are produced recombinantly using techniques as heretofore disclosed to produce ankyrin proteins of the present invention. Antibodies raised against defined proteins or mimetopes can be advantageous because such antibodies are not substantially contaminated with antibodies against other substances that might otherwise cause interference in a diagnostic assay or side effects if used in a therapeutic composition.

Antibodies of the present invention have a variety of potential uses that are within the scope of the present invention. For example, such antibodies can be used (a) as therapeutic compounds to passively immunize an animal in order to protect the animal from parasitic helminths susceptible to treatment by such antibodies, (b) as reagents in assays to detect infection by such helminths and/or (c) as tools to screen expression libraries and/or to recover desired proteins of the present invention from a mixture of proteins and other contaminants. Furthermore, antibodies of the present invention can be used to target cytotoxic agents to parasitic helminths in order to directly kill such helminths. Targeting can be accomplished by conjugating (i.e., stably joining) such antibodies to the cytotoxic agents using techniques known to those skilled in the art. Suitable cytotoxic agents are known to those skilled in the art.

One embodiment of the present invention is a therapeutic composition that, when administered to an animal in an effective manner, is capable of protecting that animal from disease caused by a parasitic helminth. Therapeutic compositions of the present invention include at least one of the following protective compounds: an isolated Dirofilaria or Brugia ankyrin protein or a mimetope thereof, an isolated Dirofilaria or Brugia ankyrin nucleic acid molecule, an isolated antibody that selectively binds to a Dirofilaria or Brugia ankyrin protein, an inhibitor of ankyrin function identified by its ability to bind to a Dirofilaria or Brugia ankyrin protein and thereby impede development and/or migration of the parasite, and a mixture thereof (i.e., combination of at least two of the compounds). As used herein, a protective compound refers to a compound that, when administered to an animal in an effective manner, is able to treat, ameliorate, and/or prevent disease caused by a parasitic helminth. Preferred helminths to target are heretofore disclosed. Examples of proteins, nucleic acid molecules, antibodies and inhibitors of the present invention are disclosed herein.

The present invention also includes a therapeutic composition comprising at least one Dirofilaria or Brugia ankyrin-based compound of the present invention in combination with at least one additional compound protective against one or more infectious agents. Examples of such compounds and infectious agents are disclosed herein.

Therapeutic compositions of the present invention can be administered to any animal susceptible to such therapy, preferably to mammals, and more preferably to dogs, cats, humans, ferrets, horses, cattle, sheep and other pets, economic food animals and/or zoo animals. Preferred animals to protect against heartworm disease include dogs, cats, humans and ferrets, with dogs and cats being particularly preferred. The preferred animals to protect against elephantiasis and hydrocele include humans.

In one embodiment, a therapeutic composition of the present invention can be administered to the vector in which the parasitic helminth develops, such as to a mosquito in order to prevent the spread of heartworm. Such administration could be oral or by developing transgenic vectors capable of producing at least one therapeutic composition of the present invention. In another embodiment, an insect vector, such as a mosquito, can ingest therapeutic compositions present in the blood of a host that has been administered a therapeutic composition of the present invention.

In order to protect an animal from disease caused by a parasitic helminth, a therapeutic composition of the present invention is administered to the animal in an effective manner such that the composition is capable of protecting that animal from a disease caused by a parasitic helminth. Therapeutic compositions of the present invention can be administered to animals prior to infection in order to prevent infection (i.e., as a preventative vaccine) and/or can be administered to animals after infection in order to treat disease caused by the parasitic helminth (i.e., as a therapeutic vaccine).

Therapeutic compositions of the present invention can be formulated in an excipient that the animal to be treated can tolerate. Examples of such excipients include water, saline, Ringer's solution, dextrose solution, Hank's solution, and other aqueous physiologically balanced salt solutions. Nonaqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, m- or o-cresol, formalin and benzyl alcohol. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration.

In one embodiment of the present invention, a therapeutic composition can include an adjuvant. Adjuvants are agents that are capable of enhancing the immune response of an animal to a specific antigen. Suitable adjuvants include, but are not limited to, cytokines, chemokines, and compounds that induce the production of cytokines and chemokines (e.g., granulocyte macrophage colony stimulating factor (GM-CSF), granulocyte colony stimulating factor (G-CSF), macrophage colony stimulating factor (M-CSF), colony stimulating factor (CSF), erythropoietin (EPO), interleukin 2 (IL-2), interleukin-3 (IL-3), interleukin 4 (IL-4), interleukin 5 (IL-5), interleukin 6 (IL-6), interleukin 7 (IL-7), interleukin 8 (IL-8), interleukin 10 (IL-10), interleukin 12 (IL-12), interferon gamma, interferon gamma inducing factor I (IGIF), transforming growth factor beta, RANTES (regulated upon activation, normal T-cell expressed and presumably secreted), macrophage inflammatory proteins (e.g., MIP-1 alpha and MIP-1 beta), and Leishmania elongation initiating factor (LEIF)); bacterial components (e.g., endotoxins, in particular superantigens, exotoxins and cell wall components); aluminum-based salts; calcium-based salts; silica; polynucleotides; toxoids; serum proteins, viral coat proteins; block copolymer adjuvants (e.g., Hunter's Titermax™ adjuvant (Vaxcel™, Inc. Norcross, Ga.), Ribi adjuvants (Ribi ImmunoChem Research, Inc., Hamilton, Mont.); and saponins and their derivatives (e.g., Quil A (Superfos Biosector A/S, Denmark). Protein adjuvants of the present invention can be delivered in the form of the protein themselves or of nucleic acid molecules encoding such proteins using the methods described herein.

In one embodiment of the present invention, a therapeutic composition can include a carrier. Carriers include compounds that increase the half-life of a therapeutic composition in the treated animal. Suitable carriers include, but are not limited to, polymeric controlled release vehicles, biodegradable implants, liposomes, bacteria, viruses, other cells, oils, esters, and glycols.

One embodiment of the present invention is a controlled release formulation that is capable of slowly releasing a composition of the present invention into an animal. As used herein, a controlled release formulation comprises a composition of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, liposhperes, and transdermal delivery systems. Other controlled release formulations of the present invention include liquids that, upon administration to an animal, form a solid or a gel in situ. Preferred controlled release formulations are biodegradable (i.e., bioerodible).

A preferred controlled release formulation of the present invention is capable of releasing a composition of the present invention into the blood of the treated animal at a constant rate sufficient to attain therapeutic dose levels of the composition to protect an animal from disease caused by parasitic helminths. The therapeutic composition is preferably released over a period of time ranging from about 1 to about 12 months. A controlled release formulation of the present invention is capable of effecting a treatment preferably for at least about 1 month, more preferably for at least about 3 months, even more preferably for at least about 6 months, even more preferably for at least about 9 months, and even more preferably for at least about 12 months.

Therapeutic compositions of the present invention can be administered to animals prior to infection in order to prevent infection and/or can be administered to animals after infection in order to treat disease caused by the parasitic helminth. For example, proteins, mimetopes thereof, and antibodies thereof can be used as immunotherapeutic agents. Acceptable protocols to administer therapeutic compositions in an effective manner include individual dose size, number of doses, frequency of dose administration, and mode of administration. Determination of such protocols can be accomplished by those skilled in the art. A suitable single dose is a dose that is capable of protecting an animal from disease when administered one or more times over a suitable time period. For example, a preferred single dose of a protein, mimetope or antibody therapeutic composition is from about 1 microgram ($\mu$g) to about 10 milligrams (mg) of the therapeutic composition per kilogram body weight of the animal. Booster vaccinations can be administered from about 2 weeks to several years after the original administration. Booster administrations preferably are administered when the immune response of the animal becomes insufficient to protect the animal from disease. A preferred administration schedule is one in which from about 10 $\mu$g to about 1 mg of the therapeutic composition per kg body weight of the animal is administered from about one to about two times over a time period of from about 2 weeks to about 12 months. Modes of administration can include, but are not limited to, subcutaneous, intradermal, intravenous, intranasal, oral, transdermal and intramuscular routes.

According to one embodiment, a nucleic acid molecule of the present invention can be administered to an animal in a fashion to enable expression of that nucleic acid molecule into a protective protein or protective RNA (e.g., antisense RNA, ribozyme, triple helix forms or RNA drug) in the animal. Nucleic acid molecules can be delivered to an animal in a variety of methods including, but not limited to, (a) administering a naked (i.e., not packaged in a viral coat or cellular membrane) nucleic acid as a genetic vaccine (e.g., as naked DNA or RNA molecules, such as is taught, for example in Wolff et al., 1990, Science 247, 1465–1468) or (b) administering a nucleic acid molecule packaged as a recombinant virus vaccine or as a recombinant cell vaccine (i.e., the nucleic acid molecule is delivered by a viral or cellular vehicle).

A genetic (i.e., naked nucleic acid) vaccine of the present invention includes a nucleic acid molecule of the present invention and preferably includes a recombinant molecule of the present invention that preferably is replication, or otherwise amplification, competent. A genetic vaccine of the present invention can comprise one or more nucleic acid molecules of the present invention in the form of, for example, a dicistronic recombinant molecule. Preferred genetic vaccines include at least a portion of a viral genome (i.e., a viral vector). Preferred viral vectors include those based on alphaviruses, poxviruses, adenoviruses, herpesviruses, picornaviruses, and retroviruses, with those based on alphaviruses (such as sindbis or Semliki forest virus), species-specific herpesviruses and poxviruses being particularly preferred. Any suitable transcription control sequence can be used, including those disclosed as suitable for protein production. Particularly preferred transcription control sequences include cytomegalovirus immediate early (preferably in conjunction with Intron-A), Rous sarcoma virus long terminal repeat, and tissue-specific transcription control sequences, as well as transcription control sequences endogenous to viral vectors if viral vectors are used. The incorporation of a "strong" polyadenylation signal is also preferred.

Genetic vaccines of the present invention can be administered in a variety of ways, with intramuscular, subcutaneous, intradermal, transdermal, intranasal and oral routes of administration being preferred. A preferred single dose of a genetic vaccine ranges from about 1 nanogram (ng) to about 600 $\mu$g, depending on the route of administration and/or method of delivery, as can be determined by those skilled in the art. Suitable delivery methods include, for example, by injection, as drops, aerosolized and/or topically. Genetic vaccines of the present invention can be contained in an aqueous excipient (e.g., phosphate buffered saline) alone or in a carrier (e.g., lipid-based vehicles).

A recombinant virus vaccine of the present invention includes a recombinant molecule of the present invention that is packaged in a viral coat and that can be expressed in an animal after administration. Preferably, the recombinant molecule is packaging- or replication-deficient and/or encodes an attenuated virus. A number of recombinant viruses can be used, including, but not limited to, those based on alphaviruses, poxviruses, adenoviruses, herpesviruses, picomaviruses, and retroviruses. Preferred recombinant virus vaccines are those based on alphaviruses (such as Sindbis virus), raccoon poxviruses, species-specific herpesviruses and species-specific poxviruses. An example of methods to produce and use alphavirus recombinant virus vaccines are disclosed in PCT Publication No. WO 94/17813, by Xiong et al., published Aug. 18, 1994, which is herein incorporated by reference in its entirety.

When administered to an animal, a recombinant virus vaccine of the present invention infects cells within the immunized animal and directs the production of a protective protein or RNA nucleic acid molecule that is capable of protecting the animal from disease caused by a parasitic helminth as disclosed herein. For example, a recombinant virus vaccine comprising an ankyrin nucleic acid molecule of the present invention is administered according to a protocol that results in the animal producing a sufficient immune response to protect itself from heartworm. A preferred single dose of a recombinant virus vaccine of the present invention is from about $1\times10^4$ to about $1\times10^8$ virus plaque forming units (pfu) per kilogram body weight of the animal. Administration protocols are similar to those described herein for protein-based vaccines, with subcutaneous, intramuscular, intranasal and oral administration routes being preferred.

A recombinant cell vaccine of the present invention includes recombinant cells of the present invention that express at least one protein of the present invention. Preferred recombinant cells for this embodiment include Salmonella, E. coli, Listeria, Mycobacterium, S. frugiperda, yeast, (including Saccharomyces cerevisiae and Pichia pastoris), BHK, CV-1, myoblast G8, COS (e.g., COS-7), Vero, MDCK and CRFK recombinant cells. Recombinant cell vaccines of the present invention can be administered in a variety of ways but have the advantage that they can be administered orally, preferably at doses ranging from about $10^8$ to about $10^{12}$ cells per kilogram body weight. Administration protocols are similar to those described herein for protein-based vaccines. Recombinant cell vaccines can comprise whole cells, cells stripped of cell walls or cell lysates.

The efficacy of a therapeutic composition of the present invention to protect an animal from disease caused by a parasitic helminth can be tested in a variety of ways including, but not limited to, detection of protective antibodies (using, for example, proteins or mimetopes of the present invention), detection of cellular immunity within the treated animal, or challenge of the treated animal with the parasitic helminth to determine whether the treated animal is resistant to disease. Challenge studies can include implantation of chambers including parasitic helminth larvae into the treated animal and/or direct administration of larvae to the treated animal. In one embodiment, therapeutic compositions can be tested in animal models such as mice. Such techniques are known to those skilled in the art.

One preferred embodiment of the present invention is the use of Dirofilaria or Brugia ankyrin proteins, nucleic acid molecules, antibodies and inhibitors of the present invention, to protect an animal from heartworm. It is particularly preferred to prevent L3 that are delivered to the animal by the mosquito intermediate host from migrating from the site of inoculation and/or maturing into adult worms. As such, preferred therapeutic compositions are those that are able to inhibit at least one step in the portion of the parasite's development cycle that includes L3, third molt, L4, fourth molt, immature adult prior to entering the circulatory system. In dogs, this portion of the development cycle is about 70 days. Particularly preferred therapeutic compositions include D. immitis ankyrin-based therapeutic compositions of the present invention. Such compositions include D. immitis ankyrin nucleic acid molecules, D. immitis ankyrin proteins and mimetopes thereof, anti-D. immitis ankyrin antibodies, and inhibitors of D. immitis ankyrin function. Therapeutic compositions are administered to animals in a manner effective to protect the animals from heartworm. Additional protection may be obtained by administering additional protective compounds, including other parasitic helminth proteins, nucleic acid molecules, antibodies and inhibitory compounds, as disclosed herein.

One therapeutic composition of the present invention includes an inhibitor of Dirofilaria or Brugia ankyrin function, i.e., a compound capable of substantially interfering with the function of a Dirofilaria or Brugia ankyrin protein susceptible to inhibition. For example, an isolated protein or mimetope thereof is administered in an amount and manner that elicits (i.e., stimulates) an immune response that is sufficient, upon interaction with a native ankyrin protein, to protect the animal from the disease. Similarly, an antibody of the present invention, when administered to an animal in an effective manner, is administered in an amount so as to be present in the animal at a titer that is sufficient, upon interaction of that antibody with a native ankyrin protein, to protect the animal from the disease, at least temporarily. Oligonucleotide nucleic acid molecules of the present invention can also be administered in an effective manner, thereby reducing expression of Dirofilaria or Brugia ankyrin proteins in order to interfere with development of parasitic helminths targeted in accordance with the present invention. Methods to identify certain functions, i.e., protein-binding capabilities, of Dirofilaria or Brugia ankyrin proteins of the present invention are disclosed herein.

One embodiment of the present invention is a method to identify proteins that specifically interact with an ankyrin protein of the present invention. The method can comprise the steps of a) identifying and isolating a protein-binding domain of an isolated Dirofilaria or Brugia ankyrin protein; b) contacting that protein-binding domain with isolated parasitic helminth proteins under conditions such that a parasitic helminth protein and the protein-binding domain can selectively interact and/or bind to each other, using, for example, the yeast two-hybrid system see, for example, Luban, et al., 1995, *Curr. Opin. Biotechnol.*, 6, 59–64; and c) identifying those proteins that specifically bind to the isolated ankyrin protein-binding domain. Additional methods to identify protein-protein interactions with the protein-binding domains of an isolated ankyrin protein of the present invention are known to those skilled in the art. Examples include Biacore® screening, confocal immunofluorescent microscopy, and immunoprecipitations.

An inhibitor of ankyrin function can be identified using Dirofilaria or Brugia ankyrin proteins of the present invention. One embodiment of the present invention is a method to identify a compound capable of inhibiting ankyrin function of a parasitic helminth. Such a method includes the steps of: (a) identifying a protein binding or regulatory activity of an isolated ankyrin protein in vitro; (b) identifying a putative compound capable of binding to and/or inhibiting the identified protein binding or regulatory activity of the isolated ankyrin protein; (c) contacting D. immitis L3 larvae with the putative inhibitory compound under conditions in which, in the absence of the compound, the larvae are able to molt to the L4 stage; and (d) determining if the putative compound inhibits molting. Putative inhibitory compounds to screen include small organic molecules, antibodies (including mimetopes thereof), and ligand analogs. Such compounds are also screened to identify those that are substantially not toxic in host animals.

Inhibitors of ankyrin function identified by such a method can be tested for their ability to block development and/or migration of parasitic helminths, and particularly of *D. immitis* and *B. malayi*, in vivo. Preferred ankyrin proteins to inhibit are those produced by parasitic helminths, even more preferred ankyrin proteins to inhibit are those produced by filariid nematodes. A particularly preferred inhibitor of the present invention is capable of protecting an animal from heartworm disease, elephantiasis and/or hydrocele. It is also within the scope of the present invention to use inhibitors of the present invention to target diseases caused by parasitic helminths in animals. Compositions comprising inhibitors of ankyrin function can be administered to animals in an effective manner to protect animals from disease caused by parasitic helminths, and preferably to protect animals from heartworm disease, elephantiasis and/or hydrocele. Effective amounts and dosing regimens can be determined using techniques known to those skilled in the art.

It is also within the scope of the present invention to use isolated proteins, mimetopes, nucleic acid molecules and antibodies of the present invention as diagnostic reagents to detect infection by parasitic helminths. Such diagnostic reagents can be supplemented with additional compounds that can specifically detect all phases of the parasite's life cycle. Methods to use such diagnostic reagents to diagnose parasitic helminth infection are well known to those skilled in the art. Suitable and preferred parasitic helminths to detect are those to which therapeutic compositions of the present invention are targeted. Particularly preferred parasitic helminths to detect using diagnostic reagents of the present invention are *D. immitis* and *B. malayi.*

The following examples are provided for the purposes of illustration and are not intended to limit the scope of the present invention.

EXAMPLES

It is to be noted that the examples include a number of molecular biology, microbiology, immunology and biochemistry techniques considered to be familiar to those skilled in the art. Disclosure of such techniques can be found, for example, in Sambrook et al., ibid. and Ausubel, et al., 1993, *Current Protocols in Molecular Biology*, Greene/ Wiley Interscience, New York, N.Y., and related references. Ausubel, et al., ibid. is herein incorporated by reference in its entirety. DNA sequence analyses and protein translations were carried out using the DNAsis program (available from Hitachi Software, San Bruno, Calif.), and the default settings for the analysis program. It should also be noted that because nucleic acid sequencing technology, and in particular the sequencing of PCR products, is not entirely error-free, that the nucleic acid and deduced protein sequences presented herein represent apparent nucleic acid sequences of the nucleic acid molecules encoding *D. immitis* ankyrin proteins of the present invention.

Example 1

This example describes the isolation and sequencing of several *D. immitis* ankyrin nucleic acid molecules. It is to be noted that some of the nucleic acid molecules disclosed in this example were isolated by PCR with degenerate primers and/or primers not fully identical to the *D. immitis* sequences. The authentic *D. immitis* nucleotide sequences were verified on overlapping nucleic acid molecules, and thus the nucleotide sequences of the nucleic acid molecules disclosed in this example are fully representative of *D. immitis* sequences.

A. As a first step in the isolation of a full-length ankyrin cDNA molecule from *D. immitis*, a *D. immitis* ankyrin nucleic acid molecule of about 937 nucleotides, denoted herein as nDiAnk$_{937}$, was isolated from a *D. immitis* cDNA library by PCR amplification for use as a probe, as follows. A *D. immitis* 48-hour L3 cDNA library was constructed in the Uni-ZAP® XR vector (available from Stratagene Cloning Systems, La Jolla, Calif.), using Stratagene's ZAP-cDNA® Synthesis Kit protocol and L3 mRNAs (i.e., messenger RNAs isolated from *D. immitis* third-stage larvae, harvested at 48 hours). Initially, degenerate primers were designed based on conserved regions of the *C. elegans* unc-44 gene described in Otsuka, et al., ibid. These initial attempts to PCR-amplify an ankyrin-related nucleic acid molecule from the *D. immitis* cDNA library were unsuccessful. In a second attempt, PCR primers were designed based on the *Onchocerca volvulus* E1 gene disclosed in Erttmann, et al., 1996a, ibid. These primers included forward primer OVANKY 554+, having the nucleotide sequence 5' CATCAATTTTTGGAATTTTCTGG 3', denoted herein as SEQ ID NO:42 and reverse primer OVANKY 1464−, having the nucleotide sequence 5' CGTT-TACAGCAACATCATCCTC 3', denoted herein as SEQ ID NO:43. Several attempts to amplify an ankyrin-related nucleic acid molecule from the *D. immitis* cDNA library with these primers using standard PCR amplification conditions were likewise unsuccessful. Finally, the same primers were used in a modified amplification procedure called "touchdown" PCR. This procedure included the following amplification cycles: six cycles of 94° C. for 30 sec, 58° C. for 45 sec, and 72° C. for 3 min; six cycles of 94° C. for 30 sec, 56° C. for 45 sec, and 72° C. for 3 min; and 20 cycles of 94° C. for 30 sec, 50° C. for 45 sec, and 72° C. for 3 min. An about 937-base-pair (bp) DNA fragment was detected in the PCR reaction by agarose gel electrophoresis. The PCR-amplified fragment, denoted herein as nDiAnk$_{937}$, was excised from the gel and purified using the QIAquick™ kit (available from Qiagen, Chatsworth, Calif.) as per manufacturer's instructions. The resultant 937-bp DNA fragment was subcloned into the pCRII™ vector (available from Invitrogen, San Diego, Calif.) according to the manufacturer's instructions.

The nucleic acid molecule nDiAnk$_{937}$ was sequenced by the Sanger dideoxy chain termination method, using the PRISM™ Ready Dye Terminator Cycle Sequencing Kit with AmpliTaq® DNA Polymerase, FS (available from the Perkin-Elmer Corporation, Norwalk, Conn.). PCR extensions were done in the GeneAmp™ PCR System 9600 (available from Perkin-Elmer). Excess dye terminators were removed from extension products using the Centriflex™ Gel Filtration Cartridge (available from Advanced Genetics Technologies Corporation, Gaithersburg, Md.) following the standard protocol. Samples were resuspended according to ABI protocols and were run on a Perkin-Elmer ABI PRISM™ 377 Automated DNA Sequencer. The resulting nucleic acid sequence of nDiAnk$_{937}$ is presented herein as SEQ ID NO:1 (the coding strand) and SEQ ID NO:3 (the complementary strand).

Translation of SEQ ID NO:1 yields a protein of about 312 amino acids, denoted herein as PDiAnk$_{312}$, the amino acid sequence of which is presented in SEQ ID NO:2, assuming a first in-frame codon extending from nucleotide 1 to nucleotide 3 of SEQ ID NO:1. The coding region encoding PDiAnk$_{315}$ is presented herein as nDiAnk$_{936}$, which has the nucleotide sequence SEQ ID NO:4 (the coding strand) and SEQ ID NO:5 (the complementary strand).

B. An additional ankyrin nucleic acid molecule of about 1029 bp, containing the authentic 3' end of a *D. immitis* ankyrin coding region, was isolated as follows.

Nucleic acid molecule nDiAnk$_{937}$, isolated as disclosed in Example 1A, was used as a hybridization probe to screen a *D. immitis* 48-hour L3 cDNA library. Nucleic acid molecule nDiAnk$_{937}$ was labeled with $\alpha$-[$^{32}$P]dATP using the Megaprime™ Kit, available from Amersham, Arlington Heights, Ill. The labeled probe was then hybridized and washed under stringent conditions (i.e., allowing at most about 3% bp mismatch) to about $5 \times 10^5$ plaque forming units of an *D. immitis* 48-hour L3 cDNA library, constructed as disclosed in Example 1A. Fifteen plaques that hybridized with the labeled probe were selected and subjected to three rounds of plaque purification. The size and identity of the bacteriophage clones that hybridized with the probe were identified by PCR amplification using vector-specific primers, and subsequent Southern hybridization of the separated PCR-amplified DNA fragments, using nDiAnk$_{937}$ as a probe. Of these 15 clones, none had inserts larger than about 1.1 kilobases (kb). One positively hybridizing clone having an insert of about 1029 bp was chosen for further study. The insert from this cDNA clone, denoted herein as nDiAnk$_{1029}$, was PCR-amplified with a T3/T7 primer set (available from Stratagene), and was subcloned into the pCRII™ vector. The resulting plasmid, containing nucleic acid molecule nDiAnk$_{1029}$, was subjected to automated sequencing as described in Example 1A. The nucleotide sequence of nDiAnk$_{1029}$ is presented herein as SEQ ID NO:6 (the coding strand) and SEQ ID NO:8 (the complementary strand). The 443 nucleotides on the 3' end of nDiAnk$_{937}$ lined up with 100% identity to the 443 nucleotides on the 5' end of nDiANK$_{1029}$.

Translation of SEQ ID NO:6 yields a protein of about 270 amino acids, denoted herein as PDiAnk$_{270}$, the amino acid sequence of which is presented in SEQ ID NO:7, assuming a first in-frame codon extending from nucleotide 2 to nucleotide 4 of SEQ ID NO:6, and a termination codon extending from nucleotide 812 to nucleotide 814 of SEQ ID NO:6. The coding region encoding PDiAnk$_{270}$, not including the termination codon, is presented herein as nDiAnk$_{810}$, which has the nucleotide sequence SEQ ID NO:9 (the coding strand) and SEQ ID NO:10 (the complementary strand). The 147 amino acid residues on the C-terminal end of PDiAnk$_{312}$ (disclosed in Example 1A) lined up with 100% identity to the 147 amino acid residues on the N-terminal end of PDiAnk$_{270}$. PDiAnk$_{270}$ thus represents approximately 123 amino acids of new *D. immitis* ankyrin amino acid sequence. The presence of a termination codon and a poly-A tail on nDiAnk$_{1029}$ indicates that nDiAnk$_{1029}$ represents the authentic 3' end of the *D. immitis* ankyrin messenger RNA that was reverse-transcribed into cDNA.

C. An additional ankyrin nucleic acid molecule of about 600 bp was isolated by PCR-amplification from a *D. immitis* 48-hour L3 cDNA library, as follows.

Since nDiAnk$_{937}$ (isolated as disclosed in Example 1A) extended beyond the 5' end of nDiAnk$_{1029}$ (isolated as disclosed in Example 1B) by 495 bp, nDiAnk$_{1029}$ did not appear to represent a full-length ankyrin cDNA molecule. Furthermore, nDiAnk$_{937}$ did not appear to contain the authentic 5' end of a full-length ankyrin cDNA molecule. This result suggested that the *D. immitis* ankyrin messenger RNA was larger, but was not represented as cDNA at hybridization-detectable levels in the *D. immitis* L3 cDNA library utilized in these experiments. Therefore, isolation of additional portions of a full-length *D. immitis* ankyrin nucleic acid molecule were carried out by PCR amplification. An about 600-bp *D. immitis* ankyrin nucleic acid molecule was amplified by PCR from a *D. immitis* 48-hour L3 cDNA library, constructed as described in Example 1A, using primers designed according to ankyrin nucleic acid sequences of *D. immitis*, derived as described in Example 1A, and *O. volvulus*, derived from the nucleotide sequence reported in Erttmann, et al., 1996a, ibid. The primers included forward primer OVANKY-1+, having the nucleotide sequence 5' GCACAACCAGTTCCGCAAGAAA 3', denoted herein as SEQ ID NO:44 and reverse primer DIANKY-1–, having the nucleotide sequence 5' GGTTAT-TGGAAGAAGATTTCC 3', denoted herein as SEQ ID NO:45. DIANKY-1– was designed to hybridize to nucleotides 22–42 of SEQ ID NO:1, i.e., about 22–42 nucleotides downstream of the 5'-end of nDiAnk$_{937}$. Amplification was accomplished using the "touchdown" PCR protocol as described in Example 1A. A PCR product of about 600 bp was observed upon agarose gel electrophoresis of the PCR reaction, which is denoted herein as nDiAnk$_{600}$. The PCR product was gel purified and subcloned into the pCRII vector as described in Example 1A. The nucleotide sequence of nDiAnk$_{600}$ was determined, and is presented herein as SEQ ID NO:11 (the coding strand) and SEQ ID NO:13 (the complementary strand). The 42 nucleotides on the 3' end of nDiAnk$_{600}$ lined up with 100% identity to the 42 nucleotides on the 5' end of nDiANK$_{937}$ (disclosed in Example 1A).

Translation of SEQ ID NO:11 yields a protein of about 200 amino acids, denoted herein as PDiAnk$_{200}$, the amino acid sequence of which is presented in SEQ ID NO:12, assuming a first in-frame codon extending from nucleotide 1 to nucleotide 3 of SEQ ID NO:11. The 14 amino acid residues on the C-terminal end of PDiAnk$_{200}$ lined up with 100% identity to the 14 amino acid residues on the N-terminal end of PDiAnk$_{312}$ (disclosed in Example 1A). PDiAnk$_{200}$ thus represents approximately 186 amino acids of new *D. immitis* ankyrin amino acid sequence.

D. An additional *D. immitis* ankyrin nucleic acid molecule of about 1228 bp was isolated from a *D. immitis* 48-h L3 cDNA library by nested PCR, as follows.

In order to clone additional *D. immitis* ankyrin nucleic acid molecules, three degenerate forward primers were designed based on *C. elegans* UNC-44 DNA sequences reported in Otsuka, et al., ibid. These primers were paired with various *D. immitis* reverse primers reverse primers in several unsuccessful attempts to isolate additional *D. immitis* ankyrin nucleic acid molecules from a *D. immitis* 48-h L3 cDNA library by standard PCR amplification. Finally, an additional *D. immitis* ankyrin nucleic acid molecule was isolated when two of the *C. elegans*-derived primers were used with two *D. immitis*-derived primers in a nested PCR. The two forward primers were: CEANKY-3+, having the nucleotide sequence 5' CAYCARGCNGCNCARCARG-GNCA 3', denoted herein as SEQ ID NO:46, and CEANKY-4+, having the nucleotide sequence 5' GTNGAYGAYGT-NACNGTNGAYTA 3', denoted herein as SEQ ID NO:47. A standard PCR amplification was performed using as a template a *D. immitis* 48-hour L3 cDNA library constructed as described in Example 1A, using forward primer CEANKY-4+ and reverse primer DIANKY-1–, as disclosed in Example 1C. No distinct nucleic acid molecules were observed from this PCR reaction upon gel electrophoresis, but a smear of indistinguishable PCR products was evident. A very small aliquot of this initial PCR reaction was subsequently used as a template for a second PCR, using forward primer CEANKY-3+, which was predicted to anneal internal to CEANKY-4+, and reverse primer DLIANKY-2–, having the nucleotide sequence 5' GGAATTTGCGACGACGCG-GTTC 3', denoted herein as SEQ ID NO:48, which was designed to hybridize to nucleotides 76–97 of SEQ ID NO:11, i.e., about 76–97 nucleotides downstream of the 5'-end of nDiAnk$_{600}$. This second amplification produced a single predominant PCR product of about 1228 bp, as viewed by separation on an agarose gel, denoted herein as nDiAnk$_{1228}$. This PCR product was gel purified and subcloned into plasmid pCRII as described in Example 1A. The nucleotide sequence of nDiAnk$_{1228}$ was determined, and is presented herein as SEQ ID NO:14 (the coding strand) and SEQ ID NO:16 (the complementary strand). The 97 nucleotides on the 3' end of nDiAnk$_{1228}$ lined up with 100% identity to the 97 nucleotides on the 5' end of nDiANK$_{600}$ (disclosed in Example 1C).

Translation of SEQ ID NO:14 yields a protein of about 409 amino acids, denoted herein as PDiAnk$_{409}$, the amino acid sequence of which is presented in SEQ ID NO:15, assuming a first in-frame codon extending from nucleotide 1 to nucleotide 3 of SEQ ID NO:14. The coding region encoding PDiAnk$_{409}$ is presented herein as nDiAnk$_{1227}$, which has the nucleotide sequence SEQ ID NO:17 (the coding strand) and SEQ ID NO:18 (the complementary strand). The 32 amino acid residues on the C-terminal end of PDiAnk$_{409}$ lined up with 100% identity to the 32 amino acid residues on the N-terminal end of PDiAnk$_{200}$ disclosed in Example 1C). PDiAnk$_{409}$ thus represents about 377 amino acids of new *D. immitis* ankyrin amino acid sequence.

E. An additional ankyrin nucleic acid molecule of about 573 bp was isolated by PCR from a *D. immitis* 48-hour L3 cDNA library, as follows.

An about 573-bp *D. immitis* ankyrin nucleic acid molecule was amplified by standard PCR from a *D. immitis* 48-hour L3 cDNA library constructed as described in Example 1A using a primer designed according to ankyrin nucleic acid sequences of *D. immitis*, derived as described in Example 1D, and an M13 reverse primer. The primers included forward primer M13 reverse, having the nucleotide sequence 5' CAGGAAACAGCTATGAC 3', denoted herein as SEQ ID NO:49 and reverse primer DIANKY-3–, having the nucleotide sequence 5' TGGAGTTTGTCCTGTCGAT-GTATG 3', denoted herein as SEQ ID NO:50. DIANKY-3– was designed to hybridize to nucleotides 73–96 of SEQ ID NO:14, i.e., about 73–96 nucleotides downstream of the 5'-end of nDiAnk$_{1228}$. A PCR product of about 573 bp was observed upon agarose gel electrophoresis of the PCR reaction, which is denoted herein as nDiAnk$_{573}$. The PCR product was gel purified and subcloned into the pCRII vector as described in Example 1A. The nucleotide sequence of nDiAnk$_{573}$ was determined, and is presented herein as SEQ ID NO:19 (the coding strand) and SEQ ID NO:21 (the complementary strand). The 96 nucleotides on the 3' end of nDiAnk$_{573}$ lined up with 100% identity to the 96 nucleotides on the 5' end of nDiANK$_{1228}$ (disclosed in Example 1D).

Translation of SEQ ID NO:19 yields a protein of about 191 amino acids, denoted herein as PDiAnk$_{191}$, the amino acid sequence of which is presented in SEQ ID NO:20, assuming a first in-frame codon extending from nucleotide 1 to nucleotide 3 of SEQ ID NO:19. The 32 amino acid residues on the C-terminal end of PDiAnk$_{191}$ lined up with 100% identity to the 32 amino acid residues on the N-terminal end of PDiAnk$_{409}$ (disclosed in Example 1D). PDiAnk$_{191}$ thus represents approximately 159 amino acids of new D. immitis ankyrin amino acid sequence.

F. An additional ankyrin nucleic acid molecule of about 911 bp was isolated from first-strand reverse transcriptase cDNA syntheses of D. immitis adult messenger RNA by PCR, as follows.

Attempts to isolate additional portions of a D. immitis ankyrin nucleic acid molecule from a cDNA library were unsuccessful. Therefore, additional portions were isolated from first-strand reverse transcriptase cDNA syntheses of *D. immitis* adult messenger RNA, by PCR amplification. A *D. immitis*-specific reverse primer was designed near the 5' terminus of $nDiAnk_{573}$ described in Example 1E above. This primer, denoted as DIANKY-4–, having the nucleotide sequence 5' GCTTTGCTTTCAGCATTCGCATTTGCC 3', denoted herein as SEQ ID NO:5 1, along with degenerate forward primer CEANKY-4+, described in Example 1D, were used in PCR amplifications of first-strand reverse transcriptase cDNA syntheses of *D. immitis* adult messenger RNA, prepared by standard methods. DIANKY-4– was designed to hybridize to nucleotides 138–164 of SEQ ID NO:19, i.e., about 138–164 nucleotides downstream of the 5'-end of $nDiAnk_{573}$. A PCR product of about 911 bp, visualized by agarose gel electrophoresis, was obtained by PCR amplification using as a template first strand cDNA syntheses of either adult female or adult male *D. immitis* messenger RNA using these primers. It should be noted that PCR amplifications performed with three other degenerate forward primers, designed from the UNC-44 nucleotide sequence of Otsuka, et al., ibid., in conjunction with *D. immitis* reverse primers, did not result in the successful amplification of *D. immitis* ankyrin nucleic acid molecules. The 911-bp PCR products were excised from the agarose gel on which they were separated, and bathed in a small volume of Tris-EDTA buffer. Ten microliter aliquots of these excised products in TE were used as template for reamplification PCRs, using the same primers, to verify the product. More intense bands of exactly the same size, denoted herein as $nDiAnk_{911}$, were produced by these second round PCRs, as seen by separation on an agarose gel.

Nucleic acid molecules from both the first and second PCR reactions were gel purified and subcloned into plasmid pCRII as described in Example 1A. The subcloned DNA products were submitted for automated sequencing. Sequence analysis revealed that the inserts of all PCR products were identical, and are denoted herein as SEQ ID NO:22 (the coding strand) and SEQ ID NO:24 (the complementary strand). The 164 nucleotides on the 3' end of $nDiAnk_{911}$ lined up with 100% identity to the 164 nucleotides on the 5' end of $nDiANK_{573}$ (disclosed in Example 1E).

Translation of SEQ ID NO:22 yields a protein of about 303 amino acids, denoted herein as $PDiAnk_{303}$, the amino acid sequence of which is presented in SEQ ID NO:23, assuming a first in-frame codon extending from nucleotide 1 to nucleotide 3 of SEQ ID NO:22. The coding region encoding $PDiAnk_{303}$ is presented herein as $nDiAnk_{909}$, which has the nucleotide sequence SEQ ID NO:25 (the coding strand) and SEQ ID NO:26 (the complementary strand). The 54 amino acid residues on the C-terminal end of $PDiAnk_{303}$ lined up with 100% identity to the 54 amino acid residues on the N-terminal end of the $PDiAnk_{191}$ (disclosed in Example 1E). $PDiAnk_{303}$ thus represents approximately 249 amino acids of new *D. immitis* ankyrin amino acid sequence.

G. An additional ankyrin nucleic acid molecule of about 1096 bp, containing sequences representing the authentic 5' end of a *D. immitis* ankyrin messenger RNA, was isolated from first-strand reverse transcriptase cDNA syntheses of *D. immitis* adult messenger RNA by PCR, as follows.

A *D. immitis*-specific reverse primer was designed near the 5' terminus of $nDiAnk_{911}$ described in Example 1F above. This primer, denoted DIANKY-7–, having the nucleotide sequence 5' GTGAGATAGTCAACAGTAACATCATCC 3', denoted herein as SEQ ID NO:53, was designed to hybridize to nucleotides 3–29 of SEQ ID NO:22, i.e., about 3–29 nucleotides downstream of the 5'-end of $nDiAnk_{91}$,. DIANKY-7– was used along with a sense primer designed according to the nematode splice leader (SL) in PCR amplifications of first-strand reverse transcriptase cDNA syntheses of *D. immitis* adult messenger RNA, prepared by standard methods. Most, but not all nematode messenger RNAs have the SL at their 5' ends, and the presence of the 5' SL sequence is indicative of an apparently full length cDNA molecule. See, for example Blaxter and Liu, 1996, *Int. J. Parasitol.* 26, 1025–1033, which is herein incorporated by reference in its entirety. The splice leader primer, denoted DiSL, has the nucleotide sequence 5' GGTTTAATTACCCAAGTTTGAG 3', denoted herein as SEQ ID NO:52. Using these primers, PCR products of about 1096 bp were obtained using adult male and adult female mRNAs as templates. These nucleic acid molecules were gel-purified using the QIAquick™ kit as per manufacturer's instructions. The yield of these purifications was low, so one microliter each of the purified DNA products were used as templates in reamplification PCRs using the same primers. More intense products of precisely the same size, collectively denoted herein as $nDiANK_{1096}$, were obtained from the reamplification PCRs, and were subcloned into plasmid pCRII as described in Example 1A. One of the subcloned nucleic acid molecules was submitted for automated nucleic acid sequencing. Sequence analysis suggested that $nDiAnk_{1096}$, the sequence of which is represented herein as SEQ ID NO:27 (the coding strand) and SEQ ID NO:29 (the complementary strand), represented the authentic 5' end of a *D. immitis* ankyrin messenger RNA. The 5' end of $nDiAnk_{1096}$ included the spliced leader sequence, 28 nucleotides of 5' untranslated sequence, and the starting methionine of the coding sequence. The 29 nucleotides on the 3' end of $nDiAnk_{1096}$ lined up with 100% identity to the 29 nucleotides on the 5' end of $nDiANK_{911}$ (disclosed in Example 1F).

Translation of SEQ ID NO:27 yields a protein of about 348 amino acids, denoted herein as $PDiAnk_{348}$, the amino acid sequence of which is presented in SEQ ID NO:28, assuming a start codon extending from nucleotide 51 to nucleotide 53 of SEQ ID NO:27. The nucleic acid molecule representing the coding region encoding $PDiAnk_{348}$, denoted herein as $nDiAnk_{1044}$, is presented herein as SEQ ID NO:30 (the coding strand) and SEQ ID NO:31 (the complementary strand). The about 9 amino acid residues on the C-terminal end of PDiAnk$_{348}$ lined up with about 100% identity to the about 9 amino acid residues on the N-terminal end of the PDiAnk$_{303}$ (disclosed in Example 1F). PDi-Ank$_{348}$ thus represents approximately 339 amino acids of new *D. immitis* ankyrin amino acid sequence.

H. A composite nucleotide sequence of a full-length *D. immitis* ankyrin gene was compiled as follows.

A *D. immitis* ankyrin nucleic acid molecule of 5503 bp, denoted herein as nDiAnk$_{5503}$, including an apparently full-length coding region, was compiled by aligning the overlapping nucleic acid sequences SEQ ID NO:1, SEQ ID NO:6, SEQ ID NO:11, SEQ ID NO:14, SEQ ID NO:19, SEQ ID NO:22, and SEQ ID NO:27. The composite full-length nucleic acid molecule has a nucleic acid sequence presented herein as SEQ ID NO:32 (the coding strand) and SEQ ID NO:34 (the complementary strand). SEQ ID NO:32 contains the 5' nematode spliced leader sequence extending from about nucleotide 1 through about nucleotide 27, and a 28 bp 5' non-coding region extending from about nucleotide 28 through about nucleotide 50.

Translation of SEQ ID NO:32 yields a full-length protein of about 1745 amino acids, denoted PDiAnk$_{1745}$, assuming a start codon extending from nucleotide 51 through nucleotide 53 of SEQ ID NO:32, and a stop codon extending from nucleotide 5286 through nucleotide 5285 of SEQ ID NO:32. The resulting amino acid sequence is presented as SEQ ID NO:33. The coding region encoding PDiAnk$_{1745}$, not including the termination codon is denoted herein as nDiANK$_{5235}$, and has the nucleotide sequence SEQ ID NO:35 (the coding strand) and SEQ ID NO:36 (the complementary strand). SEQ ID NO:35 is predicted to encode a protein with a molecular mass of about 191.7 kD and with a predicted pI of about 5.76, as calculated by the DNAsis program.

A homology search of a non-redundant protein database was performed with SEQ ID NO:33, using the blastp program available through the BLAST™ network of the National Center for Biotechnology Information (NCBI) (National Library of Medicine, National Institutes of Health, Baltimore, Md.), available on the World Wide Web. This database includes SwissProt+PIR+SPupdate+GenPept+GPUpdate+PDB databases. The highest scoring match of the homology search at the amino acid level was GenBank™ accession number gi|1208874, a *C. elegans* ankyrin-like protein, to which SEQ ID NO:33 showed about 69% identity, spanning from about amino acid 1 through about amino acid 1745 of SEQ ID NO:33. The second highest scoring match of the homology search at the amino acid level was GenBank™ accession number gi|406288, a human brain ankyrin protein (variant I, Ankyrin$_B$), to which SEQ ID NO:33 showed about 51% identity, spanning from about amino acid 1 through about amino acid 1745. SEQ ID NO:33 was also compared to the sequence of the *O. volvulus* E1 protein as disclosed by Erttmann, et al., 1996a, ibid. A region of SEQ ID NO:33 spanning from about amino acid 1282 to about amino acid 1745 showed about 78% identity to the full-length *O. volvulus* E1 protein of 467 amino acids. At the nucleotide level, the coding region represented in SEQ ID NO:35 was compared to the cDNA encoding the *O. volvulus* E1 protein. A region of SEQ ID NO:35 spanning from about nucleotide 3423 to about nucleotide 5574 showed about 88% nucleic acid identity to the cDNA containing a full-length coding region of 1401 nucleotides encoding the *O. volvulus* E1 protein.

Example 2

This Example discloses an analysis of the predicted functional domains of a full-length *D. immitis* ankyrin protein.

Based on comparisons with mammalian ankyrin proteins, as well as the protein encoded by the *C. elegans* UNC-44 gene, the putative positions of the three functional domains of ankyrin proteins were identified in SEQ ID NO:33, the amino acid sequence of an apparent full-length *D. immitis* ankyrin protein, namely PDiAnk$_{1745}$, isolated as disclosed in Example 1. While not being bound by theory, an N-terminal membrane protein-binding domain is predicted to extend from about amino acid 1 to about amino acid 880 of SEQ ID NO:33, a spectrin-binding domain is predicted to extend from about amino acid 881 to about amino acid 1398 of SEQ ID NO:33, and a regulatory domain is predicted to extend from about amino acid 1399 to about amino acid 1745 of SEQ ID NO:33.

The N-terminal membrane protein-binding domain of PDiAnk$_{1745}$ is further characterized by the presence of 24 tandemly arrayed repeats, most of which comprise about 33 amino acid residues. These repeat regions are listed in Table 1, designated by numbers, along with a general consensus sequence pattern. The terms "start" and "end" in Table 1 refer to the sequential amino acid numbers in SEQ ID NO:33 corresponding to the first and last amino acid, respectively, of each repeat listed in Table 1. The first and the twenty-fourth repeats are not as well conserved as the other repeats. To the inventor's knowledge, this is the first disclosure of ankyrin-like repeats in a parasitic nematode.

TABLE 1

Ankyrin-like repeats of PDiAnk1745

| No. | START | | | | END |
|---|---|---|---|---|---|
| 01 | 36 | ESSASFLRAA | RAGNLDRVLE | LLRSGTDINT CNA | 68 |
| 02 | 69 | NGLNALHLAS | KEGHHEVVRE | LLKRKADVDA ATR | 101 |
| 03 | 102 | KGNTALHIAS | LAGQELIVTV | LVENGANVNV QSL | 134 |
| 04 | 135 | NGFTPLYMAA | QENHESVVRY | LLAHNANQAL STE | 167 |
| 05 | 168 | DGFTPLAVAL | QQGHDRVVAV | LLENDTRGK~ ~~~ | 196 |
| 06 | 197 | VRLPALHIAA | KKDDTKAATL | LLQNEHNSDV TSK | 229 |
| 07 | 230 | SGFTPLHIAA | HYGNENVAQL | LLEKGANVNY QAR | 262 |
| 08 | 263 | HNISPLHVAT | KWGRTNMVSL | LLAHGAVIDC RTR | 295 |
| 09 | 296 | DLLTPLHCAS | RSGHDQVVDL | LLEKGAPISA KTK | 328 |
| 10 | 329 | NGLAPLHMAA | Q~~~~~~~~ | ~~~~~~~VDD VTV | 345 |
| 11 | 346 | DYLTPLHVAA | HCGHVRVAKL | LLDRNADPNA RAL | 378 |
| 12 | 379 | NGFTPLHIAC | KKNRIKIVEL | LLKYHAAIEA TTE | 411 |
| 13 | 412 | SGLSPLHVAA | FMGAINIVIY | LLQQGANADV ATV | 444 |
| 14 | 445 | RGETPLHLAA | RANQTDIVRV | LVRNGAQVDA AAR | 477 |
| 15 | 478 | ELQTPLHIAS | RLGNTDIVIL | LLQANASPNA ATR | 510 |
| 16 | 511 | DLYTPLHIAA | KEGQEEVAAI | LMDHGTDKTL LTK | 543 |
| 17 | 544 | KGFTPLHLAA | KYGNLPVAKS | LLERGTPVDI EGK | 576 |
| 18 | 577 | NQVTPLHVAA | HYNNDKVALL | LLENGASAHA AAK | 609 |
| 19 | 610 | NGYTPLHIAA | KKNQMDIAST | LLHYKANANA ESK | 642 |
| 20 | 643 | AGFTPLHLAA | QEGHREMAAL | LIENGAKVGA QAR | 675 |
| 21 | 676 | NGLTPMHLCA | QEDRVSVAEE | LVKENAAJDP KTK | 708 |

TABLE 1-continued

Ankyrin-like repeats of PDiAnk1745

| No. | START |  |  |  |  | END |
|---|---|---|---|---|---|---|
| 22 | 709 | AGYTPLHVAC | HFGQINMVRF | LIEHGARVSV | ITR | 741 |
| 23 | 742 | ASYTPLHQAA | QQGHNSVVRY | LLEHGASPNV | HTS | 774 |
| 24 | 775 | TGQTPLSIAE | RLGYVSVVEA | LKTITETTVI | TET | 807 |
| Consensus |  | -G-TPLH-AA | --GH---V--<br>A | LL--GA--N-<br>D | --- |  |

Repeat regions 01 through 24 as disclosed in Table 1 are presented herein as SEQ ID NO:61 through SEQ ID NO:84, respectively. The consensus sequence is presented herein as SEQ ID NO:85. A novel feature of the membrane-binding domain of PDiAnk$_{1745}$ is repeat No. 10 (SEQ ID NO:70), which apparently comprises only 17 amino acids. While not being bound by theory, this shortened repeat is unique among ankyrin proteins.

Example 3

This Example demonstrates the use of *D. immitis* nucleic acid molecules of the present invention to obtain, by PCR amplification, an ankyrin nucleic acid molecule from a related filariid nematode, *Brugia malayi*.

A *B. malayi* ankyrin nucleic acid molecule was PCR amplified from a first-strand cDNA synthesis of messenger RNA prepared from *B. malayi* adult female worms, as follows. The PCR primers included forward primer CEANKY 4+, as disclosed in Example 1D, and reverse primer DIANKY 4-, as disclosed in Example 1F. An about 908-bp nucleic acid molecule was amplified in a PCR amplification of a first-strand reverse transcriptase cDNA synthesis of *B. malayi* adult female messenger RNA, prepared by standard methods, and is herein denoted as nBmAnk$_{908}$.

Nucleic acid molecule nBmAnk$_{908}$ was gel purified and subcloned into plasmid pCRII, and sequenced as described in Example 1A. The sequence is presented as SEQ ID NO:37 (the coding strand) and SEQ ID NO:39 (the complementary strand). Translation of SEQ ID NO:37 yields a non-full-length protein of about 302 amino acids, herein denoted as PBmAnk$_{302}$, assuming a first in-frame codon extending from nucleotide 1 through nucleotide 3 of SEQ ID NO:37. The resulting amino acid sequence is presented as SEQ ID NO:38. The coding region encoding PBmAnk$_{302}$ is herein denoted as nBmANK$_{906}$, and has the nucleotide sequence SEQ ID NO:40 (the coding strand) and SEQ ID NO:41 (the complementary strand).

A homology search of a non-redundant protein database was performed on SEQ ID NO:38 using the BLAST network. The homology spans from about amino acid 1 through amino acid 302 of SEQ ID NO:38. The highest scoring match of the homology search at the amino acid level was GenBank accession number A57282, a *C. elegans* ankyrin-like protein, which was about 86% identical to SEQ ID NO:38 through a region extending from about amino acid 353 through about amino acid 654 of A57282. The *B. malayi* ankyrin nucleic acid molecule and protein sequences represented by SEQ ID NO:37 and SEQ ID NO:38, respectively, had no similarity to the *O. volvulus* E1 nucleic acid molecule and protein disclosed by Erttmann, et al., 1996a, ibid.

The amino acid sequence of SEQ ID NO:38 was also compared to PDiAnk$_{1745}$ (i.e., SEQ ID NO:33 of the present invention). PBmAnk$_{302}$ had 95% identity to the region of SEQ ID NO:33 spanning from about amino acid 341 through about amino acid 642.

Example 4

The following experiment was performed in order to confirm the origin of the ankyrin gene in the *D. immitis* genome, and to identify genomic restriction fragments associating with a partial ankyrin cDNA clone. The experiment also evaluates if multiple copies of the ankyrin gene are present in the *D. immitis* genome. Four enzymes were each used individually to digest about 10 micrograms of *D. immitis* genomic DNA each. A Southern blot containing genomic DNA samples restricted with Sau3A-I, EcoRI, HindIII, and XhoI, respectively, was hybridized under stringent conditions using nDiAnk$_{937}$, isolated as disclosed in Example 1A, labeled with the radioactive isotope $^{32}$P. The nDiAnk$_{937}$ probe hybridized to three bands of 460 bp, 550 bp, and 770 bp in the genomic restriction digestion using Sau3A-I. A single band of 5490 bp hybridized in the EcoRI digestion. Two bands of 930 bp and 3330 bp hybridized in the HindIII digestion. Two bands also hybridized in the XhoI digestion (which of the four enzymes digested the genomic DNA most incompletely), one of 3330 bp and one of 43,200 bp, the latter appearing in a band representing undigested DNA. This experiment confirmed the *D. immitis* origin of ankyrin nucleic acid molecules of the present invention. While not being bound by theory, since no EcoRI sites are present within the full-length coding region of nDiAnk$_{1745}$, the single EcoRI genomic fragment hybridizing with the nDiAnk$_{937}$ probe suggests that at least the portion of nDiAnk$_{1745}$ included in nDiAnk$_{937}$ is present as a single copy in the *D. immitis* genome.

Example 5

This Example discloses the production of a recombinant molecule and a recombinant cell of the present invention.

Recombinant molecule pTrc-nDiAnk$_{1866}$, containing a *D. immitis* ankyrin nucleic acid molecule operatively linked to trc transcription control sequences and to a fusion sequence encoding the T7 tag and a poly-histidine segment, was produced in the following manner. An about 1866-nucleotide DNA fragment containing nucleotides spanning from about 3423 through about 5288 of SEQ ID NO:32, herein denoted as nDiAnk$_{1866}$, was PCR-amplified by "touchdown" PCR from *D. immitis* L3 and LA cDNA libraries produced by the methods described in Example 1A, using sense primer OVANKY 1+ (SEQ ID NO:44, as described in Example 1C), and DIANKY-, having the nucleotide sequence 5' CCGGAATTCTTATTCAT-GAACGCTTTGCCCTTT 3', herein denoted as SEQ ID NO:55, EcoRI site in bold. DIANKY- was designed to anneal to a region of SEQ ID NO:32 extending from nucleotide 5365 through nucleotide 5288. This PCR product was gel-purified using the QIAquick™ kit as per manufacturer's instructions. The yield of this purification was low, so one microliter of the purified DNA product was used as template in a reamplification PCR (standard PCR) using forward primer DIANKY 3+, having the nucleotide sequence 5' CGCGGATCCGGCACAACCAGTTCCG-CAAGAA 3', herein denoted as SEQ ID NO:54, BamHI site in bold, and antisense primer DIANKY-, as described above. DIANKY 3+ was designed to anneal to the PCR product generated above, but shares 17/20 bp in common with nucleotides 3423 through 3443 of SEQ ID NO:32. A more intense product of approximately the same size, denoted herein as nDiAnk$_{1866}$, was obtained from the reamplification PCR. Recombinant molecule pTrc-nDiAnk$_{1866}$ was produced by digesting the PCR-amplified DNA fragment with BamHI and EcoRI restriction endonucleases, gel purifying the resulting fragment and directionally subcloning it into expression vector pTrcHisB (available from Invitrogen) that had been cleaved with BamHI and EcoRI and gel purified.

Recombinant molecule pTrc-nDiAnk$_{1866}$ was transformed into E. coli to form recombinant cell E. coli:pTrc-nDiAnk$_{1866}$ using standard techniques.

Example 6

This Example discloses the production of additional recombinant molecules and recombinant cells of the present invention. Also described is an analysis of the nucleic acid sequence encoding each of the three domains described above, as well as an analysis of the amino acid sequence of each.

A. Recombinant molecule pTrc-$nDiAnk_{1056}$, containing a *D. immitis* ankyrin nucleic acid molecule encoding the predicted membrane protein-binding domain (disclosed in Example 2), operatively linked to trc transcription control sequences and to a fusion sequence encoding the T7 tag and a poly-histidine segment, was produced in the following manner. An about 1056-nucleotide DNA fragment spanning from about nucleotide 1356 through about nucleotide 2411 of SEQ ID NO:32, denoted herein as $nDiAnk_{1056}$, was RT-PCR-amplified from four different *D. immitis* messenger RNA templates. The templates were as follows: 48-hour L3 (i.e., third-stage larvae harvested at 48 hours), 6-day L4 (i.e., fourth stage larvae harvested at 6 days), adult female, and adult male *D. immitis* mRNAs. The PCR primers included DIANKY REP+, having the nucleotide sequence 5' CGCGGATTCGCGCGGTGCTAATGCAGATGTGGC 3', denoted herein as SEQ ID NO:56, BamHI site in bold, and reverse primer DIANKY REP−, having the nucleotide sequence 5' CCGGAATTCCGGTTACCCTAGACGTTCAGCAATCG 3', denoted herein as SEQ ID NO:57, EcoRI site in bold. The amplification produced a product of the predicted size from each of the four mRNA templates. This result indicates that the portion of the *D. immitis* ankyrin gene encoding the putative membrane protein-binding domain is expressed in at least two larval stages and in male and female adult parasites. Recombinant molecule pTrc-$nDiAnk_{1056}$ was produced by BamHI and EcoRI restriction endonuclease digesting the PCR-amplified DNA fragments produced using the 48-hour L3 *D. immitis* mRNA as the template, gel purifying the resulting fragment and directionally subcloning it into expression vector pTrcHisB (available from Invitrogen) which was cleaved with BamHI and EcoRI and gel purified.

The nucleic acid molecule encoding the N-terminal membrane protein-binding domain, referred to herein as $nDiAnk_{1056}$ (the nucleic acid sequence of the coding and non-coding strands of which are herein referred to as SEQ ID NO:138 and SEQ ID NO:140, respectively) encodes a 352 amino acid sequence herein referred to as SEQ ID NO:139. A homology search of a non-redundant protein database was performed with SEQ ID NO:139, using the blastp program available through the BLAST198 network of the NCBI, as described above. The highest scoring match of the homology search at the amino acid level was to GenBank™ accession number pir||A57282, a *C. elegans* ankyrin-related protein fragment, UNC-44, to which SEQ ID NO:139 showed about 80% identity, spanning from about amino acid 1 through about amino acid 352 of SEQ ID NO:139. The highest scoring match of a homology search at the nucleotide level was to a nucleotide sequence encoding *C. elegans* ankyrin-related protein, GenBank™ accession number gb|U21734|CEU21734. A region of SEQ ID NO:138 spanning from about nucleotide 1 through about nucleotide 263 was found to share about 71% identity with a region of gb|U21734|CEU21734 spanning from nucleotide 4126 to nucleotide 4388. In addition, a region of SEQ ID NO:138 spanning from about nucleotide 262 through about nucleotide 896 was found to share about 68% identity with a region of gb|U21734|CEU21734 spanning from nucleotide 4743 to nucleotide 5377.

B. Recombinant molecule pTrc-$nDiAnk_{1266}$, containing a *D. immitis* ankyrin nucleic acid molecule encoding the predicted spectrin-binding domain (disclosed in Example 2), operatively linked to trc transcription control sequences and to a fusion sequence encoding the T7 tag and a poly-histidine segment, was produced in the following manner. An about 1266-nucleotide DNA fragment spanning from about nucleotide 2850 through about nucleotide 4115 of SEQ ID NO:32, denoted herein as $nDiAnk_{1266}$, was RT-PCR-amplified from the four different *D. immitis* messenger RNA templates described in Example 6A above. The PCR primers included DIANKY SPECT B+, having the nucleotide sequence 5' CCGGGATCCGCGCGCACGTGGAGGAGCAATGCGT 3', denoted herein as SEQ ID NO:58, BamHI site in bold, and reverse primer DIANKY SPECT B−, having the nucleotide sequence 5' CGCGAATTCCGGTTATTCGTTGTCCGTGTGAGTGCG 3', denoted herein as SEQ ID NO:59, EcoRI site in bold. The amplification produced a product of the predicted size from each of the four mRNA templates. This result indicates that the portion of the *D. immitis* ankyrin gene encoding the putative spectrin-binding domain is expressed in at least two larval stages and in male and female adult parasites. Recombinant molecule pTrc-$nDiAnk_{1266}$ was produced by BamHI and EcoRI restriction endonuclease digesting the PCR-amplified DNA fragments produced using the 48-hour L3 *D. immitis* mRNA as the template, gel purifying the resulting fragment and directionally subcloning it into expression vector pTrcHisB (available from Invitrogen) which was cleaved with BamHI and EcoRI and gel purified.

The nucleic acid molecule encoding the predicted spectrin-binding domain, referred to herein as $nDiAnk_{1266}$ (the nucleic acid sequence of the coding and non-coding strands of which are herein referred to as SEQ ID NO:141 and SEQ ID NO:143, respectively) encodes a 422 amino acid sequence herein referred to as SEQ ID NO:142. A homology search of a non-redundant protein database was performed with SEQ ID NO:142, using the blastp program available through the BLAST™ network of the NCBI, as described above. The highest scoring match of the homology search at the amino acid level was to GenBank™ accession number gi|1208873, a *C. elegans* ankyrin-related protein, to which SEQ ID NO:142 showed about 90% identity, spanning from about amino acid 1 through about amino acid 422 of SEQ ID NO:142. The highest scoring match of a homology search at the nucleotide level was to a nucleotide sequence encoding *C. elegans* ankyrin-related protein fragment, UNC-44, GenBank™ accession number gb|U21732|CEU21732. A region of SEQ ID NO:141 spanning from about nucleotide 1 through about nucleotide 1266 was found to share about 73% identity with a region of gb|U21732|CEU21732 spanning from nucleotide 337 to nucleotide 1602.

C. Recombinant molecule pTrc-$nDiAnk_{864}$, containing a *D. immitis* ankyrin nucleic acid molecule encoding the predicted regulatory domain (disclosed in Example 2), operatively linked to trc transcription control sequences and to a fusion sequence encoding the T7 tag and a polyhistidine segment, was produced in the following manner. An about 864-nucleotide DNA fragment spanning from about nucleotide 4425 through about nucleotide 5288 of SEQ ID NO:32, denoted herein as nDiAnk$_{864}$, was RT-PCR-amplified from the four different *D. immitis* messenger RNA templates described in Example 6A above. The PCR primers included DIANKY REG+, having the nucleotide sequence 5' CGCGGATCCGCGCCAACTAGTTGGTCT-TGAAGCAGTC 3', denoted herein as SEQ ID NO:60, BamHI site in bold, and reverse primer DIANKY-, having the nucleotide sequence 5' CCGGAATTCTTATTCAT-GAACGCTTTGCCCTTT 3', denoted herein as SEQ ID NO:55, EcoRI site in bold. The amplification produced a product of the predicted size from each of the four mRNA templates. This result indicates that the portion of the *D. immitis* ankyrin gene encoding the putative regulatory domain is expressed in at least two larval stages and in male and female adult parasites. Recombinant molecule pTrc-nDiAnk$_{864}$ was produced by BamHI and EcoRI restriction endonuclease digesting the PCR-amplified DNA fragments produced using the 48-hour L3 *D. immitis* mRNA as the template, gel purifying the resulting fragment and directionally subcloning it into expression vector pTrcHisB (available from Invitrogen) which was cleaved with BamHI and EcoRI and gel purified.

The nucleic acid molecule encoding the N-terminal membrane protein-binding domain, referred to herein as nDiAnk$_{864}$ (the nucleic acid sequence of the coding and non-coding strands of which are herein referred to as SEQ ID NO:144 and SEQ ID NO:146, respectively) encodes a 864 amino acid sequence herein referred to as SEQ ID NO:145. A homology search of a non-redundant protein database was performed with SEQ ID NO:145, using the blastp program available through the BLAST™ network of the NCBI, as described above. The highest scoring match of the homology search at the amino acid level was to GenBank™ accession number gnl|PID|e2791, the *O. volvulus* E1 protein, to which SEQ ID NO:145 showed about 75% identity, spanning from about amino acid 1 through about amino acid 108 of SEQ ID NO:145. The highest scoring match of a homology search at the nucleotide level was to an mRNA sequence encoding the *O. volvulus* E1 protein, GenBank™ accession number emb|X84359|OVMRNAANH. A region of SEQ ID NO:144 spanning from about nucleotide 1 through about nucleotide 367 was found to share about 84% identity with a region of emb|X84359|OVMRNAANH spanning from nucleotide 996 to nucleotide 1362. In addition, a region of SEQ ID NO:144 spanning from about nucleotide 358 through about nucleotide 498 was found to share about 95% identity with a region of emb|X84359|OVMRNAANH spanning from nucleotide 1350 to nucleotide 1490.

Recombinant molecules pTrc-nDiAnk$_{1056}$, pTrc-nDiAnk$_{1266}$, and pTrc-nDiAnk$_{864}$ were transformed into *E. coli* to form recombinant cells *E. coli*:pTrc-nDiAnk$_{1056}$, *E. coli*:pTrc-nDiAnk$_{1266}$, and *E. coli*:pTrc-nDiAnk$_{864}$ using standard techniques.

Example 7

This example demonstrates the production of *D. immitis* ankyrin proteins of the present invention in prokaryotic cells.

Recombinant cell *E. coli*:pTrc-nDiAnk$_{1866}$, produced as described in Example 5, was cultured in shake-flasks containing an enriched bacterial growth medium containing 0.1 mg/ml ampicillin at about 37° C. When the cells reached an OD$_{600}$ of about 0.5, expression of *D. immitis* nucleic acid molecule nDiAnk$_{1866}$ was induced by addition of about 0.5 mM IPTG, and the cells were cultured for about 3 hr at about 37° C. Protein production was monitored by SDS-polyacrylamide gel electrophoresis (SDS-PAGE) of recombinant cell lysates, followed by Coomassie blue staining, using standard techniques. Recombinant cell *E. coli*:pTrc-nDiAnk$_{1866}$ produced a fusion protein, denoted herein as PHIS-PDiANK$_{622}$, that migrated with an apparent molecular weight of about 98 kD, although the predicted molecular weight is only about 74 kD. While not being bound by theory, the difference between the observed and predicted molecular weights may be attributed to the known acidity of the regulatory domains of ankyrin proteins, which is known by those skilled in the art to reduce the binding of SDS to the protein, thereby resulting in an aberrant migration in SDS-PAGE.

Immunoblot analysis of recombinant cell *E. coli*:pTrc-nDiAnk$_{1866}$ lysates indicated that the about 98-kD protein was able to bind to a T7 tag monoclonal antibody (available from Novagen, Inc., Madison, Wis.) directed against the fusion portion of the recombinant PHIS-PDiANK$_{622}$ fusion protein.

Recombinant cells *E. coli*:pTrc-nDiAnk$_{1056}$, *E. coli*:pTrc-nDiAnk$_{1266}$, and *E. coli*:pTrc-nDiAnk$_{864}$, produced as described above, were cultured separately in shake-flasks containing an enriched bacterial growth medium containing 0.1 mg/ml ampicillin at about 37° C. When the cells reached an OD$_{600}$ of about 0.5, expression of *D. immitis* nucleic acid molecules nDiAnk$_{1056}$, nDiAnk$_{1266}$, and nDiAnk$_{864}$, respectively, was induced by addition of about 0.5 mM IPTG, and the cells were cultured for about 3 hr at about 37° C. Protein production was monitored by SDS-PAGyacrylamide gel electrophoresis (SDS-PAGE) of recombinant cell lysates, followed by Coomassie blue staining, using standard techniques. Recombinant cells *E. coli*:pTrc-nDiAnk$_{1056}$, *E. coli*:pTrc-nDiAnk$_{1266}$, and *E. coli*:pTrc-nDiAnk$_{864}$, produced fusion proteins denoted herein as PHIS-PDiANK$_{352}$, PHIS-PDiANK$_{422}$, and PHIS-PDiANK$_{288}$, respectively.

Example 8

This example discloses the purification of the *D. immitis* ankyrin membrane protein-binding fusion protein, the *D. immitis* ankyrin spectrin-binding domain fusion protein, and the *D. immitis* regulatory domain fusion protein. The designation and expression of each domain are described herein. Also described is the production of antibodies directed against the fusion proteins of each domain, respectively.

The procedures for purifying the fusion proteins representing each of the different domains (PHIS-PDiANK$_{352}$, PHIS-PDiANK$_{422}$, and PHIS-PDiANK$_{288}$) were essentially the same for each, and were as follows. *E. coli* expressed fusion protein was separated from other proteins by metal ion affinity chromatography. The soluble portion of the protein was suspended in 1× PBS and applied to a 1 ml HiTrap Chelating column (available from Pharmacia Biotech, Piscataway, N.J.) charged with nickel (Ni$^{++}$) ions. The purification scheme was performed using standard FPLC techniques utilizing the BioRad Biologic Chromatography System (available from BioRad Laboratories, Hercules, Calif.). The fusion protein was eluted using an imidazole gradient. Fractions collected following separation were analyzed by separation on SDS-PAGE gels, and detected by Coomassie Blue staining and Western blotting. Immunoblotting was performed using standard techniques for transfer to nitrocellulose and fusion proteins were detected using a T7-tag Mab. FPLC fractions containing the fusion protein of interest were pooled and the concentration of protein was determined by a BioRad Protein Assay (available from BioRad Laboratories).

Antisera to the three *D. immitis* ankyrin domains (the three antisera also referred to herein as rabbit anti-DiANK$_{352}$, rabbit anti-DiANK$_{422}$, and rabbit anti-DiANK$_{288}$, antisera, respectively) were produced as follows: One rabbit for each fusion protein (3 total) was immunized subcutaneously with 50 μg of purified fusion protein in Complete Freund's Adjuvant (available from Sigma, St. Louis, Mo.). Each rabbit was boosted two times, using the same dose of fusion protein as was used for the original immunization, in Incomplete Freund's adjuvant, with two weeks between immunizations. Serum samples were collected between immunizations, and then every other week following the second boost. Serum from each bleed was stored separately at −20° C. until use.

Example 9

This example describes the identification of ankyrin antibodies in the rabbit polyclonal antisera raised against each of the three *D. immitis* ankyrin domains. Rabbit anti-DiANK$_{352}$, rabbit anti-DiANK$_{422}$, and rabbit anti-DiANK$_{288}$ antisera, produced as described above, were used to identify the original *E. coli* fusion proteins used to immunize the respective rabbits. This was done to verify that antibodies against the fusion protein were indeed the major product of the immunization.

Each of the purified fusion proteins (representing each of the functional domains described above) was run on a 14% Tris-glycine SDS-PAGE gel for 2.5 hours at 150 V. Approximately 3 μg of protein was run per lane on the gel, and then transferred to a nitrocellulose membrane by standard methods. Following transfer, the membranes were blocked in 5% dry milk for one hour at room temperature. Each membrane was then incubated for one hour with antisera representing the three domains. Each antisera was used at dilutions of 1:500 and 1:2000 in 1× TBST. Following appropriate washing, each membrane was incubated another one hour with an alkaline phosphatase labeled anti-rabbit secondary antibody. Detection of protein was obtained using the substrate NBT/BCIP (Gibco BRL, Gaithersburg, Md.). Each antiserum identified the corresponding fusion protein of the predicted size, which matches the size of the recombinant protein originally used for immunization and polyclonal antibody production.

Example 10

This example describes the isolation and sequencing of several *D. immitis* ankyrin genomic nucleic acid molecules from adult *D. immitis* genomic DNA. As in the above examples describing the isolation of ankyrin cDNA molecules, some of the nucleic acid molecules disclosed in this example were isolated by PCR with degenerate primers and/or primers not fully identical to the *D. immitis* sequences. As described above, the authentic *D. immitis* nucleotide sequences were verified on overlapping nucleic acid molecules, and thus the nucleotide sequences of the nucleic acid molecules disclosed in this example are fully representative of *D. immitis* genomic DNA sequences.

Genomic DNA was prepared from whole adult worms using standard DNA extraction methods, well known in the art. This genomic DNA was then used as the template for "touchdown" PCR as described above. The new primers used for amplification of genomic DNA were based on the nucleic acid sequence of *D. immitis* ankyrin nucleic acid molecule herein disclosed. In addition, some of the primers used to amplify genomic DNA are described above, and had been used successfully to amplify *D. immitis* ankyrin cDNA nucleic acid sequences. These primers are summarized in Table 2.

TABLE 2

| Primer Location relative to SEQ ID NO:32 | SEQ ID NO: | Primer |
|---|---|---|
| 51–73 a | 147 | CGCGGATCCG CATGAGTAAT CCTATAGTCG AGGG |
| 486–506 b | 148 | TACAACAGAT TCGTGATTTT C |
| 726–743 a | 149 | GTGACTTCGA AAAGCGGC |
| 1070–1097 b | 53 | GTGAGATAGT CAACAGTAAC ATCATCC |
| 1356–1375 a | 56 | CGCGGATTCG CGCGGTGCTA ATGCAGATGT GGC |
| 1952–1978 b | 51 | GCTTTGCTTT CAGCATTCGC ATTTGCC |
| 2133–2156 a | 150 | GAACTAGTGA AAGAAAACGC AGCC |
| 2292–2314 b | 151 | GTAACGTACA ACACTGTTAT GCCC |
| 2310–2333 a | 46 | CAYCARGCNG CNCARCARGG NCA |
| 2392–2411 b | 57 | CCGGAATTCC GGTTACCCTA GACGTTCAGC AATCG |
| 2553–2576 a | 152 | GGTGAAGATA ATCAGATCAC AGCC |
| 2760–2780 b | 153 | CGATGCATCT AAGGAAGGAT C |
| 2760–2780 a | 154 | GATCCTTCCT TAGATGCATC G |
| 2886–2909 b | 155 | CGGTGGTATA ATGATTCTGA CACC |
| 2850–2870 a | 58 | CGCGGATCCG CGCGCACGTG GAGGAGCAAT GCGT |
| 3078–3104 b | 156 | CTCTCTCTCT CGTCCACGAA GTGATGC |
| 4425–4448 a | 60 | CGCGGATCCG CGCCAACTAG TTGGTCTTGA AGCAGTC |
| 4896–4917 b | 43 | CGTTTACAGC AACATCATCC TC |
| 4824–4841 a | 157 | CGCACTGAAC GACATGTG |
| 5040–5060 b | 158 | CTCATGTGTT GTCTGACAAC C |
| 5163–5183 a | 159 | GGATTAAGTA GCGGGGATGC A |
| 5319–5339 b | 160 | GCAACATAGG CATGTGCGAG A |

Table 2 lists the primers used for PCR amplification of *D. immitis* ankyrin nucleic acid sequences from genomic DNA. Endonuclease cleavage sites added as linkers to some of the primers are noted in bold. "a" or "b" after the primer location designation denotes that the primer corresponds to the sense or antisense strand, respectively, of ankyrin DNA. Table 2 also lists the location of these primer sequences relative to the sequence of full-length *D. immitis* ankyrin cDNA (SEQ ID NO:32, the coding strand; note that the location of the second member of each primer pair (denoted with the designation, "b") is also listed relative to SEQ ID NO:32, although the sequence of these primers is the reverse complement of the listed portion of SEQ ID NO:32).

Amplification with the primers listed in Table 2 was performed in parallel using genomic DNA as the template for one set of amplification reactions, and cDNA (as described above) as the template in the parallel set of control amplification reactions. The amplification reaction products were detected by agarose gel electrophoresis, and the presence of introns in genomic DNA fragments was detected by observing a shift in the molecular weight of the genomic DNA amplification product relative to the cDNA product produced with the same primers. The PCR-amplified fragments representing genomic DNA were excised from the gel and purified as described above. The resultant DNA fragments were subcloned, as above, into the pCRII™ vector according to the manufacturer's instructions. Sequencing of these fragments was performed as described above.

Example 11

This Example describes ankyrin introns and exons, and provides an analysis of the nucleic acid sequence encoding the exons and introns described above. Also included is an analysis of the amino acid sequence of each exon.

Sequence analysis revealed the location and sequence of eleven exons in the nucleic acid sequence encoding D. immitis ankyrin. By comparing the D. immitis ankyrin cDNA sequence with the genomic sequence, the size and sequence of these eleven exons have been identified.

TABLE 3

| SEQ ID NO: | Name/Location relative to SEQ ID NO:32 | Designation |
|---|---|---|
| 86 | Exon 51–152 | DiAnk-ex$_{102}$ |
| 88 | Exon 153–353 | DiAnk-ex$_{201}$ |
| 90 | Exon 848–1034 | DiAnk-ex$_{187}$ |
| 92 | Exon 1035–1068 | DiAnk-ex$_{34}$ |
| 94 | Exon 1464–1613 | DiAnk-ex$_{150}$ |
| 96 | Exon 2212–2372 | DiAnk-ex$_{161}$ |
| 98 | Exon 2825–2957 | DiAnk-ex$_{133}$ |
| 100 | Exon 4495–4673 | DiAnk-ex$_{179}$ |
| 102 | Exon 4674–4857 | DiAnk-ex$_{184}$ |
| 104 | Exon 4858–5015 | DiAnk-ex$_{158}$ |
| 106 | Exon 5230–5288 | DiAnk-ex$_{59}$ |

The eleven exons that have been fully sequenced, and their locations relative to SEQ ID NO:32 are listed in Table 3, as are their corresponding SEQ ID NO:s. The exon name indicates the location of each exon relative to the D. immitis cDNA sequence, SEQ ID NO:32 (i.e., the nucleotides in the cDNA sequence that represent the exon). The exon designation includes as a subscript the size, in nucleotides, of the exon. The reverse complements of the nucleic acid sequences herein denoted SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, and SEQ ID NO:106, are herein denoted SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, and SEQ ID NO:107, respectively. The amino acid sequences encoded by nucleic acid SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, and SEQ ID NO:106 are herein denoted SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, and SEQ ID NO:106, respectively.

A homology search of a non-redundant protein database was performed with each of the listed exons, using the blastx program available through the BLAST™, using the default settings. The blastx sequence analysis program translates a nucleic acid sequence in all six possible reading frames, and compares the results from each translation with the sequences in the database. The results of the blastx analysis is summarized as follows: Analysis of the amino acid sequence coded by SEQ ID NO:86 (herein denoted SEQ ID NO:161) revealed no significant homologies. The highest scoring match for the protein encoded by SEQ ID NO:88 (herein denoted SEQ ID NO:162) was to GenBank™ accession number g|1208875, a C. elegans ankyrin-related protein. Nucleotide 4 through about nucleotide 183 of SEQ ID NO:88 encodes a protein that showed about 83% identity to g|1208875. The highest scoring match for the protein encoded by SEQ ID NO:90 (herein denoted SEQ ID NO:163) was to GenBank™ accession number gi|1208776, a C. elegans ankyrin-related protein. Nucleotide 3 through about nucleotide 180 of SEQ ID NO:90 encodes a protein that showed about 82% identity to gi|1208776. The highest scoring match for the protein encoded by SEQ ID NO:92 (herein denoted SEQ ID NO:164) was to GenBank™ accession number gi|1208776, a C. elegans ankyrin-related protein. Nucleotide 1 through nucleotide 33 of SEQ ID NO:92 encodes a protein that showed 100% identity to gi|1208776. The highest scoring match for the protein encoded by SEQ ID NO:94 (herein denoted SEQ ID NO:165) was to GenBank™ accession number gi|1814196, a C. elegans ankyrin-related protein, AO13. Nucleotide 1 through nucleotide 150 of SEQ ID NO:94 encodes a protein that showed about 86% identity to gi|1814196. The highest scoring match for the protein encoded by SEQ ID NO:96 (herein denoted SEQ ID NO:166) was to GenBank™ accession number gi|1814196, a C. elegans ankyrin-related protein, AO13. Nucleotide 3 through nucleotide 161 of SEQ ID NO:96 encodes a protein that showed about 73% identity to gi|1814196. The highest scoring match for the protein encoded by SEQ ID NO:98 (herein denoted SEQ ID NO:167) was to GenBank™ accession number gi|1814196, a C. elegans ankyrin-related protein, AO13. Nucleotide 2 through nucleotide 133 of SEQ ID NO:98 encodes a protein that showed about 88% identity to gi|1814196. The highest scoring match for the protein encoded by SEQ ID NO:100 (herein denoted SEQ ID NO:168) was to GenBank™ accession number gnl|PID|e2792, an O. volvulus E1 protein. Nucleotide 6 through nucleotide 179 of SEQ ID NO:100 encodes a protein that showed about 74% identity to gnl|PID|e2792. The highest scoring match for the protein encoded by SEQ ID NO:102 (herein denoted SEQ ID NO:169) was to GenBank™ accession number gnl|PID|e2792, an O. volvulus E1 protein. Nucleotide 1 through nucleotide 75 of SEQ ID NO:102 encodes a protein that showed about 64% identity to gi|1814196. In addition, nucleotide 136 through nucleotide 183 of SEQ ID NO:102 encodes a protein that showed about 93% identity to gi|1814196. The highest scoring match for the protein encoded by SEQ ID NO:104 (herein denoted SEQ ID NO:170) was to GenBank™ accession number gnl|PID|e2792, an O. volvulus E1 protein. Nucleotide 3 through nucleotide 110 of SEQ ID NO:104 encodes a protein that showed about 74% identity to gnl|PID|e2792. The highest scoring match for the protein encoded by SEQ ID NO:106 (herein denoted SEQ ID NO:171) was to GenBank™ accession number gnl|PID|e2792, an O. volvulus E1 protein. Nucleotide 3 through nucleotide 56 of SEQ ID NO:106 encodes a protein that showed about 94% identity to gnl|PID|e2792.

Seventeen introns were identified as described above, 15 of which have now been fully sequenced and analyzed. By comparing the D. immitis ankyrin cDNA sequence with the genomic sequence, the locations of these seventeen introns have been identified. The fifteen introns that have been fully sequenced, and their locations relative to SEQ ID NO:32 are listed in Table 4.

TABLE 4

| SEQ ID NO: | Name/Location relative to SEQ ID NO:32 | Designation |
|---|---|---|
| 108 | Intron 152–153 | DiAnk-int$_{92}$ |
| 110 | Intron 353–354 | DiAnk-int$_{118}$ |
| 112 | Intron 847–848 | DiAnk-int$_{248}$ |
| 114 | Intron 1034–1035 | DiAnk-int$_{94}$ |
| 116 | Intron 1068–1069 | DiAnk-int$_{48}$ |
| 118 | Intron 1463–1464 | DiAnk-int$_{200}$ |
| 120 | Intron 1613–1614 | DiAnk-int$_{82}$ |
| 122 | Intron 1784–1785 | DiAnk-int$_{213}$ |
| 124 | Intron 2211–2212 | DiAnk-int$_{76}$ |
| 126 | Intron 2372–2373 | DiAnk-int$_{231}$ |
| 128 | Intron 2957–2958 | DiAnk-int$_{78}$ |
| 130 | Intron 4494–4495 | DiAnk-int$_{110}$ |
| 132 | Intron 4673–4674 | DiAnk-int$_{89}$ |
| 134 | Intron 4857–4858 | DiAnk-int$_{95}$ |
| 136 | Intron 5015–5016 | DiAnk-int$_{301}$ |

Table 4 lists the introns and their corresponding SEQ ID NO:s. The intron name indicates the location of each intron relative to the *D. immitis* cDNA sequence, SEQ ID NO:32 (i.e., the nucleotides in the cDNA sequence between which the intron exists in the genomic DNA sequence). The intron designation includes as a subscript the size, in nucleotides, of the intron. The reverse complements of the nucleic acid sequences denoted SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:130, SEQ ID NO:132, SEQ ID NO:134, and SEQ ID NO:136, are herein denoted SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, SEQ ID NO:135, and SEQ ID NO:137, respectively.

---

SEQUENCE LISTING (1) GENERAL INFORMATION:

(iii) NUMBER OF SEQUENCES: 171

(2) INFORMATION FOR SEQ ID NO:1:

(i) SEQUENCE CHARACTERISTICS:
      (A) LENGTH: 937 nucleotides
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 1..936

(xi) SEQUENCE DESCRIPTION: SEQ ID NO:1:

```
CAT CAG TTT TTG GAA TTT TCT GGA AAT CTT CTT CCA ATA ACC          42
His Gln Phe Leu Glu Phe Ser Gly Asn Leu Leu Pro Ile Thr
1               5                   10

AAG AGT GGT GAC CAA CTT TCT CTT TAT TTT CTA CCA TTC CAA          84
Lys Ser Gly Asp Gln Leu Ser Leu Tyr Phe Leu Pro Phe Gln
15                  20                  25

GAA AAT CGT CTT GCT TTC ATG GTA AAG ATA CGC ACT CAC ACG         126
Glu Asn Arg Leu Ala Phe Met Val Lys Ile Arg Thr His Thr
    30                  35                  40

GAC AAC GAA ACT GCA GCT GAT GGC CGG ATA GTA TTT ATG AAA         168
Asp Asn Glu Thr Ala Ala Asp Gly Arg Ile Val Phe Met Lys
        45                  50                  55

GAA CCA AAA TTG AGA GCC GAA AAT TTA CCT CCG CAG ACG CCA         210
Glu Pro Lys Leu Arg Ala Glu Asn Leu Pro Pro Gln Thr Pro
            60                  65                  70

GTG TGT ACT CTT GCA ATC ACT CTT CCG GAA TAC ACT GGG CCG         252
Val Cys Thr Leu Ala Ile Thr Leu Pro Glu Tyr Thr Gly Pro
                75                  80

GAG CCG ATG GTT TCC AAA AAA CTC TTC TAT TCG GAA GCT TCT         294
Glu Pro Met Val Ser Lys Lys Leu Phe Tyr Ser Glu Ala Ser
85                  90                  95

TTG ACT GAG AAA TAC GTT GGA GCT TTC CAT GAA ACT GCT GAA         336
Leu Thr Glu Lys Tyr Val Gly Ala Phe His Glu Thr Ala Glu
```

```
            100                 105                 110
CCT GAT AAC TTG CCA CTA GCA CAT GTT GCA CTA TTA ATT GGC              378
Pro Asp Asn Leu Pro Leu Ala His Val Ala Leu Leu Ile Gly
            115                 120                 125

GCT GAT TGG CAT CGG TTA GCT CGA GCG CTT GAA GTA CCT GAT              420
Ala Asp Trp His Arg Leu Ala Arg Ala Leu Glu Val Pro Asp
        130                 135                 140

ATT GAT ATA CGA CAA GTT CGA CAT CAA CTA GTT GGT CTT GAA              462
Ile Asp Ile Arg Gln Val Arg His Gln Leu Val Gly Leu Glu
                145                 150

GCA GTC ACT ATT CTA CGT ATT TGG ATA TTT TTG AAG AAA GAA              504
Ala Val Thr Ile Leu Arg Ile Trp Ile Phe Leu Lys Lys Glu
155                 160                 165

CAA GCT ACG CCC GTT GCT TTG CGA TCA GCA TTG CAG CGA ATA              546
Gln Ala Thr Pro Val Ala Leu Arg Ser Ala Leu Gln Arg Ile
    170                 175                 180

GGA CGT GAT GAT GTT GTA CGA GAA ATG GAT CGA GCT GAA AAG              588
Gly Arg Asp Asp Val Val Arg Glu Met Asp Arg Ala Glu Lys
        185                 190                 195

CTA GAT GGT TTA GAA GGA ACA CCT GTA TCG CAT ATT TCT GGA              630
Leu Asp Gly Leu Glu Gly Thr Pro Val Ser His Ile Ser Gly
                200                 205                 210

CCC TCA ATA ACT CTG TCA TCT ACT TTG CTA GAG GTA GCA GGC              672
Pro Ser Ile Thr Leu Ser Ser Thr Leu Leu Glu Val Ala Gly
215                 220

GAC AGA CGT CGT CAC GCC GAG GTA ACA ATG GCG CAA CAG CGA              714
Asp Arg Arg Arg His Ala Glu Val Thr Met Ala Gln Gln Arg
225                 230                 235

TTG GCA CAA GAA CCG TTT TTT CAG CAA GTA GGG TAT AAT GGG              756
Leu Ala Gln Glu Pro Phe Phe Gln Gln Val Gly Tyr Asn Gly
    240                 245                 250

ACA CCT GGA GAT CCA GAA GAA CCC AAA GAA CAG TCA TTC CAC              798
Thr Pro Gly Asp Pro Glu Glu Pro Lys Glu Gln Ser Phe His
        255                 260                 265

GAA GAG GAA GAG GAA GTT GCA GTT TCA GAA ATT CGA ACA GTT              840
Glu Glu Glu Glu Glu Val Ala Val Ser Glu Ile Arg Thr Val
                270                 275                 280

GTG CGC ACT GAA CGA CAT GTG CAT GAT TCG GAA AAT GGT CCT              882
Val Arg Thr Glu Arg His Val His Asp Ser Glu Asn Gly Pro
                    285                 290

ATT GTG GAA GAG CGT ACA ATA ACA ACT ACG TAT GAG GAT GAT              924
Ile Val Glu Glu Arg Thr Ile Thr Thr Thr Tyr Glu Asp Asp
295                 300                 305

GTT GCT GTA AAC G                                                    937
Val Ala Val Asn
    310

(2) INFORMATION FOR SEQ ID NO:2:

(i) SEQUENCE CHARACTERISTICS:
        (A) LENGTH:   312 amino acids
        (B) TYPE:     amino acid
        (D) TOPOLOGY: linear (ii) MOLECULE TYPE: protein (xi) SEQUENCE DESCRIPTION: SEQ ID NO:2:

His Gln Phe Leu Glu Phe Ser Gly Asn Leu Leu Pro Ile Thr
1               5                   10

Lys Ser Gly Asp Gln Leu Ser Leu Tyr Phe Leu Pro Phe Gln
15                  20                  25
```

```
Glu Asn Arg Leu Ala Phe Met Val Lys Ile Arg Thr His Thr
    30              35                  40

Asp Asn Glu Thr Ala Ala Asp Gly Arg Ile Val Phe Met Lys
    45                  50                  55

Glu Pro Lys Leu Arg Ala Glu Asn Leu Pro Pro Gln Thr Pro
        60                  65              70

Val Cys Thr Leu Ala Ile Thr Leu Pro Glu Tyr Thr Gly Pro
            75                  80

Glu Pro Met Val Ser Lys Lys Leu Phe Tyr Ser Glu Ala Ser
85              90                  95

Leu Thr Glu Lys Tyr Val Gly Ala Phe His Glu Thr Ala Glu
    100             105                 110

Pro Asp Asn Leu Pro Leu Ala His Val Ala Leu Leu Ile Gly
        115             120                 125

Ala Asp Trp His Arg Leu Ala Arg Ala Leu Glu Val Pro Asp
            130             135                 140

Ile Asp Ile Arg Gln Val Arg His Gln Leu Val Gly Leu Glu
                145             150

Ala Val Thr Ile Leu Arg Ile Trp Ile Phe Leu Lys Lys Glu
155             160                 165

Gln Ala Thr Pro Val Ala Leu Arg Ser Ala Leu Gln Arg Ile
    170             175                 180

Gly Arg Asp Asp Val Val Arg Glu Met Asp Arg Ala Glu Lys
        185             190                 195

Leu Asp Gly Leu Glu Gly Thr Pro Val Ser His Ile Ser Gly
        200             205                 210

Pro Ser Ile Thr Leu Ser Ser Thr Leu Leu Glu Val Ala Gly
            215                 220

Asp Arg Arg Arg His Ala Glu Val Thr Met Ala Gln Gln Arg
225             230                 235

Leu Ala Gln Glu Pro Phe Phe Gln Gln Val Gly Tyr Asn Gly
    240             245                 250

Thr Pro Gly Asp Pro Glu Glu Pro Lys Glu Gln Ser Phe His
        255             260                 265

Glu Glu Glu Glu Glu Val Ala Val Ser Glu Ile Arg Thr Val
            270                 275             280

Val Arg Thr Glu Arg His Val His Asp Ser Glu Asn Gly Pro
                285                 290

Ile Val Glu Glu Arg Thr Ile Thr Thr Thr Tyr Glu Asp Asp
295                 300                 305

Val Ala Val Asn
    310

(2) INFORMATION FOR SEQ ID NO:3:

(i) SEQUENCE CHARACTERISTICS:
        (A) LENGTH: 937 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

CGTTTACAGC AACATCATCC TCATACGTAG TTGTTATTGT ACGCTCTTCC                50
```

| | |
|---|---|
| ACAATAGGAC CATTTTCCGA ATCATGCACA TGTCGTTCAG TGCGCACAAC | 100 |
| TGTTCGAATT TCTGAAACTG CAACTTCCTC TTCCTCTTCG TGGAATGACT | 150 |
| GTTCTTTGGG TTCTTCTGGA TCTCCAGGTG TCCCATTATA CCCTACTTGC | 200 |
| TGAAAAAACG GTTCTTGTGC CAATCGCTGT TGCGCCATTG TTACCTCGGC | 250 |
| GTGACGACGT CTGTCGCCTG CTACCTCTAG CAAAGTAGAT GACAGAGTTA | 300 |
| TTGAGGGTCC AGAAATATGC GATACAGGTG TTCCTTCTAA ACCATCTAGC | 350 |
| TTTTCAGCTC GATCCATTTC TCGTACAACA TCATCACGTC CTATTCGCTG | 400 |
| CAATGCTGAT CGCAAAGCAA CGGGCGTAGC TTGTTCTTTC TTCAAAAATA | 450 |
| TCCAAATACG TAGAATAGTG ACTGCTTCAA GACCAACTAG TTGATGTCGA | 500 |
| ACTTGTCGTA TATCAATATC AGGTACTTCA AGCGCTCGAG CTAACCGATG | 550 |
| CCAATCAGCG CCAATTAATA GTGCAACATG TGCTAGTGGC AAGTTATCAG | 600 |
| GTTCAGCAGT TTCATGGAAA GCTCCAACGT ATTTCTCAGT CAAAGAAGCT | 650 |
| TCCGAATAGA AGAGTTTTTT GGAAACCATC GGCTCCGGCC CAGTGTATTC | 700 |
| CGGAAGAGTG ATTGCAAGAG TACACACTGG CGTCTGCGGA GGTAAATTTT | 750 |
| CGGCTCTCAA TTTTGGTTCT TTCATAAATA CTATCCGGCC ATCAGCTGCA | 800 |
| GTTTCGTTGT CCGTGTGAGT GCGTATCTTT ACCATGAAAG CAAGACGATT | 850 |
| TTCTTGGAAT GGTAGAAAAT AAAGAGAAAG TTGGTCACCA CTCTTGGTTA | 900 |
| TTGGAAGAAG ATTTCCAGAA AATTCCAAAA ACTGATG | 937 |

(2) INFORMATION FOR SEQ ID NO:4:

(i) SEQUENCE CHARACTERISTICS:
        (A) LENGTH: 936 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

| | |
|---|---|
| CATCAGTTTT TGGAATTTTC TGGAAATCTT CTTCCAATAA CCAAGAGTGG | 50 |
| TGACCAACTT TCTCTTTATT TTCTACCATT CCAAGAAAAT CGTCTTGCTT | 100 |
| TCATGGTAAA GATACGCACT CACACGGACA ACGAAACTGC AGCTGATGGC | 150 |
| CGGATAGTAT TTATGAAAGA ACCAAAATTG AGAGCCGAAA ATTTACCTCC | 200 |
| GCAGACGCCA GTGTGTACTC TTGCAATCAC TCTTCCGGAA TACACTGGGC | 250 |
| CGGAGCCGAT GGTTTCCAAA AAACTCTTCT ATTCGGAAGC TTCTTTGACT | 300 |
| GAGAAATACG TTGGAGCTTT CCATGAAACT GCTGAACCTG ATAACTTGCC | 350 |
| ACTAGCACAT GTTGCACTAT TAATTGGCGC TGATTGGCAT CGGTTAGCTC | 400 |
| GAGCGCTTGA AGTACCTGAT ATTGATATAC GACAAGTTCG ACATCAACTA | 450 |
| GTTGGTCTTG AAGCAGTCAC TATTCTACGT ATTTGGATAT TTTTGAAGAA | 500 |
| AGAACAAGCT ACGCCCGTTG CTTTGCGATC AGCATTGCAG CGAATAGGAC | 550 |
| GTGATGATGT TGTACGAGAA ATGGATCGAG CTGAAAAGCT AGATGGTTTA | 600 |
| GAAGGAACAC CTGTATCGCA TATTTCTGGA CCCTCAATAA CTCTGTCATC | 650 |
| TACTTTGCTA GAGGTAGCAG GCGACAGACG TCGTCACGCC GAGGTAACAA | 700 |
| TGGCGCAACA GCGATTGGCA CAAGAACCGT TTTTTCAGCA AGTAGGGTAT | 750 |

| | |
|---|---|
| AATGGGACAC CTGGAGATCC AGAAGAACCC AAAGAACAGT CATTCCACGA | 800 |
| AGAGGAAGAG GAAGTTGCAG TTTCAGAAAT TCGAACAGTT GTGCGCACTG | 850 |
| AACGACATGT GCATGATTCG GAAAATGGTC CTATTGTGGA AGAGCGTACA | 900 |
| ATAACAACTA CGTATGAGGA TGATGTTGCT GTAAAC | 936 |

(2) INFORMATION FOR SEQ ID NO:5:

(i) SEQUENCE CHARACTERISTICS:
        (A) LENGTH: 936 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

| | |
|---|---|
| GTTTACAGCA ACATCATCCT CATACGTAGT TGTTATTGTA CGCTCTTCCA | 50 |
| CAATAGGACC ATTTTCCGAA TCATGCACAT GTCGTTCAGT GCGCACAACT | 100 |
| GTTCGAATTT CTGAAACTGC AACTTCCTCT TCCTCTTCGT GGAATGACTG | 150 |
| TTCTTTGGGT TCTTCTGGAT CTCCAGGTGT CCCATTATAC CCTACTTGCT | 200 |
| GAAAAAACGG TTCTTGTGCC AATCGCTGTT GCGCCATTGT TACCTCGGCG | 250 |
| TGACGACGTC TGTCGCCTGC TACCTCTAGC AAAGTAGATG ACAGAGTTAT | 300 |
| TGAGGGTCCA GAAATATGCG ATACAGGTGT TCCTTCTAAA CCATCTAGCT | 350 |
| TTTCAGCTCG ATCCATTTCT CGTACAACAT CATCACGTCC TATTCGCTGC | 400 |
| AATGCTGATC GCAAAGCAAC GGGCGTAGCT TGTTCTTTCT TCAAAAATAT | 450 |
| CCAAATACGT AGAATAGTGA CTGCTTCAAG ACCAACTAGT TGATGTCGAA | 500 |
| CTTGTCGTAT ATCAATATCA GGTACTTCAA GCGCTCGAGC TAACCGATGC | 550 |
| CAATCAGCGC CAATTAATAG TGCAACATGT GCTAGTGGCA AGTTATCAGG | 600 |
| TTCAGCAGTT TCATGGAAAG CTCCAACGTA TTTCTCAGTC AAAGAAGCTT | 650 |
| CCGAATAGAA GAGTTTTTTG GAAACCATCG GCTCCGGCCC AGTGTATTCC | 700 |
| GGAAGAGTGA TTGCAAGAGT ACACACTGGC GTCTGCGGAG GTAAATTTTC | 750 |
| GGCTCTCAAT TTTGGTTCTT TCATAAATAC TATCCGGCCA TCAGCTGCAG | 800 |
| TTTCGTTGTC CGTGTGAGTG CGTATCTTTA CCATGAAAGC AAGACGATTT | 850 |
| TCTTGGAATG GTAGAAAATA AAGAGAAAGT TGGTCACCAC TCTTGGTTAT | 900 |
| TGGAAGAAGA TTTCCAGAAA ATTCCAAAAA CTGATG | 936 |

(2) INFORMATION FOR SEQ ID NO:6:

(i) SEQUENCE CHARACTERISTICS:
        (A) LENGTH: 1029 nucleotides
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 2..811

(xi) SEQUENCE DESCRIPTION: SEQ ID NO:6:

| | |
|---|---|
| G AAG AAA GAA CAA GCT ACG CCC GTT GCT TTG CGA TCA GCA<br>   Lys Lys Glu Gln Ala Thr Pro Val Ala Leu Arg Ser Ala<br>   1             5                    10 | 40 |

-continued

```
TTG CAG CGA ATA GGA CGT GAT GAT GTT GTA CGA GAA ATG GAT            82
Leu Gln Arg Ile Gly Arg Asp Asp Val Val Arg Glu Met Asp
     15                  20                  25

CGA GCT GAA AAG CTA GAT GGT TTA GAA GGA ACA CCT GTA TCG           124
Arg Ala Glu Lys Leu Asp Gly Leu Glu Gly Thr Pro Val Ser
         30                  35                  40

CAT ATT TCT GGA CCC TCA ATA ACT CTG TCA TCT ACT TTG CTA           166
His Ile Ser Gly Pro Ser Ile Thr Leu Ser Ser Thr Leu Leu
             45                  50                  55

GAG GTA GCA GGC GAC AGA CGT CGT CAC GCC GAG GTA ACA ATG           208
Glu Val Ala Gly Asp Arg Arg Arg His Ala Glu Val Thr Met
                 60                  65

GCG CAA CAG CGA TTG GCA CAA GAA CCG TTT TTT CAG CAA GTA           250
Ala Gln Gln Arg Leu Ala Gln Glu Pro Phe Phe Gln Gln Val
70                  75                  80

GGG TAT AAT GGG ACA CCT GGA GAT CCA GAA GAA CCC AAA GAA           292
Gly Tyr Asn Gly Thr Pro Gly Asp Pro Glu Glu Pro Lys Glu
         85                  90                  95

CAG TCA TTC CAC GAA GAG GAA GAG GAA GTT GCA GTT TCA GAA           334
Gln Ser Phe His Glu Glu Glu Glu Glu Val Ala Val Ser Glu
             100                 105                 110

ATT CGA ACA GTT GTG CGC ACT GAA CGA CAT GTG CAT GAT TCG           376
Ile Arg Thr Val Val Arg Thr Glu Arg His Val His Asp Ser
                 115                 120                 125

GAA AAT GGT CCT ATT GTG GAA GAG CGT ACA ATA ACA ACT ACG           418
Glu Asn Gly Pro Ile Val Glu Glu Arg Thr Ile Thr Thr Thr
                     130                 135

TAT GAG GAT GAT GTT GCT GTA AAC GAA GAA GAA ATT GTT GAC           460
Tyr Glu Asp Asp Val Ala Val Asn Glu Glu Glu Ile Val Asp
140                 145                 150

AAA ATA GTG CCT CTC AAC GAA GAG GAG CAA GAA AAA TGG GAT           502
Lys Ile Val Pro Leu Asn Glu Glu Glu Gln Glu Lys Trp Asp
         155                 160                 165

CGA ATG GTT CGA GAA GTG GAA ATG AAT TTT GAG CAA CAA GAA           544
Arg Met Val Arg Glu Val Glu Met Asn Phe Glu Gln Gln Glu
             170                 175                 180

ACA TCA AAA GAA GGA ACG TTT GGT TGT CAG ACA ACA CAT GAG           586
Thr Ser Lys Glu Gly Thr Phe Gly Cys Gln Thr Thr His Glu
                 185                 190                 195

AAA GAA AAA GAT GAT GAT GGT GGC AGT CTG AAG ACG ACA ATG           628
Lys Glu Lys Asp Asp Asp Gly Gly Ser Leu Lys Thr Thr Met
                     200                 205

AAA GAT AGT CAC GTA AGG CAG ATT TTC TTC GAT GGA GGT GAG           670
Lys Asp Ser His Val Arg Gln Ile Phe Phe Asp Gly Gly Glu
210                 215                 220

ACA TCC GCT AAT GAA ACA GGA TTA AGT AGC GGG GAT GCA GAC           712
Thr Ser Ala Asn Glu Thr Gly Leu Ser Ser Gly Asp Ala Asp
         225                 230                 235

ACT ATT ATG ACT CCA ACG ACA AAG GAG GAT AAT CAT GTT ATA           754
Thr Ile Met Thr Pro Thr Thr Lys Glu Asp Asn His Val Ile
             240                 245                 250

GAC GTA ATG GAG GAA AGG CGA ACT GAT GAA GAG GCC AAA GGG           796
Asp Val Met Glu Glu Arg Arg Thr Asp Glu Glu Ala Lys Gly
                 255                 260                 265

CAA AGC GTT CAT GAA TAA TCTGGATCCA CAAATTGATT TAAATCGCAA          844
Gln Ser Val His Glu
                     270

TCTCGCACAT GCCTATGTTG CTAATATTTA ATGAAATTTT TCAAAGCAAT            894
```

```
AATTTGAATG CTGTTTGGGC TTCCCATATT GTTAAAGCGT TTTCCATCGT            944

CCATTCACTT TTTGTTTTTG CTGTAGTCTG TAACTGCTAC TCTTGATAAA            994

TTTGCTCCAG TAAAAAAAAA AAAAAAAAAA AAAAA                           1029
```

(2) INFORMATION FOR SEQ ID NO:7:

(i) SEQUENCE CHARACTERISTICS:
        (A) LENGTH: 270 amino acids
        (B) TYPE: amino acid
        (D) TOPOLOGY: linear (ii) MOLECULE TYPE: protein (xi) SEQUENCE DESCRIPTION: SEQ ID NO:7:

```
Lys Lys Glu Gln Ala Thr Pro Val Ala Leu Arg Ser Ala Leu
 1               5                  10

Gln Arg Ile Gly Arg Asp Val Val Arg Glu Met Asp Arg
 15              20                  25

Ala Glu Lys Leu Asp Gly Leu Glu Gly Thr Pro Val Ser His
     30              35                  40

Ile Ser Gly Pro Ser Ile Thr Leu Ser Ser Thr Leu Leu Glu
         45              50                  55

Val Ala Gly Asp Arg Arg Arg His Ala Glu Val Thr Met Ala
             60              65                  70

Gln Gln Arg Leu Ala Gln Glu Pro Phe Phe Gln Gln Val Gly
                 75              80

Tyr Asn Gly Thr Pro Gly Asp Pro Glu Glu Pro Lys Glu Gln
 85              90                  95

Ser Phe His Glu Glu Glu Glu Val Ala Val Ser Glu Ile
     100             105                 110

Arg Thr Val Val Arg Thr Glu Arg His Val His Asp Ser Glu
         115             120                 125

Asn Gly Pro Ile Val Glu Glu Arg Thr Ile Thr Thr Tyr
             130             135                 140

Glu Asp Asp Val Ala Val Asn Glu Glu Glu Ile Val Asp Lys
                 145             150

Ile Val Pro Leu Asn Glu Glu Gln Glu Lys Trp Asp Arg
 155             150                 165

Met Val Arg Glu Val Glu Met Asn Phe Glu Gln Gln Glu Thr
     170             175                 180

Ser Lys Glu Gly Thr Phe Gly Cys Gln Thr Thr His Glu Lys
         185             190                 195

Glu Lys Asp Asp Asp Gly Gly Ser Leu Lys Thr Thr Met Lys
             200             205                 210

Asp Ser His Val Arg Gln Ile Phe Phe Asp Gly Gly Glu Thr
                 215             220

Ser Ala Asn Glu Thr Gly Leu Ser Ser Gly Asp Ala Asp Thr
 225             230             235

Ile Met Thr Pro Thr Thr Lys Glu Asp Asn His Val Ile Asp
     240             245             250

Val Met Glu Glu Arg Arg Thr Asp Glu Glu Ala Lys Gly Gln
         255             260             265

Ser Val His Glu
         270
```

(2) INFORMATION FOR SEQ ID NO:8:

(i) SEQUENCE CHARACTERISTICS:
        (A) LENGTH: 1029 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

```
TTTTTTTTTT TTTTTTTTTT TTTTACTGGA GCAAATTTAT CAAGAGTAGC        50

AGTTACAGAC TACAGCAAAA ACAAAAGTG AATGGACGAT GGAAAACGCT        100

TTAACAATAT GGGAAGCCCA AACAGCATTC AAATTATTGC TTTGAAAAAT       150

TTCATTAAAT ATTAGCAACA TAGGCATGTG CGAGATTGCG ATTTAAATCA       200

ATTTGTGGAT CCAGATTATT CATGAACGCT TTGCCCTTTG GCCTCTTCAT       250

CAGTTCGCCT TTCCTCCATT ACGTCTATAA CATGATTATC CTCCTTTGTC       300

GTTGGAGTCA TAATAGTGTC TGCATCCCCG CTACTTAATC CTGTTTCATT       350

AGCGGATGTC TCACCTCCAT CGAAGAAAAT CTGCCTTACG TGACTATCTT       400

TCATTGTCGT CTTCAGACTG CCACCATCAT CATCTTTTTC TTTCTCATGT       450

GTTGTCTGAC AACCAAACGT TCCTTCTTTT GATGTTTCTT GTTGCTCAAA       500

ATTCATTTCC ACTTCTCGAA CCATTCGATC CCATTTTTCT TGCTCCTCTT       550

CGTTGAGAGG CACTATTTTG TCAACAATTT CTTCTTCGTT TACAGCAACA       600

TCATCCTCAT ACGTAGTTGT TATTGTACGC TCTTCCACAA TAGGACCATT       650

TTCCGAATCA TGCACATGTC GTTCAGTGCG CACAACTGTT CGAATTTCTG       700

AAACTGCAAC TTCCTCTTCC TCTTCGTGGA ATGACTGTTC TTTGGGTTCT       750

TCTGGATCTC CAGGTGTCCC ATTATACCCT ACTTGCTGAA AAAACGGTTC       800

TTGTGCCAAT CGCTGTTGCG CCATTGTTAC CTCGGCGTGA CGACGTCTGT       850

CGCCTGCTAC CTCTAGCAAA GTAGATGACA GAGTTATTGA GGGTCCAGAA       900

ATATGCGATA CAGGTGTTCC TTCTAAACCA TCTAGCTTTT CAGCTCGATC       950

CATTTCTCGT ACAACATCAT CACGTCCTAT TCGCTGCAAT GCTGATCGCA      1000

AAGCAACGGG CGTAGCTTGT TCTTTCTTC                             1029
```

(2) INFORMATION FOR SEQ ID NO:9:

(i) SEQUENCE CHARACTERISTICS:
        (A) LENGTH: 810 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

```
AAGAAAGAAC AAGCTACGCC CGTTGCTTTG CGATCAGCAT TGCAGCGAAT        50

AGGACGTGAT GATGTTGTAC GAGAAATGGA TCGAGCTGAA AAGCTAGATG       100

GTTTAGAAGG AACACCTGTA TCGCATATTT CTGGACCCTC AATAACTCTG       150

TCATCTACTT TGCTAGAGGT AGCAGGCGAC AGACGTCGTC ACGCCGAGGT       200

AACAATGGCG CAACAGCGAT TGGCACAAGA ACCGTTTTTT CAGCAAGTAG       250

GGTATAATGG GACACCTGGA GATCCAGAAG AACCCAAAGA ACAGTCATTC       300
```

```
CACGAAGAGG AAGAGGAAGT TGCAGTTTCA GAAATTCGAA CAGTTGTGCG              350

CACTGAACGA CATGTGCATG ATTCGGAAAA TGGTCCTATT GTGGAAGAGC              400

GTACAATAAC AACTACGTAT GAGGATGATG TTGCTGTAAA CGAAGAAGAA              450

ATTGTTGACA AAATAGTGCC TCTCAACGAA GAGGAGCAAG AAAAATGGGA              500

TCGAATGGTT CGAGAAGTGG AAATGAATTT TGAGCAACAA GAAACATCAA              550

AAGAAGGAAC GTTTGGTTGT CAGACAACAC ATGAGAAAGA AAAAGATGAT              600

GATGGTGGCA GTCTGAAGAC GACAATGAAA GATAGTCACG TAAGGCAGAT              650

TTTCTTCGAT GGAGGTGAGA CATCCGCTAA TGAAACAGGA TTAAGTAGCG              700

GGGATGCAGA CACTATTATG ACTCCAACGA CAAAGGAGGA TAATCATGTT              750

ATAGACGTAA TGGAGGAAAG GCGAACTGAT GAAGAGGCCA AAGGGCAAAG              800

CGTTCATGAA                                                         810
```

(2) INFORMATION FOR SEQ ID NO:10:

(i) SEQUENCE CHARACTERISTICS:
        (A) LENGTH:  810 nucleotides
        (B) TYPE:  nucleic acid
        (C) STRANDEDNESS:  single
        (D) TOPOLOGY:  linear (ii) MOLECULE TYPE:  cDNA (xi) SEQUENCE DESCRIPTION:  SEQ ID NO:10:

```
TTCATGAACG CTTTGCCCTT TGGCCTCTTC ATCAGTTCGC CTTTCCTCCA               50

TTACGTCTAT AACATGATTA TCCTCCTTTG TCGTTGGAGT CATAATAGTG              100

TCTGCATCCC CGCTACTTAA TCCTGTTTCA TTAGCGGATG TCTCACCTCC              150

ATCGAAGAAA ATCTGCCTTA CGTGACTATC TTTCATTGTC GTCTTCAGAC              200

TGCCACCATC ATCATCTTTT TCTTTCTCAT GTGTTGTCTG ACAACCAAAC              250

GTTCCTTCTT TTGATGTTTC TTGTTGCTCA AAATTCATTT CCACTTCTCG              300

AACCATTCGA TCCCATTTTT CTTGCTCCTC TTCGTTGAGA GGCACTATTT              350

TGTCAACAAT TTCTTCTTCG TTTACAGCAA CATCATCCTC ATACGTAGTT              400

GTTATTGTAC GCTCTTCCAC AATAGGACCA TTTTCCGAAT CATGCACATG              450

TCGTTCAGTG CGCACAACTG TTCGAATTTC TGAAACTGCA ACTTCCTCTT              500

CCTCTTCGTG GAATGACTGT TCTTTGGGTT CTTCTGGATC TCCAGGTGTC              550

CCATTATACC CTACTTGCTG AAAAAACGGT TCTTGTGCCA ATCGCTGTTG              600

CGCCATTGTT ACCTCGGCGT GACGACGTCT GTCGCCTGCT ACCTCTAGCA              650

AAGTAGATGA CAGAGTTATT GAGGGTCCAG AAATATGCGA TACAGGTGTT              700

CCTTCTAAAC CATCTAGCTT TTCAGCTCGA TCCATTTCTC GTACAACATC              750

ATCACGTCCT ATTCGCTGCA ATGCTGATCG CAAAGCAACG GGCGTAGCTT              800

GTTCTTTCTT                                                         810
```

(2) INFORMATION FOR SEQ ID NO:11:

(i) SEQUENCE CHARACTERISTICS:
        (A) LENGTH:  600 nucleotides
        (B) TYPE:  nucleic acid
        (C) STRANDEDNESS:  single
        (D) TOPOLOGY:  linear (ii) MOLECULE TYPE:  cDNA (ix) FEATURE:
      (A) NAME/KEY: CDS
      (B) LOCATION: 1..600

(xi) SEQUENCE DESCRIPTION: SEQ ID NO:11:

| | | | | | | | | | | | | | |
|---|---|---|---|---|---|---|---|---|---|---|---|---|---|
| GCC | CAG | CCA | GTT | CCA | CAA | GAG | ATA | GTC | ACT | CGT | TTA | CAT | GGG | 42 |
| Ala | Gln | Pro | Val | Pro | Gln | Glu | Ile | Val | Thr | Arg | Leu | His | Gly | |
| 1 | | | 5 | | | | | 10 | | | | | | |

```
GCC CAG CCA GTT CCA CAA GAG ATA GTC ACT CGT TTA CAT GGG                  42
Ala Gln Pro Val Pro Gln Glu Ile Val Thr Arg Leu His Gly
1               5                   10

AAT AGA GTC GCT GTT TCT CCA ATT GTA ACT GTT GAA CCG CGT                  84
Asn Arg Val Ala Val Ser Pro Ile Val Thr Val Glu Pro Arg
 15                  20                  25

CGT CGC AAA TTC CAT AAG CCC ATA ACG CTG TGC ATA CCA TTG                 126
Arg Arg Lys Phe His Lys Pro Ile Thr Leu Cys Ile Pro Leu
     30                  35                  40

CCA CAA AGC TCA AAT AAA GGA ATG TTA ACA CAA TAT AGT GGC                 168
Pro Gln Ser Ser Asn Lys Gly Met Leu Thr Gln Tyr Ser Gly
         45                  50                  55

CAA CCA GGA CAG GAA CCA CCG ACG CTG CGT TTA CTC TGC AGT                 210
Gln Pro Gly Gln Glu Pro Pro Thr Leu Arg Leu Leu Cys Ser
             60                  65                  70

AAA ACT GGA GGT TCT TCT CCT GCA CAG TGG GAA GAT ATT ACT                 252
Lys Thr Gly Gly Ser Ser Pro Ala Gln Trp Glu Asp Ile Thr
                 75                  80

GGA ACT ACC CAG TTA ACA TTT ACT GGT GAG GAC GTT TCA TTT                 294
Gly Thr Thr Gln Leu Thr Phe Thr Gly Glu Asp Val Ser Phe
85                  90                  95

ACA ACT ACG GTT TCT GCT CGA TTT TGG TTG ATG GAT TGC CAA                 336
Thr Thr Thr Val Ser Ala Arg Phe Trp Leu Met Asp Cys Gln
    100                 105                 110

ACT CCG CGA GAT GCG GCA CGA ATG GCA CAA GAA GTT TAC AAT                 378
Thr Pro Arg Asp Ala Ala Arg Met Ala Gln Glu Val Tyr Asn
        115                 120                 125

GAA GCA ATT GCA GTT CCT TAT ATG GCT AAA TTT CTT ATT TTT                 420
Glu Ala Ile Ala Val Pro Tyr Met Ala Lys Phe Leu Ile Phe
            130                 135                 140

GCT CGA CGA ACT TTT CCT GCC GAA GGA CAG TTG AGA TTG TTT                 462
Ala Arg Arg Thr Phe Pro Ala Glu Gly Gln Leu Arg Leu Phe
                145                 150

TGT ATG ACT GAT GAT CGG GAA GAT AAA ACC CTG GAA AAA CAA                 504
Cys Met Thr Asp Asp Arg Glu Asp Lys Thr Leu Glu Lys Gln
155                 160                 165

GAA CGT TTC ATT GAA ATT GCG AAA TCG AAA GAT GTA GAA GTC                 546
Glu Arg Phe Ile Glu Ile Ala Lys Ser Lys Asp Val Glu Val
    170                 175                 180

TTA AGT GGG CGA CAT CAG TTT TTG GAA TTT TCT GGA AAT CTT                 588
Leu Ser Gly Arg His Gln Phe Leu Glu Phe Ser Gly Asn Leu
        185                 190                 195

CTT CCA ATA ACC                                                         600
Leu Pro Ile Thr
            200
```

(2) INFORMATION FOR SEQ ID NO:12:

(i) SEQUENCE CHARACTERISTICS:
        (A) LENGTH: 200 amino acids
        (B) TYPE: amino acid
        (D) TOPOLOGY: linear (ii) MOLECULE TYPE: protein (xi) SEQUENCE DESCRIPTION: SEQ ID NO:12:

```
Ala Gln Pro Val Pro Gln Glu Ile Val Thr Arg Leu His Gly
 1               5                  10

Asn Arg Val Ala Val Ser Pro Ile Val Thr Val Glu Pro Arg
15                  20                  25

Arg Arg Lys Phe His Lys Pro Ile Thr Leu Cys Ile Pro Leu
    30                  35                  40

Pro Gln Ser Ser Asn Lys Gly Met Leu Thr Gln Tyr Ser Gly
        45                  50                  55

Gln Pro Gly Gln Glu Pro Pro Thr Leu Arg Leu Leu Cys Ser
            60                  65                  70

Lys Thr Gly Gly Ser Ser Pro Ala Gln Trp Glu Asp Ile Thr
                75                  80

Gly Thr Thr Gln Leu Thr Phe Thr Gly Glu Asp Val Ser Phe
85                  90                  95

Thr Thr Thr Val Ser Ala Arg Phe Trp Leu Met Asp Cys Gln
        100                 105                 110

Thr Pro Arg Asp Ala Ala Arg Met Ala Gln Glu Val Tyr Asn
            115                 120                 125

Glu Ala Ile Ala Val Pro Tyr Met Ala Lys Phe Leu Ile Phe
                130                 135                 140

Ala Arg Arg Thr Phe Pro Ala Glu Gly Gln Leu Arg Leu Phe
                    145                 150

Cys Met Thr Asp Asp Arg Glu Asp Lys Thr Leu Glu Lys Gln
155                 160                 165

Glu Arg Phe Ile Glu Ile Ala Lys Ser Lys Asp Val Glu Val
    170                 175                 180

Leu Ser Gly Arg His Gln Phe Leu Glu Phe Ser Gly Asn Leu
        185                 190                 195

Leu Pro Ile Thr
        200

(2) INFORMATION FOR SEQ ID NO:13:

(i) SEQUENCE CHARACTERISTICS:
        (A) LENGTH:  600 nucleotides
        (B) TYPE:  nucleic acid
        (C) STRANDEDNESS:  single
        (D) TOPOLOGY:  linear (ii) MOLECULE TYPE:  cDNA (xi) SEQUENCE DESCRIPTION:  SEQ ID NO:13:

GGTTATTGGA AGAAGATTTC CAGAAAATTC CAAAAACTGA TGTCGCCCAC            50

TTAAGACTTC TACATCTTTC GATTTCGCAA TTTCAATGAA ACGTTCTTGT           100

TTTTCCAGGG TTTTATCTTC CCGATCATCA GTCATACAAA ACAATCTCAA           150

CTGTCCTTCG GCAGGAAAAG TTCGTCGAGC AAAAATAAGA AATTTAGCCA           200

TATAAGGAAC TGCAATTGCT TCATTGTAAA CTTCTTGTGC CATTCGTGCC           250

GCATCTCGCG GAGTTTGGCA ATCCATCAAC CAAAATCGAG CAGAAACCGT           300

AGTTGTAAAT GAAACGTCCT CACCAGTAAA TGTTAACTGG GTAGTTCCAG           350

TAATATCTTC CCACTGTGCA GGAGAAGAAC CTCCAGTTTT ACTGCAGAGT           400

AAACGCAGCG TCGGTGGTTC CTGTCCTGGT TGGCCACTAT ATTGTGTTAA           450

CATTCCTTTA TTTGAGCTTT GTGGCAATGG TATGCACAGC GTTATGGGCT           500

TATGGAATTT GCGACGACGC GGTTCAACAG TTACAATTGG AGAAACAGCG           550
```

ACTCTATTCC CATGTAAACG AGTGACTATC TCTTGTGGAA CTGGCTGGGC        600

(2) INFORMATION FOR SEQ ID NO:14:

(i) SEQUENCE CHARACTERISTICS:
        (A) LENGTH: 1228 nucleotides
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1227

(xi) SEQUENCE DESCRIPTION: SEQ ID NO:14:

```
CAT CAA GCT GCT CAG CAA GGG CAT AAC AGT GTT GTA CGT TAC         42
His Gln Ala Ala Gln Gln Gly His Asn Ser Val Val Arg Tyr
1               5                   10

TTG TTG GAA CAT GGT GCA AGT CCA AAT GTT CAT ACA TCG ACA         84
Leu Leu Glu His Gly Ala Ser Pro Asn Val His Thr Ser Thr
15                  20                  25

GGA CAA ACT CCA TTA TCG ATT GCT GAA CGT CTA GGG TAT GTA        126
Gly Gln Thr Pro Leu Ser Ile Ala Glu Arg Leu Gly Tyr Val
30                  35                  40

TCC GTG GTT GAA GCG CTT AAA ACA ATT ACC GAG ACT ACT GTG        168
Ser Val Val Glu Ala Leu Lys Thr Ile Thr Glu Thr Thr Val
45                  50                  55

ATA ACG GAG ACC ACA ACC GTT ACT GAA GAA AGA TAT AAA CCT        210
Ile Thr Glu Thr Thr Thr Val Thr Glu Glu Arg Tyr Lys Pro
60                  65                  70

CAG AAT CCC GAA GCA ATG AAT GAA ACC ATG TTT TCC GAT TCC        252
Gln Asn Pro Glu Ala Met Asn Glu Thr Met Phe Ser Asp Ser
75                  80

GAA GAT GAA GGT GAA GAT AAT CAG ATC ACA GCC AAT GCT CAT        294
Glu Asp Glu Gly Glu Asp Asn Gln Ile Thr Ala Asn Ala His
85                  90                  95

GCT CAT GAT TTC TCA GAA AGC CTC ACA AAA GGT TTG CAC GAT        336
Ala His Asp Phe Ser Glu Ser Leu Thr Lys Gly Leu His Asp
100                 105                 110

TCA ACT GGT GTA CAT TTG ATT CAT GCC ACA GAA CCG ACA TTG        378
Ser Thr Gly Val His Leu Ile His Ala Thr Glu Pro Thr Leu
115                 120                 125

TCA CGA AGT CCG GAA GTG GAA GGT ACG GAT GGC GAT TTG GAT        420
Ser Arg Ser Pro Glu Val Glu Gly Thr Asp Gly Asp Leu Asp
130                 135                 140

GCC TTA ATT CGT AAA GCA CAA CAT GAA CCA ATT ACT ACA GCG        462
Ala Leu Ile Arg Lys Ala Gln His Glu Pro Ile Thr Thr Ala
145                 150

ATG GCC GAT CCT TCC TTA GAT GCA TCG CTT CCT GAC AAT GTT        504
Met Ala Asp Pro Ser Leu Asp Ala Ser Leu Pro Asp Asn Val
155                 160                 165

ACG ATA ATG AGA ACT ACC ATG CAA CCT AGT TTT TTA ATT TCG        546
Thr Ile Met Arg Thr Thr Met Gln Pro Ser Phe Leu Ile Ser
170                 175                 180

TTT ATG GTG GAT GCA CGT GGA GGA GCA ATG CGT GGT TGT AGG        588
Phe Met Val Asp Ala Arg Gly Gly Ala Met Arg Gly Cys Arg
185                 190                 195

CAT TCC GGT GTC AGA ATC ATT ATA CCA CCG AGG AAA GCG CCG        630
His Ser Gly Val Arg Ile Ile Ile Pro Pro Arg Lys Ala Pro
200                 205                 210
```

-continued

```
CAA CCT ACA CGG GTC ACA TGC AGA TAC CTT GGA AAG GAC AAG            672
Gln Pro Thr Arg Val Thr Cys Arg Tyr Leu Gly Lys Asp Lys
215                 220

TTA GCG CAT CCA CCA CCA TTA AGT GAA GGT GAA GCG CTC GCN            714
Leu Ala His Pro Pro Pro Leu Ser Glu Gly Glu Ala Leu Ala
225                 230                 235

TCA CGT ATA CTT GAA ATG GCA CCA CAT GGA GCA AAA TTC TTA            756
Ser Arg Ile Leu Glu Met Ala Pro His Gly Ala Lys Phe Leu
240                 245                 250

GGC CCT GTT ATA TTG GAA GTA CCA CAT TTT GCA TCA CTT CGT            798
Gly Pro Val Ile Leu Glu Val Pro His Phe Ala Ser Leu Arg
255                 260                 265

GGA CGA GAG AGA GAG ATT GTC ATT TTG CGT TCT GAT GAT GGG            840
Gly Arg Glu Arg Glu Ile Val Ile Leu Arg Ser Asp Asp Gly
270                 275                 280

CAG CAT TGG AAA GAG CAT CAG CTT GAA GCA ACA GAA GAT GCT            882
Gln His Trp Lys Glu His Gln Leu Glu Ala Thr Glu Asp Ala
285                 290

GTA CAA GAG GTG CTC AAT GAA TCG TTT GAT GCA GAA GAG TTG            924
Val Gln Glu Val Leu Asn Glu Ser Phe Asp Ala Glu Glu Leu
295                 300                 305

TCG CAA CTT GAT GAT TTG CAT ACA TCA CGG ATT ACG CGT ATC            966
Ser Gln Leu Asp Asp Leu His Thr Ser Arg Ile Thr Arg Ile
310                 315                 320

CTG ACC AAT GAT TTC CCA ATG TAT TTC GCG GTC GTT ACT CGT           1008
Leu Thr Asn Asp Phe Pro Met Tyr Phe Ala Val Val Thr Arg
325                 330                 335

GTG CGG CAA GAA GTG CAC TGT GTT GGT CCA GAA GGT GGT GTA           1050
Val Arg Gln Glu Val His Cys Val Gly Pro Glu Gly Gly Val
340                 345                 350

ATA CTC TCT TCA GTT GTT CCT CAT GTG CAG GCC ATA TTT CCG           1092
Ile Leu Ser Ser Val Val Pro His Val Gln Ala Ile Phe Pro
355                 360

GAT GGT TCC TTG ACT AAG ACG ATC AAA GTA TCT GTG CAA GCC           1134
Asp Gly Ser Leu Thr Lys Thr Ile Lys Val Ser Val Gln Ala
365                 370                 375

CAG CCA GTT CCA CAA GAG ATA GTC ACT CGT TTA CAT GGG AAT           1176
Gln Pro Val Pro Gln Glu Ile Val Thr Arg Leu His Gly Asn
380                 385                 390

AGA GTC GCT GTT TCT CCA ATT GTA ACT GTT GAA CCG CGT CGT           1218
Arg Val Ala Val Ser Pro Ile Val Thr Val Glu Pro Arg Arg
395                 400                 405

CGC AAA TTC C                                                      1228
Arg Lys Phe
```

(2) INFORMATION FOR SEQ ID NO:15:

(i) SEQUENCE CHARACTERISTICS:
        (A) LENGTH: 409 amino acids
        (B) TYPE: amino acid
        (D) TOPOLOGY: linear (ii) MOLECULE TYPE: protein (xi) SEQUENCE DESCRIPTION: SEQ ID NO:15:

```
His Gln Ala Ala Gln Gln Gly His Asn Ser Val Val Arg Tyr
 1               5                  10

Leu Leu Glu His Gly Ala Ser Pro Asn Val His Thr Ser Thr
15                  20                  25

Gly Gln Thr Pro Leu Ser Ile Ala Glu Arg Leu Gly Tyr Val
```

-continued

```
            30                  35                  40
Ser Val Val Glu Ala Leu Lys Thr Ile Thr Glu Thr Thr Val
            45                  50                  55
Ile Thr Glu Thr Thr Thr Val Thr Glu Glu Arg Tyr Lys Pro
            60                  65                  70
Gln Asn Pro Glu Ala Met Asn Glu Thr Met Phe Ser Asp Ser
            75                  80
Glu Asp Glu Gly Glu Asp Asn Gln Ile Thr Ala Asn Ala His
85                  90                  95
Ala His Asp Phe Ser Glu Ser Leu Thr Lys Gly Leu His Asp
    100                 105                 110
Ser Thr Gly Val His Leu Ile His Ala Thr Glu Pro Thr Leu
            115                 120                 125
Ser Arg Ser Pro Glu Val Glu Gly Thr Asp Gly Asp Leu Asp
            130                 135                 140
Ala Leu Ile Arg Lys Ala Gln His Glu Pro Ile Thr Thr Ala
                145                 150
Met Ala Asp Pro Ser Leu Asp Ala Ser Leu Pro Asp Asn Val
155                 160                 165
Thr Ile Met Arg Thr Thr Met Gln Pro Ser Phe Leu Ile Ser
    170                 175                 180
Phe Met Val Asp Ala Arg Gly Gly Ala Met Arg Gly Cys Arg
            185                 190                 195
His Ser Gly Val Arg Ile Ile Pro Pro Arg Lys Ala Pro
            200                 205                 210
Gln Pro Thr Arg Val Thr Cys Arg Tyr Leu Gly Lys Asp Lys
            215                 220
Leu Ala His Pro Pro Leu Ser Glu Gly Glu Ala Leu Ala
225                 230                 235
Ser Arg Ile Leu Glu Met Ala Pro His Gly Ala Lys Phe Leu
    240                 245                 250
Gly Pro Val Ile Leu Glu Val Pro His Phe Ala Ser Leu Arg
            255                 260                 265
Gly Arg Glu Arg Glu Ile Val Ile Leu Arg Ser Asp Asp Gly
            270                 275                 280
Gln His Trp Lys Glu His Gln Leu Glu Ala Thr Glu Asp Ala
                285                 290
Val Gln Glu Val Leu Asn Glu Ser Phe Asp Ala Glu Glu Leu
295                 300                 305
Ser Gln Leu Asp Asp Leu His Thr Ser Arg Ile Thr Arg Ile
    310                 315                 320
Leu Thr Asn Asp Phe Pro Met Tyr Phe Ala Val Val Thr Arg
    325                 330                 335
Val Arg Gln Glu Val His Cys Val Gly Pro Glu Gly Gly Val
            340                 345                 350
Ile Leu Ser Ser Val Val Pro His Val Gln Ala Ile Phe Pro
                355                 360
Asp Gly Ser Leu Thr Lys Thr Ile Lys Val Ser Val Gln Ala
365                 370                 375
Gln Pro Val Pro Gln Glu Ile Val Thr Arg Leu His Gly Asn
    380                 385                 390
Arg Val Ala Val Ser Pro Ile Val Thr Val Glu Pro Arg Arg
    395                 400                 405
```

Arg Lys Phe (2) INFORMATION FOR SEQ ID NO:16:

(i) SEQUENCE CHARACTERISTICS:
        (A) LENGTH: 1228 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

```
GGAATTTGCG ACGACGCGGT TCAACAGTTA CAATTGGAGA AACAGCGACT            50
CTATTCCCAT GTAAACGAGT GACTATCTCT TGTGGAACTG GCTGGGCTTG           100
CACAGATACT TTGATCGTCT TAGTCAAGGA ACCATCCGGA AATATGGCCT           150
GCACATGAGG AACAACTGAA GAGAGTATTA CACCACCTTC TGGACCAACA           200
CAGTGCACTT CTTGCCGCAC ACGAGTAACG ACCGCGAAAT ACATTGGGAA           250
ATCATTGGTC AGGATACGCG TAATCCGTGA TGTATGCAAA TCATCAAGTT           300
GCGACAACTC TTCTGCATCA AACGATTCAT TGAGCACCTC TTGTACAGCA           350
TCTTCTGTTG CTTCAAGCTG ATGCTCTTTC CAATGCTGCC CATCATCAGA           400
ACGCAAAATG ACAATCTCTC TCTCTCGTCC ACGAAGTGAT GCAAAATGTG           450
GTACTTCCAA TATAACAGGG CCTAAGAATT TTGCTCCATG TGGTGCCATT           500
TCAAGTATAC GTGANGCGAG CGCTTCACCT TCACTTAATG GTGGTGGATG           550
CGCTAACTTG TCCTTTCCAA GGTATCTGCA TGTGACCCGT GTAGGTTGCG           600
GCGCTTTCCT CGGTGGTATA ATGATTCTGA CACCGGAATG CCTACAACCA           650
CGCATTGCTC CTCCACGTGC ATCCACCATA AACGAAATTA AAAAACTAGG           700
TTGCATGGTA GTTCTCATTA TCGTAACATT GTCAGGAAGC GATGCATCTA           750
AGGAAGGATC GGCCATCGCT GTAGTAATTG GTTCATGTTG TGCTTTACGA           800
ATTAAGGCAT CCAAATCGCC ATCCGTACCT TCCACTTCCG GACTTCGTGA           850
CAATGTCGGT TCTGTGGCAT GAATCAAATG TACACCAGTT GAATCGTGCA           900
AACCTTTTGT GAGGCTTTCT GAGAAATCAT GAGCATGAGC ATTGGCTGTG           950
ATCTGATTAT CTTCACCTTC ATCTTCGGAA TCGGAAAACA TGGTTTCATT          1000
CATTGCTTCG GGATTCTGAG GTTTATATCT TTCTTCAGTA ACGGTTGTGG          1050
TCTCCGTTAT CACAGTAGTC TCGGTAATTG TTTTAAGCGC TTCAACCACG          1100
GATACATACC CTAGACGTTC AGCAATCGAT AATGGAGTTT GTCCTGTCGA          1150
TGTATGAACA TTTGGACTTG CACCATGTTC CAACAAGTAA CGTACAACAC          1200
TGTTATGCCC TTGCTGAGCA GCTTGATG                                 1228
```

(2) INFORMATION FOR SEQ ID NO:17:

(i) SEQUENCE CHARACTERISTICS:
        (A) LENGTH: 1227 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

| | |
|---|---|
| CATCAAGCTG CTCAGCAAGG GCATAACAGT GTTGTACGTT ACTTGTTGGA | 50 |
| ACATGGTGCA AGTCCAAATG TTCATACATC GACAGGACAA ACTCCATTAT | 100 |
| CGATTGCTGA ACGTCTAGGG TATGTATCCG TGGTTGAAGC GCTTAAAACA | 150 |
| ATTACCGAGA CTACTGTGAT AACGGAGACC ACAACCGTTA CTGAAGAAAG | 200 |
| ATATAAACCT CAGAATCCCG AAGCAATGAA TGAAACCATG TTTTCCGATT | 250 |
| CCGAAGATGA AGGTGAAGAT AATCAGATCA CAGCCAATGC TCATGCTCAT | 300 |
| GATTTCTCAG AAAGCCTCAC AAAAGGTTTG CACGATTCAA CTGGTGTACA | 350 |
| TTTGATTCAT GCCACAGAAC CGACATTGTC ACGAAGTCCG GAAGTGGAAG | 400 |
| GTACGGATGG CGATTTGGAT GCCTTAATTC GTAAAGCACA ACATGAACCA | 450 |
| ATTACTACAG CGATGGCCGA TCCTTCCTTA GATGCATCGC TTCCTGACAA | 500 |
| TGTTACGATA ATGAGAACTA CCATGCAACC TAGTTTTTTA ATTTCGTTTA | 550 |
| TGGTGGATGC ACGTGGAGGA GCAATGCGTG GTTGTAGGCA TTCCGGTGTC | 600 |
| AGAATCATTA TACCACCGAG GAAAGCGCCG CAACCTACAC GGGTCACATG | 650 |
| CAGATACCTT GGAAAGGACA AGTTAGCGCA TCCACCACCA TTAAGTGAAG | 700 |
| GTGAAGCGCT CGCNTCACGT ATACTTGAAA TGGCACCACA TGGAGCAAAA | 750 |
| TTCTTAGGCC CTGTTATATT GGAAGTACCA CATTTTGCAT CACTTCGTGG | 800 |
| ACGAGAGAGA GAGATTGTCA TTTTGCGTTC TGATGATGGG CAGCATTGGA | 850 |
| AAGAGCATCA GCTTGAAGCA ACAGAAGATG CTGTACAAGA GGTGCTCAAT | 900 |
| GAATCGTTTG ATGCAGAAGA GTTGTCGCAA CTTGATGATT TGCATACATC | 950 |
| ACGGATTACG CGTATCCTGA CCAATGATTT CCCAATGTAT TTCGCGGTCG | 1000 |
| TTACTCGTGT GCGGCAAGAA GTGCACTGTG TTGGTCCAGA AGGTGGTGTA | 1050 |
| ATACTCTCTT CAGTTGTTCC TCATGTGCAG GCCATATTTC CGGATGGTTC | 1100 |
| CTTGACTAAG ACGATCAAAG TATCTGTGCA AGCCCAGCCA GTTCCACAAG | 1150 |
| AGATAGTCAC TCGTTTACAT GGGAATAGAG TCGCTGTTTC TCCAATTGTA | 1200 |
| ACTGTTGAAC CGCGTCGTCG CAAATTC | 1227 |

(2) INFORMATION FOR SEQ ID NO:18:

(i) SEQUENCE CHARACTERISTICS:
        (A) LENGTH: 1227 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

| | |
|---|---|
| GAATTTGCGA CGACGCGGTT CAACAGTTAC AATTGGAGAA ACAGCGACTC | 50 |
| TATTCCCATG TAAACGAGTG ACTATCTCTT GTGGAACTGG CTGGGCTTGC | 100 |
| ACAGATACTT TGATCGTCTT AGTCAAGGAA CCATCCGGAA ATATGGCCTG | 150 |
| CACATGAGGA ACAACTGAAG AGAGTATTAC ACCACCTTCT GGACCAACAC | 200 |
| AGTGCACTTC TTGCCGCACA CGAGTAACGA CCGCGAAATA CATTGGGAAA | 250 |
| TCATTGGTCA GGATACGCGT AATCCGTGAT GTATGCAAAT CATCAAGTTG | 300 |
| CGACAACTCT TCTGCATCAA ACGATTCATT GAGCACCTCT TGTACAGCAT | 350 |
| CTTCTGTTGC TTCAAGCTGA TGCTCTTTCC AATGCTGCCC ATCATCAGAA | 400 |

-continued

```
CGCAAAATGA CAATCTCTCT CTCTCGTCCA CGAAGTGATG CAAAATGTGG            450

TACTTCCAAT ATAACAGGGC CTAAGAATTT TGCTCCATGT GGTGCCATTT            500

CAAGTATACG TGANGCGAGC GCTTCACCTT CACTTAATGG TGGTGGATGC            550

GCTAACTTGT CCTTTCCAAG GTATCTGCAT GTGACCCGTG TAGGTTGCGG            600

CGCTTTCCTC GGTGGTATAA TGATTCTGAC ACCGGAATGC CTACAACCAC            650

GCATTGCTCC TCCACGTGCA TCCACCATAA CGAAATTAA AAAACTAGGT             700

TGCATGGTAG TTCTCATTAT CGTAACATTG TCAGGAAGCG ATGCATCTAA            750

GGAAGGATCG GCCATCGCTG TAGTAATTGG TTCATGTTGT GCTTTACGAA            800

TTAAGGCATC CAAATCGCCA TCCGTACCTT CCACTTCCGG ACTTCGTGAC            850

AATGTCGGTT CTGTGGCATG AATCAAATGT ACACCAGTTG AATCGTGCAA            900

ACCTTTTGTG AGGCTTTCTG AGAAATCATG AGCATGAGCA TTGGCTGTGA            950

TCTGATTATC TTCACCTTCA TCTTCGGAAT CGGAAAACAT GGTTTCATTC           1000

ATTGCTTCGG GATTCTGAGG TTTATATCTT TCTTCAGTAA CGGTTGTGGT           1050

CTCCGTTATC ACAGTAGTCT CGGTAATTGT TTTAAGCGCT TCAACCACGG           1100

ATACATACCC TAGACGTTCA GCAATCGATA ATGGAGTTTG TCCTGTCGAT           1150

GTATGAACAT TTGGACTTGC ACCATGTTCC AACAAGTAAC GTACAACACT           1200

GTTATGCCCT TGCTGAGCAG CTTGATG                                   1227

(2) INFORMATION FOR SEQ ID NO:19:

(i) SEQUENCE CHARACTERISTICS:
        (A) LENGTH:  573 nucleotides
        (B) TYPE:  nucleic acid
        (C) STRANDEDNESS:  single
        (D) TOPOLOGY:  linear (ii) MOLECULE TYPE:  cDNA (ix) FEATURE:
        (A) NAME/KEY:  CDS
        (B) LOCATION:  1..573

(xi) SEQUENCE DESCRIPTION:  SEQ ID NO:19:

AAT AAC GAC AAG GTA GCA TTG TTA CTT CTA GAA AAT GGT GCT            42
Asn Asn Asp Lys Val Ala Leu Leu Leu Leu Glu Asn Gly Ala
1               5                   10

TCT GCA CAT GCC GCT GCC AAG AAT GGG TAC ACT CCT TTA CAT            84
Ser Ala His Ala Ala Ala Lys Asn Gly Tyr Thr Pro Leu His
15                  20                  25

ATT GCC GCG AAG AAG AAT CAG ATG GAT ATT GCT AGC ACT CTC           126
Ile Ala Ala Lys Lys Asn Gln Met Asp Ile Ala Ser Thr Leu
30                  35                  40

CTT CAT TAT AAG GCA AAT GCG AAT GCT GAA AGC AAA GCT GGC           168
Leu His Tyr Lys Ala Asn Ala Asn Ala Glu Ser Lys Ala Gly
45                  50                  55

TTT ACA CCA CTT CAT CTT GCC GCC CAG GAG GGC CAT CGC GAA           210
Phe Thr Pro Leu His Leu Ala Ala Gln Glu Gly His Arg Glu
60                  65                  70

ATG GCT GCG TTA TTA ATT GAA AAT GGA GCA AAA GTT GGA GCT           252
Met Ala Ala Leu Leu Ile Glu Asn Gly Ala Lys Val Gly Ala
75                  80

CAG GCA AGG AAT GGC TTG ACA CCA ATG CAT TTA TGT GCA CAG           294
Gln Ala Arg Asn Gly Leu Thr Pro Met His Leu Cys Ala Gln
85                  90                  95
```

-continued

```
GAG GAT CGT GTG AGC GTA GCA GAA GAA CTA GTG AAA GAA AAC            336
Glu Asp Arg Val Ser Val Ala Glu Glu Leu Val Lys Glu Asn
100             105                 110

GCA GCC ATT GAT CCC AAA ACG AAA GCA GGA TAT ACG CCG TTA            378
Ala Ala Ile Asp Pro Lys Thr Lys Ala Gly Tyr Thr Pro Leu
115             120                 125

CAT GTT GCT TGC CAT TTT GGA CAA ATA AAC ATG GTC CGT TTC            420
His Val Ala Cys His Phe Gly Gln Ile Asn Met Val Arg Phe
130             135                 140

TTG ATT GAG CAT GGC GCA CGA GTT TCA GTT ATT ACT CGT GCT            462
Leu Ile Glu His Gly Ala Arg Val Ser Val Ile Thr Arg Ala
145             150

TCC TAT ACT CCT CTG CAT CAA GCT GCT CAG CAA GGG CAT AAC            504
Ser Tyr Thr Pro Leu His Gln Ala Ala Gln Gln Gly His Asn
155             160                 165

AGT GTT GTA CGT TAC TTG TTG GAA CAT GGT GCA AGT CCA AAT            546
Ser Val Val Arg Tyr Leu Leu Glu His Gly Ala Ser Pro Asn
170             175                 180

GTT CAT ACA TCG ACA GGA CAA ACT CCA                                573
Val His Thr Ser Thr Gly Gln Thr Pro
185             190
```

(2) INFORMATION FOR SEQ ID NO:20:

(i) SEQUENCE CHARACTERISTICS:
        (A) LENGTH: 191 amino acids
        (B) TYPE: amino acid
        (D) TOPOLOGY: linear (ii) MOLECULE TYPE: protein (xi) SEQUENCE DESCRIPTION: SEQ ID NO:20:

```
Asn Asn Asp Lys Val Ala Leu Leu Leu Glu Asn Gly Ala
1               5                   10

Ser Ala His Ala Ala Lys Asn Gly Tyr Thr Pro Leu His
15              20                  25

Ile Ala Ala Lys Lys Asn Gln Met Asp Ile Ala Ser Thr Leu
30              35                  40

Leu His Tyr Lys Ala Asn Ala Asn Ala Glu Ser Lys Ala Gly
                45                  50              55

Phe Thr Pro Leu His Leu Ala Ala Gln Glu Gly His Arg Glu
                60                  65                  70

Met Ala Ala Leu Leu Ile Glu Asn Gly Ala Lys Val Gly Ala
                75                  80

Gln Ala Arg Asn Gly Leu Thr Pro Met His Leu Cys Ala Gln
85                  90                  95

Glu Asp Arg Val Ser Val Ala Glu Glu Leu Val Lys Glu Asn
    100                 105                 110

Ala Ala Ile Asp Pro Lys Thr Lys Ala Gly Tyr Thr Pro Leu
                115                 120                 125

His Val Ala Cys His Phe Gly Gln Ile Asn Met Val Arg Phe
                    130                 135                 140

Leu Ile Glu His Gly Ala Arg Val Ser Val Ile Thr Arg Ala
                    145                 150

Ser Tyr Thr Pro Leu His Gln Ala Ala Gln Gln Gly His Asn
155                 160                 165

Ser Val Val Arg Tyr Leu Leu Glu His Gly Ala Ser Pro Asn
    170                 175                 180
```

```
Val His Thr Ser Thr Gly Gln Thr Pro
        185                 190
```

(2) INFORMATION FOR SEQ ID NO:21:

(i) SEQUENCE CHARACTERISTICS:
        (A) LENGTH: 573 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:21:

```
TGGAGTTTGT CCTGTCGATG TATGAACATT TGGACTTGCA CCATGTTCCA           50

ACAAGTAACG TACAACACTG TTATGCCCTT GCTGAGCAGC TTGATGCAGA          100

GGAGTATAGG AAGCACGAGT AATAACTGAA ACTCGTGCGC CATGCTCAAT          150

CAAGAAACGG ACCATGTTTA TTTGTCCAAA ATGGCAAGCA ACATGTAACG          200

GCGTATATCC TGCTTTCGTT TTGGGATCAA TGGCTGCGTT TTCTTTCACT          250

AGTTCTTCTG CTACGCTCAC ACGATCCTCC TGTGCACATA AATGCATTGG          300

TGTCAAGCCA TTCCTTGCCT GAGCTCCAAC TTTTGCTCCA TTTTCAATTA          350

ATAACGCAGC CATTTCGCGA TGGCCCTCCT GGGCGGCAAG ATGAAGTGGT          400

GTAAAGCCAG CTTTGCTTTC AGCATTCGCA TTTGCCTTAT AATGAAGGAG          450

AGTGCTAGCA ATATCCATCT GATTCTTCTT CGCGGCAATA TGTAAAGGAG          500

TGTACCCATT CTTGGCAGCG GCATGTGCAG AAGCACCATT TTCTAGAAGT          550

AACAATGCTA CCTTGTCGTT ATT                                      573
```

(2) INFORMATION FOR SEQ ID NO:22:

(i) SEQUENCE CHARACTERISTICS:
        (A) LENGTH: 911 nucleotides
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..909

(xi) SEQUENCE DESCRIPTION: SEQ ID NO:22:

```
GTG GAT GAT GTT ACT GTT GAC TAT CTC ACT CCT CTT CAT GTG          42
Val Asp Asp Val Thr Val Asp Tyr Leu Thr Pro Leu His Val
1               5                   10

GCT GCT CAT TGC GGA CAT GTC CGT GTC GCT AAA CTT TTG CTG          84
Ala Ala His Cys Gly His Val Arg Val Ala Lys Leu Leu Leu
15                  20                  25

GAT CGT AAT GCT GAC CCG AAT GCT CGA GCT CTC AAT GGC TTC         126
Asp Arg Asn Ala Asp Pro Asn Ala Arg Ala Leu Asn Gly Phe
30                  35                  40

ACA CCG CTG CAT ATC GCT TGC AAA AAA AAT CGC ATT AAA ATT         168
Thr Pro Leu His Ile Ala Cys Lys Lys Asn Arg Ile Lys Ile
45                  50                  55

GTC GAA CTG CTA CTG AAA TAC CAC GCT GCA ATC GAA GCA ACT         210
Val Glu Leu Leu Leu Lys Tyr His Ala Ala Ile Glu Ala Thr
60                  65                  70

ACT GAA TCC GGT CTC TCA CCG CTG CAT GTC GCT GCT TTT ATG         252
Thr Glu Ser Gly Leu Ser Pro Leu His Val Ala Ala Phe Met
```

```
                                                                                   75                          80
GGT GCT ATA AAC ATT GTC ATC TAT TTA CTA CAA CAA GGT GCT                              294
Gly Ala Ile Asn Ile Val Ile Tyr Leu Leu Gln Gln Gly Ala
 85                          90                      95

AAT GCA GAT GTG GCT ACA GTA CGC GGT GAA ACG CCT CTT CAT                              336
Asn Ala Asp Val Ala Thr Val Arg Gly Glu Thr Pro Leu His
100                         105                     110

TTA GCT GCA CGA GCA AAC CAA ACG GAC ATT GTT CGT GTT TTG                              378
Leu Ala Ala Arg Ala Asn Gln Thr Asp Ile Val Arg Val Leu
115                         120                     125

GTG CGT AAT GGA GCA CAG GTG GAT GCT GCT GCT CGT GAA CTA                              420
Val Arg Asn Gly Ala Gln Val Asp Ala Ala Ala Arg Glu Leu
130                         135                     140

CAA ACT CCA CTG CAC ATT GCA TCA CGT CTT GGT AAT ACC GAC                              462
Gln Thr Pro Leu His Ile Ala Ser Arg Leu Gly Asn Thr Asp
145                         150

ATC GTC ATT TTG TTG CTG CAG GCT AAT GCA TCA CCA AAT GCT                              504
Ile Val Ile Leu Leu Leu Gln Ala Asn Ala Ser Pro Asn Ala
155                         160                     165

GCC ACA AGA GAT CTT TAT ACT CCT CTT CAT ATT GCT GCC AAG                              546
Ala Thr Arg Asp Leu Tyr Thr Pro Leu His Ile Ala Ala Lys
170                         175                     180

GAG GGG CAA GAG GAA GTG GCA GCA ATA TTG ATG GAT CAT GGA                              588
Glu Gly Gln Glu Glu Val Ala Ala Ile Leu Met Asp His Gly
185                         190                     195

ACC GAC AAG ACA CTG CTC ACG AAA AAG GGT TTT ACG CCG TTG                              630
Thr Asp Lys Thr Leu Leu Thr Lys Lys Gly Phe Thr Pro Leu
200                         205                     210

CAT TTA GCT GCT AAG TAT GGC AAT TTG CCG GTC GCG AAA TCA                              672
His Leu Ala Ala Lys Tyr Gly Asn Leu Pro Val Ala Lys Ser
215                         220

TTG CTA GAA CGA GGA ACA CCG GTT GAC ATT GAA GGC AAG AAT                              714
Leu Leu Glu Arg Gly Thr Pro Val Asp Ile Glu Gly Lys Asn
225                         230                     235

CAG GTA ACA CCT CTG CAT GTA GCG GCA CAT TAC AAT AAC GAC                              756
Gln Val Thr Pro Leu His Val Ala Ala His Tyr Asn Asn Asp
240                         245                     250

AAG GTA GCA TTG TTA CTT CTA GAA AAT GGT GCT TCT GCA CAT                              798
Lys Val Ala Leu Leu Leu Leu Glu Asn Gly Ala Ser Ala His
255                         260                     265

GCC GCT GCC AAG AAT GGG TAC ACT CCT TTA CAT ATT GCC GCG                              840
Ala Ala Ala Lys Asn Gly Tyr Thr Pro Leu His Ile Ala Ala
270                         275                     280

AAG AAG AAT CAG ATG GAT ATT GCT AGC ACT CTC CTT CAT TAT                              882
Lys Lys Asn Gln Met Asp Ile Ala Ser Thr Leu Leu His Tyr
285                         290

AAG GCA AAT GCG AAT GCT GAA AGC AAA GC                                               911
Lys Ala Asn Ala Asn Ala Glu Ser Lys
295                         300
```

(2) INFORMATION FOR SEQ ID NO:23:

(i) SEQUENCE CHARACTERISTICS:
        (A) LENGTH: 303 amino acids
        (B) TYPE: amino acid
        (D) TOPOLOGY: linear (ii) MOLECULE TYPE: protein (xi) SEQUENCE DESCRIPTION: SEQ ID NO:23:

Val Asp Asp Val Thr Val Asp Tyr Leu Thr Pro Leu His Val

```
 1               5                    10
Ala Ala His Cys Gly His Val Arg Val Ala Lys Leu Leu Leu
15                   20                  25

Asp Arg Asn Ala Asp Pro Asn Ala Arg Ala Leu Asn Gly Phe
   30                  35                  40

Thr Pro Leu His Ile Ala Cys Lys Lys Asn Arg Ile Lys Ile
         45                  50                  55

Val Glu Leu Leu Leu Lys Tyr His Ala Ala Ile Glu Ala Thr
             60                  65                  70

Thr Glu Ser Gly Leu Ser Pro Leu His Val Ala Ala Phe Met
                75                  80

Gly Ala Ile Asn Ile Val Ile Tyr Leu Leu Gln Gln Gly Ala
85                  90                  95

Asn Ala Asp Val Ala Thr Val Arg Gly Glu Thr Pro Leu His
    100                 105                 110

Leu Ala Ala Arg Ala Asn Gln Thr Asp Ile Val Arg Val Leu
            115                 120                 125

Val Arg Asn Gly Ala Gln Val Asp Ala Ala Ala Arg Glu Leu
                130                 135                 140

Gln Thr Pro Leu His Ile Ala Ser Arg Leu Gly Asn Thr Asp
                    145                 150

Ile Val Ile Leu Leu Leu Gln Ala Asn Ala Ser Pro Asn Ala
155                 160                 165

Ala Thr Arg Asp Leu Tyr Thr Pro Leu His Ile Ala Ala Lys
    170                 175                 180

Glu Gly Gln Glu Val Ala Ala Ile Leu Met Asp His Gly
            185                 190                 195

Thr Asp Lys Thr Leu Leu Thr Lys Lys Gly Phe Thr Pro Leu
                200                 205                 210

His Leu Ala Ala Lys Tyr Gly Asn Leu Pro Val Ala Lys Ser
                    215                 220

Leu Leu Glu Arg Gly Thr Pro Val Asp Ile Glu Gly Lys Asn
225                 230                 235

Gln Val Thr Pro Leu His Val Ala Ala His Tyr Asn Asn Asp
    240                 245                 250

Lys Val Ala Leu Leu Leu Leu Glu Asn Gly Ala Ser Ala His
            255                 260                 265

Ala Ala Ala Lys Asn Gly Tyr Thr Pro Leu His Ile Ala Ala
                270                 275                 280

Lys Lys Asn Gln Met Asp Ile Ala Ser Thr Leu Leu His Tyr
                    285                 290

Lys Ala Asn Ala Asn Ala Glu Ser Lys
295                 300
```

(2) INFORMATION FOR SEQ ID NO:24:

(i) SEQUENCE CHARACTERISTICS:
        (A) LENGTH: 911 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:24:

GCTTTGCTTT CAGCATTCGC ATTTGCCTTA TAATGAAGGA GAGTGCTAGC    50

-continued

```
AATATCCATC TGATTCTTCT TCGCGGCAAT ATGTAAAGGA GTGTACCCAT         100

TCTTGGCAGC GGCATGTGCA GAAGCACCAT TTTCTAGAAG TAACAATGCT         150

ACCTTGTCGT TATTGTAATG TGCCGCTACA TGCAGAGGTG TTACCTGATT         200

CTTGCCTTCA ATGTCAACCG GTGTTCCTCG TTCTAGCAAT GATTTCGCGA         250

CCGGCAAATT GCCATACTTA GCAGCTAAAT GCAACGGCGT AAAACCCTTT         300

TTCGTGAGCA GTGTCTTGTC GGTTCCATGA TCCATCAATA TTGCTGCCAC         350

TTCCTCTTGC CCCTCCTTGG CAGCAATATG AAGAGGAGTA TAAAGATCTC         400

TTGTGGCAGC ATTTGGTGAT GCATTAGCCT GCAGCAACAA AATGACGATG         450

TCGGTATTAC CAAGACGTGA TGCAATGTGC AGTGGAGTTT GTAGTTCACG         500

AGCAGCAGCA TCCACCTGTG CTCCATTACG CACCAAAACA CGAACAATGT         550

CCGTTTGGTT TGCTCGTGCA GCTAAATGAA GAGGCGTTTC ACCGCGTACT         600

GTAGCCACAT CTGCATTAGC ACCTTGTTGT AGTAAATAGA TGACAATGTT         650

TATAGCACCC ATAAAAGCAG CGACATGCAG CGGTGAGAGA CCGGATTCAG         700

TAGTTGCTTC GATTGCAGCG TGGTATTTCA GTAGCAGTTC GACAATTTTA         750

ATGCGATTTT TTTTGCAAGC GATATGCAGC GGTGTGAAGC CATTGAGAGC         800

TCGAGCATTC GGGTCAGCAT TACGATCCAG CAAAAGTTTA GCGACACGGA         850

CATGTCCGCA ATGAGCAGCC ACATGAAGAG GAGTGAGATA GTCAACAGTA         900

ACATCATCCA C                                                   911
```

(2) INFORMATION FOR SEQ ID NO:25:

(i) SEQUENCE CHARACTERISTICS:
        (A) LENGTH: 909 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:25:

```
GTGGATGATG TTACTGTTGA CTATCTCACT CCTCTTCATG TGGCTGCTCA          50

TTGCGGACAT GTCCGTGTCG CTAAACTTTT GCTGGATCGT AATGCTGACC         100

CGAATGCTCG AGCTCTCAAT GGCTTCACAC CGCTGCATAT CGCTTGCAAA         150

AAAAATCGCA TTAAAATTGT CGAACTGCTA CTGAAATACC ACGCTGCAAT         200

CGAAGCAACT ACTGAATCCG GTCTCTCACC GCTGCATGTC GCTGCTTTTA         250

TGGGTGCTAT AAACATTGTC ATCTATTTAC TACAACAAGG TGCTAATGCA         300

GATGTGGCTA CAGTACGCGG TGAAACGCCT CTTCATTTAG CTGCACGAGC         350

AAACCAAACG GACATTGTTC GTGTTTTGGT GCGTAATGGA GCACAGGTGG         400

ATGCTGCTGC TCGTGAACTA CAAACTCCAC TGCACATTGC ATCACGTCTT         450

GGTAATACCG ACATCGTCAT TTTGTTGCTG CAGGCTAATG CATCACCAAA         500

TGCTGCCACA AGAGATCTTT ATACTCCTCT TCATATTGCT GCCAAGGAGG         550

GGCAAGAGGA AGTGGCAGCA ATATTGATGG ATCATGGAAC CGACAAGACA         600

CTGCTCACGA AAAGGGTTT TACGCCGTTG CATTTAGCTG CTAAGTATGG          650

CAATTTGCCG GTCGCGAAAT CATTGCTAGA ACGAGGAACA CCGGTTGACA         700

TTGAAGGCAA GAATCAGGTA ACACCTCTGC ATGTAGCGGC ACATTACAAT         750
```

```
AACGACAAGG TAGCATTGTT ACTTCTAGAA AATGGTGCTT CTGCACATGC           800

CGCTGCCAAG AATGGGTACA CTCCTTTACA TATTGCCGCG AAGAAGAATC           850

AGATGGATAT TGCTAGCACT CTCCTTCATT ATAAGGCAAA TGCGAATGCT           900

GAAAGCAAA                                                       909
```

(2) INFORMATION FOR SEQ ID NO:26:

(i) SEQUENCE CHARACTERISTICS:
        (A) LENGTH: 909 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:26:

```
TTTGCTTTCA GCATTCGCAT TGCCTTATA ATGAAGGAGA GTGCTAGCAA            50

TATCCATCTG ATTCTTCTTC GCGGCAATAT GTAAAGGAGT GTACCCATTC          100

TTGGCAGCGG CATGTGCAGA AGCACCATTT TCTAGAAGTA ACAATGCTAC          150

CTTGTCGTTA TTGTAATGTG CCGCTACATG CAGAGGTGTT ACCTGATTCT          200

TGCCTTCAAT GTCAACCGGT GTTCCTCGTT CTAGCAATGA TTTCGCGACC          250

GGCAAATTGC CATACTTAGC AGCTAAATGC AACGGCGTAA AACCCTTTTT          300

CGTGAGCAGT GTCTTGTCGG TTCCATGATC CATCAATATT GCTGCCACTT          350

CCTCTTGCCC CTCCTTGGCA GCAATATGAA GAGGAGTATA AAGATCTCTT          400

GTGGCAGCAT TTGGTGATGC ATTAGCCTGC AGCAACAAAA TGACGATGTC          450

GGTATTACCA AGACGTGATG CAATGTGCAG TGGAGTTTGT AGTTCACGAG          500

CAGCAGCATC CACCTGTGCT CCATTACGCA CCAAAACACG AACAATGTCC          550

GTTTGGTTTG CTCGTGCAGC TAAATGAAGA GGCGTTTCAC CGCGTACTGT          600

AGCCACATCT GCATTAGCAC CTTGTTGTAG TAAATAGATG ACAATGTTTA          650

TAGCACCCAT AAAAGCAGCG ACATGCAGCG GTGAGAGACC GGATTCAGTA          700

GTTGCTTCGA TTGCAGCGTG GTATTTCAGT AGCAGTTCGA CAATTTTAAT          750

GCGATTTTTT TTGCAAGCGA TATGCAGCGG TGTGAAGCCA TTGAGAGCTC          800

GAGCATTCGG GTCAGCATTA CGATCCAGCA AAAGTTTAGC GACACGGACA          850

TGTCCGCAAT GAGCAGCCAC ATGAAGAGGA GTGAGATAGT CAACAGTAAC          900

ATCATCCAC                                                      909
```

(2) INFORMATION FOR SEQ ID NO:27:

(i) SEQUENCE CHARACTERISTICS:
        (A) LENGTH: 1096 nucleotides
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 51..1094

(xi) SEQUENCE DESCRIPTION: SEQ ID NO:27:

```
GGTTTAATTA CCCAAGTTTG AGGCGGCTGA CTGATATAAC TCAACTATTG           50
```

```
ATG AGT AAT CCT ATA GTC GAG GGA AGT GGC TGG CCC GCA GAA        92
Met Ser Asn Pro Ile Val Glu Gly Ser Gly Trp Pro Ala Glu
1               5                   10

CCA AAA GAT TCA CAA CAT CAA CAA CAA ATT CCT GAT GAT AAC       134
Pro Lys Asp Ser Gln His Gln Gln Gln Ile Pro Asp Asp Asn
15                  20                  25

AGT CAA CAT TCC AAC AAA GGT GAG AGC AGT GCA AGT TTT TTA       176
Ser Gln His Ser Asn Lys Gly Glu Ser Ser Ala Ser Phe Leu
30                  35                  40

CGA GCA GCA AGA GCT GGA AAT TTG GAT CGT GTA CTT GAA CTA       218
Arg Ala Ala Arg Ala Gly Asn Leu Asp Arg Val Leu Glu Leu
45                  50                  55

CTT CGT TCG GGC ACC GAT ATC AAC ACA TGC AAT GCG AAT GGC       260
Leu Arg Ser Gly Thr Asp Ile Asn Thr Cys Asn Ala Asn Gly
60                  65                  70

CTT AAT GCA TTG CAT CTG GCC TCC AAA GAA GGT CAT CAT GAA       302
Leu Asn Ala Leu His Leu Ala Ser Lys Glu Gly His His Glu
75                  80

GTG GTC CGC GAA CTT CTG AAA AGA AAA GCA GAT GTT GAT GCT       344
Val Val Arg Glu Leu Leu Lys Arg Lys Ala Asp Val Asp Ala
85                  90                  95

GCC ACT AGA AAG GGT AAC ACA GCG TTA CAT ATA GCA TCA TTG       386
Ala Thr Arg Lys Gly Asn Thr Ala Leu His Ile Ala Ser Leu
100                 105                 110

GCA GGA CAA GAA CTA ATC GTC ACA GTA CTT GTT GAA AAT GGT       428
Ala Gly Gln Glu Leu Ile Val Thr Val Leu Val Glu Asn Gly
115                 120                 125

GCT AAT GTT AAC GTA CAA TCA CTA AAC GGT TTT ACA CCA CTT       470
Ala Asn Val Asn Val Gln Ser Leu Asn Gly Phe Thr Pro Leu
130                 135                 140

TAC ATG GCT GCA CAA GAA AAT CAC GAA TCT GTT GTA CGC TAT       512
Tyr Met Ala Ala Gln Glu Asn His Glu Ser Val Val Arg Tyr
145                 150

CTT CTT GCC CAC AAT GCC AAT CAA GCT TTA AGT ACA GAA GAC       554
Leu Leu Ala His Asn Ala Asn Gln Ala Leu Ser Thr Glu Asp
155                 160                 165

GGT TTT ACG CCA CTG GCA GTT GCC TTG CAA CAA GGT CAC GAT       596
Gly Phe Thr Pro Leu Ala Val Ala Leu Gln Gln Gly His Asp
170                 175                 180

CGT GTG GTC GCT GTT TTG CTT GAA AAT GAC ACG CGC GGG AAA       638
Arg Val Val Ala Val Leu Leu Glu Asn Asp Thr Arg Gly Lys
185                 190                 195

GTG CGC TTG CCA GCA CTG CAT ATT GCT GCT AAA AAA GAT GAT       680
Val Arg Leu Pro Ala Leu His Ile Ala Ala Lys Lys Asp Asp
200                 205                 210

ACG AAA GCA GCT ACG CTA TTA CTT CAA AAT GAG CAT AAC TCG       722
Thr Lys Ala Ala Thr Leu Leu Leu Gln Asn Glu His Asn Ser
215                 220

GAT GTG ACT TCG AAA AGC GGC TTT ACT CCG CTT CAT ATC GCC       764
Asp Val Thr Ser Lys Ser Gly Phe Thr Pro Leu His Ile Ala
225                 230                 235

GCT CAC TAT GGA AAT GAG AAC GTA GCA CAA CTG CTA CTC GAA       806
Ala His Tyr Gly Asn Glu Asn Val Ala Gln Leu Leu Leu Glu
240                 245                 250

AAG GGA GCC AAT GTG AAT TAC CAA GCG AGA CAT AAC ATA AGT       848
Lys Gly Ala Asn Val Asn Tyr Gln Ala Arg His Asn Ile Ser
255                 260                 265

CCG TTA CAC GTT GCA ACA AAA TGG GGT CGT ACA AAC ATG GTT       890
Pro Leu His Val Ala Thr Lys Trp Gly Arg Thr Asn Met Val
270                 275                 280
```

```
TCG TTA TTG TTG GCT CAT GGG GCC GTA ATT GAC TGT CGC ACA           932
Ser Leu Leu Leu Ala His Gly Ala Val Ile Asp Cys Arg Thr
285                 290

CGT GAT TTA CTA ACA CCA TTA CAC TGT GCT TCT CGT TCA GGT           974
Arg Asp Leu Leu Thr Pro Leu His Cys Ala Ser Arg Ser Gly
295                 300             305

CAT GAT CAA GTT GTT GAT TTG TTG CTT GAA AAA GGA GCT CCA          1016
His Asp Gln Val Val Asp Leu Leu Leu Glu Lys Gly Ala Pro
310                 315             320

ATC AGT GCT AAG ACA AAA AAT GGT TTG GCT CCC TTA CAT ATG          1058
Ile Ser Ala Lys Thr Lys Asn Gly Leu Ala Pro Leu His Met
325                 330             335

GCA GCA CAG GTG GAT GAT GTT ACT GTT GAC TAT CTC AC               1096
Ala Ala Gln Val Asp Asp Val Thr Val Asp Tyr Leu
340                 345
```

(2) INFORMATION FOR SEQ ID NO:28:

(i) SEQUENCE CHARACTERISTICS:
        (A) LENGTH: 348 amino acids
        (B) TYPE: amino acid
        (D) TOPOLOGY: linear (ii) MOLECULE TYPE: protein (xi) SEQUENCE DESCRIPTION: SEQ ID NO:28:

```
Met Ser Asn Pro Ile Val Glu Gly Ser Gly Trp Pro Ala Glu
1               5                   10

Pro Lys Asp Ser Gln His Gln Gln Ile Pro Asp Asn
15              20              25

Ser Gln His Ser Asn Lys Gly Glu Ser Ser Ala Ser Phe Leu
            30              35              40

Arg Ala Ala Arg Ala Gly Asn Leu Asp Arg Val Leu Glu Leu
        45              50              55

Leu Arg Ser Gly Thr Asp Ile Asn Thr Cys Asn Ala Asn Gly
            60              65              70

Leu Asn Ala Leu His Leu Ala Ser Lys Glu Gly His His Glu
            75              80

Val Val Arg Glu Leu Leu Lys Arg Lys Ala Asp Val Asp Ala
85              90              95

Ala Thr Arg Lys Gly Asn Thr Ala Leu His Ile Ala Ser Leu
            100             105             110

Ala Gly Gln Glu Leu Ile Val Thr Val Leu Val Glu Asn Gly
            115             120             125

Ala Asn Val Asn Val Gln Ser Leu Asn Gly Phe Thr Pro Leu
            130             135             140

Tyr Met Ala Ala Gln Glu Asn His Glu Ser Val Val Arg Tyr
                145             150

Leu Leu Ala His Asn Ala Asn Gln Ala Leu Ser Thr Glu Asp
155             160             165

Gly Phe Thr Pro Leu Ala Val Ala Leu Gln Gln Gly His Asp
    170             175             180

Arg Val Val Ala Val Leu Leu Glu Asn Asp Thr Arg Gly Lys
        185             190             195

Val Arg Leu Pro Ala Leu His Ile Ala Ala Lys Lys Asp Asp
            200             205             210

Thr Lys Ala Ala Thr Leu Leu Leu Gln Asn Glu His Asn Ser
```

```
                    215                     220
Asp Val Thr Ser Lys Ser Gly Phe Thr Pro Leu His Ile Ala
225                 230                 235

Ala His Tyr Gly Asn Glu Asn Val Ala Gln Leu Leu Leu Glu
    240                 245                 250

Lys Gly Ala Asn Val Asn Tyr Gln Ala Arg His Asn Ile Ser
        255                 260                 265

Pro Leu His Val Ala Thr Lys Trp Gly Arg Thr Asn Met Val
            270                 275                 280

Ser Leu Leu Leu Ala His Gly Ala Val Ile Asp Cys Arg Thr
                285                 290

Arg Asp Leu Leu Thr Pro Leu His Cys Ala Ser Arg Ser Gly
295                 300                 305

His Asp Gln Val Val Asp Leu Leu Leu Glu Lys Gly Ala Pro
    310                 315                 320

Ile Ser Ala Lys Thr Lys Asn Gly Leu Ala Pro Leu His Met
        325                 330                 335

Ala Ala Gln Val Asp Asp Val Thr Val Asp Tyr Leu
            340                 345
```

(2) INFORMATION FOR SEQ ID NO:29:

(i) SEQUENCE CHARACTERISTICS:
        (A) LENGTH: 1096 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:29:

```
GTGAGATAGT CAACAGTAAC ATCATCCACC TGTGCTGCCA TATGTAAGGG            50

AGCCAAACCA TTTTTTGTCT TAGCACTGAT TGGAGCTCCT TTTTCAAGCA           100

ACAAATCAAC AACTTGATCA TGACCTGAAC GAGAAGCACA GTGTAATGGT           150

GTTAGTAAAT CACGTGTGCG ACAGTCAATT ACGGCCCCAT GAGCCAACAA           200

TAACGAAACC ATGTTTGTAC GACCCCATTT TGTTGCAACG TGTAACGGAC           250

TTATGTTATG TCTCGCTTGG TAATTCACAT TGGCTCCCTT TTCGAGTAGC           300

AGTTGTGCTA CGTTCTCATT TCCATAGTGA GCGGCGATAT GAAGCGGAGT           350

AAAGCCGCTT TTCGAAGTCA CATCCGAGTT ATGCTCATTT TGAAGTAATA           400

GCGTAGCTGC TTTCGTATCA TCTTTTTTAG CAGCAATATG CAGTGCTGGC           450

AAGCGCACTT TCCCGCGCGT GTCATTTTCA AGCAAAACAG CGACCACACG           500

ATCGTGACCT TGTTGCAAGG CAACTGCCAG TGGCGTAAAA CCGTCTTCTG           550

TACTTAAAGC TTGATTGGCA TTGTGGGCAA GAAGATAGCG TACAACAGAT           600

TCGTGATTTT CTTGTGCAGC CATGTAAAGT GGTGTAAAAC CGTTTAGTGA           650

TTGTACGTTA ACATTAGCAC CATTTTCAAC AAGTACTGTG ACGATTAGTT           700

CTTGTCCTGC CAATGATGCT ATATGTAACG CTGTGTTACC CTTTCTAGTG           750

GCAGCATCAA CATCTGCTTT TCTTTTCAGA AGTTCGCGGA CCACTTCATG           800

ATGACCTTCT TTGGAGGCCA GATGCAATGC ATTAAGGCCA TTCGCATTGC           850

ATGTGTTGAT ATCGGTGCCC GAACGAAGTA GTTCAAGTAC ACGATCCAAA           900

TTTCCAGCTC TTGCTGCTCG TAAAAAACTT GCACTGCTCT CACCTTTGTT           950
```

```
GGAATGTTGA CTGTTATCAT CAGGAATTTG TTGTTGATGT TGTGAATCTT              1000

TTGGTTCTGC GGGCCAGCCA CTTCCCTCGA CTATAGGATT ACTCATCAAT              1050

AGTTGAGTTA TATCAGTCAG CCGCCTCAAA CTTGGGTAAT TAAACC                  1096

(2) INFORMATION FOR SEQ ID NO:30:

(i) SEQUENCE CHARACTERISTICS:
        (A) LENGTH: 1044 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:30:

ATGAGTAATC CTATAGTCGA GGGAAGTGGC TGGCCCGCAG AACCAAAAGA                50

TTCACAACAT CAACAACAAA TTCCTGATGA TAACAGTCAA CATTCCAACA               100

AAGGTGAGAG CAGTGCAAGT TTTTTACGAG CAGCAAGAGC TGGAAATTTG               150

GATCGTGTAC TTGAACTACT TCGTTCGGGC ACCGATATCA ACACATGCAA               200

TGCGAATGGC CTTAATGCAT TGCATCTGGC CTCCAAAGAA GGTCATCATG               250

AAGTGGTCCG CGAACTTCTG AAAAGAAAAG CAGATGTTGA TGCTGCCACT               300

AGAAAGGGTA ACACAGCGTT ACATATAGCA TCATTGGCAG ACAAGAACT                350

AATCGTCACA GTACTTGTTG AAAATGGTGC TAATGTTAAC GTACAATCAC               400

TAAACGGTTT TACACCACTT TACATGGCTG CACAAGAAAA TCACGAATCT               450

GTTGTACGCT ATCTTCTTGC CCACAATGCC AATCAAGCTT TAAGTACAGA               500

AGACGGTTTT ACGCCACTGG CAGTTGCCTT GCAACAAGGT CACGATCGTG               550

TGGTCGCTGT TTTGCTTGAA AATGACACGC GCGGGAAAGT GCGCTTGCCA               600

GCACTGCATA TTGCTGCTAA AAAAGATGAT ACGAAAGCAG CTACGCTATT               650

ACTTCAAAAT GAGCATAACT CGGATGTGAC TTCGAAAAGC GGCTTTACTC               700

CGCTTCATAT CGCCGCTCAC TATGGAAATG AGAACGTAGC ACAACTGCTA               750

CTCGAAAAGG GAGCCAATGT GAATTACCAA GCGAGACATA ACATAAGTCC               800

GTTACACGTT GCAACAAAAT GGGGTCGTAC AAACATGGTT TCGTTATTGT               850

TGGCTCATGG GGCCGTAATT GACTGTCGCA CACGTGATTT ACTAACACCA               900

TTACACTGTG CTTCTCGTTC AGGTCATGAT CAAGTTGTTG ATTTGTTGCT               950

TGAAAAAGGA GCTCCAATCA GTGCTAAGAC AAAAAATGGT TTGGCTCCCT              1000

TACATATGGC AGCACAGGTG GATGATGTTA CTGTTGACTA TCTC                    1044

(2) INFORMATION FOR SEQ ID NO:31:

(i) SEQUENCE CHARACTERISTICS:
        (A) LENGTH: 1044 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:31:

GAGATAGTCA ACAGTAACAT CATCCACCTG TGCTGCCATA TGTAAGGGAG                50

CCAAACCATT TTTTGTCTTA GCACTGATTG GAGCTCCTTT TTCAAGCAAC               100
```

-continued

```
AAATCAACAA CTTGATCATG ACCTGAACGA GAAGCACAGT GTAATGGTGT            150

TAGTAAATCA CGTGTGCGAC AGTCAATTAC GGCCCCATGA GCCAACAATA            200

ACGAAACCAT GTTTGTACGA CCCCATTTTG TTGCAACGTG TAACGGACTT            250

ATGTTATGTC TCGCTTGGTA ATTCACATTG GCTCCCTTTT CGAGTAGCAG            300

TTGTGCTACG TTCTCATTTC CATAGTGAGC GGCGATATGA AGCGGAGTAA            350

AGCCGCTTTT CGAAGTCACA TCCGAGTTAT GCTCATTTTG AAGTAATAGC            400

GTAGCTGCTT TCGTATCATC TTTTTTAGCA GCAATATGCA GTGCTGGCAA            450

GCGCACTTTC CCGCGCGTGT CATTTTCAAG CAAAACAGCG ACCACACGAT            500

CGTGACCTTG TTGCAAGGCA ACTGCCAGTG GCGTAAAACC GTCTTCTGTA            550

CTTAAAGCTT GATTGGCATT GTGGGCAAGA AGATAGCGTA CAACAGATTC            600

GTGATTTTCT TGTGCAGCCA TGTAAAGTGG TGTAAAACCG TTTAGTGATT            650

GTACGTTAAC ATTAGCACCA TTTTCAACAA GTACTGTGAC GATTAGTTCT            700

TGTCCTGCCA ATGATGCTAT ATGTAACGCT GTGTTACCCT TTCTAGTGGC            750

AGCATCAACA TCTGCTTTTC TTTTCAGAAG TTCGCGGACC ACTTCATGAT            800

GACCTTCTTT GGAGGCCAGA TGCAATGCAT TAAGGCCATT CGCATTGCAT            850

GTGTTGATAT CGGTGCCCGA ACGAAGTAGT TCAAGTACAC GATCCAAATT            900

TCCAGCTCTT GCTGCTCGTA AAAAACTTGC ACTGCTCTCA CCTTTGTTGG            950

AATGTTGACT GTTATCATCA GGAATTTGTT GTTGATGTTG TGAATCTTTT           1000

GGTTCTGCGG GCCAGCCACT TCCCTCGACT ATAGGATTAC TCAT                 1044
```

(2) INFORMATION FOR SEQ ID NO:32:

(i) SEQUENCE CHARACTERISTICS:
        (A) LENGTH: 5503 nucleotides
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 51..5285

(xi) SEQUENCE DESCRIPTION: SEQ ID NO:32:

```
GGTTTAATTA CCCAAGTTTG AGGCGGCTGA CTGATATAAC TCAACTATTG             50

ATG AGT AAT CCT ATA GTC GAG GGA AGT GGC TGG CCC GCA GAA            92
Met Ser Asn Pro Ile Val Glu Gly Ser Gly Trp Pro Ala Glu
1               5                   10

CCA AAA GAT TCA CAA CAT CAA CAA CAA ATT CCT GAT GAT AAC           134
Pro Lys Asp Ser Gln His Gln Gln Gln Ile Pro Asp Asp Asn
 15                  20                  25

AGT CAA CAT TCC AAC AAA GGT GAG AGC AGT GCA AGT TTT TTA           176
Ser Gln His Ser Asn Lys Gly Glu Ser Ser Ala Ser Phe Leu
30                  35                  40

CGA GCA GCA AGA GCT GGA AAT TTG GAT CGT GTA CTT GAA CTA           218
Arg Ala Ala Arg Ala Gly Asn Leu Asp Arg Val Leu Glu Leu
45                  50                  55

CTT CGT TCG GGC ACC GAT ATC AAC ACA TGC AAT GCG AAT GGC           260
Leu Arg Ser Gly Thr Asp Ile Asn Thr Cys Asn Ala Asn Gly
60                  65                  70

CTT AAT GCA TTG CAT CTG GCC TCC AAA GAA GGT CAT CAT GAA           302
Leu Asn Ala Leu His Leu Ala Ser Lys Glu Gly His His Glu
```

```
                    75                      80
GTG GTC CGC GAA CTT CTG AAA AGA AAA GCA GAT GTT GAT GCT              344
Val Val Arg Glu Leu Leu Lys Arg Lys Ala Asp Val Asp Ala
 85                      90                      95

GCC ACT AGA AAG GGT AAC ACA GCG TTA CAT ATA GCA TCA TTG              386
Ala Thr Arg Lys Gly Asn Thr Ala Leu His Ile Ala Ser Leu
100                     105                     110

GCA GGA CAA GAA CTA ATC GTC ACA GTA CTT GTT GAA AAT GGT              428
Ala Gly Gln Glu Leu Ile Val Thr Val Leu Val Glu Asn Gly
115                     120                     125

GCT AAT GTT AAC GTA CAA TCA CTA AAC GGT TTT ACA CCA CTT              470
Ala Asn Val Asn Val Gln Ser Leu Asn Gly Phe Thr Pro Leu
130                     135                     140

TAC ATG GCT GCA CAA GAA AAT CAC GAA TCT GTT GTA CGC TAT              512
Tyr Met Ala Ala Gln Glu Asn His Glu Ser Val Val Arg Tyr
145                     150

CTT CTT GCC CAC AAT GCC AAT CAA GCT TTA AGT ACA GAA GAC              554
Leu Leu Ala His Asn Ala Asn Gln Ala Leu Ser Thr Glu Asp
155                     160                     165

GGT TTT ACG CCA CTG GCA GTT GCC TTG CAA CAA GGT CAC GAT              596
Gly Phe Thr Pro Leu Ala Val Ala Leu Gln Gln Gly His Asp
170                     175                     180

CGT GTG GTC GCT GTT TTG CTT GAA AAT GAC ACG CGC GGG AAA              638
Arg Val Val Ala Val Leu Leu Glu Asn Asp Thr Arg Gly Lys
185                     190                     195

GTG CGC TTG CCA GCA CTG CAT ATT GCT GCT AAA AAA GAT GAT              680
Val Arg Leu Pro Ala Leu His Ile Ala Ala Lys Lys Asp Asp
200                     205                     210

ACG AAA GCA GCT ACG CTA TTA CTT CAA AAT GAG CAT AAC TCG              722
Thr Lys Ala Ala Thr Leu Leu Leu Gln Asn Glu His Asn Ser
215                     220

GAT GTG ACT TCG AAA AGC GGC TTT ACT CCG CTT CAT ATC GCC              764
Asp Val Thr Ser Lys Ser Gly Phe Thr Pro Leu His Ile Ala
225                     230                     235

GCT CAC TAT GGA AAT GAG AAC GTA GCA CAA CTG CTA CTC GAA              806
Ala His Tyr Gly Asn Glu Asn Val Ala Gln Leu Leu Leu Glu
240                     245                     250

AAG GGA GCC AAT GTG AAT TAC CAA GCG AGA CAT AAC ATA AGT              848
Lys Gly Ala Asn Val Asn Tyr Gln Ala Arg His Asn Ile Ser
255                     260                     265

CCG TTA CAC GTT GCA ACA AAA TGG GGT CGT ACA AAC ATG GTT              890
Pro Leu His Val Ala Thr Lys Trp Gly Arg Thr Asn Met Val
270                     275                     280

TCG TTA TTG TTG GCT CAT GGG GCC GTA ATT GAC TGT CGC ACA              932
Ser Leu Leu Leu Ala His Gly Ala Val Ile Asp Cys Arg Thr
285                     290

CGT GAT TTA CTA ACA CCA TTA CAC TGT GCT TCT CGT TCA GGT              974
Arg Asp Leu Leu Thr Pro Leu His Cys Ala Ser Arg Ser Gly
295                     300                     305

CAT GAT CAA GTT GTT GAT TTG TTG CTT GAA AAA GGA GCT CCA             1016
His Asp Gln Val Val Asp Leu Leu Leu Glu Lys Gly Ala Pro
310                     315                     320

ATC AGT GCT AAG ACA AAA AAT GGT TTG GCT CCC TTA CAT ATG             1058
Ile Ser Ala Lys Thr Lys Asn Gly Leu Ala Pro Leu His Met
325                     330                     335

GCA GCA CAG GTG GAT GAT GTT ACT GTT GAC TAT CTC ACT CCT             1100
Ala Ala Gln Val Asp Asp Val Thr Val Asp Tyr Leu Thr Pro
340                     345                     350

CTT CAT GTG GCT GCT CAT TGC GGA CAT GTC CGT GTC GCT AAA             1142
Leu His Val Ala Ala His Cys Gly His Val Arg Val Ala Lys
```

```
Leu His Val Ala Ala His Cys Gly His Val Arg Val Ala Lys
355                 360

CTT TTG CTG GAT CGT AAT GCT GAC CCG AAT GCT CGA GCT CTC        1184
Leu Leu Leu Asp Arg Asn Ala Asp Pro Asn Ala Arg Ala Leu
365                 370                 375

AAT GGC TTC ACA CCG CTG CAT ATC GCT TGC AAA AAA AAT CGC        1226
Asn Gly Phe Thr Pro Leu His Ile Ala Cys Lys Lys Asn Arg
380                 385                 390

ATT AAA ATT GTC GAA CTG CTA CTG AAA TAC CAC GCT GCA ATC        1268
Ile Lys Ile Val Glu Leu Leu Leu Lys Tyr His Ala Ala Ile
395                 400                 405

GAA GCA ACT ACT GAA TCC GGT CTC TCA CCG CTG CAT GTC GCT        1310
Glu Ala Thr Thr Glu Ser Gly Leu Ser Pro Leu His Val Ala
410                 415                 420

GCT TTT ATG GGT GCT ATA AAC ATT GTC ATC TAT TTA CTA CAA        1352
Ala Phe Met Gly Ala Ile Asn Ile Val Ile Tyr Leu Leu Gln
425                 430

CAA GGT GCT AAT GCA GAT GTG GCT ACA GTA CGC GGT GAA ACG        1394
Gln Gly Ala Asn Ala Asp Val Ala Thr Val Arg Gly Glu Thr
435                 440                 445

CCT CTT CAT TTA GCT GCA CGA GCA AAC CAA ACG GAC ATT GTT        1436
Pro Leu His Leu Ala Ala Arg Ala Asn Gln Thr Asp Ile Val
450                 455                 460

CGT GTT TTG GTG CGT AAT GGA GCA CAG GTG GAT GCT GCT GCT        1478
Arg Val Leu Val Arg Asn Gly Ala Gln Val Asp Ala Ala Ala
465                 470                 475

CGT GAA CTA CAA ACT CCA CTG CAC ATT GCA TCA CGT CTT GGT        1520
Arg Glu Leu Gln Thr Pro Leu His Ile Ala Ser Arg Leu Gly
480                 485                 490

AAT ACC GAC ATC GTC ATT TTG TTG CTG CAG GCT AAT GCA TCA        1562
Asn Thr Asp Ile Val Ile Leu Leu Leu Gln Ala Asn Ala Ser
495                 500

CCA AAT GCT GCC ACA AGA GAT CTT TAT ACT CCT CTT CAT ATT        1604
Pro Asn Ala Ala Thr Arg Asp Leu Tyr Thr Pro Leu His Ile
505                 510                 515

GCT GCC AAG GAG GGG CAA GAG GAA GTG GCA GCA ATA TTG ATG        1646
Ala Ala Lys Glu Gly Gln Glu Glu Val Ala Ala Ile Leu Met
520                 525                 530

GAT CAT GGA ACC GAC AAG ACA CTG CTC ACG AAA AAG GGT TTT        1688
Asp His Gly Thr Asp Lys Thr Leu Leu Thr Lys Lys Gly Phe
535                 540                 545

ACG CCG TTG CAT TTA GCT GCT AAG TAT GGC AAT TTG CCG GTC        1730
Thr Pro Leu His Leu Ala Ala Lys Tyr Gly Asn Leu Pro Val
550                 555                 560

GCG AAA TCA TTG CTA GAA CGA GGA ACA CCG GTT GAC ATT GAA        1772
Ala Lys Ser Leu Leu Glu Arg Gly Thr Pro Val Asp Ile Glu
565                 570

GGC AAG AAT CAG GTA ACA CCT CTG CAT GTA GCG GCA CAT TAC        1814
Gly Lys Asn Gln Val Thr Pro Leu His Val Ala Ala His Tyr
575                 580                 585

AAT AAC GAC AAG GTA GCA TTG TTA CTT CTA GAA AAT GGT GCT        1856
Asn Asn Asp Lys Val Ala Leu Leu Leu Leu Glu Asn Gly Ala
590                 595                 600

TCT GCA CAT GCC GCT GCC AAG AAT GGG TAC ACT CCT TTA CAT        1898
Ser Ala His Ala Ala Ala Lys Asn Gly Tyr Thr Pro Leu His
605                 610                 615

ATT GCC GCG AAG AAG AAT CAG ATG GAT ATT GCT AGC ACT CTC        1940
Ile Ala Ala Lys Lys Asn Gln Met Asp Ile Ala Ser Thr Leu
620                 625                 630
```

```
CTT CAT TAT AAG GCA AAT GCG AAT GCT GAA AGC AAA GCT GGC      1982
Leu His Tyr Lys Ala Asn Ala Asn Ala Glu Ser Lys Ala Gly
635                 640

TTT ACA CCA CTT CAT CTT GCC GCC CAG GAG GGC CAT CGC GAA      2024
Phe Thr Pro Leu His Leu Ala Ala Gln Glu Gly His Arg Glu
645                 650                 655

ATG GCT GCG TTA TTA ATT GAA AAT GGA GCA AAA GTT GGA GCT      2066
Met Ala Ala Leu Leu Ile Glu Asn Gly Ala Lys Val Gly Ala
660                 665                 670

CAG GCA AGG AAT GGC TTG ACA CCA ATG CAT TTA TGT GCA CAG      2108
Gln Ala Arg Asn Gly Leu Thr Pro Met His Leu Cys Ala Gln
675                 680                 685

GAG GAT CGT GTG AGC GTA GCA GAA GAA CTA GTG AAA GAA AAC      2150
Glu Asp Arg Val Ser Val Ala Glu Glu Leu Val Lys Glu Asn
690                 695                 700

GCA GCC ATT GAT CCC AAA ACG AAA GCA GGA TAT ACG CCG TTA      2192
Ala Ala Ile Asp Pro Lys Thr Lys Ala Gly Tyr Thr Pro Leu
705                 710

CAT GTT GCT TGC CAT TTT GGA CAA ATA AAC ATG GTC CGT TTC      2234
His Val Ala Cys His Phe Gly Gln Ile Asn Met Val Arg Phe
715                 720                 725

TTG ATT GAG CAT GGC GCA CGA GTT TCA GTT ATT ACT CGT GCT      2276
Leu Ile Glu His Gly Ala Arg Val Ser Val Ile Thr Arg Ala
730                 735                 740

TCC TAT ACT CCT CTG CAT CAA GCT GCT CAG CAA GGG CAT AAC      2318
Ser Tyr Thr Pro Leu His Gln Ala Ala Gln Gln Gly His Asn
745                 750                 755

AGT GTT GTA CGT TAC TTG TTG GAA CAT GGT GCA AGT CCA AAT      2360
Ser Val Val Arg Tyr Leu Leu Glu His Gly Ala Ser Pro Asn
760                 765                 770

GTT CAT ACA TCG ACA GGA CAA ACT CCA TTA TCG ATT GCT GAA      2402
Val His Thr Ser Thr Gly Gln Thr Pro Leu Ser Ile Ala Glu
775                 780

CGT CTA GGG TAT GTA TCC GTG GTT GAA GCG CTT AAA ACA ATT      2444
Arg Leu Gly Tyr Val Ser Val Val Glu Ala Leu Lys Thr Ile
785                 790                 795

ACC GAG ACT ACT GTG ATA ACG GAG ACC ACA ACC GTT ACT GAA      2486
Thr Glu Thr Thr Val Ile Thr Glu Thr Thr Thr Val Thr Glu
800                 805                 810

GAA AGA TAT AAA CCT CAG AAT CCC GAA GCA ATG AAT GAA ACC      2528
Glu Arg Tyr Lys Pro Gln Asn Pro Glu Ala Met Asn Glu Thr
815                 820                 825

ATG TTT TCC GAT TCC GAA GAT GAA GGT GAA GAT AAT CAG ATC      2570
Met Phe Ser Asp Ser Glu Asp Glu Gly Glu Asp Asn Gln Ile
830                 835                 840

ACA GCC AAT GCT CAT GCT CAT GAT TTC TCA GAA AGC CTC ACA      2612
Thr Ala Asn Ala His Ala His Asp Phe Ser Glu Ser Leu Thr
845                 850

AAA GGT TTG CAC GAT TCA ACT GGT GTA CAT TTG ATT CAT GCC      2654
Lys Gly Leu His Asp Ser Thr Gly Val His Leu Ile His Ala
855                 860                 865

ACA GAA CCG ACA TTG TCA CGA AGT CCG GAA GTG GAA GGT ACG      2696
Thr Glu Pro Thr Leu Ser Arg Ser Pro Glu Val Glu Gly Thr
870                 875                 880

GAT GGC GAT TTG GAT GCC TTA ATT CGT AAA GCA CAA CAT GAA      2738
Asp Gly Asp Leu Asp Ala Leu Ile Arg Lys Ala Gln His Glu
885                 890                 895

CCA ATT ACT ACA GCG ATG GCC GAT CCT TCC TTA GAT GCA TCG      2780
Pro Ile Thr Thr Ala Met Ala Asp Pro Ser Leu Asp Ala Ser
900                 905                 910
```

```
                                                         -continued

CTT CCT GAC AAT GTT ACG ATA ATG AGA ACT ACC ATG CAA CCT                    2822
Leu Pro Asp Asn Val Thr Ile Met Arg Thr Thr Met Gln Pro
915                 920

AGT TTT TTA ATT TCG TTT ATG GTG GAT GCA CGT GGA GGA GCA                    2864
Ser Phe Leu Ile Ser Phe Met Val Asp Ala Arg Gly Gly Ala
925                 930                 935

ATG CGT GGT TGT AGG CAT TCC GGT GTC AGA ATC ATT ATA CCA                    2906
Met Arg Gly Cys Arg His Ser Gly Val Arg Ile Ile Ile Pro
940                 945                 950

CCG AGG AAA GCG CCG CAA CCT ACA CGG GTC ACA TGC AGA TAC                    2948
Pro Arg Lys Ala Pro Gln Pro Thr Arg Val Thr Cys Arg Tyr
955                 960                 965

CTT GGA AAG GAC AAG TTA GCG CAT CCA CCA CCA TTA AGT GAA                    2990
Leu Gly Lys Asp Lys Leu Ala His Pro Pro Pro Leu Ser Glu
970                 975                 980

GGT GAA GCG CTC GCN TCA CGT ATA CTT GAA ATG GCA CCA CAT                    3032
Gly Glu Ala Leu Ala Ser Arg Ile Leu Glu Met Ala Pro His
985                 990

GGA GCA AAA TTC TTA GGC CCT GTT ATA TTG GAA GTA CCA CAT                    3074
Gly Ala Lys Phe Leu Gly Pro Val Ile Leu Glu Val Pro His
995                 1000                1005

TTT GCA TCA CTT CGT GGA CGA GAG AGA GAG ATT GTC ATT TTG                    3116
Phe Ala Ser Leu Arg Gly Arg Glu Arg Glu Ile Val Ile Leu
1010                1015                1020

CGT TCT GAT GAT GGG CAG CAT TGG AAA GAG CAT CAG CTT GAA                    3158
Arg Ser Asp Asp Gly Gln His Trp Lys Glu His Gln Leu Glu
1025                1030                1035

GCA ACA GAA GAT GCT GTA CAA GAG GTG CTC AAT GAA TCG TTT                    3200
Ala Thr Glu Asp Ala Val Gln Glu Val Leu Asn Glu Ser Phe
1040                1045                1050

GAT GCA GAA GAG TTG TCG CAA CTT GAT GAT TTG CAT ACA TCA                    3242
Asp Ala Glu Glu Leu Ser Gln Leu Asp Asp Leu His Thr Ser
1055                1060

CGG ATT ACG CGT ATC CTG ACC AAT GAT TTC CCA ATG TAT TTC                    3284
Arg Ile Thr Arg Ile Leu Thr Asn Asp Phe Pro Met Tyr Phe
1065                1070                1075

GCG GTC GTT ACT CGT GTG CGG CAA GAA GTG CAC TGT GTT GGT                    3326
Ala Val Val Thr Arg Val Arg Gln Glu Val His Cys Val Gly
1080                1085                1090

CCA GAA GGT GGT GTA ATA CTC TCT TCA GTT GTT CCT CAT GTG                    3368
Pro Glu Gly Gly Val Ile Leu Ser Ser Val Val Pro His Val
1095                1100                1105

CAG GCC ATA TTT CCG GAT GGT TCC TTG ACT AAG ACG ATC AAA                    3410
Gln Ala Ile Phe Pro Asp Gly Ser Leu Thr Lys Thr Ile Lys
1110                1115                1120

GTA TCT GTG CAA GCC CAG CCA GTT CCA CAA GAG ATA GTC ACT                    3452
Val Ser Val Gln Ala Gln Pro Val Pro Gln Glu Ile Val Thr
1125                1130

CGT TTA CAT GGG AAT AGA GTC GCT GTT TCT CCA ATT GTA ACT                    3494
Arg Leu His Gly Asn Arg Val Ala Val Ser Pro Ile Val Thr
1135                1140                1145

GTT GAA CCG CGT CGT CGC AAA TTC CAT AAG CCC ATA ACG CTG                    3536
Val Glu Pro Arg Arg Arg Lys Phe His Lys Pro Ile Thr Leu
1150                1155                1160

TGC ATA CCA TTG CCA CAA AGC TCA AAT AAA GGA ATG TTA ACA                    3578
Cys Ile Pro Leu Pro Gln Ser Ser Asn Lys Gly Met Leu Thr
1165                1170                1175

CAA TAT AGT GGC CAA CCA GGA CAG GAA CCA CCG ACG CTG CGT                    3620
Gln Tyr Ser Gly Gln Pro Gly Gln Glu Pro Pro Thr Leu Arg
```

-continued

| | |
|---|---|
| 1180 1185 1190 | |
| TTA CTC TGC AGT AAA ACT GGA GGT TCT TCT CCT GCA CAG TGG<br>Leu Leu Cys Ser Lys Thr Gly Gly Ser Ser Pro Ala Gln Trp<br>1195                   1200 | 3662 |
| GAA GAT ATT ACT GGA ACT ACC CAG TTA ACA TTT ACT GGT GAG<br>Glu Asp Ile Thr Gly Thr Thr Gln Leu Thr Phe Thr Gly Glu<br>1205                   1210                1215 | 3704 |
| GAC GTT TCA TTT ACA ACT ACG GTT TCT GCT CGA TTT TGG TTG<br>Asp Val Ser Phe Thr Thr Thr Val Ser Ala Arg Phe Trp Leu<br>1220                   1225                1230 | 3746 |
| ATG GAT TGC CAA ACT CCG CGA GAT GCG GCA CGA ATG GCA CAA<br>Met Asp Cys Gln Thr Pro Arg Asp Ala Ala Arg Met Ala Gln<br>1235                   1240                1245 | 3788 |
| GAA GTT TAC AAT GAA GCA ATT GCA GTT CCT TAT ATG GCT AAA<br>Glu Val Tyr Asn Glu Ala Ile Ala Val Pro Tyr Met Ala Lys<br>1250                   1255                1260 | 3830 |
| TTT CTT ATT TTT GCT CGA CGA ACT TTT CCT GCC GAA GGA CAG<br>Phe Leu Ile Phe Ala Arg Arg Thr Phe Pro Ala Glu Gly Gln<br>1265                   1270 | 3872 |
| TTG AGA TTG TTT TGT ATG ACT GAT GAT CGG GAA GAT AAA ACC<br>Leu Arg Leu Phe Cys Met Thr Asp Asp Arg Glu Asp Lys Thr<br>1275                   1280                1285 | 3914 |
| CTG GAA AAA CAA GAA CGT TTC ATT GAA ATT GCG AAA TCG AAA<br>Leu Glu Lys Gln Glu Arg Phe Ile Glu Ile Ala Lys Ser Lys<br>1290                   1295                1300 | 3956 |
| GAT GTA GAA GTC TTA AGT GGG CGA CAT CAG TTT TTG GAA TTT<br>Asp Val Glu Val Leu Ser Gly Arg His Gln Phe Leu Glu Phe<br>1305                   1310                1315 | 3998 |
| TCT GGA AAT CTT CTT CCA ATA ACC AAG AGT GGT GAC CAA CTT<br>Ser Gly Asn Leu Leu Pro Ile Thr Lys Ser Gly Asp Gln Leu<br>1320                   1325                1330 | 4040 |
| TCT CTT TAT TTT CTA CCA TTC CAA GAA AAT CGT CTT GCT TTC<br>Ser Leu Tyr Phe Leu Pro Phe Gln Glu Asn Arg Leu Ala Phe<br>1335                   1340 | 4082 |
| ATG GTA AAG ATA CGC ACT CAC ACG GAC AAC GAA ACT GCA GCT<br>Met Val Lys Ile Arg Thr His Thr Asp Asn Glu Thr Ala Ala<br>1345                   1350                1355 | 4124 |
| GAT GGC CGG ATA GTA TTT ATG AAA GAA CCA AAA TTG AGA GCC<br>Asp Gly Arg Ile Val Phe Met Lys Glu Pro Lys Leu Arg Ala<br>1360                   1365                1370 | 4166 |
| GAA AAT TTA CCT CCG CAG ACG CCA GTG TGT ACT CTT GCA ATC<br>Glu Asn Leu Pro Pro Gln Thr Pro Val Cys Thr Leu Ala Ile<br>1375                   1380                1385 | 4208 |
| ACT CTT CCG GAA TAC ACT GGG CCG GAG CCG ATG GTT TCC AAA<br>Thr Leu Pro Glu Tyr Thr Gly Pro Glu Pro Met Val Ser Lys<br>1390                   1395                1400 | 4250 |
| AAA CTC TTC TAT TCG GAA GCT TCT TTG ACT GAG AAA TAC GTT<br>Lys Leu Phe Tyr Ser Glu Ala Ser Leu Thr Glu Lys Tyr Val<br>1405                   1410 | 4292 |
| GGA GCT TTC CAT GAA ACT GCT GAA CCT GAT AAC TTG CCA CTA<br>Gly Ala Phe His Glu Thr Ala Glu Pro Asp Asn Leu Pro Leu<br>1415                   1420                1425 | 4334 |
| GCA CAT GTT GCA CTA TTA ATT GGC GCT GAT TGG CAT CGG TTA<br>Ala His Val Ala Leu Leu Ile Gly Ala Asp Trp His Arg Leu<br>1430                     1435                1440 | 4376 |
| GCT CGA GCG CTT GAA GTA CCT GAT ATT GAT ATA CGA CAA GTT<br>Ala Arg Ala Leu Glu Val Pro Asp Ile Asp Ile Arg Gln Val<br>1445                   1450                1455 | 4418 |
| CGA CAT CAA CTA GTT GGT CTT GAA GCA GTC ACT ATT CTA CGT | 4460 |

```
Arg His Gln Leu Val Gly Leu Glu Ala Val Thr Ile Leu Arg
1460                1465                1470

ATT TGG ATA TTT TTG AAG AAA GAA CAA GCT ACG CCC GTT GCT        4502
Ile Trp Ile Phe Leu Lys Lys Glu Gln Ala Thr Pro Val Ala
1475                1480

TTG CGA TCA GCA TTG CAG CGA ATA GGA CGT GAT GAT GTT GTA        4544
Leu Arg Ser Ala Leu Gln Arg Ile Gly Arg Asp Asp Val Val
1485                1490                1495

CGA GAA ATG GAT CGA GCT GAA AAG CTA GAT GGT TTA GAA GGA        4586
Arg Glu Met Asp Arg Ala Glu Lys Leu Asp Gly Leu Glu Gly
1500                1505                1510

ACA CCT GTA TCG CAT ATT TCT GGA CCC TCA ATA ACT CTG TCA        4628
Thr Pro Val Ser His Ile Ser Gly Pro Ser Ile Thr Leu Ser
1515                1520                1525

TCT ACT TTG CTA GAG GTA GCA GGC GAC AGA CGT CGT CAC GCC        4670
Ser Thr Leu Leu Glu Val Ala Gly Asp Arg Arg Arg His Ala
1530                1535                1540

GAG GTA ACA ATG GCG CAA CAG CGA TTG GCA CAA GAA CCG TTT        4712
Glu Val Thr Met Ala Gln Gln Arg Leu Ala Gln Glu Pro Phe
1545                1550

TTT CAG CAA GTA GGG TAT AAT GGG ACA CCT GGA GAT CCA GAA        4754
Phe Gln Gln Val Gly Tyr Asn Gly Thr Pro Gly Asp Pro Glu
1555                1560                1565

GAA CCC AAA GAA CAG TCA TTC CAC GAA GAG GAA GAG GAA GTT        4796
Glu Pro Lys Glu Gln Ser Phe His Glu Glu Glu Glu Glu Val
1570                1575                1580

GCA GTT TCA GAA ATT CGA ACA GTT GTG CGC ACT GAA CGA CAT        4838
Ala Val Ser Glu Ile Arg Thr Val Val Arg Thr Glu Arg His
1585                1590                1595

GTG CAT GAT TCG GAA AAT GGT CCT ATT GTG GAA GAG CGT ACA        4880
Val His Asp Ser Glu Asn Gly Pro Ile Val Glu Glu Arg Thr
1600                1605                1610

ATA ACA ACT ACG TAT GAG GAT GAT GTT GCT GTA AAC GAA GAA        4922
Ile Thr Thr Thr Tyr Glu Asp Asp Val Ala Val Asn Glu Glu
1615                1620

GAA ATT GTT GAC AAA ATA GTG CCT CTC AAC GAA GAG GAG CAA        4964
Glu Ile Val Asp Lys Ile Val Pro Leu Asn Glu Glu Glu Gln
1625                1630                1635

GAA AAA TGG GAT CGA ATG GTT CGA GAA GTG GAA ATG AAT TTT        5006
Glu Lys Trp Asp Arg Met Val Arg Glu Val Glu Met Asn Phe
1640                1645                1650

GAG CAA CAA GAA ACA TCA AAA GAA GGA ACG TTT GGT TGT CAG        5048
Glu Gln Gln Glu Thr Ser Lys Glu Gly Thr Phe Gly Cys Gln
1655                1660                1665

ACA ACA CAT GAG AAA GAA AAA GAT GAT GAT GGT GGC AGT CTG        5090
Thr Thr His Glu Lys Glu Lys Asp Asp Asp Gly Gly Ser Leu
1670                1675                1680

AAG ACG ACA ATG AAA GAT AGT CAC GTA AGG CAG ATT TTC TTC        5132
Lys Thr Thr Met Lys Asp Ser His Val Arg Gln Ile Phe Phe
1685                1690

GAT GGA GGT GAG ACA TCC GCT AAT GAA ACA GGA TTA AGT AGC        5174
Asp Gly Gly Glu Thr Ser Ala Asn Glu Thr Gly Leu Ser Ser
1695                1700                1705

GGG GAT GCA GAC ACT ATT ATG ACT CCA ACG ACA AAG GAG GAT        5216
Gly Asp Ala Asp Thr Ile Met Thr Pro Thr Thr Lys Glu Asp
1710                1715                1720

AAT CAT GTT ATA GAC GTA ATG GAG GAA AGG CGA ACT GAT GAA        5258
Asn His Val Ile Asp Val Met Glu Glu Arg Arg Thr Asp Glu
1725                1730                1735
```

-continued

```
GAG GCC AAA GGG CAA AGC GTT CAT GAA TAA TCTGGATCCA          5298
Glu Ala Lys Gly Gln Ser Val His Glu
1740                    1745

CAAATTGATT TAAATCGCAA TCTCGCACAT GCCTATGTTG CTAATATTTA        5348

ATGAAATTTT TCAAAGCAAT AATTTGAATG CTGTTTGGGC TTCCCATATT        5398

GTTAAAGCGT TTTCCATCGT CCATTCACTT TTTGTTTTTG CTGTAGTCTG        5448

TAACTGCTAC TCTTGATAAA TTTGCTCCAG TAAAAAAAAA AAAAAAAAA         5498

AAAAA                                                        5503
```

(2) INFORMATION FOR SEQ ID NO:33:

(i) SEQUENCE CHARACTERISTICS:
        (A) LENGTH: 1745 amino acids
        (B) TYPE: amino acid
        (D) TOPOLOGY: linear (ii) MOLECULE TYPE: protein (xi) SEQUENCE DESCRIPTION: SEQ ID NO:33:

```
Met Ser Asn Pro Ile Val Glu Gly Ser Gly Trp Pro Ala Glu
1               5                   10

Pro Lys Asp Ser Gln His Gln Gln Ile Pro Asp Asn
15                  20                  25

Ser Gln His Ser Asn Lys Gly Glu Ser Ala Ser Phe Leu
    30                  35                  40

Arg Ala Ala Arg Ala Gly Asn Leu Asp Arg Val Leu Glu Leu
        45                  50                  55

Leu Arg Ser Gly Thr Asp Ile Asn Thr Cys Asn Ala Asn Gly
            60                  65                  70

Leu Asn Ala Leu His Leu Ala Ser Lys Glu Gly His His Glu
                75                  80

Val Val Arg Glu Leu Leu Lys Arg Lys Ala Asp Val Asp Ala
85                  90                  95

Ala Thr Arg Lys Gly Asn Thr Ala Leu His Ile Ala Ser Leu
    100                 105                 110

Ala Gly Gln Glu Leu Ile Val Thr Val Leu Val Glu Asn Gly
        115                 120                 125

Ala Asn Val Asn Val Gln Ser Leu Asn Gly Phe Thr Pro Leu
            130                 135                 140

Tyr Met Ala Ala Gln Glu Asn His Glu Ser Val Val Arg Tyr
                145                 150

Leu Leu Ala His Asn Ala Asn Gln Ala Leu Ser Thr Glu Asp
155                 160                 165

Gly Phe Thr Pro Leu Ala Val Ala Leu Gln Gln Gly His Asp
    170                 175                 180

Arg Val Ala Val Leu Leu Glu Asn Asp Thr Arg Gly Lys
        185                 190                 195

Val Arg Leu Pro Ala Leu His Ile Ala Ala Lys Lys Asp Asp
            200                 205                 210

Thr Lys Ala Ala Thr Leu Leu Leu Gln Asn Glu His Asn Ser
                215                 220

Asp Val Thr Ser Lys Ser Gly Phe Thr Pro Leu His Ile Ala
225                 230                 235

Ala His Tyr Gly Asn Glu Asn Val Ala Gln Leu Leu Leu Glu
    240                 245                 250
```

-continued

```
Lys Gly Ala Asn Val Asn Tyr Gln Ala Arg His Asn Ile Ser
        255                 260                 265

Pro Leu His Val Ala Thr Lys Trp Gly Arg Thr Asn Met Val
        270                 275                 280

Ser Leu Leu Leu Ala His Gly Ala Val Ile Asp Cys Arg Thr
        285                 290

Arg Asp Leu Leu Thr Pro Leu His Cys Ala Ser Arg Ser Gly
295             300                 305

His Asp Gln Val Val Asp Leu Leu Glu Lys Gly Ala Pro
        310                 315                 320

Ile Ser Ala Lys Thr Lys Asn Gly Leu Ala Pro Leu His Met
        325                 330                 335

Ala Ala Gln Val Asp Asp Val Thr Val Asp Tyr Leu Thr Pro
        340                 345                 350

Leu His Val Ala Ala His Cys Gly His Val Arg Val Ala Lys
        355                 360

Leu Leu Leu Asp Arg Asn Ala Asp Pro Asn Ala Arg Ala Leu
365             370                 375

Asn Gly Phe Thr Pro Leu His Ile Ala Cys Lys Lys Asn Arg
        380                 385                 390

Ile Lys Ile Val Glu Leu Leu Leu Lys Tyr His Ala Ala Ile
        395                 400                 405

Glu Ala Thr Thr Glu Ser Gly Leu Ser Pro Leu His Val Ala
        410                 415                 420

Ala Phe Met Gly Ala Ile Asn Ile Val Ile Tyr Leu Leu Gln
        425                 430

Gln Gly Ala Asn Ala Asp Val Ala Thr Val Arg Gly Glu Thr
435             440                 445

Pro Leu His Leu Ala Ala Arg Ala Asn Gln Thr Asp Ile Val
        450                 455                 460

Arg Val Leu Val Arg Asn Gly Ala Gln Val Asp Ala Ala Ala
        465                 470                 475

Arg Glu Leu Gln Thr Pro Leu His Ile Ala Ser Arg Leu Gly
        480                 485                 490

Asn Thr Asp Ile Val Ile Leu Leu Gln Ala Asn Ala Ser
        495                 500

Pro Asn Ala Ala Thr Arg Asp Leu Tyr Thr Pro Leu His Ile
505             510                 515

Ala Ala Lys Glu Gly Gln Glu Val Ala Ala Ile Leu Met
        520                 525                 530

Asp His Gly Thr Asp Lys Thr Leu Leu Thr Lys Lys Gly Phe
        535                 540                 545

Thr Pro Leu His Leu Ala Ala Lys Tyr Gly Asn Leu Pro Val
        550                 555                 560

Ala Lys Ser Leu Leu Glu Arg Gly Thr Pro Val Asp Ile Glu
        565                 570

Gly Lys Asn Gln Val Thr Pro Leu His Val Ala Ala His Tyr
575             580                 585

Asn Asn Asp Lys Val Ala Leu Leu Leu Leu Glu Asn Gly Ala
        590                 595                 600

Ser Ala His Ala Ala Ala Lys Asn Gly Tyr Thr Pro Leu His
        605                 610                 615
```

-continued

Ile Ala Ala Lys Lys Asn Gln Met Asp Ile Ala Ser Thr Leu
            620                 625                 630

Leu His Tyr Lys Ala Asn Ala Asn Ala Glu Ser Lys Ala Gly
            635                 640

Phe Thr Pro Leu His Leu Ala Ala Gln Glu Gly His Arg Glu
645             650                 655

Met Ala Ala Leu Leu Ile Glu Asn Gly Ala Lys Val Gly Ala
    660                 665                 670

Gln Ala Arg Asn Gly Leu Thr Pro Met His Leu Cys Ala Gln
        675                 680                 685

Glu Asp Arg Val Ser Val Ala Glu Glu Leu Val Lys Glu Asn
            690                 695                 700

Ala Ala Ile Asp Pro Lys Thr Lys Ala Gly Tyr Thr Pro Leu
                705                 710

His Val Ala Cys His Phe Gly Gln Ile Asn Met Val Arg Phe
715             720                 725

Leu Ile Glu His Gly Ala Arg Val Ser Val Ile Thr Arg Ala
    730                 735                 740

Ser Tyr Thr Pro Leu His Gln Ala Ala Gln Gln Gly His His Asn
        745                 750                 755

Ser Val Val Arg Tyr Leu Leu Glu His Gly Ala Ser Pro Asn
            760                 765                 770

Val His Thr Ser Thr Gly Gln Thr Pro Leu Ser Ile Ala Glu
                775                 780

Arg Leu Gly Tyr Val Ser Val Glu Ala Leu Lys Thr Ile
785             790                 795

Thr Glu Thr Thr Val Ile Thr Glu Thr Thr Thr Val Thr Glu
    800                 805                 810

Glu Arg Tyr Lys Pro Gln Asn Pro Glu Ala Met Asn Glu Thr
        815                 820                 825

Met Phe Ser Asp Ser Glu Asp Glu Gly Glu Asp Asn Gln Ile
            830                 835                 840

Thr Ala Asn Ala His Ala His Asp Phe Ser Glu Ser Leu Thr
                845                 850

Lys Gly Leu His Asp Ser Thr Gly Val His Leu Ile His Ala
855             860                 865

Thr Glu Pro Thr Leu Ser Arg Ser Pro Glu Val Glu Gly Thr
    870                 875                 880

Asp Gly Asp Leu Asp Ala Leu Ile Arg Lys Ala Gln His Glu
        885                 890                 895

Pro Ile Thr Thr Ala Met Ala Asp Pro Ser Leu Asp Ala Ser
            900                 905                 910

Leu Pro Asp Asn Val Thr Ile Met Arg Thr Thr Met Gln Pro
                915                 920

Ser Phe Leu Ile Ser Phe Met Val Asp Ala Arg Gly Gly Ala
925             930                 935

Met Arg Gly Cys Arg His Ser Gly Val Arg Ile Ile Pro
    940                 945                 950

Pro Arg Lys Ala Pro Gln Pro Thr Arg Val Thr Cys Arg Tyr
        955                 960                 965

Leu Gly Lys Asp Lys Leu Ala His Pro Pro Leu Ser Glu
            970                 975                 980

Gly Glu Ala Leu Ala Ser Arg Ile Leu Glu Met Ala Pro His

-continued

```
                985                 990
Gly Ala Lys Phe Leu Gly Pro Val Ile Leu Glu Val Pro His
995             1000                1005

Phe Ala Ser Leu Arg Gly Arg Glu Arg Glu Ile Val Ile Leu
    1010                1015                1020

Arg Ser Asp Asp Gly Gln His Trp Lys Glu His Gln Leu Glu
        1025                1030                1035

Ala Thr Glu Asp Ala Val Gln Glu Val Leu Asn Glu Ser Phe
            1040                1045                1050

Asp Ala Glu Glu Leu Ser Gln Leu Asp Asp Leu His Thr Ser
                1055                1060

Arg Ile Thr Arg Ile Leu Thr Asn Asp Phe Pro Met Tyr Phe
1065                1070                1075

Ala Val Val Thr Arg Val Arg Gln Glu Val His Cys Val Gly
    1080                1085                1090

Pro Glu Gly Gly Val Ile Leu Ser Ser Val Val Pro His Val
        1095                1100                1105

Gln Ala Ile Phe Pro Asp Gly Ser Leu Thr Lys Thr Ile Lys
            1110                1115                1120

Val Ser Val Gln Ala Gln Pro Val Pro Gln Glu Ile Val Thr
                1125                1130

Arg Leu His Gly Asn Arg Val Ala Val Ser Pro Ile Val Thr
1135                1140                1145

Val Glu Pro Arg Arg Arg Lys Phe His Lys Pro Ile Thr Leu
    1150                1155                1160

Cys Ile Pro Leu Pro Gln Ser Ser Asn Lys Gly Met Leu Thr
        1165                1170                1175

Gln Tyr Ser Gly Gln Pro Gly Gln Glu Pro Pro Thr Leu Arg
            1180                1185                1190

Leu Leu Cys Ser Lys Thr Gly Gly Ser Ser Pro Ala Gln Trp
                1195                1200

Glu Asp Ile Thr Gly Thr Thr Gln Leu Thr Phe Thr Gly Glu
1205                1210                1215

Asp Val Ser Phe Thr Thr Thr Val Ser Ala Arg Phe Trp Leu
    1220                1225                1230

Met Asp Cys Gln Thr Pro Arg Asp Ala Ala Arg Met Ala Gln
        1235                1240                1245

Glu Val Tyr Asn Glu Ala Ile Ala Val Pro Tyr Met Ala Lys
            1250                1255                1260

Phe Leu Ile Phe Ala Arg Arg Thr Phe Pro Ala Glu Gly Gln
                1265                1270

Leu Arg Leu Phe Cys Met Thr Asp Asp Arg Glu Asp Lys Thr
1275                1280                1285

Leu Glu Lys Gln Glu Arg Phe Ile Glu Ile Ala Lys Ser Lys
    1290                1295                1300

Asp Val Glu Val Leu Ser Gly Arg His Gln Phe Leu Glu Phe
        1305                1310                1315

Ser Gly Asn Leu Leu Pro Ile Thr Lys Ser Gly Asp Gln Leu
            1320                1325                1330

Ser Leu Tyr Phe Leu Pro Phe Gln Glu Asn Arg Leu Ala Phe
                1335                1340

Met Val Lys Ile Arg Thr His Thr Asp Asn Glu Thr Ala Ala
1345                1350                1355
```

-continued

```
Asp Gly Arg Ile Val Phe Met Lys Glu Pro Lys Leu Arg Ala
    1360                1365                1370

Glu Asn Leu Pro Pro Gln Thr Pro Val Cys Thr Leu Ala Ile
    1375                1380                1385

Thr Leu Pro Glu Tyr Thr Gly Pro Glu Pro Met Val Ser Lys
    1390                1395                1400

Lys Leu Phe Tyr Ser Glu Ala Ser Leu Thr Glu Lys Tyr Val
            1405                1410

Gly Ala Phe His Glu Thr Ala Glu Pro Asp Asn Leu Pro Leu
1415                1420                1425

Ala His Val Ala Leu Leu Ile Gly Ala Asp Trp His Arg Leu
    1430                1435                1440

Ala Arg Ala Leu Glu Val Pro Asp Ile Asp Ile Arg Gln Val
    1445                1450                1455

Arg His Gln Leu Val Gly Leu Glu Ala Val Thr Ile Leu Arg
    1460                1465                1470

Ile Trp Ile Phe Leu Lys Lys Glu Gln Ala Thr Pro Val Ala
            1475                1480

Leu Arg Ser Ala Leu Gln Arg Ile Gly Arg Asp Asp Val Val
1485                1490                1495

Arg Glu Met Asp Arg Ala Glu Lys Leu Asp Gly Leu Glu Gly
    1500                1505                1510

Thr Pro Val Ser His Ile Ser Gly Pro Ser Ile Thr Leu Ser
            1515                1520                1525

Ser Thr Leu Leu Glu Val Ala Gly Asp Arg Arg Arg His Ala
            1530                1535                1540

Glu Val Thr Met Ala Gln Gln Arg Leu Ala Gln Glu Pro Phe
                1545                1550

Phe Gln Gln Val Gly Tyr Asn Gly Thr Pro Gly Asp Pro Glu
1555                1560                1565

Glu Pro Lys Glu Gln Ser Phe His Glu Glu Glu Glu Val
    1570                1575                1580

Ala Val Ser Glu Ile Arg Thr Val Arg Thr Glu Arg His
    1585                1590                1595

Val His Asp Ser Glu Asn Gly Pro Ile Val Glu Glu Arg Thr
            1600                1605                1610

Ile Thr Thr Thr Tyr Glu Asp Asp Val Ala Val Asn Glu Glu
            1615                1620

Glu Ile Val Asp Lys Ile Val Pro Leu Asn Glu Glu Glu Gln
1625                1630                1635

Glu Lys Trp Asp Arg Met Val Arg Glu Val Glu Met Asn Phe
    1640                1645                1650

Glu Gln Gln Glu Thr Ser Lys Glu Gly Thr Phe Gly Cys Gln
    1655                1660                1665

Thr Thr His Glu Lys Glu Lys Asp Asp Asp Gly Gly Ser Leu
            1670                1675                1680

Lys Thr Thr Met Lys Asp Ser His Val Arg Gln Ile Phe Phe
            1685                1690

Asp Gly Gly Glu Thr Ser Ala Asn Glu Thr Gly Leu Ser Ser
1695                1700                1705

Gly Asp Ala Asp Thr Ile Met Thr Pro Thr Thr Lys Glu Asp
    1710                1715                1720
```

```
Asn His Val Ile Asp Val Met Glu Glu Arg Arg Thr Asp Glu
    1725                1730                1735

Glu Ala Lys Gly Gln Ser Val His Glu
    1740                1745

(2) INFORMATION FOR SEQ ID NO:34:

(i) SEQUENCE CHARACTERISTICS:
        (A) LENGTH: 5503 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:34:

TTTTTTTTTT TTTTTTTTTT TTTTACTGGA GCAAATTTAT CAAGAGTAGC            50

AGTTACAGAC TACAGCAAAA ACAAAAAGTG AATGGACGAT GGAAAACGCT           100

TTAACAATAT GGGAAGCCCA AACAGCATTC AAATTATTGC TTTGAAAAAT           150

TTCATTAAAT ATTAGCAACA TAGGCATGTG CGAGATTGCG ATTTAAATCA           200

ATTTGTGGAT CCAGATTATT CATGAACGCT TTGCCCTTTG GCCTCTTCAT           250

CAGTTCGCCT TTCCTCCATT ACGTCTATAA CATGATTATC CTCCTTTGTC           300

GTTGGAGTCA TAATAGTGTC TGCATCCCCG CTACTTAATC CTGTTTCATT           350

AGCGGATGTC TCACCTCCAT CGAAGAAAAT CTGCCTTACG TGACTATCTT           400

TCATTGTCGT CTTCAGACTG CCACCATCAT CATCTTTTTC TTTCTCATGT           450

GTTGTCTGAC AACCAAACGT TCCTTCTTTT GATGTTTCTT GTTGCTCAAA           500

ATTCATTTCC ACTTCTCGAA CCATTCGATC CCATTTTTCT TGCTCCTCTT           550

CGTTGAGAGG CACTATTTTG TCAACAATTT CTTCTTCGTT TACAGCAACA           600

TCATCCTCAT ACGTAGTTGT TATTGTACGC TCTTCCACAA TAGGACCATT           650

TTCCGAATCA TGCACATGTC GTTCAGTGCG CACAACTGTT CGAATTTCTG           700

AAACTGCAAC TTCCTCTTCC TCTTCGTGGA ATGACTGTTC TTTGGGTTCT           750

TCTGGATCTC CAGGTGTCCC ATTATACCCT ACTTGCTGAA AAAACGGTTC           800

TTGTGCCAAT CGCTGTTGCG CCATTGTTAC CTCGGCGTGA CGACGTCTGT           850

CGCCTGCTAC CTCTAGCAAA GTAGATGACA GAGTTATTGA GGGTCCAGAA           900

ATATGCGATA CAGGTGTTCC TTCTAAACCA TCTAGCTTTT CAGCTCGATC           950

CATTTCTCGT ACAACATCAT CACGTCCTAT TCGCTGCAAT GCTGATCGCA          1000

AAGCAACGGG CGTAGCTTGT TCTTTCTTCA AAAATATCCA AATACGTAGA          1050

ATAGTGACTG CTTCAAGACC AACTAGTTGA TGTCGAACTT GTCGTATATC          1100

AATATCAGGT ACTTCAAGCG CTCGAGCTAA CCGATGCCAA TCAGCGCCAA          1150

TTAATAGTGC AACATGTGCT AGTGGCAAGT TATCAGGTTC AGCAGTTTCA          1200

TGGAAAGCTC CAACGTATTT CTCAGTCAAA GAAGCTTCCG AATAGAAGAG          1250

TTTTTTGGAA ACCATCGGCT CCGGCCCAGT GTATTCCGGA AGAGTGATTG          1300

CAAGAGTACA CACTGGCGTC TGCGGAGGTA AATTTTCGGC TCTCAATTTT          1350

GGTTCTTTCA TAAATACTAT CCGGCCATCA GCTGCAGTTT CGTTGTCCGT          1400

GTGAGTGCGT ATCTTTACCA TGAAAGCAAG ACGATTTTCT TGGAATGGTA          1450

GAAAATAAAG AGAAAGTTGG TCACCACTCT TGGTTATTGG AAGAAGATTT          1500
```

```
CCAGAAAATT CCAAAAACTG ATGTCGCCCA CTTAAGACTT CTACATCTTT      1550

CGATTTCGCA ATTTCAATGA AACGTTCTTG TTTTTCCAGG GTTTTATCTT      1600

CCCGATCATC AGTCATACAA AACAATCTCA ACTGTCCTTC GGCAGGAAAA      1650

GTTCGTCGAG CAAAAATAAG AAATTTAGCC ATATAAGGAA CTGCAATTGC      1700

TTCATTGTAA ACTTCTTGTG CCATTCGTGC CGCATCTCGC GGAGTTTGGC      1750

AATCCATCAA CCAAAATCGA GCAGAAACCG TAGTTGTAAA TGAAACGTCC      1800

TCACCAGTAA ATGTTAACTG GGTAGTTCCA GTAATATCTT CCCACTGTGC      1850

AGGAGAAGAA CCTCCAGTTT TACTGCAGAG TAAACGCAGC GTCGGTGGTT      1900

CCTGTCCTGG TTGGCCACTA TATTGTGTTA ACATTCCTTT ATTTGAGCTT      1950

TGTGGCAATG GTATGCACAG CGTTATGGGC TTATGGAATT TGCGACGACG      2000

CGGTTCAACA GTTACAATTG GAGAAACAGC GACTCTATTC CCATGTAAAC      2050

GAGTGACTAT CTCTTGTGGA ACTGGCTGGG CTTGCACAGA TACTTTGATC      2100

GTCTTAGTCA AGGAACCATC CGGAAATATG GCCTGCACAT GAGGAACAAC      2150

TGAAGAGAGT ATTACACCAC CTTCTGGACC AACACAGTGC ACTTCTTGCC      2200

GCACACGAGT AACGACCGCG AAATACATTG GAAATCATT GGTCAGGATA       2250

CGCGTAATCC GTGATGTATG CAAATCATCA AGTTGCGACA ACTCTTCTGC      2300

ATCAAACGAT TCATTGAGCA CCTCTTGTAC AGCATCTTCT GTTGCTTCAA      2350

GCTGATGCTC TTTCCAATGC TGCCCATCAT CAGAACGCAA AATGACAATC      2400

TCTCTCTCTC GTCCACGAAG TGATGCAAAA TGTGGTACTT CCAATATAAC      2450

AGGGCCTAAG AATTTTGCTC CATGTGGTGC CATTTCAAGT ATACGTGANG      2500

CGAGCGCTTC ACCTTCACTT AATGGTGGTG GATGCGCTAA CTTGTCCTTT      2550

CCAAGGTATC TGCATGTGAC CCGTGTAGGT TGCGGCGCTT TCCTCGGTGG      2600

TATAATGATT CTGACACCGG AATGCCTACA ACCACGCATT GCTCCTCCAC      2650

GTGCATCCAC CATAAACGAA ATTAAAAAAC TAGGTTGCAT GGTAGTTCTC      2700

ATTATCGTAA CATTGTCAGG AAGCGATGCA TCTAAGGAAG GATCGGCCAT      2750

CGCTGTAGTA ATTGGTTCAT GTTGTGCTTT ACGAATTAAG GCATCCAAAT      2800

CGCCATCCGT ACCTTCCACT TCCGGACTTC GTGACAATGT CGGTTCTGTG      2850

GCATGAATCA AATGTACACC AGTTGAATCG TGCAAACCTT TTGTGAGGCT      2900

TTCTGAGAAA TCATGAGCAT GAGCATTGGC TGTGATCTGA TTATCTTCAC      2950

CTTCATCTTC GGAATCGGAA AACATGGTTT CATTCATTGC TTCGGGATTC      3000

TGAGGTTTAT ATCTTTCTTC AGTAACGGTT GTGGTCTCCG TTATCACAGT      3050

AGTCTCGGTA ATTGTTTTAA GCGCTTCAAC CACGGATACA TACCCTAGAC      3100

GTTCAGCAAT CGATAATGGA GTTTGTCCTG TCGATGTATG AACATTTGGA      3150

CTTGCACCAT GTTCCAACAA GTAACGTACA ACACTGTTAT GCCCTTGCTG      3200

AGCAGCTTGA TGCAGAGGAG TATAGGAAGC ACGAGTAATA ACTGAAACTC      3250

GTGCGCCATG CTCAATCAAG AAACGGACCA TGTTTATTTG TCCAAAATGG      3300

CAAGCAACAT GTAACGGCGT ATATCCTGCT TTCGTTTTGG GATCAATGGC      3350

TGCGTTTTCT TTCACTAGTT CTTCTGCTAC GCTCACACGA TCCTCCTGTG      3400

CACATAAATG CATTGGTGTC AAGCCATTCC TTGCCTGAGC TCCAACTTTT      3450

GCTCCATTTT CAATTAATAA CGCAGCCATT TCGCGATGGC CCTCCTGGGC      3500
```

-continued

| | |
|---|---|
| GGCAAGATGA AGTGGTGTAA AGCCAGCTTT GCTTTCAGCA TTCGCATTTG | 3550 |
| CCTTATAATG AAGGAGAGTG CTAGCAATAT CCATCTGATT CTTCTTCGCG | 3600 |
| GCAATATGTA AAGGAGTGTA CCCATTCTTG GCAGCGGCAT GTGCAGAAGC | 3650 |
| ACCATTTTCT AGAAGTAACA ATGCTACCTT GTCGTTATTG TAATGTGCCG | 3700 |
| CTACATGCAG AGGTGTTACC TGATTCTTGC CTTCAATGTC AACCGGTGTT | 3750 |
| CCTCGTTCTA GCAATGATTT CGCGACCGGC AAATTGCCAT ACTTAGCAGC | 3800 |
| TAAATGCAAC GGCGTAAAAC CCTTTTTCGT GAGCAGTGTC TTGTCGGTTC | 3850 |
| CATGATCCAT CAATATTGCT GCCACTTCCT CTTGCCCCTC CTTGGCAGCA | 3900 |
| ATATGAAGAG GAGTATAAAG ATCTCTTGTG GCAGCATTTG GTGATGCATT | 3950 |
| AGCCTGCAGC AACAAAATGA CGATGTCGGT ATTACCAAGA CGTGATGCAA | 4000 |
| TGTGCAGTGG AGTTTGTAGT TCACGAGCAG CAGCATCCAC CTGTGCTCCA | 4050 |
| TTACGCACCA AAACACGAAC AATGTCCGTT TGGTTTGCTC GTGCAGCTAA | 4100 |
| ATGAAGAGGC GTTTCACCGC GTACTGTAGC CACATCTGCA TTAGCACCTT | 4150 |
| GTTGTAGTAA ATAGATGACA ATGTTTATAG CACCCATAAA AGCAGCGACA | 4200 |
| TGCAGCGGTG AGAGACCGGA TTCAGTAGTT GCTTCGATTG CAGCGTGGTA | 4250 |
| TTTCAGTAGC AGTTCGACAA TTTTAATGCG ATTTTTTTTG CAAGCGATAT | 4300 |
| GCAGCGGTGT GAAGCCATTG AGAGCTCGAG CATTCGGGTC AGCATTACGA | 4350 |
| TCCAGCAAAA GTTTAGCGAC ACGGACATGT CCGCAATGAG CAGCCACATG | 4400 |
| AAGAGGAGTG AGATAGTCAA CAGTAACATC ATCCACCTGT GCTGCCATAT | 4450 |
| GTAAGGGAGC CAAACCATTT TTTGTCTTAG CACTGATTGG AGCTCCTTTT | 4500 |
| TCAAGCAACA AATCAACAAC TTGATCATGA CCTGAACGAG AAGCACAGTG | 4550 |
| TAATGGTGTT AGTAAATCAC GTGTGCGACA GTCAATTACG GCCCCATGAG | 4600 |
| CCAACAATAA CGAAACCATG TTTGTACGAC CCCATTTTGT TGCAACGTGT | 4650 |
| AACGGACTTA TGTTATGTCT CGCTTGGTAA TTCACATTGG CTCCCTTTTC | 4700 |
| GAGTAGCAGT TGTGCTACGT TCTCATTTCC ATAGTGAGCG GCGATATGAA | 4750 |
| GCGGAGTAAA GCCGCTTTTC GAAGTCACAT CCGAGTTATG CTCATTTTGA | 4800 |
| AGTAATAGCG TAGCTGCTTT CGTATCATCT TTTTTAGCAG CAATATGCAG | 4850 |
| TGCTGGCAAG CGCACTTTCC CGCGCGTGTC ATTTTCAAGC AAAACAGCGA | 4900 |
| CCACACGATC GTGACCTTGT TGCAAGGCAA CTGCCAGTGG CGTAAAACCG | 4950 |
| TCTTCTGTAC TTAAAGCTTG ATTGGCATTG TGGGCAAGAA GATAGCGTAC | 5000 |
| AACAGATTCG TGATTTTCTT GTGCAGCCAT GTAAAGTGGT GTAAAACCGT | 5050 |
| TTAGTGATTG TACGTTAACA TTAGCACCAT TTTCAACAAG TACTGTGACG | 5100 |
| ATTAGTTCTT GTCCTGCCAA TGATGCTATA TGTAACGCTG TGTTACCCTT | 5150 |
| TCTAGTGGCA GCATCAACAT CTGCTTTTCT TTTCAGAAGT TCGCGGACCA | 5200 |
| CTTCATGATG ACCTTCTTTG GAGGCCAGAT GCAATGCATT AAGGCCATTC | 5250 |
| GCATTGCATG TGTTGATATC GGTGCCCGAA CGAAGTAGTT CAAGTACACG | 5300 |
| ATCCAAATTT CCAGCTCTTG CTGCTCGTAA AAAACTTGCA CTGCTCTCAC | 5350 |
| CTTTGTTGGA ATGTTGACTG TTATCATCAG GAATTTGTTG TTGATGTTGT | 5400 |
| GAATCTTTTG GTTCTGCGGG CCAGCCACTT CCCTCGACTA TAGGATTACT | 5450 |

```
CATCAATAGT TGAGTTATAT CAGTCAGCCG CCTCAAACTT GGGTAATTAA         5500

ACC                                                           5503

(2) INFORMATION FOR SEQ ID NO:35:

(i) SEQUENCE CHARACTERISTICS:
        (A) LENGTH: 5235 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:35:

ATGAGTAATC CTATAGTCGA GGGAAGTGGC TGGCCCGCAG AACCAAAAGA          50

TTCACAACAT CAACAACAAA TTCCTGATGA TAACAGTCAA CATTCCAACA         100

AAGGTGAGAG CAGTGCAAGT TTTTTACGAG CAGCAAGAGC TGGAAATTTG         150

GATCGTGTAC TTGAACTACT TCGTTCGGGC ACCGATATCA ACACATGCAA         200

TGCGAATGGC CTTAATGCAT TGCATCTGGC CTCCAAAGAA GGTCATCATG         250

AAGTGGTCCG CGAACTTCTG AAAAGAAAAG CAGATGTTGA TGCTGCCACT         300

AGAAAGGGTA ACACAGCGTT ACATATAGCA TCATTGGCAG ACAAGAACT          350

AATCGTCACA GTACTTGTTG AAAATGGTGC TAATGTTAAC GTACAATCAC         400

TAAACGGTTT TACACCACTT TACATGGCTG ACAAGAAAA TCACGAATCT          450

GTTGTACGCT ATCTTCTTGC CCACAATGCC AATCAAGCTT TAAGTACAGA         500

AGACGGTTTT ACGCCACTGG CAGTTGCCTT GCAACAAGGT CACGATCGTG         550

TGGTCGCTGT TTTGCTTGAA AATGACACGC GCGGGAAAGT GCGCTTGCCA         600

GCACTGCATA TTGCTGCTAA AAAAGATGAT ACGAAAGCAG CTACGCTATT         650

ACTTCAAAAT GAGCATAACT CGGATGTGAC TTCGAAAAGC GGCTTTACTC         700

CGCTTCATAT CGCCGCTCAC TATGGAAATG AGAACGTAGC ACAACTGCTA         750

CTCGAAAAGG GAGCCAATGT GAATTACCAA GCGAGACATA ACATAAGTCC         800

GTTACACGTT GCAACAAAAT GGGGTCGTAC AAACATGGTT TCGTTATTGT         850

TGGCTCATGG GGCCGTAATT GACTGTCGCA CACGTGATTT ACTAACACCA         900

TTACACTGTG CTTCTCGTTC AGGTCATGAT CAAGTTGTTG ATTTGTTGCT         950

TGAAAAAGGA GCTCCAATCA GTGCTAAGAC AAAAAATGGT TTGGCTCCCT        1000

TACATATGGC AGCACAGGTG GATGATGTTA CTGTTGACTA TCTCACTCCT        1050

CTTCATGTGG CTGCTCATTG CGGACATGTC CGTGTCGCTA AACTTTTGCT        1100

GGATCGTAAT GCTGACCCGA ATGCTCGAGC TCTCAATGGC TTCACACCGC        1150

TGCATATCGC TTGCAAAAAA AATCGCATTA AAATTGTCGA ACTGCTACTG        1200

AAATACCACG CTGCAATCGA AGCAACTACT GAATCCGGTC TCTCACCGCT        1250

GCATGTCGCT GCTTTTATGG GTGCTATAAA CATTGTCATC TATTTACTAC        1300

AACAAGGTGC TAATGCAGAT GTGGCTACAG TACGCGGTGA AACGCCTCTT        1350

CATTTAGCTG CACGAGCAAA CCAAACGGAC ATTGTTCGTG TTTTGGTGCG        1400

TAATGGAGCA CAGGTGGATG CTGCTGCTCG TGAACTACAA ACTCCACTGC        1450

ACATTGCATC ACGTCTTGGT AATACCGACA TCGTCATTTT GTTGCTGCAG        1500

GCTAATGCAT CACCAAATGC TGCCACAAGA GATCTTTATA CTCCTCTTCA        1550
```

| | |
|---|---|
| TATTGCTGCC AAGGAGGGGC AAGAGGAAGT GGCAGCAATA TTGATGGATC | 1600 |
| ATGGAACCGA CAAGACACTG CTCACGAAAA AGGGTTTTAC GCCGTTGCAT | 1650 |
| TTAGCTGCTA AGTATGGCAA TTTGCCGGTC GCGAAATCAT TGCTAGAACG | 1700 |
| AGGAACACCG GTTGACATTG AAGGCAAGAA TCAGGTAACA CCTCTGCATG | 1750 |
| TAGCGGCACA TTACAATAAC GACAAGGTAG CATTGTTACT TCTAGAAAAT | 1800 |
| GGTGCTTCTG CACATGCCGC TGCCAAGAAT GGGTACACTC CTTTACATAT | 1850 |
| TGCCGCGAAG AAGAATCAGA TGGATATTGC TAGCACTCTC CTTCATTATA | 1900 |
| AGGCAAATGC GAATGCTGAA AGCAAAGCTG GCTTTACACC ACTTCATCTT | 1950 |
| GCCGCCCAGG AGGGCCATCG CGAAATGGCT GCGTTATTAA TTGAAAATGG | 2000 |
| AGCAAAAGTT GGAGCTCAGG CAAGGAATGG CTTGACACCA ATGCATTTAT | 2050 |
| GTGCACAGGA GGATCGTGTG AGCGTAGCAG AAGAACTAGT GAAAGAAAAC | 2100 |
| GCAGCCATTG ATCCCAAAAC GAAAGCAGGA TATACGCCGT TACATGTTGC | 2150 |
| TTGCCATTTT GGACAAATAA ACATGGTCCG TTTCTTGATT GAGCATGGCG | 2200 |
| CACGAGTTTC AGTTATTACT CGTGCTTCCT ATACTCCTCT GCATCAAGCT | 2250 |
| GCTCAGCAAG GGCATAACAG TGTTGTACGT TACTTGTTGG AACATGGTGC | 2300 |
| AAGTCCAAAT GTTCATACAT CGACAGGACA AACTCCATTA TCGATTGCTG | 2350 |
| AACGTCTAGG GTATGTATCC GTGGTTGAAG CGCTTAAAAC AATTACCGAG | 2400 |
| ACTACTGTGA TAACGGAGAC CACAACCGTT ACTGAAGAAA GATATAAACC | 2450 |
| TCAGAATCCC GAAGCAATGA ATGAAACCAT GTTTTCCGAT TCCGAAGATG | 2500 |
| AAGGTGAAGA TAATCAGATC ACAGCCAATG CTCATGCTCA TGATTTCTCA | 2550 |
| GAAAGCCTCA CAAAAGGTTT GCACGATTCA ACTGGTGTAC ATTTGATTCA | 2600 |
| TGCCACAGAA CCGACATTGT CACGAAGTCC GGAAGTGGAA GGTACGGATG | 2650 |
| GCGATTTGGA TGCCTTAATT CGTAAAGCAC AACATGAACC AATTACTACA | 2700 |
| GCGATGGCCG ATCCTTCCTT AGATGCATCG CTTCCTGACA ATGTTACGAT | 2750 |
| AATGAGAACT ACCATGCAAC CTAGTTTTTT AATTTCGTTT ATGGTGGATG | 2800 |
| CACGTGGAGG AGCAATGCGT GGTTGTAGGC ATTCCGGTGT CAGAATCATT | 2850 |
| ATACCACCGA GGAAAGCGCC GCAACCTACA CGGGTCACAT GCAGATACCT | 2900 |
| TGGAAAGGAC AAGTTAGCGC ATCCACCACC ATTAAGTGAA GGTGAAGCGC | 2950 |
| TCGCNTCACG TATACTTGAA ATGGCACCAC ATGGAGCAAA ATTCTTAGGC | 3000 |
| CCTGTTATAT TGGAAGTACC ACATTTTGCA TCACTTCGTG GACGAGAGAG | 3050 |
| AGAGATTGTC ATTTTGCGTT CTGATGATGG GCAGCATTGG AAAGAGCATC | 3100 |
| AGCTTGAAGC AACAGAAGAT GCTGTACAAG AGGTGCTCAA TGAATCGTTT | 3150 |
| GATGCAGAAG AGTTGTCGCA ACTTGATGAT TTGCATACAT CACGGATTAC | 3200 |
| GCGTATCCTG ACCAATGATT TCCCAATGTA TTTCGCGGTC GTTACTCGTG | 3250 |
| TGCGGCAAGA AGTGCACTGT GTTGGTCCAG AAGGTGGTGT AATACTCTCT | 3300 |
| TCAGTTGTTC CTCATGTGCA GGCCATATTT CCGGATGGTT CCTTGACTAA | 3350 |
| GACGATCAAA GTATCTGTGC AAGCCCAGCC AGTTCCACAA GAGATAGTCA | 3400 |
| CTCGTTTACA TGGGAATAGA GTCGCTGTTT CTCCAATTGT AACTGTTGAA | 3450 |
| CCGCGTCGTC GCAAATTCCA TAAGCCCATA CGCTGTGCA TACCATTGCC | 3500 |
| ACAAAGCTCA AATAAAGGAA TGTTAACACA ATATAGTGGC CAACCAGGAC | 3550 |

-continued

```
AGGAACCACC GACGCTGCGT TTACTCTGCA GTAAAACTGG AGGTTCTTCT          3600

CCTGCACAGT GGGAAGATAT TACTGGAACT ACCCAGTTAA CATTTACTGG          3650

TGAGGACGTT TCATTTACAA CTACGGTTTC TGCTCGATTT TGGTTGATGG          3700

ATTGCCAAAC TCCGCGAGAT GCGGCACGAA TGGCACAAGA AGTTTACAAT          3750

GAAGCAATTG CAGTTCCTTA TATGGCTAAA TTTCTTATTT TTGCTCGACG          3800

AACTTTTCCT GCCGAAGGAC AGTTGAGATT GTTTTGTATG ACTGATGATC          3850

GGGAAGATAA AACCCTGGAA AAACAAGAAC GTTTCATTGA AATTGCGAAA          3900

TCGAAAGATG TAGAAGTCTT AAGTGGGCGA CATCAGTTTT TGGAATTTTC          3950

TGGAAATCTT CTTCCAATAA CCAAGAGTGG TGACCAACTT TCTCTTTATT          4000

TTCTACCATT CCAAGAAAAT CGTCTTGCTT TCATGGTAAA GATACGCACT          4050

CACACGGACA ACGAAACTGC AGCTGATGGC CGGATAGTAT TTATGAAAGA          4100

ACCAAAATTG AGAGCCGAAA ATTTACCTCC GCAGACGCCA GTGTGTACTC          4150

TTGCAATCAC TCTTCCGGAA TACACTGGGC CGGAGCCGAT GGTTTCCAAA          4200

AAACTCTTCT ATTCGGAAGC TTCTTTGACT GAGAAATACG TTGGAGCTTT          4250

CCATGAAACT GCTGAACCTG ATAACTTGCC ACTAGCACAT GTTGCACTAT          4300

TAATTGGCGC TGATTGGCAT CGGTTAGCTC GAGCGCTTGA AGTACCTGAT          4350

ATTGATATAC GACAAGTTCG ACATCAACTA GTTGGTCTTG AAGCAGTCAC          4400

TATTCTACGT ATTTGGATAT TTTTGAAGAA AGAACAAGCT ACGCCCGTTG          4450

CTTTGCGATC AGCATTGCAG CGAATAGGAC GTGATGATGT TGTACGAGAA          4500

ATGGATCGAG CTGAAAAGCT AGATGGTTTA GAAGGAACAC CTGTATCGCA          4550

TATTTCTGGA CCCTCAATAA CTCTGTCATC TACTTTGCTA GAGGTAGCAG          4600

GCGACAGACG TCGTCACGCC GAGGTAACAA TGGCGCAACA GCGATTGGCA          4650

CAAGAACCGT TTTTTCAGCA AGTAGGGTAT AATGGGACAC CTGGAGATCC          4700

AGAAGAACCC AAAGAACAGT CATTCCACGA AGAGGAAGAG GAAGTTGCAG          4750

TTTCAGAAAT TCGAACAGTT GTGCGCACTG AACGACATGT GCATGATTCG          4800

GAAAATGGTC CTATTGTGGA AGAGCGTACA ATAACAACTA CGTATGAGGA          4850

TGATGTTGCT GTAAACGAAG AAGAAATTGT TGACAAAATA GTGCCTCTCA          4900

ACGAAGAGGA GCAAGAAAAA TGGGATCGAA TGGTTCGAGA AGTGGAAATG          4950

AATTTTGAGC AACAAGAAAC ATCAAAAGAA GGAACGTTTG GTTGTCAGAC          5000

AACACATGAG AAAGAAAAAG ATGATGATGG TGGCAGTCTG AAGACGACAA          5050

TGAAAGATAG TCACGTAAGG CAGATTTTCT TCGATGGAGG TGAGACATCC          5100

GCTAATGAAA CAGGATTAAG TAGCGGGGAT GCAGACACTA TTATGACTCC          5150

AACGACAAAG GAGGATAATC ATGTTATAGA CGTAATGGAG GAAAGGCGAA          5200

CTGATGAAGA GGCCAAAGGG CAAAGCGTTC ATGAA                          5235
```

(2) INFORMATION FOR SEQ ID NO:36:

(i) SEQUENCE CHARACTERISTICS:
        (A) LENGTH: 5235 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:36:

| | | | | |
|---|---|---|---|---|
| TTCATGAACG | CTTTGCCCTT | TGGCCTCTTC | ATCAGTTCGC | CTTTCCTCCA | 50 |
| TTACGTCTAT | AACATGATTA | TCCTCCTTTG | TCGTTGGAGT | CATAATAGTG | 100 |
| TCTGCATCCC | CGCTACTTAA | TCCTGTTTCA | TTAGCGGATG | TCTCACCTCC | 150 |
| ATCGAAGAAA | ATCTGCCTTA | CGTGACTATC | TTTCATTGTC | GTCTTCAGAC | 200 |
| TGCCACCATC | ATCATCTTTT | TCTTTCTCAT | GTGTTGTCTG | ACAACCAAAC | 250 |
| GTTCCTTCTT | TTGATGTTTC | TTGTTGCTCA | AAATTCATTT | CCACTTCTCG | 300 |
| AACCATTCGA | TCCCATTTTT | CTTGCTCCTC | TTCGTTGAGA | GGCACTATTT | 350 |
| TGTCAACAAT | TTCTTCTTCG | TTTACAGCAA | CATCATCCTC | ATACGTAGTT | 400 |
| GTTATTGTAC | GCTCTTCCAC | AATAGGACCA | TTTTCCGAAT | CATGCACATG | 450 |
| TCGTTCAGTG | CGCACAACTG | TTCGAATTTC | TGAAACTGCA | ACTTCCTCTT | 500 |
| CCTCTTCGTG | GAATGACTGT | TCTTTGGGTT | CTTCTGGATC | TCCAGGTGTC | 550 |
| CCATTATACC | CTACTTGCTG | AAAAAACGGT | TCTTGTGCCA | ATCGCTGTTG | 600 |
| CGCCATTGTT | ACCTCGGCGT | GACGACGTCT | GTCGCCTGCT | ACCTCTAGCA | 650 |
| AAGTAGATGA | CAGAGTTATT | GAGGGTCCAG | AAATATGCGA | TACAGGTGTT | 700 |
| CCTTCTAAAC | CATCTAGCTT | TTCAGCTCGA | TCCATTTCTC | GTACAACATC | 750 |
| ATCACGTCCT | ATTCGCTGCA | ATGCTGATCG | CAAAGCAACG | GGCGTAGCTT | 800 |
| GTTCTTTCTT | CAAAAATATC | CAAATACGTA | GAATAGTGAC | TGCTTCAAGA | 850 |
| CCAACTAGTT | GATGTCGAAC | TTGTCGTATA | TCAATATCAG | GTACTTCAAG | 900 |
| CGCTCGAGCT | AACCGATGCC | AATCAGCGCC | AATTAATAGT | GCAACATGTG | 950 |
| CTAGTGGCAA | GTTATCAGGT | TCAGCAGTTT | CATGGAAAGC | TCCAACGTAT | 1000 |
| TTCTCAGTCA | AAGAAGCTTC | CGAATAGAAG | AGTTTTTTGG | AAACCATCGG | 1050 |
| CTCCGGCCCA | GTGTATTCCG | GAAGAGTGAT | TGCAAGAGTA | CACACTGGCG | 1100 |
| TCTGCGGAGG | TAAATTTTCG | GCTCTCAATT | TTGGTTCTTT | CATAAATACT | 1150 |
| ATCCGGCCAT | CAGCTGCAGT | TTCGTTGTCC | GTGTGAGTGC | GTATCTTTAC | 1200 |
| CATGAAAGCA | AGACGATTTT | CTTGGAATGG | TAGAAAATAA | AGAGAAAGTT | 1250 |
| GGTCACCACT | CTTGGTTATT | GGAAGAAGAT | TTCCAGAAAA | TTCCAAAAAC | 1300 |
| TGATGTCGCC | CACTTAAGAC | TTCTACATCT | TTCGATTTCG | CAATTTCAAT | 1350 |
| GAAACGTTCT | TGTTTTTCCA | GGGTTTTATC | TTCCCGATCA | TCAGTCATAC | 1400 |
| AAAACAATCT | CAACTGTCCT | TCGGCAGGAA | AAGTTCGTCG | AGCAAAAATA | 1450 |
| AGAAATTTAG | CCATATAAGG | AACTGCAATT | GCTTCATTGT | AAACTTCTTG | 1500 |
| TGCCATTCGT | GCCGCATCTC | GCGGAGTTTG | GCAATCCATC | AACCAAAATC | 1550 |
| GAGCAGAAAC | CGTAGTTGTA | AATGAAACGT | CCTCACCAGT | AAATGTTAAC | 1600 |
| TGGGTAGTTC | CAGTAATATC | TTCCCACTGT | GCAGGAGAAG | AACCTCCAGT | 1650 |
| TTTACTGCAG | AGTAAACGCA | GCGTCGGTGG | TTCCTGTCCT | GGTTGGCCAC | 1700 |
| TATATTGTGT | TAACATTCCT | TTATTTGAGC | TTTGTGGCAA | TGGTATGCAC | 1750 |
| AGCGTTATGG | GCTTATGGAA | TTTGCGACGA | CGCGGTTCAA | CAGTTACAAT | 1800 |
| TGGAGAAACA | GCGACTCTAT | TCCCATGTAA | ACGAGTGACT | ATCTCTTGTG | 1850 |
| GAACTGGCTG | GGCTTGCACA | GATACTTTGA | TCGTCTTAGT | CAAGGAACCA | 1900 |

-continued

| | |
|---|---|
| TCCGGAAATA TGGCCTGCAC ATGAGGAACA ACTGAAGAGA GTATTACACC | 1950 |
| ACCTTCTGGA CCAACACAGT GCACTTCTTG CCGCACACGA GTAACGACCG | 2000 |
| CGAAATACAT TGGGAAATCA TTGGTCAGGA TACGCGTAAT CCGTGATGTA | 2050 |
| TGCAAATCAT CAAGTTGCGA CAACTCTTCT GCATCAAACG ATTCATTGAG | 2100 |
| CACCTCTTGT ACAGCATCTT CTGTTGCTTC AAGCTGATGC TCTTTCCAAT | 2150 |
| GCTGCCCATC ATCAGAACGC AAAATGACAA TCTCTCTCTC TCGTCCACGA | 2200 |
| AGTGATGCAA AATGTGGTAC TTCCAATATA ACAGGGCCTA AGAATTTTGC | 2250 |
| TCCATGTGGT GCCATTTCAA GTATACGTGA NGCGAGCGCT TCACCTTCAC | 2300 |
| TTAATGGTGG TGGATGCGCT AACTTGTCCT TTCCAAGGTA TCTGCATGTG | 2350 |
| ACCCGTGTAG GTTGCGGCGC TTTCCTCGGT GGTATAATGA TTCTGACACC | 2400 |
| GGAATGCCTA CAACCACGCA TTGCTCCTCC ACGTGCATCC ACCATAAACG | 2450 |
| AAATTAAAAA ACTAGGTTGC ATGGTAGTTC TCATTATCGT AACATTGTCA | 2500 |
| GGAAGCGATG CATCTAAGGA AGGATCGGCC ATCGCTGTAG TAATTGGTTC | 2550 |
| ATGTTGTGCT TTACGAATTA AGGCATCCAA ATCGCCATCC GTACCTTCCA | 2600 |
| CTTCCGGACT TCGTGACAAT GTCGGTTCTG TGGCATGAAT CAAATGTACA | 2650 |
| CCAGTTGAAT CGTGCAAACC TTTTGTGAGG CTTTCTGAGA AATCATGAGC | 2700 |
| ATGAGCATTG GCTGTGATCT GATTATCTTC ACCTTCATCT TCGGAATCGG | 2750 |
| AAAACATGGT TTCATTCATT GCTTCGGGAT TCTGAGGTTT ATATCTTTCT | 2800 |
| TCAGTAACGG TTGTGGTCTC CGTTATCACA GTAGTCTCGG TAATTGTTTT | 2850 |
| AAGCGCTTCA ACCACGGATA CATACCCTAG ACGTTCAGCA ATCGATAATG | 2900 |
| GAGTTTGTCC TGTCGATGTA TGAACATTTG GACTTGCACC ATGTTCCAAC | 2950 |
| AAGTAACGTA CAACACTGTT ATGCCCTTGC TGAGCAGCTT GATGCAGAGG | 3000 |
| AGTATAGGAA GCACGAGTAA TAACTGAAAC TCGTGCGCCA TGCTCAATCA | 3050 |
| AGAAACGGAC CATGTTTATT TGTCCAAAAT GGCAAGCAAC ATGTAACGGC | 3100 |
| GTATATCCTG CTTTCGTTTT GGGATCAATG GCTGCGTTTT CTTTCACTAG | 3150 |
| TTCTTCTGCT ACGCTCACAC GATCCTCCTG TGCACATAAA TGCATTGGTG | 3200 |
| TCAAGCCATT CCTTGCCTGA GCTCCAACTT TTGCTCCATT TTCAATTAAT | 3250 |
| AACGCAGCCA TTTCGCGATG GCCCTCCTGG GCGGCAAGAT GAAGTGGTGT | 3300 |
| AAAGCCAGCT TTGCTTTCAG CATTCGCATT TGCCTTATAA TGAAGGAGAG | 3350 |
| TGCTAGCAAT ATCCATCTGA TTCTTCTTCG CGGCAATATG TAAAGGAGTG | 3400 |
| TACCCATTCT TGGCAGCGGC ATGTGCAGAA GCACCATTTT CTAGAAGTAA | 3450 |
| CAATGCTACC TTGTCGTTAT TGTAATGTGC CGCTACATGC AGAGGTGTTA | 3500 |
| CCTGATTCTT GCCTTCAATG TCAACCGGTG TTCCTCGTTC TAGCAATGAT | 3550 |
| TTCGCGACCG GCAAATTGCC ATACTTAGCA GCTAAATGCA ACGGCGTAAA | 3600 |
| ACCCTTTTTC GTGAGCAGTG TCTTGTCGGT TCCATGATCC ATCAATATTG | 3650 |
| CTGCCACTTC CTCTTGCCCC TCCTTGGCAG CAATATGAAG AGGAGTATAA | 3700 |
| AGATCTCTTG TGGCAGCATT TGGTGATGCA TTAGCCTGCA GCAACAAAAT | 3750 |
| GACGATGTCG GTATTACCAA GACGTGATGC AATGTGCAGT GGAGTTTGTA | 3800 |
| GTTCACGAGC AGCAGCATCC ACCTGTGCTC CATTACGCAC CAAAACACGA | 3850 |
| ACAATGTCCG TTTGGTTTGC TCGTGCAGCT AAATGAAGAG GCGTTTCACC | 3900 |

-continued

```
GCGTACTGTA GCCACATCTG CATTAGCACC TTGTTGTAGT AAATAGATGA      3950

CAATGTTTAT AGCACCCATA AAAGCAGCGA CATGCAGCGG TGAGAGACCG      4000

GATTCAGTAG TTGCTTCGAT TGCAGCGTGG TATTTCAGTA GCAGTTCGAC      4050

AATTTTAATG CGATTTTTTT TGCAAGCGAT ATGCAGCGGT GTGAAGCCAT      4100

TGAGAGCTCG AGCATTCGGG TCAGCATTAC GATCCAGCAA AAGTTTAGCG      4150

ACACGGACAT GTCCGCAATG AGCAGCCACA TGAAGAGGAG TGAGATAGTC      4200

AACAGTAACA TCATCCACCT GTGCTGCCAT ATGTAAGGGA GCCAAACCAT      4250

TTTTTGTCTT AGCACTGATT GGAGCTCCTT TTTCAAGCAA CAAATCAACA      4300

ACTTGATCAT GACCTGAACG AGAAGCACAG TGTAATGGTG TTAGTAAATC      4350

ACGTGTGCGA CAGTCAATTA CGGCCCCATG AGCCAACAAT AACGAAACCA      4400

TGTTTGTACG ACCCCATTTT GTTGCAACGT GTAACGGACT TATGTTATGT      4450

CTCGCTTGGT AATTCACATT GGCTCCCTTT TCGAGTAGCA GTTGTGCTAC      4500

GTTCTCATTT CCATAGTGAG CGGCGATATG AAGCGGAGTA AAGCCGCTTT      4550

TCGAAGTCAC ATCCGAGTTA TGCTCATTTT GAAGTAATAG CGTAGCTGCT      4600

TTCGTATCAT CTTTTTTAGC AGCAATATGC AGTGCTGGCA AGCGCACTTT      4650

CCCGCGCGTG TCATTTTCAA GCAAAACAGC GACCACACGA TCGTGACCTT      4700

GTTGCAAGGC AACTGCCAGT GGCGTAAAAC CGTCTTCTGT ACTTAAAGCT      4750

TGATTGGCAT TGTGGGCAAG AAGATAGCGT ACAACAGATT CGTGATTTTC      4800

TTGTGCAGCC ATGTAAAGTG GTGTAAAACC GTTTAGTGAT TGTACGTTAA      4850

CATTAGCACC ATTTTCAACA AGTACTGTGA CGATTAGTTC TTGTCCTGCC      4900

AATGATGCTA TATGTAACGC TGTGTTACCC TTTCTAGTGG CAGCATCAAC      4950

ATCTGCTTTT CTTTTCAGAA GTTCGCGGAC CACTTCATGA TGACCTTCTT      5000

TGGAGGCCAG ATGCAATGCA TTAAGGCCAT TCGCATTGCA TGTGTTGATA      5050

TCGGTGCCCG AACGAAGTAG TTCAAGTACA CGATCCAAAT TTCCAGCTCT      5100

TGCTGCTCGT AAAAAACTTG CACTGCTCTC ACCTTTGTTG GAATGTTGAC      5150

TGTTATCATC AGGAATTTGT TGTTGATGTT GTGAATCTTT TGGTTCTGCG      5200

GGCCAGCCAC TTCCCTCGAC TATAGGATTA CTCAT                     5235
```

(2) INFORMATION FOR SEQ ID NO:37:

(i) SEQUENCE CHARACTERISTICS:
        (A) LENGTH: 908 nucleotides
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..906

(xi) SEQUENCE DESCRIPTION: SEQ ID NO:37:

```
GAT AAT GTT ACT GTT GAC TAT CTC ACT CCT CTT CAT GTG GCC         42
Asp Asn Val Thr Val Asp Tyr Leu Thr Pro Leu His Val Ala
1               5                  10

GCC CAC TGC GGA CAT GTC CGT GTC GCT AAG CTT CTG CTG GAT         84
Ala His Cys Gly His Val Arg Val Ala Lys Leu Leu Leu Asp
15                  20                  25
```

```
CGT AAT GCC GAT TCA AAT GCT CGG GCT CTC AAT GGC TTC ACA                   126
Arg Asn Ala Asp Ser Asn Ala Arg Ala Leu Asn Gly Phe Thr
 30              35              40

CCG TTG CAC ATA GCT TGC AAA AAA AAT CGC ATT AAG GTT GTC                   168
Pro Leu His Ile Ala Cys Lys Lys Asn Arg Ile Lys Val Val
 45              50              55

GAA CTG TTG CTG AAA TAT CAT GCT GCC ATC GAG GCA ACT ACA                   210
Glu Leu Leu Leu Lys Tyr His Ala Ala Ile Glu Ala Thr Thr
 60              65              70

GAA TCC GGT CTG TCG CCG CTT CAC GTC GCT GCT TTC ATG GGT                   252
Glu Ser Gly Leu Ser Pro Leu His Val Ala Ala Phe Met Gly
 75              80

GCT ATA AAC ATC GTT ATC TAC TTA CTG CAG CAG GGT GCT AAT                   294
Ala Ile Asn Ile Val Ile Tyr Leu Leu Gln Gln Gly Ala Asn
 85              90              95

GCG AAT GTG GCT ACT GTA CGC GGT GAA ACA CCT CTT CAT TTA                   336
Ala Asn Val Ala Thr Val Arg Gly Glu Thr Pro Leu His Leu
100             105             110

GCT GCA CGA GCG AAC CAA ACC GAT ATT GTC CGT GTT TTG GTA                   378
Ala Ala Arg Ala Asn Gln Thr Asp Ile Val Arg Val Leu Val
115             120             125

CGT AAT GGA GCC CAG GTG GAT GCC GCG GCA CGT GAG CTA CAA                   420
Arg Asn Gly Ala Gln Val Asp Ala Ala Ala Arg Glu Leu Gln
130             135             140

ACA CCA TTA CAT ATT GCA TCA CGT CTT GGC AAT ACT GAT ATC                   462
Thr Pro Leu His Ile Ala Ser Arg Leu Gly Asn Thr Asp Ile
145             150

GTT ATC TTG TTG CTG CAG GCA GAC GCA TCA CCA AAT GCT GCT                   504
Val Ile Leu Leu Leu Gln Ala Asp Ala Ser Pro Asn Ala Ala
155             160             165

ACA CGG GAT CTC TAC ACT CTT CTT CAT ATT GCT GCC AAA GAG                   546
Thr Arg Asp Leu Tyr Thr Leu Leu His Ile Ala Ala Lys Glu
170             175             180

GGA CAA GAG GAG GTG GCA GCA ATA TTG ATA GAT CAT GGT TCC                   588
Gly Gln Glu Glu Val Ala Ala Ile Leu Ile Asp His Gly Ser
185             190             195

GAT AAG ACA TTG CTT ACC AAG AAA GGT TTT ACA CCG TTG CAT                   630
Asp Lys Thr Leu Leu Thr Lys Lys Gly Phe Thr Pro Leu His
200             205             210

TTA GCT GCT AAA TAC GGC AAT TTA CCG GTA GCG AAA TTA TTG                   672
Leu Ala Ala Lys Tyr Gly Asn Leu Pro Val Ala Lys Leu Leu
215             220

CTG GAA CGA GGA ACT TTG GTT GAC ATT GAA GGC AAG AAC CAG                   714
Leu Glu Arg Gly Thr Leu Val Asp Ile Glu Gly Lys Asn Gln
225             230             235

GTG ACA CCT TTG CAT GTA GCA GCA CAT TAT AAT AAC GAC AAG                   756
Val Thr Pro Leu His Val Ala Ala His Tyr Asn Asn Asp Lys
240             245             250

GTA GCG CTG CTG CTT CTA GAA AGT GGT GCT TCC GCA CAT GCC                   798
Val Ala Leu Leu Leu Glu Ser Gly Ala Ser Ala His Ala
255             260             265

GTT GCC AAG AAT GGA TAT ACT CCT TTG CAT ATT GCT GCA AAG                   840
Val Ala Lys Asn Gly Tyr Thr Pro Leu His Ile Ala Ala Lys
270             275             280

AAA AAT CAG ATG GAT ATT GCT AGC ACT CTT CTT CAT TAT AGG                   882
Lys Asn Gln Met Asp Ile Ala Ser Thr Leu Leu His Tyr Arg
285             290

GCA AAT GCG AAT GCT GAA AGC AAA GC                                        908
Ala Asn Ala Asn Ala Glu Ser Lys
```

(2) INFORMATION FOR SEQ ID NO:38:

(i) SEQUENCE CHARACTERISTICS:
        (A) LENGTH: 302 amino acids
        (B) TYPE: amino acid
        (D) TOPOLOGY: linear (ii) MOLECULE TYPE: protein (xi) SEQUENCE DESCRIPTION: SEQ ID NO:38:

```
Asp Asn Val Thr Val Asp Tyr Leu Thr Pro Leu His Val Ala
 1               5                  10
Ala His Cys Gly His Val Arg Val Ala Lys Leu Leu Leu Asp
15                  20                  25
Arg Asn Ala Asp Ser Asn Ala Arg Ala Leu Asn Gly Phe Thr
        30                  35                  40
Pro Leu His Ile Ala Cys Lys Lys Asn Arg Ile Lys Val Val
            45                  50                  55
Glu Leu Leu Leu Lys Tyr His Ala Ala Ile Glu Ala Thr Thr
                60                  65                  70
Glu Ser Gly Leu Ser Pro Leu His Val Ala Ala Phe Met Gly
                    75                  80
Ala Ile Asn Ile Val Ile Tyr Leu Leu Gln Gln Gly Ala Asn
85                  90                  95
Ala Asn Val Ala Thr Val Arg Gly Glu Thr Pro Leu His Leu
        100                 105                 110
Ala Ala Arg Ala Asn Gln Thr Asp Ile Val Arg Val Leu Val
            115                 120                 125
Arg Asn Gly Ala Gln Val Asp Ala Ala Arg Glu Leu Gln
                130                 135                 140
Thr Pro Leu His Ile Ala Ser Arg Leu Gly Asn Thr Asp Ile
                    145                 150
Val Ile Leu Leu Leu Gln Ala Asp Ala Ser Pro Asn Ala Ala
155                 160                 165
Thr Arg Asp Leu Tyr Thr Leu Leu His Ile Ala Ala Lys Glu
        170                 175                 180
Gly Gln Glu Glu Val Ala Ala Ile Leu Ile Asp His Gly Ser
            185                 190                 195
Asp Lys Thr Leu Leu Thr Lys Lys Gly Phe Thr Pro Leu His
                200                 205                 210
Leu Ala Ala Lys Tyr Gly Asn Leu Pro Val Ala Lys Leu Leu
                    215                 220
Leu Glu Arg Gly Thr Leu Val Asp Ile Glu Gly Lys Asn Gln
225                 230                 235
Val Thr Pro Leu His Val Ala Ala His Tyr Asn Asn Asp Lys
        240                 245                 250
Val Ala Leu Leu Leu Leu Glu Ser Gly Ala Ser Ala His Ala
            255                 260                 265
Val Ala Lys Asn Gly Tyr Thr Pro Leu His Ile Ala Ala Lys
                270                 275                 280
Lys Asn Gln Met Asp Ile Ala Ser Thr Leu Leu His Tyr Arg
                    285                 290
Ala Asn Ala Asn Ala Glu Ser Lys
295                 300
```

(2) INFORMATION FOR SEQ ID NO:39:

(i) SEQUENCE CHARACTERISTICS:
        (A) LENGTH: 908 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:39:

```
GCTTTGCTTT CAGCATTCGC ATTTGCCCTA TAATGAAGAA GAGTGCTAGC          50

AATATCCATC TGATTTTTCT TTGCAGCAAT ATGCAAAGGA GTATATCCAT         100

TCTTGGCAAC GGCATGTGCG GAAGCACCAC TTTCTAGAAG CAGCAGCGCT         150

ACCTTGTCGT TATTATAATG TGCTGCTACA TGCAAAGGTG TCACCTGGTT         200

CTTGCCTTCA ATGTCAACCA AAGTTCCTCG TTCCAGCAAT AATTTCGCTA         250

CCGGTAAATT GCCGTATTTA GCAGCTAAAT GCAACGGTGT AAAACCTTTC         300

TTGGTAAGCA ATGTCTTATC GGAACCATGA TCTATCAATA TTGCTGCCAC         350

CTCCTCTTGT CCCTCTTTGG CAGCAATATG AAGAAGAGTG TAGAGATCCC         400

GTGTAGCAGC ATTTGGTGAT GCGTCTGCCT GCAGCAACAA GATAACGATA         450

TCAGTATTGC CAAGACGTGA TGCAATATGT AATGGTGTTT GTAGCTCACG         500

TGCCGCGGCA TCCACCTGGG CTCCATTACG TACCAAAACA CGGACAATAT         550

CGGTTTGGTT CGCTCGTGCA GCTAAATGAA GAGGTGTTTC ACCGCGTACA         600

GTAGCCACAT TCGCATTAGC ACCCTGCTGC AGTAAGTAGA TAACGATGTT         650

TATAGCACCC ATGAAAGCAG CGACGTGAAG CGGCGACAGA CCGGATTCTG         700

TAGTTGCCTC GATGGCAGCA TGATATTTCA GCAACAGTTC GACAACCTTA         750

ATGCGATTTT TTTTGCAAGC TATGTGCAAC GGTGTGAAGC CATTGAGAGC         800

CCGAGCATTT GAATCGGCAT TACGATCCAG CAGAAGCTTA GCGACACGGA         850

CATGTCCGCA GTGGGCGGCC ACATGAAGAG GAGTGAGATA GTCAACAGTA         900

ACATTATC                                                      908
```

(2) INFORMATION FOR SEQ ID NO:40:

(i) SEQUENCE CHARACTERISTICS:
        (A) LENGTH: 906 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:40:

```
GATAATGTTA CTGTTGACTA TCTCACTCCT CTTCATGTGG CCGCCCACTG          50

CGGACATGTC CGTGTCGCTA AGCTTCTGCT GGATCGTAAT GCCGATTCAA         100

ATGCTCGGGC TCTCAATGGC TTCACACCGT TGCACATAGC TTGCAAAAAA         150

AATCGCATTA AGGTTGTCGA ACTGTTGCTG AAATATCATG CTGCCATCGA         200

GGCAACTACA GAATCCGGTC TGTCGCCGCT TCACGTCGCT GCTTTCATGG         250

GTGCTATAAA CATCGTTATC TACTTACTGC AGCAGGGTGC TAATGCGAAT         300

GTGGCTACTG TACGCGGTGA AACACCTCTT CATTTAGCTG CACGAGCGAA         350
```

-continued

| | |
|---|---|
| CCAAACCGAT ATTGTCCGTG TTTTGGTACG TAATGGAGCC CAGGTGGATG | 400 |
| CCGCGGCACG TGAGCTACAA ACACCATTAC ATATTGCATC ACGTCTTGGC | 450 |
| AATACTGATA TCGTTATCTT GTTGCTGCAG GCAGACGCAT CACCAAATGC | 500 |
| TGCTACACGG GATCTCTACA CTCTTCTTCA TATTGCTGCC AAAGAGGGAC | 550 |
| AAGAGGAGGT GGCAGCAATA TTGATAGATC ATGGTTCCGA TAAGACATTG | 600 |
| CTTACCAAGA AAGGTTTTAC ACCGTTGCAT TTAGCTGCTA AATACGGCAA | 650 |
| TTTACCGGTA GCGAAATTAT TGCTGGAACG AGGAACTTTG GTTGACATTG | 700 |
| AAGGCAAGAA CCAGGTGACA CCTTTGCATG TAGCAGCACA TTATAATAAC | 750 |
| GACAAGGTAG CGCTGCTGCT TCTAGAAAGT GGTGCTTCCG CACATGCCGT | 800 |
| TGCCAAGAAT GGATATACTC CTTTGCATAT TGCTGCAAAG AAAAATCAGA | 850 |
| TGGATATTGC TAGCACTCTT CTTCATTATA GGGCAAATGC GAATGCTGAA | 900 |
| AGCAAA | 906 |

(2) INFORMATION FOR SEQ ID NO:41:

(i) SEQUENCE CHARACTERISTICS:
        (A) LENGTH: 906 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:41:

| | |
|---|---|
| TTTGCTTTCA GCATTCGCAT TTGCCCTATA ATGAAGAAGA GTGCTAGCAA | 50 |
| TATCCATCTG ATTTTTCTTT GCAGCAATAT GCAAAGGAGT ATATCCATTC | 100 |
| TTGGCAACGG CATGTGCGGA AGCACCACTT TCTAGAAGCA GCAGCGCTAC | 150 |
| CTTGTCGTTA TTATAATGTG CTGCTACATG CAAAGGTGTC ACCTGGTTCT | 200 |
| TGCCTTCAAT GTCAACCAAA GTTCCTCGTT CCAGCAATAA TTTCGCTACC | 250 |
| GGTAAATTGC CGTATTTAGC AGCTAAATGC AACGGTGTAA AACCTTTCTT | 300 |
| GGTAAGCAAT GTCTTATCGG AACCATGATC TATCAATATT GCTGCCACCT | 350 |
| CCTCTTGTCC CTCTTTGGCA GCAATATGAA GAAGAGTGTA GAGATCCCGT | 400 |
| GTAGCAGCAT TTGGTGATGC GTCTGCCTGC AGCAACAAGA TAACGATATC | 450 |
| AGTATTGCCA AGACGTGATG CAATATGTAA TGGTGTTTGT AGCTCACGTG | 500 |
| CCGCGGCATC CACCTGGGCT CCATTACGTA CCAAAACACG GACAATATCG | 550 |
| GTTTGGTTCG CTCGTGCAGC TAAATGAAGA GGTGTTTCAC CGCGTACAGT | 600 |
| AGCCACATTC GCATTAGCAC CCTGCTGCAG TAAGTAGATA ACGATGTTTA | 650 |
| TAGCACCCAT GAAAGCAGCG ACGTGAAGCG GCGACAGACC GGATTCTGTA | 700 |
| GTTGCCTCGA TGGCAGCATG ATATTTCAGC AACAGTTCGA CAACCTTAAT | 750 |
| GCGATTTTTT TTGCAAGCTA TGTGCAACGG TGTGAAGCCA TTGAGAGCCC | 800 |
| GAGCATTTGA ATCGGCATTA CGATCCAGCA GAAGCTTAGC GACACGGACA | 850 |
| TGTCCGCAGT GGGCGGCCAC ATGAAGAGGA GTGAGATAGT CAACAGTAAC | 900 |
| ATTATC | 906 |

(2) INFORMATION FOR SEQ ID NO:42:

(i) SEQUENCE CHARACTERISTICS:

(A) LENGTH:  23 nucleotides
        (B) TYPE:  nucleic acid
        (C) STRANDEDNESS:  single
        (D) TOPOLOGY:  linear (ii) MOLECULE TYPE:  primer (xi) SEQUENCE DESCRIPTION:  SEQ ID NO:42:

CATCAATTTT TGGAATTTTC TGG                                                23

(2) INFORMATION FOR SEQ ID NO:43:

(i) SEQUENCE CHARACTERISTICS:
        (A) LENGTH:  22 nucleotides
        (B) TYPE:  nucleic acid
        (C) STRANDEDNESS:  single
        (D) TOPOLOGY:  linear (ii) MOLECULE TYPE:  primer (xi) SEQUENCE DESCRIPTION:  SEQ ID NO:43:

CGTTTACAGC AACATCATCC TC                                                 22

(2) INFORMATION FOR SEQ ID NO:44:

(i) SEQUENCE CHARACTERISTICS:
        (A) LENGTH:  22 nucleotides
        (B) TYPE:  nucleic acid
        (C) STRANDEDNESS:  single
        (D) TOPOLOGY:  linear (ii) MOLECULE TYPE:  primer (xi) SEQUENCE DESCRIPTION:  SEQ ID NO:44:

GCACAACCAG TTCCGCAAGA AA                                                 22

(2) INFORMATION FOR SEQ ID NO:45:

(i) SEQUENCE CHARACTERISTICS:
        (A) LENGTH:  21 nucleotides
        (B) TYPE:  nucleic acid
        (C) STRANDEDNESS:  single
        (D) TOPOLOGY:  linear (ii) MOLECULE TYPE:  primer (xi) SEQUENCE DESCRIPTION:  SEQ ID NO:45:

GGTTATTGGA AGAAGATTTC C                                                  21

(2) INFORMATION FOR SEQ ID NO:46:

(i) SEQUENCE CHARACTERISTICS:
        (A) LENGTH:  23 nucleotides
        (B) TYPE:  nucleic acid
        (C) STRANDEDNESS:  single
        (D) TOPOLOGY:  linear (ii) MOLECULE TYPE:  primer (ix) FEATURE:
        (A) NAME/KEY:  N = any nucleotide
        (B) LOCATION:  9, 13

(xi) SEQUENCE DESCRIPTION:  SEQ ID NO:46:

CAYCARGCNG CNCARCARGG NCA                                                23

(2) INFORMATION FOR SEQ ID NO:47:

(i) SEQUENCE CHARACTERISTICS:

(A) LENGTH:  23 nucleotides
        (B) TYPE:  nucleic acid
        (C) STRANDEDNESS:  single
        (D) TOPOLOGY:  linear (ii) MOLECULE TYPE:  primer (ix) FEATURE:
        (A) NAME/KEY:  N = any nucleotide
        (B) LOCATION:  3, 13, 16, 19

(xi) SEQUENCE DESCRIPTION:  SEQ ID NO:47:

GTNGAYGAYG TNACNGTNGA YTA                                              23

(2) INFORMATION FOR SEQ ID NO:48:

(i) SEQUENCE CHARACTERISTICS:
        (A) LENGTH:  22 nucleotides
        (B) TYPE:  nucleic acid
        (C) STRANDEDNESS:  single
        (D) TOPOLOGY:  linear (ii) MOLECULE TYPE:  primer (xi) SEQUENCE DESCRIPTION:  SEQ ID NO:48:

GGAATTTGCG ACGACGCGGT TC                                               22

(2) INFORMATION FOR SEQ ID NO:49:

(i) SEQUENCE CHARACTERISTICS:
        (A) LENGTH: 17 nucleotides
        (B) TYPE:  nucleic acid
        (C) STRANDEDNESS:  single
        (D) TOPOLOGY:  linear (ii) MOLECULE TYPE:  primer (xi) SEQUENCE DESCRIPTION:  SEQ ID NO:49:

CAGGAAACAG CTATGAC                                                     17

(2) INFORMATION FOR SEQ ID NO:50:

(i) SEQUENCE CHARACTERISTICS:
        (A) LENGTH:  24 nucleotides
        (B) TYPE:  nucleic acid
        (C) STRANDEDNESS:  single
        (D) TOPOLOGY:  linear (ii) MOLECULE TYPE:  primer (xi) SEQUENCE DESCRIPTION:  SEQ ID NO:50:

TGGAGTTTGT CCTGTCGATG TATG                                             24

(2) INFORMATION FOR SEQ ID NO:51:

(i) SEQUENCE CHARACTERISTICS:
        (A) LENGTH:  27 nucleotides
        (B) TYPE:  nucleic acid
        (C) STRANDEDNESS:  single
        (D) TOPOLOGY:  linear (ii) MOLECULE TYPE:  primer (xi) SEQUENCE DESCRIPTION:  SEQ ID NO:51:

GCTTTGCTTT CAGCATTCGC ATTTGCC                                          27

(2) INFORMATION FOR SEQ ID NO:52:

(i) SEQUENCE CHARACTERISTICS:

(A) LENGTH:  22 nucleotides
        (B) TYPE:  nucleic acid
        (C) STRANDEDNESS:  single
        (D) TOPOLOGY:  linear (ii) MOLECULE TYPE:  primer (xi) SEQUENCE DESCRIPTION:  SEQ ID NO:52:

GGTTTAATTA CCCAAGTTTG AG                                                    22

(2) INFORMATION FOR SEQ ID NO:53:

(i) SEQUENCE CHARACTERISTICS:
        (A) LENGTH:  27 nucleotides
        (B) TYPE:  nucleic acid
        (C) STRANDEDNESS:  single
        (D) TOPOLOGY:  linear (ii) MOLECULE TYPE:  primer (xi) SEQUENCE DESCRIPTION:  SEQ ID NO:53:

GTGAGATAGT CAACAGTAAC ATCATCC                                               27

(2) INFORMATION FOR SEQ ID NO:54:

(i) SEQUENCE CHARACTERISTICS:
        (A) LENGTH:  31 nucleotides
        (B) TYPE:  nucleic acid
        (C) STRANDEDNESS:  single
        (D) TOPOLOGY:  linear (ii) MOLECULE TYPE:  primer (xi) SEQUENCE DESCRIPTION:  SEQ ID NO:54:

CGCGGATCCG GCACAACCAG TTCCGCAAGA A                                          31

(2) INFORMATION FOR SEQ ID NO:55:

(i) SEQUENCE CHARACTERISTICS:
        (A) LENGTH:  30 nucleotides
        (B) TYPE:  nucleic acid
        (C) STRANDEDNESS:  single
        (D) TOPOLOGY:  linear (ii) MOLECULE TYPE:  primer (xi) SEQUENCE DESCRIPTION:  SEQ ID NO:55:

CCGGAATTCT TATTCATGAA CGCTTTGCCC                                            30

(2) INFORMATION FOR SEQ ID NO:56:

(i) SEQUENCE CHARACTERISTICS:
        (A) LENGTH:  33 nucleotides
        (B) TYPE:  nucleic acid
        (C) STRANDEDNESS:  single
        (D) TOPOLOGY:  linear (ii) MOLECULE TYPE:  primer (xi) SEQUENCE DESCRIPTION:  SEQ ID NO:56:

CGCGGATTCG CGCGGTGCTA ATGCAGATGT GGC                                        33

(2) INFORMATION FOR SEQ ID NO:57:

(i) SEQUENCE CHARACTERISTICS:
        (A) LENGTH:  35 nucleotides
        (B) TYPE:  nucleic acid
        (C) STRANDEDNESS:  single
        (D) TOPOLOGY:  linear

```
        (ii) MOLECULE TYPE: primer (xi) SEQUENCE DESCRIPTION: SEQ ID NO:57:

CCGGAATTCC GGTTACCCTA GACGTTCAGC AATCG                              35

(2) INFORMATION FOR SEQ ID NO:58:

(i) SEQUENCE CHARACTERISTICS:
             (A) LENGTH: 34 nucleotides
             (B) TYPE: nucleic acid
             (C) STRANDEDNESS: single
             (D) TOPOLOGY: linear (ii) MOLECULE TYPE: primer (xi) SEQUENCE DESCRIPTION: SEQ ID NO:58:

CGCGGATCCG CGCGCACGTG GAGGAGCAAT GCGT                               34

(2) INFORMATION FOR SEQ ID NO:59:

(i) SEQUENCE CHARACTERISTICS:
             (A) LENGTH: 36 nucleotides
             (B) TYPE: nucleic acid
             (C) STRANDEDNESS: single
             (D) TOPOLOGY: linear (ii) MOLECULE TYPE: primer (xi) SEQUENCE DESCRIPTION: SEQ ID NO:59:

CCGGAATTCC GGTTATTCGT TGTCCGTGTG AGTGCG                             36

(2) INFORMATION FOR SEQ ID NO:60:

(i) SEQUENCE CHARACTERISTICS:
             (A) LENGTH: 37 nucleotides
             (B) TYPE: nucleic acid
             (C) STRANDEDNESS: single
             (D) TOPOLOGY: linear (ii) MOLECULE TYPE: primer (xi) SEQUENCE DESCRIPTION: SEQ ID NO:60:

CGCGGATCCG CGCCAACTAG TTGGTCTTGA AGCAGTC                            37

(2) INFORMATION FOR SEQ ID NO:61:

(i) SEQUENCE CHARACTERISTICS:
             (A) LENGTH: 33 amino acids
             (B) TYPE: amino acid
             (D) TOPOLOGY: linear (ii) MOLECULE TYPE: protein (xi) SEQUENCE DESCRIPTION: SEQ ID NO:61:

Glu Ser Ser Ala Ser Phe Leu Arg Ala Ala Arg Ala Gly Asn
 1               5                  10

Leu Asp Arg Val Leu Glu Leu Leu Arg Ser Gly Thr Asp Ile
15                  20                  25

Asn Thr Cys Asn Ala
    30

(2) INFORMATION FOR SEQ ID NO:62:

(i) SEQUENCE CHARACTERISTICS:
             (A) LENGTH: 33 amino acids
             (B) TYPE: amino acid
```

(D) TOPOLOGY:  linear (ii) MOLECULE TYPE:  protein (xi) SEQUENCE DESCRIPTION:  SEQ ID NO:62:

Asn Gly Leu Asn Ala Leu His Leu Ala Ser Lys Glu Gly His
1               5                  10
His Glu Val Val Arg Glu Leu Leu Lys Arg Lys Ala Asp Val
15                  20                  25
Asp Ala Ala Thr Arg
    30

(2) INFORMATION FOR SEQ ID NO:63:

(i) SEQUENCE CHARACTERISTICS:
            (A) LENGTH:  33 amino acids
            (B) TYPE:  amino acid
            (D) TOPOLOGY:  linear (ii) MOLECULE TYPE:  protein (xi) SEQUENCE DESCRIPTION:  SEQ ID NO:63:

Lys Gly Asn Thr Ala Leu His Ile Ala Ser Leu Ala Gly Gln
1               5                  10
Glu Leu Ile Val Thr Val Leu Val Glu Asn Gly Ala Asn Val
15                  20                  25
Asn Val Gln Ser Leu
    30

(2) INFORMATION FOR SEQ ID NO:64:

(i) SEQUENCE CHARACTERISTICS:
            (A) LENGTH:  33 amino acids
            (B) TYPE:  amino acid
            (D) TOPOLOGY:  linear (ii) MOLECULE TYPE:  protein (xi) SEQUENCE DESCRIPTION:  SEQ ID NO:64:

Asn Gly Phe Thr Pro Leu Tyr Met Ala Ala Gln Glu Asn His
1               5                  10
Glu Ser Val Val Arg Tyr Leu Leu Ala His Asn Ala Asn Gln
15                  20                  25
Ala Leu Ser Thr Glu
    30

(2) INFORMATION FOR SEQ ID NO:65:

(i) SEQUENCE CHARACTERISTICS:
            (A) LENGTH:  29 amino acids
            (B) TYPE:  amino acid
            (D) TOPOLOGY:  linear (ii) MOLECULE TYPE:  protein (xi) SEQUENCE DESCRIPTION:  SEQ ID NO:65:

Asp Gly Phe Thr Pro Leu Ala Val Ala Leu Gln Gln Gly His
1               5                          20
Asp Arg Val Val Ala Val Leu Leu Glu Asn Asp Thr Arg Gly
15                  20                  25
Lys (2) INFORMATION FOR SEQ ID NO:66:

```
        (i) SEQUENCE CHARACTERISTICS:
            (A) LENGTH:  33 amino acids
            (B) TYPE:  amino acid
            (D) TOPOLOGY:  linear (ii) MOLECULE TYPE:  protein (xi) SEQUENCE DESCRIPTION:  SEQ ID NO:66:

Val Arg Leu Pro Ala Leu His Ile Ala Ala Lys Lys Asp Asp
 1               5                  10

Thr Lys Ala Ala Thr Leu Leu Leu Gln Asn Glu His Asn Ser
15                  20                  25

Asp Val Thr Ser Lys
    30

(2) INFORMATION FOR SEQ ID NO:67:

(i) SEQUENCE CHARACTERISTICS:
            (A) LENGTH:  33 amino acids
            (B) TYPE:  amino acid
            (D) TOPOLOGY:  linear (ii) MOLECULE TYPE:  protein (xi) SEQUENCE DESCRIPTION:  SEQ ID NO:67:

Ser Gly Phe Thr Pro Leu His Ile Ala Ala His Tyr Gly Asn
 1               5                  10

Glu Asn Val Ala Gln Leu Leu Leu Glu Lys Gly Ala Asn Val
15                  20                  25

Asn Tyr Gln Ala Arg
    30

(2) INFORMATION FOR SEQ ID NO:68:

(i) SEQUENCE CHARACTERISTICS:
            (A) LENGTH:  33 amino acids
            (B) TYPE:  amino acid
            (D) TOPOLOGY:  linear (ii) MOLECULE TYPE:  protein (xi) SEQUENCE DESCRIPTION:  SEQ ID NO:68:

His Asn Ile Ser Pro Leu His Val Ala Thr Lys Trp Gly Arg
 1               5                  10

Thr Asn Met Val Ser Leu Leu Leu Ala His Gly Ala Val Ile
15                  20                  25

Asp Cys Arg Thr Arg
    30

(2) INFORMATION FOR SEQ ID NO:69:

(i) SEQUENCE CHARACTERISTICS:
            (A) LENGTH:  33 amino acids
            (B) TYPE:  amino acid
            (D) TOPOLOGY:  linear (ii) MOLECULE TYPE:  protein (xi) SEQUENCE DESCRIPTION:  SEQ ID NO:69:

Asp Leu Leu Thr Pro Leu His Cys Ala Ser Arg Ser Gly His
 1               5                  10

Asp Gln Val Val Asp Leu Leu Leu Glu Lys Gly Ala Pro Ile
15                  20                  25
```

```
Ser Ala Lys Thr Lys
    30

(2) INFORMATION FOR SEQ ID NO:70:

(i) SEQUENCE CHARACTERISTICS:
        (A) LENGTH:  17 amino acids
        (B) TYPE:  amino acid
        (D) TOPOLOGY:  linear (ii) MOLECULE TYPE:  protein (xi) SEQUENCE DESCRIPTION:  SEQ ID NO:70:

Asn Gly Leu Ala Pro Leu His Met Ala Ala Gln Val Asp Asp
1               5                   10

Val Thr Val
15

(2) INFORMATION FOR SEQ ID NO:71:

(i) SEQUENCE CHARACTERISTICS:
        (A) LENGTH:  33 amino acids
        (B) TYPE:  amino acid
        (D) TOPOLOGY:  linear (ii) MOLECULE TYPE:  protein (xi) SEQUENCE DESCRIPTION:  SEQ ID NO:71:

Asp Tyr Leu Thr Pro Leu His Val Ala Ala His Cys Gly His
1               5                   10

Val Arg Val Ala Lys Leu Leu Leu Asp Arg Asn Ala Asp Pro
15                  20                  25

Asn Ala Arg Ala Leu
    30

(2) INFORMATION FOR SEQ ID NO:72:

(i) SEQUENCE CHARACTERISTICS:
        (A) LENGTH:  33 amino acids
        (B) TYPE:  amino acid
        (D) TOPOLOGY:  linear (ii) MOLECULE TYPE:  protein (xi) SEQUENCE DESCRIPTION:  SEQ ID NO:72:

Asn Gly Phe Thr Pro Leu His Ile Ala Cys Lys Lys Asn Arg
1               5                   10

Ile Lys Ile Val Glu Leu Leu Leu Lys Tyr His Ala Ala Ile
15                  20                  25

Glu Ala Thr Thr Glu
    30

(2) INFORMATION FOR SEQ ID NO:73:

(i) SEQUENCE CHARACTERISTICS:
        (A) LENGTH:  33 amino acids
        (B) TYPE:  amino acid
        (D) TOPOLOGY:  linear (ii) MOLECULE TYPE:  protein (xi) SEQUENCE DESCRIPTION:  SEQ ID NO:73:

Ser Gly Leu Ser Pro Leu His Val Ala Ala Phe Met Gly Ala
1               5                   10

Ile Asn Ile Val Ile Tyr Leu Leu Gln Gln Gly Ala Asn Ala
```

```
15              20              25

Asp Val Ala Thr Val
     30

(2) INFORMATION FOR SEQ ID NO:74:

(i) SEQUENCE CHARACTERISTICS:
        (A) LENGTH: 33 amino acids
        (B) TYPE: amino acid
        (D) TOPOLOGY: linear (ii) MOLECULE TYPE: protein (xi) SEQUENCE DESCRIPTION: SEQ ID NO:74:

Arg Gly Glu Thr Pro Leu His Leu Ala Ala Arg Ala Asn Gln
 1               5                  10

Thr Asp Ile Val Arg Val Leu Val Arg Asn Gly Ala Gln Val
15              20              25

Asp Ala Ala Ala Arg
     30

(2) INFORMATION FOR SEQ ID NO:75:

(i) SEQUENCE CHARACTERISTICS:
        (A) LENGTH: 33 amino acids
        (B) TYPE: amino acid
        (D) TOPOLOGY: linear (ii) MOLECULE TYPE: protein (xi) SEQUENCE DESCRIPTION: SEQ ID NO:75:

Glu Leu Gln Thr Pro Leu His Ile Ala Ser Arg Leu Gly Asn
 1               5                  10

Thr Asp Ile Val Ile Leu Leu Leu Gln Ala Asn Ala Ser Pro
15              20              25

Asn Ala Ala Thr Arg
     30

(2) INFORMATION FOR SEQ ID NO:76:

(i) SEQUENCE CHARACTERISTICS:
        (A) LENGTH: 33 amino acids
        (B) TYPE: amino acid
        (D) TOPOLOGY: linear (ii) MOLECULE TYPE: protein (xi) SEQUENCE DESCRIPTION: SEQ ID NO:76:

Asp Leu Tyr Thr Pro Leu His Ile Ala Ala Lys Glu Gly Gln
 1               5                  10

Glu Glu Val Ala Ala Ile Leu Met Asp His Gly Thr Asp Lys
15              20              25

Thr Leu Leu Thr Lys
     30

(2) INFORMATION FOR SEQ ID NO:77:

(i) SEQUENCE CHARACTERISTICS:
        (A) LENGTH: 33 amino acids
        (B) TYPE: amino acid
        (D) TOPOLOGY: linear (ii) MOLECULE TYPE: protein (xi) SEQUENCE DESCRIPTION: SEQ ID NO:77:
```

```
Lys Gly Phe Thr Pro Leu His Leu Ala Ala Lys Tyr Gly Asn
1               5                   10

Leu Pro Val Ala Lys Ser Leu Leu Glu Arg Gly Thr Pro Val
15                  20                  25

Asp Ile Glu Gly Lys
    30
```

(2) INFORMATION FOR SEQ ID NO:78:

(i) SEQUENCE CHARACTERISTICS:
        (A) LENGTH: 33 amino acids
        (B) TYPE: amino acid
        (D) TOPOLOGY: linear (ii) MOLECULE TYPE: protein (xi) SEQUENCE DESCRIPTION: SEQ ID NO:78:

```
Asn Gln Val Thr Pro Leu His Val Ala Ala His Tyr Asn Asn
1               5                   10

Asp Lys Val Ala Leu Leu Leu Leu Glu Asn Gly Ala Ser Ala
15                  20                  25

His Ala Ala Ala Lys
    30
```

(2) INFORMATION FOR SEQ ID NO:79:

(i) SEQUENCE CHARACTERISTICS:
        (A) LENGTH: 33 amino acids
        (B) TYPE: amino acid
        (D) TOPOLOGY: linear (ii) MOLECULE TYPE: protein (xi) SEQUENCE DESCRIPTION: SEQ ID NO:79:

```
Asn Gly Tyr Thr Pro Leu His Ile Ala Ala Lys Lys Asn Gln
1               5                   10

Met Asp Ile Ala Ser Thr Leu Leu His Tyr Lys Ala Asn Ala
15                  20                  25

Asn Ala Glu Ser Lys
    30
```

(2) INFORMATION FOR SEQ ID NO:80:

(i) SEQUENCE CHARACTERISTICS:
        (A) LENGTH: 33 amino acids
        (B) TYPE: amino acid
        (D) TOPOLOGY: linear (ii) MOLECULE TYPE: protein (xi) SEQUENCE DESCRIPTION: SEQ ID NO:80:

```
Ala Gly Phe Thr Pro Leu His Leu Ala Ala Gln Glu Gly His
1               5                   10

Arg Glu Met Ala Ala Leu Leu Ile Glu Asn Gly Ala Lys Val
15                  20                  25

Gly Ala Gln Ala Arg
    30
```

(2) INFORMATION FOR SEQ ID NO:81:

(i) SEQUENCE CHARACTERISTICS:
        (A) LENGTH: 33 amino acids
        (B) TYPE: amino acid (D) TOPOLOGY:  linear (ii) MOLECULE TYPE:  protein (xi) SEQUENCE DESCRIPTION:  SEQ ID NO:81:

Asn Gly Leu Thr Pro Met His Leu Cys Ala Gln Glu Asp Arg
1               5                  10

Val Ser Val Ala Glu Glu Leu Val Lys Glu Asn Ala Ala Ile
15                  20                  25

Asp Pro Lys Thr Lys
    30

(2) INFORMATION FOR SEQ ID NO:82:

(i) SEQUENCE CHARACTERISTICS:
        (A) LENGTH:  33 amino acids
        (B) TYPE:  amino acid
        (D) TOPOLOGY:  linear (ii) MOLECULE TYPE:  protein (xi) SEQUENCE DESCRIPTION:  SEQ ID NO:82:

Ala Gly Tyr Thr Pro Leu His Val Ala Cys His Phe Gly Gln
1               5                  10

Ile Asn Met Val Arg Phe Leu Ile Glu His Gly Ala Arg Val
15                  20                  25

Ser Val Ile Thr Arg
    30

(2) INFORMATION FOR SEQ ID NO:83:

(i) SEQUENCE CHARACTERISTICS:
        (A) LENGTH:  33 amino acids
        (B) TYPE:  amino acid
        (D) TOPOLOGY:  linear (ii) MOLECULE TYPE:  protein (xi) SEQUENCE DESCRIPTION:  SEQ ID NO:83:

Ala Ser Tyr Thr Pro Leu His Gln Ala Ala Gln Gln Gly His
1               5                  10

Asn Ser Val Val Arg Tyr Leu Leu Glu His Gly Ala Ser Pro
15                  20                  25

Asn Val His Thr Ser
    30

(2) INFORMATION FOR SEQ ID NO:84:

(i) SEQUENCE CHARACTERISTICS:
        (A) LENGTH:  33 amino acids
        (B) TYPE:  amino acid
        (D) TOPOLOGY:  linear (ii) MOLECULE TYPE:  protein (xi) SEQUENCE DESCRIPTION:  SEQ ID NO:84:

Thr Gly Gln Thr Pro Leu Ser Ile Ala Glu Arg Leu Gly Tyr
1               5                  10

Val Ser Val Val Glu Ala Leu Lys Thr Ile Thr Glu Thr Thr
15                  20                  25

Val Ile Thr Glu Thr
    30

```
(2) INFORMATION FOR SEQ ID NO:85:

(i) SEQUENCE CHARACTERISTICS:
        (A) LENGTH: 33 amino acids
        (B) TYPE: amino acid
        (D) TOPOLOGY: linear (ii) MOLECULE TYPE: protein (ix) FEATURE:
        (A) NAME/KEY: Xaa = any amino acid
        (B) LOCATION: 1, 3, 8, 11, 12, 15, 16,
            17, 19, 20, 23, 24, 27, 28,
            30, 31, 32, 33

(ix) FEATURE:
        (A) NAME/KEY: Xaa = Val or Ala
        (B) LOCATION: 18

(ix) FEATURE:
        (A) NAME/KEY: Xaa = Asn or Asp
        (B) LOCATION: 29

(xi) SEQUENCE DESCRIPTION: SEQ ID NO:85:

Xaa Gly Xaa Thr Pro Leu His Xaa Ala Ala Xaa Xaa Gly His
  1               5                  10

Xaa Xaa Xaa Xaa Xaa Xaa Leu Leu Xaa Xaa Gly Ala Xaa Xaa
 15                  20                  25

Xaa Xaa Xaa Xaa Xaa
     30

(2) INFORMATION FOR SEQ ID NO:86:

(i) SEQUENCE CHARACTERISTICS:
        (A) LENGTH: 102 nucleotides
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..102

(xi) SEQUENCE DESCRIPTION: SEQ ID NO:86:

ATG AGT AAT CCT ATA GTC GAG GGA AGT GGC TGG CCC GCA GAA          42
Met Ser Asn Pro Ile Val Glu Gly Ser Gly Trp Pro Ala Glu
  1               5                  10

CCA AAA GAT TCA CAA CAT CAA CAA CAA ATT CCT GAT GAT AAC          84
Pro Lys Asp Ser Gln His Gln Gln Gln Ile Pro Asp Asp Asn
 15                  20                  25

AGT CAA CAT TCC AAC AAA                                         102
Ser Gln His Ser Asn Lys
     30

(2) INFORMATION FOR SEQ ID NO:87:

(i) SEQUENCE CHARACTERISTICS:
        (A) LENGTH: 102 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:87:

TTTGTTGGAA TGTTGACTGT TATCATCAGG AATTTGTTGT TGATGTTGTG           50

AATCTTTTGG TTCTGCGGGC CAGCCACTTC CCTCGACTAT AGGATTACTC          100
```

```
AT                                                                      102

(2) INFORMATION FOR SEQ ID NO:88:

(i) SEQUENCE CHARACTERISTICS:
        (A) LENGTH:  201 nucleotides
        (B) TYPE:  nucleic acid
        (C) STRANDEDNESS:  single
        (D) TOPOLOGY:  linear (ii) MOLECULE TYPE:  cDNA (ix) FEATURE:
        (A) NAME/KEY:  CDS
        (B) LOCATION:  1..201

(xi) SEQUENCE DESCRIPTION:  SEQ ID NO:88:

GGT GAG AGC AGT GCA AGT TTT TTA CGA GCA GCA AGA GCT GGA                  42
Gly Glu Ser Ser Ala Ser Phe Leu Arg Ala Ala Arg Ala Gly
 1               5                  10

AAT TTG GAT CGT GTA CTT GAA CTA CTT CGT TCG GGC ACC GAT                  84
Asn Leu Asp Arg Val Leu Glu Leu Leu Arg Ser Gly Thr Asp
15                  20                  25

ATC AAC ACA TGC AAT GCG AAT GGC CTT AAT GCA TTG CAT CTG                 126
Ile Asn Thr Cys Asn Ala Asn Gly Leu Asn Ala Leu His Leu
30                  35                  40

GCC TCC AAA GAA GGT CAT CAT GAA GTG GTC CGC GAA CTT CTG                 168
Ala Ser Lys Glu Gly His His Glu Val Val Arg Glu Leu Leu
45                  50                  55

AAA AGA AAA GCA GAT GTT GAT GCT GCC ACT AGA                             201
Lys Arg Lys Ala Asp Val Asp Ala Ala Thr Arg
60                  65

(2) INFORMATION FOR SEQ ID NO:89:

(i) SEQUENCE CHARACTERISTICS:
        (A) LENGTH:  201 nucleotides
        (B) TYPE:  nucleic acid
        (C) STRANDEDNESS:  single
        (D) TOPOLOGY:  linear (ii) MOLECULE TYPE:  cDNA (xi) SEQUENCE DESCRIPTION:  SEQ ID NO:89:

TCTAGTGGCA GCATCAACAT CTGCTTTTCT TTTCAGAAGT TCGCGGACCA                   50

CTTCATGATG ACCTTCTTTG GAGGCCAGAT GCAATGCATT AAGGCCATTC                  100

GCATTGCATG TGTTGATATC GGTGCCCGAA CGAAGTAGTT CAAGTACACG                  150

ATCCAAATTT CCAGCTCTTG CTGCTCGTAA AAAACTTGCA CTGCTCTCAC                  200

C                                                                       201

(2) INFORMATION FOR SEQ ID NO:90:

(i) SEQUENCE CHARACTERISTICS:
        (A) LENGTH:  187 nucleotides
        (B) TYPE:  nucleic acid
        (C) STRANDEDNESS:  single
        (D) TOPOLOGY:  linear (ii) MOLECULE TYPE:  cDNA (ix) FEATURE:
        (A) NAME/KEY:  CDS
        (B) LOCATION:  2..187

(xi) SEQUENCE DESCRIPTION:  SEQ ID NO:90:
```

```
T CCG TTA CAC GTT GCA ACA AAA TGG GGT CGT ACA AAC ATG           40
  Pro Leu His Val Ala Thr Lys Trp Gly Arg Thr Asn Met
  1               5                   10

GTT TCG TTA TTG TTG GCT CAT GGG GCC GTA ATT GAC TGT CGC         82
Val Ser Leu Leu Leu Ala His Gly Ala Val Ile Asp Cys Arg
 15              20                  25

ACA CGT GAT TTA CTA ACA CCA TTA CAC TGT GCT TCT CGT TCA        124
Thr Arg Asp Leu Leu Thr Pro Leu His Cys Ala Ser Arg Ser
 30              35                  40

GGT CAT GAT CAA GTT GTT GAT TTG TTG CTT GAA AAA GGA GCT        166
Gly His Asp Gln Val Val Asp Leu Leu Leu Glu Lys Gly Ala
 45              50                  55

CCA ATC AGT GCT AAG ACA AAA                                    187
Pro Ile Ser Ala Lys Thr Lys
 60
```

(2) INFORMATION FOR SEQ ID NO:91:

(i) SEQUENCE CHARACTERISTICS:
        (A) LENGTH: 188 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:91:

```
TTTTGTCTTA GCACTGATTG GAGCTCCTTT TCAAGCAAC AAATCAACAA            50

CTTGATCATG ACCTGAACGA GAAGCACAGT GTAATGGTGT TAGTAAATCA          100

CGTGTGCGAC AGTCAATTAC GGCCCCATGA GCCAACAATA ACGAAACCAT          150

GTTTGTACGA CCCCATTTTG TTGCAACGTG TAACGGAC                       188
```

(2) INFORMATION FOR SEQ ID NO:92:

(i) SEQUENCE CHARACTERISTICS:
        (A) LENGTH: 34 nucleotides
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..33

(xi) SEQUENCE DESCRIPTION: SEQ ID NO:92:

```
AAT GGT TTG GCT CCC TTA CAT ATG GCA GCA CAG G                   34
Asn Gly Leu Ala Pro Leu His Met Ala Ala Gln
 1               5                  10
```

(2) INFORMATION FOR SEQ ID NO:93:

(i) SEQUENCE CHARACTERISTICS:
        (A) LENGTH: 34 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:93:

```
CCTGTGCTGC CATATGTAAG GGAGCCAAAC CATT                           34
```

(2) INFORMATION FOR SEQ ID NO:94:

(i) SEQUENCE CHARACTERISTICS:
     (A) LENGTH:  150 nucleotides
     (B) TYPE:  nucleic acid
     (C) STRANDEDNESS:  single
     (D) TOPOLOGY:  linear (ii) MOLECULE TYPE:  cDNA (ix) FEATURE:
     (A) NAME/KEY:  CDS
     (B) LOCATION:  1..150

(xi) SEQUENCE DESCRIPTION:  SEQ ID NO:94:

```
GTG GAT GCT GCT GCT CGT GAA CTA CAA ACT CCA CTG CAC ATT            42
Val Asp Ala Ala Ala Arg Glu Leu Gln Thr Pro Leu His Ile
1               5                  10

GCA TCA CGT CTT GGT AAT ACC GAC ATC GTC ATT TTG TTG CTG            84
Ala Ser Arg Leu Gly Asn Thr Asp Ile Val Ile Leu Leu Leu
15              20                  25

CAG GCT AAT GCA TCA CCA AAT GCT GCC ACA AGA GAT CTT TAT           126
Gln Ala Asn Ala Ser Pro Asn Ala Ala Thr Arg Asp Leu Tyr
30              35                  40

ACT CCT CTT CAT ATT GCT GCC AAG                                   150
Thr Pro Leu His Ile Ala Ala Lys
45              50
```

(2) INFORMATION FOR SEQ ID NO:95:

(i) SEQUENCE CHARACTERISTICS:
      (A) LENGTH:  150 nucleotides
      (B) TYPE:  nucleic acid
      (C) STRANDEDNESS:  single
      (D) TOPOLOGY:  linear (ii) MOLECULE TYPE:  cDNA (xi) SEQUENCE DESCRIPTION:  SEQ ID NO:95:

```
CTTGGCAGCA ATATGAAGAG GAGTATAAAG ATCTCTTGTG GCAGCATTTG             50

GTGATGCATT AGCCTGCAGC AACAAAATGA CGATGTCGGT ATTACCAAGA            100

CGTGATGCAA TGTGCAGTGG AGTTTGTAGT TCACGAGCAG CAGCATCCAC            150
```

(2) INFORMATION FOR SEQ ID NO:96:

(i) SEQUENCE CHARACTERISTICS:
      (A) LENGTH:  161 nucleotides
      (B) TYPE:  nucleic acid
      (C) STRANDEDNESS:  single
      (D) TOPOLOGY:  linear (ii) MOLECULE TYPE:  cDNA (ix) FEATURE:
      (A) NAME/KEY:  CDS
      (B) LOCATION:  3..161

(xi) SEQUENCE DESCRIPTION:  SEQ ID NO:96:

```
GA CAA ATA AAC ATG GTC CGT TTC TTG ATT GAG CAT GGC GCA             41
   Gln Ile Asn Met Val Arg Phe Leu Ile Glu His Gly Ala
   1               5                  10

CGA GTT TCA GTT ATT ACT CGT GCT TCC TAT ACT CCT CTG CAT            83
Arg Val Ser Val Ile Thr Arg Ala Ser Tyr Thr Pro Leu His
15              20                  25

CAA GCT GCT CAG CAA GGG CAT AAC AGT GTT GTA CGT TAC TTG           125
Gln Ala Ala Gln Gln Gly His Asn Ser Val Val Arg Tyr Leu
30              35                  40
```

```
TTG GAA CAT GGT GCA AGT CCA AAT GTT CAT ACA TCG                    161
Leu Glu His Gly Ala Ser Pro Asn Val His Thr Ser
 45                  50
```

(2) INFORMATION FOR SEQ ID NO:97:

(i) SEQUENCE CHARACTERISTICS:
        (A) LENGTH: 161 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:97:

```
CGATGTATGA ACATTTGGAC TTGCACCATG TTCCAACAAG TAACGTACAA              50

CACTGTTATG CCCTTGCTGA GCAGCTTGAT GCAGAGGAGT ATAGGAAGCA             100

CGAGTAATAA CTGAAACTCG TGCGCCATGC TCAATCAAGA AACGGACCAT             150

GTTTATTTGT C                                                       161
```

(2) INFORMATION FOR SEQ ID NO:98:

(i) SEQUENCE CHARACTERISTICS:
        (A) LENGTH: 133 nucleotides
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 2..133

(xi) SEQUENCE DESCRIPTION: SEQ ID NO:98:

```
T TTT TTA ATT TCG TTT ATG GTG GAT GCA CGT GGA GGA GCA ATG           43
  Phe Leu Ile Ser Phe Met Val Asp Ala Arg Gly Gly Ala Met
   1               5                  10

CGT GGT TGT AGG CAT TCC GGT GTC AGA ATC ATT ATA CCA CCG             85
Arg Gly Cys Arg His Ser Gly Val Arg Ile Ile Ile Pro Pro
 15                  20                  25

AGG AAA GCG CCG CAA CCT ACA CGG GTC ACA TGC AGA TAC CTT            127
Arg Lys Ala Pro Gln Pro Thr Arg Val Thr Cys Arg Tyr Leu
 30                  35                  40

GGA AAG                                                            133
Gly Lys
```

(2) INFORMATION FOR SEQ ID NO:99:

(i) SEQUENCE CHARACTERISTICS:
        (A) LENGTH: 133 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:99:

```
CTTTCCAAGG TATCTGCATG TGACCCGTGT AGGTTGCGGC GCTTTCCTCG              50

GTGGTATAAT GATTCTGACA CCGGAATGCC TACAACCACG CATTGCTCCT             100

CCACGTGCAT CCACCATAAA CGAAATTAAA AAA                               133
```

(2) INFORMATION FOR SEQ ID NO:100:

```
    (i) SEQUENCE CHARACTERISTICS:
        (A) LENGTH: 179 nucleotides
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 3..179

(xi) SEQUENCE DESCRIPTION: SEQ ID NO:100:

CC GTT GCT TTG CGA TCA GCA TTG CAG CGA ATA GGA CGT GAT            41
   Val Ala Leu Arg Ser Ala Leu Gln Arg Ile Gly Arg Asp
   1               5                  10

GAT GTT GTA CGA GAA ATG GAT CGA GCT GAA AAG CTA GAT GGT           83
Asp Val Val Arg Glu Met Asp Arg Ala Glu Lys Leu Asp Gly
15                  20                  25

TTA GAA GGA ACA CCT GTA TCG CAT ATT TCT GGA CCC TCA ATA          125
Leu Glu Gly Thr Pro Val Ser His Ile Ser Gly Pro Ser Ile
30                  35                  40

ACT CTG TCA TCT ACT TTG CTA GAG GTA GCA GGC GAC AGA CGT          167
Thr Leu Ser Ser Thr Leu Leu Glu Val Ala Gly Asp Arg Arg
45                  50                  55

CGT CAC GCC GAG                                                  179
Arg His Ala Glu (2) INFORMATION FOR SEQ ID NO:101:

(i) SEQUENCE CHARACTERISTICS:
        (A) LENGTH: 179 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:101:

CTCGGCGTGA CGACGTCTGT CGCCTGCTAC CTCTAGCAAA GTAGATGACA             50

GAGTTATTGA GGGTCCAGAA ATATGCGATA CAGGTGTTCC TTCTAAACCA            100

TCTAGCTTTT CAGCTCGATC CATTTCTCGT ACAACATCAT CACGTCCTAT            150

TCGCTGCAAT GCTGATCGCA AAGCAACGG                                   179

(2) INFORMATION FOR SEQ ID NO:102:

(i) SEQUENCE CHARACTERISTICS:
        (A) LENGTH: 184 nucleotides
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..183

(xi) SEQUENCE DESCRIPTION: SEQ ID NO:102:

GTA ACA ATG GCG CAA CAG CGA TTG GCA CAA GAA CCG TTT TTT            42
Val Thr Met Ala Gln Gln Arg Leu Ala Gln Glu Pro Phe Phe
1               5                  10

CAG CAA GTA GGG TAT AAT GGG ACA CCT GGA GAT CCA GAA GAA            84
Gln Gln Val Gly Tyr Asn Gly Thr Pro Gly Asp Pro Glu Glu
15                  20                  25
```

```
CCC AAA GAA CAG TCA TTC CAC GAA GAG GAA GAG GAA GTT GCA        126
Pro Lys Glu Gln Ser Phe His Glu Glu Glu Glu Glu Val Ala
 30                  35                  40

GTT TCA GAA ATT CGA ACA GTT GTG CGC ACT GAA CGA CAT GTG        168
Val Ser Glu Ile Arg Thr Val Val Arg Thr Glu Arg His Val
 45                  50                  55

CAT GAT TCG GAA AAT G                                          184
His Asp Ser Glu Asn
 60
```

(2) INFORMATION FOR SEQ ID NO:103:

(i) SEQUENCE CHARACTERISTICS:
        (A) LENGTH: 184 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:103:

```
CATTTTCCGA ATCATGCACA TGTCGTTCAG TGCGCACAAC TGTTCGAATT         50

TCTGAAACTG CAACTTCCTC TTCCTCTTCG TGGAATGACT GTTCTTTGGG        100

TTCTTCTGGA TCTCCAGGTG TCCCATTATA CCCTACTTGC TGAAAAAACG        150

GTTCTTGTGC AATCGCTGT TGCGCCATTG TTAC                          184
```

(2) INFORMATION FOR SEQ ID NO:104:

(i) SEQUENCE CHARACTERISTICS:
        (A) LENGTH: 158 nucleotides
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 3..158

(xi) SEQUENCE DESCRIPTION: SEQ ID NO:104:

```
GT CCT ATT GTG GAA GAG CGT ACA ATA ACA ACT ACG TAT GAG          41
   Pro Ile Val Glu Glu Arg Thr Ile Thr Thr Thr Tyr Glu
    1               5                  10

GAT GAT GTT GCT GTA AAC GAA GAA GAA ATT GTT GAC AAA ATA         83
Asp Asp Val Ala Val Asn Glu Glu Glu Ile Val Asp Lys Ile
 15                  20                  25

GTG CCT CTC AAC GAA GAG GAG CAA GAA AAA TGG GAT CGA ATG        125
Val Pro Leu Asn Glu Glu Glu Gln Glu Lys Trp Asp Arg Met
 30                  35                  40

GTT CGA GAA GTG GAA ATG AAT TTT GAG CAA CAA                    158
Val Arg Glu Val Glu Met Asn Phe Glu Gln Gln
 45                  50
```

(2) INFORMATION FOR SEQ ID NO:105:

(i) SEQUENCE CHARACTERISTICS:
        (A) LENGTH: 158 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:105:

| | |
|---|---|
| TTGTTGCTCA AAATTCATTT CCACTTCTCG AACCATTCGA TCCCATTTTT | 50 |
| CTTGCTCCTC TTCGTTGAGA GGCACTATTT TGTCAACAAT TTCTTCTTCG | 100 |
| TTTACAGCAA CATCATCCTC ATACGTAGTT GTTATTGTAC GCTCTTCCAC | 150 |
| AATAGGAC | 158 |

(2) INFORMATION FOR SEQ ID NO:106:

(i) SEQUENCE CHARACTERISTICS:
        (A) LENGTH: 59 nucleotides
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 3..59

(xi) SEQUENCE DESCRIPTION: SEQ ID NO:106:

| | |
|---|---|
| AC GTA ATG GAG GAA AGG CGA ACT GAT GAA GAG GCC AAA GGG | 41 |
|    Val Met Glu Glu Arg Arg Thr Asp Glu Glu Ala Lys Gly | |
|    1            5               10 | |
| CAA AGC GTT CAT GAA TAA | 59 |
| Gln Ser Val His Glu | |
| 15 | |

(2) INFORMATION FOR SEQ ID NO:107:

(i) SEQUENCE CHARACTERISTICS:
        (A) LENGTH: 59 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:107:

| | |
|---|---|
| TTATTCATGA ACGCTTTGCC CTTTGGCCTC TTCATCAGTT CGCCTTTCCT | 50 |
| CCATTACGT | 59 |

(2) INFORMATION FOR SEQ ID NO:108:

(i) SEQUENCE CHARACTERISTICS:
        (A) LENGTH: 92 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:108:

| | |
|---|---|
| GTATTTTCTT TATAAATGTA TATTATCGAA GGAAATAGCT GCATAAATGT | 50 |
| TAAGCCTTTT TATTGTAAGG AGGAACTAAA ATAATTTCGC AG | 92 |

(2) INFORMATION FOR SEQ ID NO:109:

(i) SEQUENCE CHARACTERISTICS:
        (A) LENGTH: 92 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:109:

```
CTGCGAAATT ATTTTAGTTC CTCCTTACAA TAAAAAGGCT TAACATTTAT                50

GCAGCTATTT CCTTCGATAA TATACATTTA TAAAGAAAAT AC                        92

(2) INFORMATION FOR SEQ ID NO:110:

(i) SEQUENCE CHARACTERISTICS:
         (A) LENGTH:  118 nucleotides
         (B) TYPE:  nucleic acid
         (C) STRANDEDNESS:  single
         (D) TOPOLOGY:  linear (ii) MOLECULE TYPE:  cDNA (xi) SEQUENCE DESCRIPTION:  SEQ ID NO:110:

GTCTTATTTG TGAATCCTTT TGTCCTTTTC TTTCTGTTGT TAATAGTTCG                50

CTTTTTCGAT TTTCACTTTT GTTGCATTGT TTATATAATC TTGCTGTTGA                100

TAATAATATT GTTTTCAG                                                   118

(2) INFORMATION FOR SEQ ID NO:111:

(i) SEQUENCE CHARACTERISTICS:
         (A) LENGTH:  118 nucleotides
         (B) TYPE:  nucleic acid
         (C) STRANDEDNESS:  single
         (D) TOPOLOGY:  linear (ii) MOLECULE TYPE:  cDNA (xi) SEQUENCE DESCRIPTION:  SEQ ID NO:111:

CTGAAAACAA TATTATTATC AACAGCAAGA TTATATAAAC AATGCAACAA                50

AAGTGAAAAT CGAAAAGCG AACTATTAAC AACAGAAAGA AAAGGACAAA                 100

AGGATTCACA AATAAGAC                                                   118

(2) INFORMATION FOR SEQ ID NO:112:

(i) SEQUENCE CHARACTERISTICS:
         (A) LENGTH:  248 nucleotides
         (B) TYPE:  nucleic acid
         (C) STRANDEDNESS:  single
         (D) TOPOLOGY:  linear (ii) MOLECULE TYPE:  cDNA (xi) SEQUENCE DESCRIPTION:  SEQ ID NO:112:

GTATGTAAAT GTATATGCTG GAAATATTAA AATGATTGAT TTAAAAAGGC                50

CATTGTAAAA ATACGATGAA GTAACTGCGT CCATAAATGG ATAACGATCT                100

TGAGAGTCAT CTGCCTGAAT TTTTTTAGAA TTCCAACACA AAGGTTTAAG                150

GCACTTGTTA AATAAATCTA GATAAGCATT TCAAAATTAT GCGTTAGATG                200

AGTATTCTAT CAATAACAGC TATTAATAAA ATTTTTTTTT TCCTTCAG                  248

(2) INFORMATION FOR SEQ ID NO:113:

(i) SEQUENCE CHARACTERISTICS:
         (A) LENGTH:  248 nucleotides
         (B) TYPE:  nucleic acid
         (C) STRANDEDNESS:  single
         (D) TOPOLOGY:  linear (ii) MOLECULE TYPE:  cDNA (xi) SEQUENCE DESCRIPTION:  SEQ ID NO:113:
```

-continued

```
CTGAAGGAAA AAAAAAATTT TATTAATAGC TGTTATTGAT AGAATACTCA        50

TCTAACGCAT AATTTTGAAA TGCTTATCTA GATTTATTTA ACAAGTGCCT       100

TAAACCTTTG TGTTGGAATT CTAAAAAAAT TCAGGCAGAT GACTCTCAAG       150

ATCGTTATCC ATTTATGGAC GCAGTTACTT CATCGTATTT TTACAATGGC       200

CTTTTTAAAT CAATCATTTT AATATTTCCA GCATATACAT TTACATAC         248
```

(2) INFORMATION FOR SEQ ID NO:114:

(i) SEQUENCE CHARACTERISTICS:
        (A) LENGTH: 94 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:114:

```
GTAAGCAGTA TAGTTTTGGG ATTCTATTTC TGTTGTTGCC TCCTTTATAG        50

TTTTCAGAGA ATTTCATTGG ATAATCAAAT ATAAAACATT GCAG              94
```

(2) INFORMATION FOR SEQ ID NO:115:

(i) SEQUENCE CHARACTERISTICS:
        (A) LENGTH: 94 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:115:

```
CTGCAATGTT TTATATTTGA TTATCCAATG AAATTCTCTG AAAACTATAA        50

AGGAGGCAAC AACAGAAATA GAATCCCAAA ACTATACTGC TTAC              94
```

(2) INFORMATION FOR SEQ ID NO:116:

(i) SEQUENCE CHARACTERISTICS:
        (A) LENGTH: 48 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:116:

```
GTGATCATGT GGACAGTGCG CGAATTCTCT TGTATCATAG AGCTCCAG          48
```

(2) INFORMATION FOR SEQ ID NO:117:

(i) SEQUENCE CHARACTERISTICS:
        (A) LENGTH: 48 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:117:

```
CTGGAGCTCT ATGATACAAG AGAATTCGCG CACTGTCCAC ATGATCAC          48
```

(2) INFORMATION FOR SEQ ID NO:118:

(i) SEQUENCE CHARACTERISTICS:
        (A) LENGTH: 200 nucleotides (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:118:

GTTAGTCGAT GTTGCATGCT TAAATACTAT CATCATTGAA AACTATTTTT          50

GCGGGAACCG GTATTTTATT CTTATTTCAG AGCATTGTTT AGTTTCGAAA         100

AGAAAGAAGA ATGCCATTCA TTCTATATGA AAGTGTATAG TATTGAAGCT         150

CCATTGCTAC AGTCATATTG AAGATTTCAT TATGTGATAT GTTTATAAAG         200

(2) INFORMATION FOR SEQ ID NO:119:

(i) SEQUENCE CHARACTERISTICS:
        (A) LENGTH: 200 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:119:

CTTTATAAAC ATATCACATA ATGAAATCTT CAATATGACT GTAGCAATGG          50

AGCTTCAATA CTATACACTT TCATATAGAA TGAATGGCAT TCTTCTTTCT         100

TTTCGAAACT AAACAATGCT CTGAAATAAG AATAAAATAC CGGTTCCCGC         150

AAAAATAGTT TTCAATGATG ATAGTATTTA AGCATGCAAC ATCGACTAAC         200

(2) INFORMATION FOR SEQ ID NO:120:

(i) SEQUENCE CHARACTERISTICS:
        (A) LENGTH: 82 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:120:

GTAAGCTTAG TGGAAAAAAG AAATATTTGC CTTTTTTAAT TAATTTAGAG          50

TGCATAAGTT ATTCAATTTC CAAATATTAT AG                            82

(2) INFORMATION FOR SEQ ID NO:121:

(i) SEQUENCE CHARACTERISTICS:
        (A) LENGTH: 82 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:121:

CTATAATATT TGGAAATTGA ATAACTTATG CACTCTAAAT TAATTAAAAA          50

AGGCAAATAT TTCTTTTTTC CACTAAGCTT AC                            82

(2) INFORMATION FOR SEQ ID NO:122:

(i) SEQUENCE CHARACTERISTICS:
        (A) LENGTH: 213 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:122:

GTGATCACTG ATATGATATT GGCGTTAAAT ATCTCTGTGT TCTTCGCAAT          50

AAATTAACTT GCCTTTTTAA GTCCGACCAG AAGACTTCCA GATACTAAAT         100

TATTTATAAT ATATTTTTAG ATTAATTCTT GCTCTTATCT TTCATTGTAA         150

ATATATTCAG TATGTTCAGA AAGATATTGA TATACGAATA TCAGTGATCA         200

TTGATTATTT TAG                                                 213

(2) INFORMATION FOR SEQ ID NO:123:

(i) SEQUENCE CHARACTERISTICS:
             (A) LENGTH: 213 nucleotides
             (B) TYPE: nucleic acid
             (C) STRANDEDNESS: single
             (D) TOPOLOGY: linear (ii) MOLECULE TYPE: cDNA (xi) SEQUENCE DESCRIPTION: SEQ ID NO:123:

CTAAAATAAT CAATGATCAC TGATATTCGT ATATCAATAT CTTTCTGAAC          50

ATACTGAATA TATTTACAAT GAAAGATAAG AGCAAGAATT AATCTAAAAA         100

TATATTATAA ATAATTTAGT ATCTGGAAGT CTTCTGGTCG ACTTAAAAA          150

GGCAAGTTAA TTTATTGCGA AGAACACAGA GATATTTAAC GCCAATATCA         200

TATCAGTGAT CAC                                                 213

(2) INFORMATION FOR SEQ ID NO:124:

(i) SEQUENCE CHARACTERISTICS:
             (A) LENGTH: 76 nucleotides
             (B) TYPE: nucleic acid
             (C) STRANDEDNESS: single
             (D) TOPOLOGY: linear (ii) MOLECULE TYPE: cDNA (xi) SEQUENCE DESCRIPTION: SEQ ID NO:124:

GTTCGATTTC TCCTCTTATG GAATTTTGTT GCTGTTCTTC TGTGTCATAC          50

TAATTATAAT ATTGAGAACG TTGCAG                                    76

(2) INFORMATION FOR SEQ ID NO:125:

(i) SEQUENCE CHARACTERISTICS:
             (A) LENGTH: 76 nucleotides
             (B) TYPE: nucleic acid
             (C) STRANDEDNESS: single
             (D) TOPOLOGY: linear (ii) MOLECULE TYPE: cDNA (xi) SEQUENCE DESCRIPTION: SEQ ID NO:125:

CTGCAACGTT CTCAATATTA TAATTAGTAT GACACAGAAG AACAGCAACA          50

AAATTCCATA AGAGGAGAAA TCGAAC                                    76

(2) INFORMATION FOR SEQ ID NO:126:

(i) SEQUENCE CHARACTERISTICS:
             (A) LENGTH: 231 nucleotides
             (B) TYPE: nucleic acid
             (C) STRANDEDNESS: single (D) TOPOLOGY:  linear (ii) MOLECULE TYPE:  cDNA (xi) SEQUENCE DESCRIPTION:  SEQ ID NO:126:

GTAATAATTG ATTAATTTGG GAAAAAAAGT AACGTGTTAT CTTCGAAATT         50

ATGAAAAATT TATGTAGGAA GGCTTTTGAG TAATAGAACC ATTAAGCTTG        100

GCATTTAAGA GAAAAACAAC CTGACTGCTG CAATGAAGAG CTTTGTAAGA        150

AAAAGAAAAG TGTATGTTTA GAAGGATTAA AATTCCATTT GTAAAGTCAC        200

TTTTTAGTGA TCCAACGTTT TCGTTTTGTA G                           231

(2) INFORMATION FOR SEQ ID NO:127:

(i) SEQUENCE CHARACTERISTICS:
           (A) LENGTH:  231 nucleotides
           (B) TYPE:  nucleic acid
           (C) STRANDEDNESS:  single
           (D) TOPOLOGY:  linear (ii) MOLECULE TYPE:  cDNA (xi) SEQUENCE DESCRIPTION:  SEQ ID NO:127:

CTACAAAACG AAAACGTTGG ATCACTAAAA AGTGACTTTA CAAATGGAAT         50

TTTAATCCTT CTAAACATAC ACTTTTCTTT TTCTTACAAA GCTCTTCATT        100

GCAGCAGTCA GGTTGTTTTT CTCTTAAATG CCAAGCTTAA TGGTTCTATT        150

ACTCAAAAGC CTTCCTACAT AAATTTTTCA TAATTTCGAA GATAACACGT        200

TACTTTTTTT CCCAAATTAA TCAATTATTA C                           231

(2) INFORMATION FOR SEQ ID NO:128:

(i) SEQUENCE CHARACTERISTICS:
           (A) LENGTH:  78 nucleotides
           (B) TYPE:  nucleic acid
           (C) STRANDEDNESS:  single
           (D) TOPOLOGY:  linear (ii) MOLECULE TYPE:  cDNA (xi) SEQUENCE DESCRIPTION:  SEQ ID NO:128:

GTTATGTTTT TAACTTTTCT TCGAAGTCAT TAGCGGATTT AATTTTAGAG         50

AGTTCTTTAT GCCGTGCTTT ATTTATAG                                78

(2) INFORMATION FOR SEQ ID NO:129:

(i) SEQUENCE CHARACTERISTICS:
           (A) LENGTH:  78 nucleotides
           (B) TYPE:  nucleic acid
           (C) STRANDEDNESS:  single
           (D) TOPOLOGY:  linear (ii) MOLECULE TYPE:  cDNA (xi) SEQUENCE DESCRIPTION:  SEQ ID NO:129:

CTATAAATAA AGCACGGCAT AAAGAACTCT CTAAAATTAA ATCCGCTAAT         50

GACTTCGAAG AAAAGTTAAA AACATAAC                                78

(2) INFORMATION FOR SEQ ID NO:130:

(i) SEQUENCE CHARACTERISTICS:
           (A) LENGTH:  110 nucleotides
           (B) TYPE:  nucleic acid (C) STRANDEDNESS:  single
          (D) TOPOLOGY:  linear (ii) MOLECULE TYPE:  cDNA (xi) SEQUENCE DESCRIPTION:  SEQ ID NO:130:

```
GTAAGTTTTA CTACAACAAC ACGAAATACT AGAAGAAAAA GACCCGTTAA            50

TAACTAAAAG TTATGTTCGA AGCAATGAAA TTGTTGCATA TTACTTTCTT           100

AAAATTACAG                                                       110
```

(2) INFORMATION FOR SEQ ID NO:131:

(i) SEQUENCE CHARACTERISTICS:
        (A) LENGTH:  110 nucleotides
        (B) TYPE:  nucleic acid
        (C) STRANDEDNESS:  single
        (D) TOPOLOGY:  linear (ii) MOLECULE TYPE:  cDNA (xi) SEQUENCE DESCRIPTION:  SEQ ID NO:131:

```
CTGTAATTTT AAGAAAGTAA TATGCAACAA TTTCATTGCT TCGAACATAA            50

CTTTTAGTTA TTAACGGGTC TTTTTCTTCT AGTATTTCGT GTTGTTGTAG           100

TAAAACTTAC                                                       110
```

(2) INFORMATION FOR SEQ ID NO:132:

(i) SEQUENCE CHARACTERISTICS:
        (A) LENGTH:  89 nucleotides
        (B) TYPE:  nucleic acid
        (C) STRANDEDNESS:  single
        (D) TOPOLOGY:  linear (ii) MOLECULE TYPE:  cDNA (xi) SEQUENCE DESCRIPTION:  SEQ ID NO:132:

```
GTATGATGGT CGTAATTAAA ATTTTCTTGG GATTTATGTC NAAAGTTAAT            50

AAACATATGC ATGCTAAAAA ACATCCGGAA TCTTTTGAG                        89
```

(2) INFORMATION FOR SEQ ID NO:133:

(i) SEQUENCE CHARACTERISTICS:
        (A) LENGTH:  89 nucleotides
        (B) TYPE:  nucleic acid
        (C) STRANDEDNESS:  single
        (D) TOPOLOGY:  linear (ii) MOLECULE TYPE:  cDNA (xi) SEQUENCE DESCRIPTION:  SEQ ID NO:133:

```
CTCAAAAGAT TCCGGATGTT TTTTAGCATG CATATGTTTA TTAACTTTNG            50

ACATAAATCC CAAGAAAATT TTAATTACGA CCATCATAC                        89
```

(2) INFORMATION FOR SEQ ID NO:134:

(i) SEQUENCE CHARACTERISTICS:
        (A) LENGTH:  95 nucleotides
        (B) TYPE:  nucleic acid
        (C) STRANDEDNESS:  single
        (D) TOPOLOGY:  linear (ii) MOLECULE TYPE:  cDNA (xi) SEQUENCE DESCRIPTION:  SEQ ID NO:134:

```
GTGAGCGAAA TTTTGATACT AAAGAATTTC AGCTTTCTTG ATGGGTGCTG          50

AAACTTATGG AATATGTAGT CAGAAATAGA TGAAGCTTGC CATAG              95

(2) INFORMATION FOR SEQ ID NO:135:

(i) SEQUENCE CHARACTERISTICS:
        (A) LENGTH:  95 nucleotides
        (B) TYPE:  nucleic acid
        (C) STRANDEDNESS:  single
        (D) TOPOLOGY:  linear (ii) MOLECULE TYPE:  cDNA (xi) SEQUENCE DESCRIPTION:  SEQ ID NO:135:

CTATGGCAAG CTTCATCTAT TTCTGACTAC ATATTCCATA AGTTTCAGCA          50

CCCATCAAGA AAGCTGAAAT TCTTTAGTAT CAAAATTTCG CTCAC              95

(2) INFORMATION FOR SEQ ID NO:136:

(i) SEQUENCE CHARACTERISTICS:
        (A) LENGTH:  301 nucleotides
        (B) TYPE:  nucleic acid
        (C) STRANDEDNESS:  single
        (D) TOPOLOGY:  linear (ii) MOLECULE TYPE:  cDNA (xi) SEQUENCE DESCRIPTION:  SEQ ID NO:136:

GTAAAAAAAG CTTCAGTAAA CTTTAATTTC TCGCTGTGAT TTTGCAGTAT          50

TGTGAATAAA ATTTTTCTCC GCCTGATTCT TTTGATGAAT CTTAATTTAA         100

AATAATTTTT GTTACCGCAT GGTATTCCTT TTGTATGATT TGTAACAAAC         150

AATTTGGAAC ATTTTTTCAA TCGGTGGGTT CGTTTTCAAA ATTACAGAAA         200

TATTGTGCTA CTGTTACTGA ATGATATTAA ATGCATTTCT GAAAAGGAAT         250

TATTTCAATG AAATGCTTTC TTAGTTAGAG GCTTACTATA ATTACTTAAA         300

G                                                             301

(2) INFORMATION FOR SEQ ID NO:137:

(i) SEQUENCE CHARACTERISTICS:
        (A) LENGTH:  301 nucleotides
        (B) TYPE:  nucleic acid
        (C) STRANDEDNESS:  single
        (D) TOPOLOGY:  linear (ii) MOLECULE TYPE:  cDNA (xi) SEQUENCE DESCRIPTION:  SEQ ID NO:137:

CTTTAAGTAA TTATAGTAAG CCTCTAACTA AGAAAGCATT TCATTGAAAT          50

AATTCCTTTT CAGAAATGCA TTTAATATCA TTCAGTAACA GTAGCACAAT         100

ATTTCTGTAA TTTTGAAAAC GAACCCACCG ATTGAAAAAA TGTTCCAAAT         150

TGTTTGTTAC AAATCATACA AAAGGAATAC CATGCGGTAA CAAAAATTAT         200

TTTAAATTAA GATTCATCAA AAGAATCAGG CGGAGAAAAA TTTTATTCAC         250

AATACTGCAA AATCACAGCG AGAAATTAAA GTTTACTGAA GCTTTTTTA          300

C                                                             301

(2) INFORMATION FOR SEQ ID NO:138:

(i) SEQUENCE CHARACTERISTICS:
```

```
        (A) LENGTH: 1056 nucleotides
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1056

(xi) SEQUENCE DESCRIPTION: SEQ ID NO:138:

GGT GCT AAT GCA GAT GTG GCT ACA GTA CGC GGT GAA ACG CCT            42
Gly Ala Asn Ala Asp Val Ala Thr Val Arg Gly Glu Thr Pro
  1               5                  10

CTT CAT TTA GCT GCA CGA GCA AAC CAA ACG GAC ATT GTT CGT            84
Leu His Leu Ala Ala Arg Ala Asn Gln Thr Asp Ile Val Arg
 15                  20                  25

GTT TTG GTG CGT AAT GGA GCA CAG GTG GAT GCT GCT GCT CGT           126
Val Leu Val Arg Asn Gly Ala Gln Val Asp Ala Ala Ala Arg
         30                  35                  40

GAA CTA CAA ACT CCA CTG CAC ATT GCA TCA CGT CTT GGT AAT           168
Glu Leu Gln Thr Pro Leu His Ile Ala Ser Arg Leu Gly Asn
                 45                  50                  55

ACC GAC ATC GTC ATT TTG TTG CTG CAG GCT AAT GCA TCA CCA           210
Thr Asp Ile Val Ile Leu Leu Leu Gln Ala Asn Ala Ser Pro
                         60                  65                  70

AAT GCT GCC ACA AGA GAT CTT TAT ACT CCT CTT CAT ATT GCT           252
Asn Ala Ala Thr Arg Asp Leu Tyr Thr Pro Leu His Ile Ala
                             75                  80

GCC AAG GAG GGG CAA GAG GAA GTG GCA GCA ATA TTG ATG GAT           294
Ala Lys Glu Gly Gln Glu Glu Val Ala Ala Ile Leu Met Asp
 85                  90                  95

CAT GGA ACC GAC AAG ACA CTG CTC ACG AAA AAG GGT TTT ACG           336
His Gly Thr Asp Lys Thr Leu Leu Thr Lys Lys Gly Phe Thr
        100                 105                 110

CCG TTG CAT TTA GCT GCT AAG TAT GGC AAT TTG CCG GTC GCG           378
Pro Leu His Leu Ala Ala Lys Tyr Gly Asn Leu Pro Val Ala
                115                 120                 125

AAA TCA TTG CTA GAA CGA GGA ACA CCG GTT GAC ATT GAA GGC           420
Lys Ser Leu Leu Glu Arg Gly Thr Pro Val Asp Ile Glu Gly
                    130                 135                 140

AAG AAT CAG GTA ACA CCT CTG CAT GTA GCG GCA CAT TAC AAT           462
Lys Asn Gln Val Thr Pro Leu His Val Ala Ala His Tyr Asn
                            145                 150

AAC GAC AAG GTA GCA TTG TTA CTT CTA GAA AAT GGT GCT TCT           504
Asn Asp Lys Val Ala Leu Leu Leu Leu Glu Asn Gly Ala Ser
155                 160                 165

GCA CAT GCC GCT GCC AAG AAT GGG TAC ACT CCT TTA CAT ATT           546
Ala His Ala Ala Ala Lys Asn Gly Tyr Thr Pro Leu His Ile
        170                 175                 180

GCC GCG AAG AAG AAT CAG ATG GAT ATT GCT AGC ACT CTC CTT           588
Ala Ala Lys Lys Asn Gln Met Asp Ile Ala Ser Thr Leu Leu
                185                 190                 195

CAT TAT AAG GCA AAT GCG AAT GCT GAA AGC AAA GCT GGC TTT           630
His Tyr Lys Ala Asn Ala Asn Ala Glu Ser Lys Ala Gly Phe
                    200                 205                 210

ACA CCA CTT CAT CTT GCC GCC CAG GAG GGC CAT CGC GAA ATG           672
Thr Pro Leu His Leu Ala Ala Gln Glu Gly His Arg Glu Met
                            215                 220

GCT GCG TTA TTA ATT GAA AAT GGA GCA AAA GTT GGA GCT CAG           714
Ala Ala Leu Leu Ile Glu Asn Gly Ala Lys Val Gly Ala Gln
```

```
                225                 230                 235
GCA AGG AAT GGC TTG ACA CCA ATG CAT TTA TGT GCA CAG GAG          756
Ala Arg Asn Gly Leu Thr Pro Met His Leu Cys Ala Gln Glu
    240                 245                 250

GAT CGT GTG AGC GTA GCA GAA GAA CTA GTG AAA GAA AAC GCA          798
Asp Arg Val Ser Val Ala Glu Glu Leu Val Lys Glu Asn Ala
        255                 260                 265

GCC ATT GAT CCC AAA ACG AAA GCA GGA TAT ACG CCG TTA CAT          840
Ala Ile Asp Pro Lys Thr Lys Ala Gly Tyr Thr Pro Leu His
            270                 275                 280

GTT GCT TGC CAT TTT GGA CAA ATA AAC ATG GTC CGT TTC TTG          882
Val Ala Cys His Phe Gly Gln Ile Asn Met Val Arg Phe Leu
                285                 290

ATT GAG CAT GGC GCA CGA GTT TCA GTT ATT ACT CGT GCT TCC          924
Ile Glu His Gly Ala Arg Val Ser Val Ile Thr Arg Ala Ser
295                 300                 305

TAT ACT CCT CTG CAT CAA GCT GCT CAG CAA GGG CAT AAC AGT          966
Tyr Thr Pro Leu His Gln Ala Ala Gln Gln Gly His Asn Ser
        310                 315                 320

GTT GTA CGT TAC TTG TTG GAA CAT GGT GCA AGT CCA AAT GTT          1008
Val Val Arg Tyr Leu Leu Glu His Gly Ala Ser Pro Asn Val
            325                 330                 335

CAT ACA TCG ACA GGA CAA ACT CCA TTA TCG ATT GCT GAA CGT          1050
His Thr Ser Thr Gly Gln Thr Pro Leu Ser Ile Ala Glu Arg
                340                 345                 350

CTA GGG                                                          1056
Leu Gly
```

(2) INFORMATION FOR SEQ ID NO:139:

(i) SEQUENCE CHARACTERISTICS:
      (A) LENGTH: 352 amino acids
      (B) TYPE: amino acid
      (D) TOPOLOGY: linear (ii) MOLECULE TYPE: Protein (xi) SEQUENCE DESCRIPTION: SEQ ID NO:139:

```
Gly Ala Asn Ala Asp Val Ala Thr Val Arg Gly Glu Thr Pro
1               5                   10

Leu His Leu Ala Ala Arg Ala Asn Gln Thr Asp Ile Val Arg
15                  20                  25

Val Leu Val Arg Asn Gly Ala Gln Val Asp Ala Ala Ala Arg
        30                  35                  40

Glu Leu Gln Thr Pro Leu His Ile Ala Ser Arg Leu Gly Asn
            45                  50                  55

Thr Asp Ile Val Ile Leu Leu Gln Ala Asn Ala Ser Pro
                60                  65                  70

Asn Ala Ala Thr Arg Asp Leu Tyr Thr Pro Leu His Ile Ala
                75                  80

Ala Lys Glu Gly Gln Glu Glu Val Ala Ala Ile Leu Met Asp
85                  90                  95

His Gly Thr Asp Lys Thr Leu Leu Thr Lys Lys Gly Phe Thr
        100                 105                 110

Pro Leu His Leu Ala Ala Lys Tyr Gly Asn Leu Pro Val Ala
            115                 120                 125

Lys Ser Leu Leu Glu Arg Gly Thr Pro Val Asp Ile Glu Gly
                130                 135                 140
```

```
Lys Asn Gln Val Thr Pro Leu His Val Ala Ala His Tyr Asn
                145                 150
Asn Asp Lys Val Ala Leu Leu Leu Glu Asn Gly Ala Ser
155                 160                 165
Ala His Ala Ala Ala Lys Asn Gly Tyr Thr Pro Leu His Ile
        170                 175                 180
Ala Ala Lys Lys Asn Gln Met Asp Ile Ala Ser Thr Leu Leu
                185                 190                 195
His Tyr Lys Ala Asn Ala Asn Ala Glu Ser Lys Ala Gly Phe
                200                 205                 210
Thr Pro Leu His Leu Ala Ala Gln Glu Gly His Arg Glu Met
                215                 220
Ala Ala Leu Leu Ile Glu Asn Gly Ala Lys Val Gly Ala Gln
225                 230                 235
Ala Arg Asn Gly Leu Thr Pro Met His Leu Cys Ala Gln Glu
        240                 245                 250
Asp Arg Val Ser Val Ala Glu Glu Leu Val Lys Glu Asn Ala
                255                 260                 265
Ala Ile Asp Pro Lys Thr Lys Ala Gly Tyr Thr Pro Leu His
                270                 275                 280
Val Ala Cys His Phe Gly Gln Ile Asn Met Val Arg Phe Leu
                285                 290
Ile Glu His Gly Ala Arg Val Ser Val Ile Thr Arg Ala Ser
295                 300                 305
Tyr Thr Pro Leu His Gln Ala Ala Gln Gln Gly His Asn Ser
        310                 315                 320
Val Val Arg Tyr Leu Leu Glu His Gly Ala Ser Pro Asn Val
                325                 330                 335
His Thr Ser Thr Gly Gln Thr Pro Leu Ser Ile Ala Glu Arg
                340                 345                 350
Leu Gly (2) INFORMATION FOR SEQ ID NO:140:

(i) SEQUENCE CHARACTERISTICS:
        (A) LENGTH:  1056 nucleotides
        (B) TYPE:  nucleic acid
        (C) STRANDEDNESS:  single
        (D) TOPOLOGY:  linear (ii) MOLECULE TYPE:  cDNA (xi) SEQUENCE DESCRIPTION:  SEQ ID NO:140:

CCCTAGACGT TCAGCAATCG ATAATGGAGT TTGTCCTGTC GATGTATGAA          50

CATTTGGACT TGCACCATGT TCCAACAAGT AACGTACAAC ACTGTTATGC         100

CCTTGCTGAG CAGCTTGATG CAGAGGAGTA TAGGAAGCAC GAGTAATAAC         150

TGAAACTCGT GCGCCATGCT CAATCAAGAA ACGGACCATG TTTATTTGTC         200

CAAAATGGCA AGCAACATGT AACGGCGTAT ATCCTGCTTT CGTTTTGGGA         250

TCAATGGCTG CGTTTTCTTT CACTAGTTCT TCTGCTACGC TCACACGATC         300

CTCCTGTGCA CATAAATGCA TTGGTGTCAA GCCATTCCTT GCCTGAGCTC         350

CAACTTTTGC TCCATTTTCA ATTAATAACG CAGCCATTTC GCGATGGCCC         400

TCCTGGGCGG CAAGATGAAG TGGTGTAAAG CCAGCTTTGC TTTCAGCATT         450

CGCATTTGCC TTATAATGAA GGAGAGTGCT AGCAATATCC ATCTGATTCT         500
```

-continued

```
TCTTCGCGGC AATATGTAAA GGAGTGTACC CATTCTTGGC AGCGGCATGT            550

GCAGAAGCAC CATTTTCTAG AAGTAACAAT GCTACCTTGT CGTTATTGTA            600

ATGTGCCGCT ACATGCAGAG GTGTTACCTG ATTCTTGCCT TCAATGTCAA            650

CCGGTGTTCC TCGTTCTAGC AATGATTTCG CGACCGGCAA ATTGCCATAC            700

TTAGCAGCTA AATGCAACGG CGTAAAACCC TTTTTCGTGA GCAGTGTCTT            750

GTCGGTTCCA TGATCCATCA ATATTGCTGC CACTTCCTCT TGCCCCTCCT            800

TGGCAGCAAT ATGAAGAGGA GTATAAAGAT CTCTTGTGGC AGCATTTGGT            850

GATGCATTAG CCTGCAGCAA CAAAATGACG ATGTCGGTAT TACCAAGACG            900

TGATGCAATG TGCAGTGGAG TTTGTAGTTC ACGAGCAGCA GCATCCACCT            950

GTGCTCCATT ACGCACCAAA ACACGAACAA TGTCCGTTTG GTTTGCTCGT           1000

GCAGCTAAAT GAAGAGGCGT TTCACCGCGT ACTGTAGCCA CATCTGCATT           1050

AGCACC                                                           1056
```

(2) INFORMATION FOR SEQ ID NO:141:

(i) SEQUENCE CHARACTERISTICS:
        (A) LENGTH: 1266 nucleotides
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1266

(xi) SEQUENCE DESCRIPTION: SEQ ID NO:141:

```
GCA CGT GGA GGA GCA ATG CGT GGT TGT AGG CAT TCC GGT GTC             42
Ala Arg Gly Gly Ala Met Arg Gly Cys Arg His Ser Gly Val
 1               5                  10

AGA ATC ATT ATA CCA CCG AGG AAA GCG CCG CAA CCT ACA CGG             84
Arg Ile Ile Ile Pro Pro Arg Lys Ala Pro Gln Pro Thr Arg
 15              20                  25

GTC ACA TGC AGA TAC CTT GGA AAG GAC AAG TTA GCG CAT CCA            126
Val Thr Cys Arg Tyr Leu Gly Lys Asp Lys Leu Ala His Pro
         30              35                  40

CCA CCA TTA AGT GAA GGT GAA GCG CTC GCN TCA CGT ATA CTT            168
Pro Pro Leu Ser Glu Gly Glu Ala Leu Ala Ser Arg Ile Leu
             45              50                  55

GAA ATG GCA CCA CAT GGA GCA AAA TTC TTA GGC CCT GTT ATA            210
Glu Met Ala Pro His Gly Ala Lys Phe Leu Gly Pro Val Ile
                 60              65                  70

TTG GAA GTA CCA CAT TTT GCA TCA CTT CGT GGA CGA GAG AGA            252
Leu Glu Val Pro His Phe Ala Ser Leu Arg Gly Arg Glu Arg
                     75              80

GAG ATT GTC ATT TTG CGT TCT GAT GAT GGG CAG CAT TGG AAA            294
Glu Ile Val Ile Leu Arg Ser Asp Asp Gly Gln His Trp Lys
 85              90                  95

GAG CAT CAG CTT GAA GCA ACA GAA GAT GCT GTA CAA GAG GTG            336
Glu His Gln Leu Glu Ala Thr Glu Asp Ala Val Gln Glu Val
         100             105                 110

CTC AAT GAA TCG TTT GAT GCA GAA GAG TTG TCG CAA CTT GAT            378
Leu Asn Glu Ser Phe Asp Ala Glu Glu Leu Ser Gln Leu Asp
             115             120                 125

GAT TTG CAT ACA TCA CGG ATT ACG CGT ATC CTG ACC AAT GAT            420
```

```
Asp Leu His Thr Ser Arg Ile Thr Arg Ile Leu Thr Asn Asp
        130                 135                 140

TTC CCA ATG TAT TTC GCG GTC GTT ACT CGT GTG CGG CAA GAA           462
Phe Pro Met Tyr Phe Ala Val Val Thr Arg Val Arg Gln Glu
            145                 150

GTG CAC TGT GTT GGT CCA GAA GGT GGT GTA ATA CTC TCT TCA           504
Val His Cys Val Gly Pro Glu Gly Gly Val Ile Leu Ser Ser
155                 160                 165

GTT GTT CCT CAT GTG CAG GCC ATA TTT CCG GAT GGT TCC TTG           546
Val Val Pro His Val Gln Ala Ile Phe Pro Asp Gly Ser Leu
        170                 175                 180

ACT AAG ACG ATC AAA GTA TCT GTG CAA GCC CAG CCA GTT CCA           588
Thr Lys Thr Ile Lys Val Ser Val Gln Ala Gln Pro Val Pro
            185                 190                 195

CAA GAG ATA GTC ACT CGT TTA CAT GGG AAT AGA GTC GCT GTT           630
Gln Glu Ile Val Thr Arg Leu His Gly Asn Arg Val Ala Val
                200                 205                 210

TCT CCA ATT GTA ACT GTT GAA CCG CGT CGT CGC AAA TTC CAT           672
Ser Pro Ile Val Thr Val Glu Pro Arg Arg Arg Lys Phe His
            215                 220

AAG CCC ATA ACG CTG TGC ATA CCA TTG CCA CAA AGC TCA AAT           714
Lys Pro Ile Thr Leu Cys Ile Pro Leu Pro Gln Ser Ser Asn
225                 230                 235

AAA GGA ATG TTA ACA CAA TAT AGT GGC CAA CCA GGA CAG GAA           756
Lys Gly Met Leu Thr Gln Tyr Ser Gly Gln Pro Gly Gln Glu
        240                 245                 250

CCA CCG ACG CTG CGT TTA CTC TGC AGT AAA ACT GGA GGT TCT           798
Pro Pro Thr Leu Arg Leu Leu Cys Ser Lys Thr Gly Gly Ser
            255                 260                 265

TCT CCT GCA CAG TGG GAA GAT ATT ACT GGA ACT ACC CAG TTA           840
Ser Pro Ala Gln Trp Glu Asp Ile Thr Gly Thr Thr Gln Leu
                270                 275                 280

ACA TTT ACT GGT GAG GAC GTT TCA TTT ACA ACT ACG GTT TCT           882
Thr Phe Thr Gly Glu Asp Val Ser Phe Thr Thr Thr Val Ser
            285                 290

GCT CGA TTT TGG TTG ATG GAT TGC CAA ACT CCG CGA GAT GCG           924
Ala Arg Phe Trp Leu Met Asp Cys Gln Thr Pro Arg Asp Ala
295                 300                 305

GCA CGA ATG GCA CAA GAA GTT TAC AAT GAA GCA ATT GCA GTT           966
Ala Arg Met Ala Gln Glu Val Tyr Asn Glu Ala Ile Ala Val
        310                 315                 320

CCT TAT ATG GCT AAA TTT CTT ATT TTT GCT CGA CGA ACT TTT          1008
Pro Tyr Met Ala Lys Phe Leu Ile Phe Ala Arg Arg Thr Phe
            325                 330                 335

CCT GCC GAA GGA CAG TTG AGA TTG TTT TGT ATG ACT GAT GAT          1050
Pro Ala Glu Gly Gln Leu Arg Leu Phe Cys Met Thr Asp Asp
                340                 345                 350

CGG GAA GAT AAA ACC CTG GAA AAA CAA GAA CGT TTC ATT GAA          1092
Arg Glu Asp Lys Thr Leu Glu Lys Gln Glu Arg Phe Ile Glu
            355                 360

ATT GCG AAA TCG AAA GAT GTA GAA GTC TTA AGT GGG CGA CAT          1134
Ile Ala Lys Ser Lys Asp Val Glu Val Leu Ser Gly Arg His
365                 370                 375

CAG TTT TTG GAA TTT TCT GGA AAT CTT CTT CCA ATA ACC AAG          1176
Gln Phe Leu Glu Phe Ser Gly Asn Leu Leu Pro Ile Thr Lys
        380                 385                 390

AGT GGT GAC CAA CTT TCT CTT TAT TTT CTA CCA TTC CAA GAA          1218
Ser Gly Asp Gln Leu Ser Leu Tyr Phe Leu Pro Phe Gln Glu
            395                 400                 405
```

```
AAT CGT CTT GCT TTC ATG GTA AAG ATA CGC ACT CAC ACG GAC              1260
Asn Arg Leu Ala Phe Met Val Lys Ile Arg Thr His Thr Asp
            410                 415                 420

AAC GAA                                                              1266
Asn Glu
```

(2) INFORMATION FOR SEQ ID NO:142:

(i) SEQUENCE CHARACTERISTICS:
        (A) LENGTH: 422 amino acids
        (B) TYPE: amino acid
        (D) TOPOLOGY: linear (ii) MOLECULE TYPE: Protein (xi) SEQUENCE DESCRIPTION: SEQ ID NO:142:

```
Ala Arg Gly Gly Ala Met Arg Gly Cys Arg His Ser Gly Val
 1               5                  10

Arg Ile Ile Ile Pro Pro Arg Lys Ala Pro Gln Pro Thr Arg
15                  20                  25

Val Thr Cys Arg Tyr Leu Gly Lys Asp Lys Leu Ala His Pro
        30                  35                  40

Pro Pro Leu Ser Glu Gly Glu Ala Leu Ala Ser Arg Ile Leu
            45                  50                  55

Glu Met Ala Pro His Gly Ala Lys Phe Leu Gly Pro Val Ile
                60                  65                  70

Leu Glu Val Pro His Phe Ala Ser Leu Arg Gly Arg Glu Arg
                    75                  80

Glu Ile Val Ile Leu Arg Ser Asp Asp Gly Gln His Trp Lys
85                  90                  95

Glu His Gln Leu Glu Ala Thr Glu Asp Ala Val Gln Glu Val
            100                 105                 110

Leu Asn Glu Ser Phe Asp Ala Glu Glu Leu Ser Gln Leu Asp
                115                 120                 125

Asp Leu His Thr Ser Arg Ile Thr Arg Ile Leu Thr Asn Asp
                    130                 135                 140

Phe Pro Met Tyr Phe Ala Val Val Thr Arg Val Arg Gln Glu
                145                 150

Val His Cys Val Gly Pro Glu Gly Gly Val Ile Leu Ser Ser
155                 160                 165

Val Val Pro His Val Gln Ala Ile Phe Pro Asp Gly Ser Leu
        170                 175                 180

Thr Lys Thr Ile Lys Val Ser Val Gln Ala Gln Pro Val Pro
            185                 190                 195

Gln Glu Ile Val Thr Arg Leu His Gly Asn Arg Val Ala Val
                200                 205                 210

Ser Pro Ile Val Thr Val Glu Pro Arg Arg Lys Phe His
                    215                 220

Lys Pro Ile Thr Leu Cys Ile Pro Leu Pro Gln Ser Ser Asn
225                 230                 235

Lys Gly Met Leu Thr Gln Tyr Ser Gly Gln Pro Gly Gln Glu
            240                 245                 250

Pro Pro Thr Leu Arg Leu Leu Cys Ser Lys Thr Gly Gly Ser
                255                 260                 265

Ser Pro Ala Gln Trp Glu Asp Ile Thr Gly Thr Thr Gln Leu
                    270                 275                 280
```

```
Thr Phe Thr Gly Glu Asp Val Ser Phe Thr Thr Thr Val Ser
            285                 290

Ala Arg Phe Trp Leu Met Asp Cys Gln Thr Pro Arg Asp Ala
295                 300                 305

Ala Arg Met Ala Gln Glu Val Tyr Asn Glu Ala Ile Ala Val
        310                 315                 320

Pro Tyr Met Ala Lys Phe Leu Ile Phe Ala Arg Arg Thr Phe
            325                 330                 335

Pro Ala Glu Gly Gln Leu Arg Leu Phe Cys Met Thr Asp Asp
                340                 345                 350

Arg Glu Asp Lys Thr Leu Glu Lys Gln Glu Arg Phe Ile Glu
            355                 360

Ile Ala Lys Ser Lys Asp Val Glu Val Leu Ser Gly Arg His
365                 370                 375

Gln Phe Leu Glu Phe Ser Gly Asn Leu Leu Pro Ile Thr Lys
        380                 385                 390

Ser Gly Asp Gln Leu Ser Leu Tyr Phe Leu Pro Phe Gln Glu
            395                 400                 405

Asn Arg Leu Ala Phe Met Val Lys Ile Arg Thr His Thr Asp
            410                 415                 420

Asn Glu (2) INFORMATION FOR SEQ ID NO:143:

(i) SEQUENCE CHARACTERISTICS:
        (A) LENGTH:   1266 nucleotides
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:143:

TTCGTTGTCC GTGTGAGTGC GTATCTTTAC CATGAAAGCA AGACGATTTT           50

CTTGGAATGG TAGAAAATAA AGAGAAAGTT GGTCACCACT CTTGGTTATT          100

GGAAGAAGAT TTCCAGAAAA TTCCAAAAAC TGATGTCGCC CACTTAAGAC          150

TTCTACATCT TTCGATTTCG CAATTTCAAT GAAACGTTCT TGTTTTTCCA          200

GGGTTTTATC TTCCCGATCA TCAGTCATAC AAAACAATCT CAACTGTCCT          250

TCGGCAGGAA AAGTTCGTCG AGCAAAAATA AGAAATTTAG CCATATAAGG          300

AACTGCAATT GCTTCATTGT AAACTTCTTG TGCCATTCGT GCCGCATCTC          350

GCGGAGTTTG GCAATCCATC AACCAAAATC GAGCAGAAAC CGTAGTTGTA          400

AATGAAACGT CCTCACCAGT AAATGTTAAC TGGGTAGTTC CAGTAATATC          450

TTCCCACTGT GCAGGAGAAG AACCTCCAGT TTTACTGCAG AGTAAACGCA          500

GCGTCGGTGG TTCCTGTCCT GGTTGGCCAC TATATTGTGT TAACATTCCT          550

TTATTTGAGC TTTGTGGCAA TGGTATGCAC AGCGTTATGG GCTTATGGAA          600

TTTGCGACGA CGCGGTTCAA CAGTTACAAT GGAGAAACA GCGACTCTAT           650

TCCCATGTAA ACGAGTGACT ATCTCTTGTG GAACTGGCTG GCTTGCACA           700

GATACTTTGA TCGTCTTAGT CAAGGAACCA TCCGGAAATA TGGCCTGCAC          750

ATGAGGAACA ACTGAAGAGA GTATTACACC ACCTTCTGGA CCAACACAGT          800

GCACTTCTTG CCGCACACGA GTAACGACCG CGAAATACAT TGGGAAATCA          850
```

```
TTGGTCAGGA TACGCGTAAT CCGTGATGTA TGCAAATCAT CAAGTTGCGA                900

CAACTCTTCT GCATCAAACG ATTCATTGAG CACCTCTTGT ACAGCATCTT                950

CTGTTGCTTC AAGCTGATGC TCTTTCCAAT GCTGCCCATC ATCAGAACGC               1000

AAAATGACAA TCTCTCTCTC TCGTCCACGA AGTGATGCAA AATGTGGTAC               1050

TTCCAATATA ACAGGGCCTA AGAATTTTGC TCCATGTGGT GCCATTTCAA               1100

GTATACGTGA NGCGAGCGCT TCACCTTCAC TTAATGGTGG TGGATGCGCT               1150

AACTTGTCCT TTCCAAGGTA TCTGCATGTG ACCCGTGTAG GTTGCGGCGC               1200

TTTCCTCGGT GGTATAATGA TTCTGACACC GGAATGCCTA CAACCACGCA               1250

TTGCTCCTCC ACGTGC                                                    1266
```

(2) INFORMATION FOR SEQ ID NO:144:

(i) SEQUENCE CHARACTERISTICS:
        (A) LENGTH: 864 nucleotides
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..861

(xi) SEQUENCE DESCRIPTION: SEQ ID NO:144:

```
CAA CTA GTT GGT CTT GAA GCA GTC ACT ATT CTA CGT ATT TGG                 42
Gln Leu Val Gly Leu Glu Ala Val Thr Ile Leu Arg Ile Trp
 1               5                  10

ATA TTT TTG AAG AAA GAA CAA GCT ACG CCC GTT GCT TTG CGA                 84
Ile Phe Leu Lys Lys Glu Gln Ala Thr Pro Val Ala Leu Arg
15                  20                  25

TCA GCA TTG CAG CGA ATA GGA CGT GAT GAT GTT GTA CGA GAA                126
Ser Ala Leu Gln Arg Ile Gly Arg Asp Asp Val Val Arg Glu
        30                  35                  40

ATG GAT CGA GCT GAA AAG CTA GAT GGT TTA GAA GGA ACA CCT                168
Met Asp Arg Ala Glu Lys Leu Asp Gly Leu Glu Gly Thr Pro
                45                  50                  55

GTA TCG CAT ATT TCT GGA CCC TCA ATA ACT CTG TCA TCT ACT                210
Val Ser His Ile Ser Gly Pro Ser Ile Thr Leu Ser Ser Thr
                    60                  65                  70

TTG CTA GAG GTA GCA GGC GAC AGA CGT CGT CAC GCC GAG GTA                252
Leu Leu Glu Val Ala Gly Asp Arg Arg Arg His Ala Glu Val
                        75                  80

ACA ATG GCG CAA CAG CGA TTG GCA CAA GAA CCG TTT TTT CAG                294
Thr Met Ala Gln Gln Arg Leu Ala Gln Glu Pro Phe Phe Gln
85                  90                  95

CAA GTA GGG TAT AAT GGG ACA CCT GGA GAT CCA GAA GAA CCC                336
Gln Val Gly Tyr Asn Gly Thr Pro Gly Asp Pro Glu Glu Pro
       100                 105                 110

AAA GAA CAG TCA TTC CAC GAA GAG GAA GAG GAA GTT GCA GTT                378
Lys Glu Gln Ser Phe His Glu Glu Glu Glu Glu Val Ala Val
               115                 120                 125

TCA GAA ATT CGA ACA GTT GTG CGC ACT GAA CGA CAT GTG CAT                420
Ser Glu Ile Arg Thr Val Val Arg Thr Glu Arg His Val His
                   130                 135                 140

GAT TCG GAA AAT GGT CCT ATT GTG GAA GAG CGT ACA ATA ACA                462
Asp Ser Glu Asn Gly Pro Ile Val Glu Glu Arg Thr Ile Thr
                       145                 150
```

```
ACT ACG TAT GAG GAT GAT GTT GCT GTA AAC GAA GAA GAA ATT      504
Thr Thr Tyr Glu Asp Asp Val Ala Val Asn Glu Glu Glu Ile
155                 160                 165

GTT GAC AAA ATA GTG CCT CTC AAC GAA GAG GAG CAA GAA AAA      546
Val Asp Lys Ile Val Pro Leu Asn Glu Glu Glu Gln Glu Lys
        170                 175                 180

TGG GAT CGA ATG GTT CGA GAA GTG GAA ATG AAT TTT GAG CAA      588
Trp Asp Arg Met Val Arg Glu Val Glu Met Asn Phe Glu Gln
                185                 190                 195

CAA GAA ACA TCA AAA GAA GGA ACG TTT GGT TGT CAG ACA ACA      630
Gln Glu Thr Ser Lys Glu Gly Thr Phe Gly Cys Gln Thr Thr
                    200                 205                 210

CAT GAG AAA GAA AAA GAT GAT GAT GGT GGC AGT CTG AAG ACG      672
His Glu Lys Glu Lys Asp Asp Asp Gly Gly Ser Leu Lys Thr
                        215                 220

ACA ATG AAA GAT AGT CAC GTA AGG CAG ATT TTC TTC GAT GGA      714
Thr Met Lys Asp Ser His Val Arg Gln Ile Phe Phe Asp Gly
225                 230                 235

GGT GAG ACA TCC GCT AAT GAA ACA GGA TTA AGT AGC GGG GAT      756
Gly Glu Thr Ser Ala Asn Glu Thr Gly Leu Ser Ser Gly Asp
    240                 245                 250

GCA GAC ACT ATT ATG ACT CCA ACG ACA AAG GAG GAT AAT CAT      798
Ala Asp Thr Ile Met Thr Pro Thr Thr Lys Glu Asp Asn His
                255                 260                 265

GTT ATA GAC GTA ATG GAG GAA AGG CGA ACT GAT GAA GAG GCC      840
Val Ile Asp Val Met Glu Glu Arg Arg Thr Asp Glu Glu Ala
                    270                 275                 280

AAA GGG CAA AGC GTT CAT GAA TAA                              864
Lys Gly Gln Ser Val His Glu
                285
```

(2) INFORMATION FOR SEQ ID NO:145:

(i) SEQUENCE CHARACTERISTICS:
        (A) LENGTH: 287 amino acids
        (B) TYPE: amino acid
        (D) TOPOLOGY: linear (ii) MOLECULE TYPE: Protein (xi) SEQUENCE DESCRIPTION: SEQ ID NO:145:

```
Gln Leu Val Gly Leu Glu Ala Val Thr Ile Leu Arg Ile Trp
1               5                   10

Ile Phe Leu Lys Lys Glu Gln Ala Thr Pro Val Ala Leu Arg
15                  20                  25

Ser Ala Leu Gln Arg Ile Gly Arg Asp Asp Val Val Arg Glu
        30                  35                  40

Met Asp Arg Ala Glu Lys Leu Asp Gly Leu Glu Gly Thr Pro
            45                  50                  55

Val Ser His Ile Ser Gly Pro Ser Ile Thr Leu Ser Ser Thr
                60                  65                  70

Leu Leu Glu Val Ala Gly Asp Arg Arg Arg His Ala Glu Val
                    75                  80

Thr Met Ala Gln Gln Arg Leu Ala Gln Glu Pro Phe Phe Gln
85                  90                  95

Gln Val Gly Tyr Asn Gly Thr Pro Gly Asp Pro Glu Glu Pro
            100                 105                 110

Lys Glu Gln Ser Phe His Glu Glu Glu Glu Val Ala Val
                115                 120                 125
```

```
Ser Glu Ile Arg Thr Val Val Arg Thr Glu Arg His Val His
            130                 135                 140

Asp Ser Glu Asn Gly Pro Ile Val Glu Glu Arg Thr Ile Thr
                145                 150

Thr Thr Tyr Glu Asp Asp Val Ala Val Asn Glu Glu Glu Ile
155                 160                 165

Val Asp Lys Ile Val Pro Leu Asn Glu Glu Gln Glu Lys
            170                 175                 180

Trp Asp Arg Met Val Arg Glu Val Glu Met Asn Phe Glu Gln
                185                 190                 195

Gln Glu Thr Ser Lys Glu Gly Thr Phe Gly Cys Gln Thr Thr
                200                 205                 210

His Glu Lys Glu Lys Asp Asp Gly Gly Ser Leu Lys Thr
                215                     220

Thr Met Lys Asp Ser His Val Arg Gln Ile Phe Phe Asp Gly
225                 230                 235

Gly Glu Thr Ser Ala Asn Glu Thr Gly Leu Ser Ser Gly Asp
            240                 245                 250

Ala Asp Thr Ile Met Thr Pro Thr Thr Lys Glu Asp Asn His
                255                 260                 265

Val Ile Asp Val Met Glu Glu Arg Arg Thr Asp Glu Glu Ala
            270                 275                 280

Lys Gly Gln Ser Val His Glu
                285

(2) INFORMATION FOR SEQ ID NO:146:

(i) SEQUENCE CHARACTERISTICS:
        (A) LENGTH:   864 nucleotides
        (B) TYPE:  nucleic acid
        (C) STRANDEDNESS:  single
        (D) TOPOLOGY:  linear (ii) MOLECULE TYPE:  cDNA (xi) SEQUENCE DESCRIPTION: SEQ ID NO:146:

TTATTCATGA ACGCTTTGCC CTTTGGCCTC TTCATCAGTT CGCCTTTCCT            50

CCATTACGTC TATAACATGA TTATCCTCCT TTGTCGTTGG AGTCATAATA           100

GTGTCTGCAT CCCCGCTACT TAATCCTGTT TCATTAGCGG ATGTCTCACC           150

TCCATCGAAG AAAATCTGCC TTACGTGACT ATCTTTCATT GTCGTCTTCA           200

GACTGCCACC ATCATCATCT TTTTCTTTCT CATGTGTTGT CTGACAACCA           250

AACGTTCCTT CTTTTGATGT TTCTTGTTGC TCAAAATTCA TTTCCACTTC           300

TCGAACCATT CGATCCCATT TTTCTTGCTC CTCTTCGTTG AGAGGCACTA           350

TTTTGTCAAC AATTTCTTCT TCGTTTACAG CAACATCATC CTCATACGTA           400

GTTGTTATTG TACGCTCTTC CACAATAGGA CCATTTTCCG AATCATGCAC           450

ATGTCGTTCA GTGCGCACAA CTGTTCGAAT TTCTGAAACT GCAACTTCCT           500

CTTCCTCTTC GTGGAATGAC TGTTCTTTGG GTTCTTCTGG ATCTCCAGGT           550

GTCCCATTAT ACCCTACTTG CTGAAAAAAC GGTTCTTGTG CCAATCGCTG           600

TTGCGCCATT GTTACCTCGG CGTGACGACG TCTGTCGCCT GCTACCTCTA           650

GCAAAGTAGA TGACAGAGTT ATTGAGGGTC CAGAAATATG CGATACAGGT           700

GTTCCTTCTA AACCATCTAG CTTTTCAGCT CGATCCATTT CTCGTACAAC           750
```

```
ATCATCACGT CCTATTCGCT GCAATGCTGA TCGCAAAGCA ACGGGCGTAG              800

CTTGTTCTTT CTTCAAAAAT ATCCAAATAC GTAGAATAGT GACTGCTTCA              850

AGACCAACTA GTTG                                                     864
```

(2) INFORMATION FOR SEQ ID NO:147:

(i) SEQUENCE CHARACTERISTICS:
        (A) LENGTH: 34 nucleotides
        (B) TYPE: nucleic acid
        (C) STRANDEDNESS: single
        (D) TOPOLOGY: linear (ii) MOLECULE TYPE: Primer (xi) SEQUENCE DESCRIPTION: SEQ ID NO:147:

```
CGCGGATCCG CATGAGTAAT CCTATAGTCG AGGG                                34
```

(2) INFORMATION FOR SEQ ID NO:148:

(i) SEQUENCE CHARACTERISTICS:
        (A) LENGTH: 21 nucleotides
        (B) TYPE: nucleic acid
        (C) STRANDEDNESS: single
        (D) TOPOLOGY: linear (ii) MOLECULE TYPE: Primer (xi) SEQUENCE DESCRIPTION: SEQ ID NO:148:

```
TACAACAGAT TCGTGATTTT C                                              21
```

(2) INFORMATION FOR SEQ ID NO:149:

(i) SEQUENCE CHARACTERISTICS:
        (A) LENGTH: 18 nucleotides
        (B) TYPE: nucleic acid
        (C) STRANDEDNESS: single
        (D) TOPOLOGY: linear (ii) MOLECULE TYPE: Primer (xi) SEQUENCE DESCRIPTION: SEQ ID NO:149:

```
GTGACTTCGA AAAGCGGC                                                  18
```

(2) INFORMATION FOR SEQ ID NO:150:

(i) SEQUENCE CHARACTERISTICS:
        (A) LENGTH: 24 nucleotides
        (B) TYPE: nucleic acid
        (C) STRANDEDNESS: single
        (D) TOPOLOGY: linear (ii) MOLECULE TYPE: Primer (xi) SEQUENCE DESCRIPTION: SEQ ID NO:150:

```
GAACTAGTGA AAGAAAACGC AGCC                                           24
```

(2) INFORMATION FOR SEQ ID NO:151:

(i) SEQUENCE CHARACTERISTICS:
        (A) LENGTH: 24 nucleotides
        (B) TYPE: nucleic acid
        (C) STRANDEDNESS: single
        (D) TOPOLOGY: linear (ii) MOLECULE TYPE: Primer (xi) SEQUENCE DESCRIPTION: SEQ ID NO:151:

```
GTAACGTACA ACACTGTTAT GCCC                                           24
```

(2) INFORMATION FOR SEQ ID NO:152:

(i) SEQUENCE CHARACTERISTICS:
            (A) LENGTH:  24 nucleotides
            (B) TYPE:  nucleic acid
            (C) STRANDEDNESS:  single
            (D) TOPOLOGY:  linear (ii) MOLECULE TYPE:  Primer (xi) SEQUENCE DESCRIPTION:  SEQ ID NO:152:

GGTGAAGATA ATCAGATCAC AGCC                                                24

(2) INFORMATION FOR SEQ ID NO:153:

(i) SEQUENCE CHARACTERISTICS:
            (A) LENGTH:  21 nucleotides
            (B) TYPE:  nucleic acid
            (C) STRANDEDNESS:  single
            (D) TOPOLOGY:  linear (ii) MOLECULE TYPE:  Primer (xi) SEQUENCE DESCRIPTION:  SEQ ID NO:153:

CGATGCATCT AAGGAAGGAT C                                                   21

(2) INFORMATION FOR SEQ ID NO:154:

(i) SEQUENCE CHARACTERISTICS:
            (A) LENGTH:  21 nucleotides
            (B) TYPE:  nucleic acid
            (C) STRANDEDNESS:  single
            (D) TOPOLOGY:  linear (ii) MOLECULE TYPE:  Primer (xi) SEQUENCE DESCRIPTION:  SEQ ID NO:154:

GATCCTTCCT TAGATGCATC G                                                   21

(2) INFORMATION FOR SEQ ID NO:155:

(i) SEQUENCE CHARACTERISTICS:
            (A) LENGTH:  24 nucleotides
            (B) TYPE:  nucleic acid
            (C) STRANDEDNESS:  single
            (D) TOPOLOGY:  linear (ii) MOLECULE TYPE:  Primer (xi) SEQUENCE DESCRIPTION:  SEQ ID NO:155:

CGGTGGTATA ATGATTCTGA CACC                                                24

(2) INFORMATION FOR SEQ ID NO:156:

(i) SEQUENCE CHARACTERISTICS:
            (A) LENGTH:  27 nucleotides
            (B) TYPE:  nucleic acid
            (C) STRANDEDNESS:  single
            (D) TOPOLOGY:  linear (ii) MOLECULE TYPE:  Primer (xi) SEQUENCE DESCRIPTION:  SEQ ID NO:156:

CTCTCTCTCT CGTCCACGAA GTGATGC                                             27

(2) INFORMATION FOR SEQ ID NO:157:

(i) SEQUENCE CHARACTERISTICS:
            (A) LENGTH:  18 nucleotides
            (B) TYPE:  nucleic acid
            (C) STRANDEDNESS:  single
            (D) TOPOLOGY:  linear (ii) MOLECULE TYPE:  Primer (xi) SEQUENCE DESCRIPTION: SEQ ID NO:157:

CGCACTGAAC GACATGTG                                                        18

(2) INFORMATION FOR SEQ ID NO:158:

(i) SEQUENCE CHARACTERISTICS:
            (A) LENGTH: 21 nucleotides
            (B) TYPE: nucleic acid
            (C) STRANDEDNESS: single
            (D) TOPOLOGY: linear (ii) MOLECULE TYPE: Primer (xi) SEQUENCE DESCRIPTION: SEQ ID NO:158:

CTCATGTGTT GTCTGACAAC C                                                    21

(2) INFORMATION FOR SEQ ID NO:159:

(i) SEQUENCE CHARACTERISTICS:
            (A) LENGTH: 21 nucleotides
            (B) TYPE: nucleic acid
            (C) STRANDEDNESS: single
            (D) TOPOLOGY: linear (ii) MOLECULE TYPE: Primer (xi) SEQUENCE DESCRIPTION: SEQ ID NO:159:

GGATTAAGTA GCGGGGATGC A                                                    21

(2) INFORMATION FOR SEQ ID NO:160:

(i) SEQUENCE CHARACTERISTICS:
            (A) LENGTH: 21 nucleotides
            (B) TYPE: nucleic acid
            (C) STRANDEDNESS: single
            (D) TOPOLOGY: linear (ii) MOLECULE TYPE: Primer (xi) SEQUENCE DESCRIPTION: SEQ ID NO:160:

GCAACATAGG CATGTGCGAG A                                                    21

(2) INFORMATION FOR SEQ ID NO:161:

(i) SEQUENCE CHARACTERISTICS:
            (A) LENGTH: 34 amino acids
            (B) TYPE: amino acid
            (D) TOPOLOGY: linear (ii) MOLECULE TYPE: Protein (xi) SEQUENCE DESCRIPTION: SEQ ID NO:161:

Met Ser Asn Pro Ile Val Glu Gly Ser Gly Trp Pro Ala Glu
 1               5                  10

Pro Lys Asp Ser Gln His Gln Gln Gln Ile Pro Asp Asp Asn
15                  20                  25

Ser Gln His Ser Asn Lys
    30

(2) INFORMATION FOR SEQ ID NO:162:

(i) SEQUENCE CHARACTERISTICS:
            (A) LENGTH: 67 amino acids
            (B) TYPE: amino acid
            (D) TOPOLOGY: linear (ii) MOLECULE TYPE: Protein (xi) SEQUENCE DESCRIPTION: SEQ ID NO:162:

Gly Glu Ser Ser Ala Ser Phe Leu Arg Ala Ala Arg Ala Gly

```
            1               5                  10
Asn Leu Asp Arg Val Leu Glu Leu Arg Ser Gly Thr Asp
 15              20              25

Ile Asn Thr Cys Asn Ala Asn Gly Leu Asn Ala Leu His Leu
         30              35              40

Ala Ser Lys Glu Gly His His Glu Val Val Arg Glu Leu Leu
         45              50              55

Lys Arg Lys Ala Asp Val Asp Ala Ala Thr Arg
             60              65
```

(2) INFORMATION FOR SEQ ID NO:163:

(i) SEQUENCE CHARACTERISTICS:
        (A) LENGTH: 62 amino acids
        (B) TYPE: amino acid
        (D) TOPOLOGY: linear (ii) MOLECULE TYPE: Protein (xi) SEQUENCE DESCRIPTION: SEQ ID NO:163:

```
Pro Leu His Val Ala Thr Lys Trp Gly Arg Thr Asn Met
 1               5                  10

Val Ser Leu Leu Leu Ala His Gly Ala Val Ile Asp Cys Arg
 15              20              25

Thr Arg Asp Leu Leu Thr Pro Leu His Cys Ala Ser Arg Ser
         30              35              40

Gly His Asp Gln Val Val Asp Leu Leu Glu Lys Gly Ala
             45              50              55

Pro Ile Ser Ala Lys Thr Lys
             60
```

(2) INFORMATION FOR SEQ ID NO:164:

(i) SEQUENCE CHARACTERISTICS:
        (A) LENGTH: 11 amino acids
        (B) TYPE: amino acid
        (D) TOPOLOGY: linear (ii) MOLECULE TYPE: Protein (xi) SEQUENCE DESCRIPTION: SEQ ID NO:164:

```
Asn Gly Leu Ala Pro Leu His Met Ala Ala Gln
 1               5                  10
```

(2) INFORMATION FOR SEQ ID NO:165:

(i) SEQUENCE CHARACTERISTICS:
        (A) LENGTH: 50 amino acids
        (B) TYPE: amino acid
        (D) TOPOLOGY: linear (ii) MOLECULE TYPE: Protein (xi) SEQUENCE DESCRIPTION: SEQ ID NO:165:

```
Val Asp Ala Ala Ala Arg Glu Leu Gln Thr Pro Leu His Ile
 1               5                  10

Ala Ser Arg Leu Gly Asn Thr Asp Ile Val Ile Leu Leu Leu
 15              20              25

Gln Ala Asn Ala Ser Pro Asn Ala Ala Thr Arg Asp Leu Tyr
         30              35              40

Thr Pro Leu His Ile Ala Ala Lys
             45              50
```

(2) INFORMATION FOR SEQ ID NO:166:

(i) SEQUENCE CHARACTERISTICS:
        (A) LENGTH: 53 amino acids
        (B) TYPE: amino acid
        (D) TOPOLOGY: linear (ii) MOLECULE TYPE: Protein (xi) SEQUENCE DESCRIPTION: SEQ ID NO:166:

Gln Ile Asn Met Val Arg Phe Leu Ile Glu His Gly Ala
 1               5                  10

Arg Val Ser Val Ile Thr Arg Ala Ser Tyr Thr Pro Leu His
15                  20                  25

Gln Ala Ala Gln Gln Gly His Asn Ser Val Val Arg Tyr Leu
        30                  35                  40

Leu Glu His Gly Ala Ser Pro Asn Val His Thr Ser
            45                  50

(2) INFORMATION FOR SEQ ID NO:167:

(i) SEQUENCE CHARACTERISTICS:
        (A) LENGTH: 44 amino acids
        (B) TYPE: amino acid
        (D) TOPOLOGY: linear (ii) MOLECULE TYPE: Protein (xi) SEQUENCE DESCRIPTION: SEQ ID NO:167:

Phe Leu Ile Ser Phe Met Val Asp Ala Arg Gly Gly Ala Met
 1               5                  10

Arg Gly Cys Arg His Ser Gly Val Arg Ile Ile Pro Pro
15                  20                  25

Arg Lys Ala Pro Gln Pro Thr Arg Val Thr Cys Arg Tyr Leu
        30                  35                  40

Gly Lys (2) INFORMATION FOR SEQ ID NO:168:

(i) SEQUENCE CHARACTERISTICS:
        (A) LENGTH: 59 amino acids
        (B) TYPE: amino acid
        (D) TOPOLOGY: linear (ii) MOLECULE TYPE: Protein (xi) SEQUENCE DESCRIPTION: SEQ ID NO:168:

Val Ala Leu Arg Ser Ala Leu Gln Arg Ile Gly Arg Asp
 1               5                  10

Asp Val Val Arg Glu Met Asp Arg Ala Glu Lys Leu Asp Gly
15                  20                  25

Leu Glu Gly Thr Pro Val Ser His Ile Ser Gly Pro Ser Ile
        30                  35                  40

Thr Leu Ser Ser Thr Leu Leu Glu Val Ala Gly Asp Arg Arg
            45                  50                  55

Arg His Ala Glu (2) INFORMATION FOR SEQ ID NO:169:

(i) SEQUENCE CHARACTERISTICS:
        (A) LENGTH: 61 amino acids
        (B) TYPE: amino acid

```
          (D) TOPOLOGY:  linear (ii) MOLECULE TYPE:  Protein (xi) SEQUENCE DESCRIPTION:  SEQ ID NO:169:

Val Thr Met Ala Gln Gln Arg Leu Ala Gln Glu Pro Phe Phe
1               5                   10

Gln Gln Val Gly Tyr Asn Gly Thr Pro Gly Asp Pro Glu Glu
15                  20                  25

Pro Lys Glu Gln Ser Phe His Glu Glu Glu Glu Val Ala
        30              35              40

Val Ser Glu Ile Arg Thr Val Val Arg Thr Glu Arg His Val
            45              50              55

His Asp Ser Glu Asn
            60

(2) INFORMATION FOR SEQ ID NO:170:

(i) SEQUENCE CHARACTERISTICS:
        (A) LENGTH:  52 amino acids
        (B) TYPE:  amino acid
        (D) TOPOLOGY:  linear (ii) MOLECULE TYPE:  Protein (xi) SEQUENCE DESCRIPTION:  SEQ ID NO:170:

Pro Ile Val Glu Glu Arg Thr Ile Thr Thr Thr Tyr Glu
1               5                   10

Asp Asp Val Ala Val Asn Glu Glu Glu Ile Val Asp Lys Ile
15                  20                  25

Val Pro Leu Asn Glu Glu Glu Gln Glu Lys Trp Asp Arg Met
        30              35              40

Val Arg Glu Val Glu Met Asn Phe Glu Gln Gln
            45              50

(2) INFORMATION FOR SEQ ID NO:171:

(i) SEQUENCE CHARACTERISTICS:
        (A) LENGTH:  18 amino acids
        (B) TYPE:  amino single
        (D) TOPOLOGY:  linear (ii) MOLECULE TYPE:  Protein (xi) SEQUENCE DESCRIPTION:  SEQ ID NO:171:

Val Met Glu Glu Arg Arg Thr Asp Glu Glu Ala Lys Gly
1               5                   10

Gln Ser Val His Glu
```

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. An isolated ankyrin nucleic acid molecule wherein said nucleic acid molecule is a Dirofilaria or Brugia nucleic acid molecule that hybridizes to a nucleic acid molecule having a nucleic acid sequence selected from the group consisting of SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEO ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:130, SEQ ID NO:132, SEQ ID NO:134, SEQ ID NO:136; SEQ ID NO:138, SEQ ID NO:140, SEQ ID NO:141, SEQ ID NO:143, SEQ ID NO:144 and SEQ ID NO:146 under conditions comprising (a) hybridizing in a solution comprising 2×SSC and 0% formamide, at a temperature of 37° C., and (b) washing in 1×SSC and 0% formamide at a temperature of 49° C.

2. The ankyrin nucleic acid molecule of claim 1, wherein said nucleic acid molecule is selected from the group consisting of a *Dirofilaria immitis* ankyrin nucleic acid molecule and a *Brugia malayi* ankyrin nucleic acid molecule.

3. The ankyrin nucleic acid molecule of claim 1, wherein said nucleic acid molecule comprises a nucleic acid sequence selected from the group consisting of: a nucleic acid sequence selected from the group consisting of SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:130, SEQ ID NO:132, SEQ ID NO:134, SEQ ID NO:136; SEQ ID NO:138, SEQ ID NO:140, SEQ ID NO:141, SEQ ID NO:143, SEQ ID NO:144, and SEQ ID NO:146; and an allelic variant of a nucleic acid sequence selected from the group consisting of the above-listed sequences.

4. The ankyrin nucleic acid molecule of claim 1, wherein said ankyrin nucleic acid molecule comprises a nucleic acid sequence that encodes an ankyrin protein.

5. The ankyrin nucleic acid molecule of claim 1, wherein said nucleic acid molecule is selected from the group consisting of: a nucleic acid molecule selected from the group consisting of DiAnk-int$_{92}$, DiAnk-int$_{118}$, DiAnk-int$_{248}$, DiAnk-int$_{94}$, DiAnk-int$_{48}$, DiAnk-int$_{200}$, DiAnk-int$_{82}$, DiAnk-int$_{213}$, DiAnk-int$_{76}$, DiAnk-int$_{231}$, DiAnk-int$_{78}$, DiAnk-int$_{110}$, DiAnk-int$_{89}$, DiAnk-int$_{95}$, DiAnk-int$_{301}$, DiAnk-ex$_{102}$, DiAnk-ex$_{201}$, DiAnk-ex$_{187}$, DiAnk-ex$_{34}$, DiAnk-ex$_{150}$, DiAnk-ex$_{161}$, DiAnk-ex$_{133}$, DiAnk-ex$_{179}$, DiAnk-ex$_{184}$, DiAnk-ex$_{158}$, DiAnk-ex$_{59}$, nDiAnk$_{1056}$, nDiAnk$_{1266}$, and nDiAnk$_{864}$; and an allelic variant of a nucleic acid molecule selected from the group consisting of DiAnk-int$_{92}$, DiAnk-int$_{118}$, DiAnk-int$_{248}$, DiAnk-int$_{94}$, DiAnk-int$_{48}$, DiAnk-int$_{200}$, DiAnk-int$_{82}$, DiAnk-int$_{213}$, DiAnk-int$_{76}$, DiAnk-int$_{231}$, DiAnk-int$_{78}$, DiAnk-int$_{110}$, DiAnk-int$_{89}$, DiAnk-int$_{95}$, DiAnk-int$_{301}$, DiAnk-ex$_{102}$, DiAnk-ex$_{201}$, DiAnk-ex$_{187}$, DiAnk-ex$_{34}$, DiAnk-ex$_{150}$, DiAnk-ex161, DiAnk-ex$_{133}$, DiAnk-ex$_{179}$, DiAnk-ex$_{184}$, DiAnk-ex$_{158}$, DiAnk-ex$_{59}$, nDiAnk$_{1056}$, nDiAnk$_{1266}$, and nDiAnk$_{864}$.

6. The ankyrin nucleic acid molecule of claim 1, wherein said nucleic acid molecule encodes a protein selected from the group consisting of a protein that shares at least about 85% identity with PDiANK$_{352}$, a protein that shares at least about 95% identity with PDiAnk$_{422}$, and a protein that shares at least about 80% identity with PDiANK$_{288}$.

7. The ankyrin nucleic acid molecule of claim 1, wherein said nucleic acid molecule encodes a protein comprising an amino acid sequence selected from the group consisting of an amino acid sequence that shares at least about 85% identity with SEQ ID NO:139, an amino acid sequence that shares at least about 95% identity with SEQ ID NO:142, an amino acid sequence that shares at least about 75% identity with SEQ ID NO:145, an amino acid sequence that shares at least about 75% identity with SEQ ID NO:161, an amino acid sequence that shares at least about 85% identity with SEQ ID NO:162, an amino acid sequence that shares at least about 85% identity with SEQ ID NO:163, an amino acid sequence that shares at least about 100% identity with SEQ ID NO:164, an amino acid sequence that shares at least about 90% identity with SEQ ID NO:165, an amino acid sequence that shares at least about 75% identity with SEQ ID NO:166, an amino acid sequence that shares at least about 90% identity with SEQ ID NO:167, an amino acid sequence that shares at least about 80% identity with SEQ ID NO:168, an amino acid sequence that shares at least about 95% identity with SEQ ID NO:169, an amino acid sequence that shares at least about 75% identity with SEQ ID NO:170, and an amino acid sequence that shares at least about 95% identity with SEQ ID NO:171.

8. The ankyrin nucleic acid molecule of claim 1, wherein said nucleic acid molecule is selected from the group consisting of: a nucleic acid molecule encoding a protein comprising an amino acid sequence selected from the group consisting of SEQ ID NO:139, SEQ ID NO:142, SEQ ID NO:145, SEQ ID NO:161, SEQ ID NO:162, SEQ ID NO:163, SEQ ID NO:164, SEQ ID NO:165, SEQ ID NO:166, SEQ ID NO:167, SEQ ID NO:168, SEQ ID NO:169, SEQ ID NO:170, and SEQ ID NO:171; and an allelic variant of a nucleic acid molecule encoding a protein comprising an amino acid sequence selected from the group consisting of SEQ ID NO:139, SEQ ID NO:142, SEQ ID NO:145, SEQ ID NO:161, SEQ ID NO:162, SEQ ID NO:163, SEQ ID NO:164, SEQ ID NO:165, SEQ ID NO:166, SEQ ID NO:167, SEQ ID NO:168, SEQ ID NO:169, SEQ ID NO:170, and SEQ ID NO:171.

9. A recombinant molecule comprising an ankyrin nucleic acid molecule as set forth in claim 1 operatively linked to a transcription control sequence.

10. A recombinant virus comprising an ankyrin nucleic acid molecule as set forth in claim 1.

11. A recombinant cell comprising an ankyrin nucleic acid molecule as set forth in claim 1.

12. An isolated ankyrin nucleic acid molecule that hybridizes to a nucleic acid molecule having a nucleic acid sequence selected from the group consisting of SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:130, SEQ ID NO:132, SEQ ID NO:134, SEQ ID NO:136; SEQ ID NO:138, SEQ ID NO:140, SEQ ID NO:141, SEQ ID NO:143, SEQ ID NO:144 and SEQ ID NO:146 underhybridization and wash conditions which allow 30% or less base-pair mismatch, wherein such conditions are determined by a formula:

$$T_m = 81.5° C. + 16.6 \log M + 0.41(\% G+C) - 500/n - 0.61 (\% \text{formamide}),$$

wherein $T_m$ represents the temperature at which two complementary nucleic acid molecule strands will disassociate, assuming 100% complementarity between the two strands, n represents the number of nucleotides in the shorter strand of the duplex being hybridized and log M represents the ionic strengths of the hybridization and wash solutions in moles/liter;

wherein said wash is conducted at a temperature of $T_m$ minus 30° C.

13. A recombinant molecule comprising an ankyrin nucleic acid molecule as set forth in claim 12 operatively linked to a transcription control sequence.

14. A recombinant virus comprising an ankyrin nucleic acid molecule as set forth in claim 12.

15. A recombinant cell comprising an ankyrin nucleic acid molecule as set forth in claim 12.

16. A composition comprising an excipient and an isolated ankyrin nucleic acid molecule wherein said nucleic acid molecule is a Dirofilaria or Brugia nucleic acid molecule that hybridizes to a nucleic acid molecule having a nucleic acid sequence selected from the group consisting of SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:130, SEQ ID NO:132, SEQ ID NO:134, SEQ ID NO:136, SEQ ID NO:138, SEQ ID NO:140, SEQ ID NO:141, SEQ ID NO:143, SEQ ID NO:144 and SEQ ID NO:146 under conditions comprising (a) hybridizing in a solution comprising 2×SSC and 0% formamide, at a temperature of 37° C., and (b) washing in 1×SSC and 0% formamide at a temperature of 49° C.

17. The composition of claim 16, wherein said protective compound is selected from the group consisting of a genetic vaccine, a recombinant virus vaccine and a recombinant cell vaccine.

18. The composition of claim 16, wherein said composition further comprises a component selected from the group consisting of an adjuvant, a carrier, and a mixture thereof.

19. A method to produce an ankyrin protein, said method comprising culturing in an effective medium a cell capable of expressing said protein, said protein being encoded by a Dirofilaria or Brugia nucleic acid molecule that hybridizes to a nucleic acid molecule having a nucleic acid sequence selected from the group consisting of SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:140, SEQ ID NO:143 and SEQ ID NO:146 under conditions comprising (a) hybridizing in a solution comprising 2×SSC and 0% formamide, at a temperature of 37° C., and (b) washing in 1×SSC and 0% formamide at a temperature of 49° C.

* * * * *

UNITED STATES PATENT AND TRADEMARK OFFICE
CERTIFICATE OF CORRECTION

PATENT NO : 6,063,599
DATED : May 16, 2000
INVENTOR(S) : Tang et al.

It is certified that error appears in the above-identified patent and that said Letters Patent is hereby corrected as shown below:

Claim 1, column 234, line 56, delete "SEO" and insert --SEQ--.
Claim 1, column 234, line 66, delete "37° C.," and insert --37°C,--.
Claim 1, column 234, line 67, delete "49° C" and insert --49°C--.
Claim 6, column 235, line 50, delete "encodcs" and insert --encodes--.
Claim 12, column 236, line 49, delete "underhybridization" and insert --under hybridization--.
Claim 12, column 236, line 54, delete "81.5° C." and insert --81.5°C--.
Claim 12, column 236, line 64, delete "30° C" and insert --30°C--.
Claim 16, column 238, line 1, delete "37° C.," and insert --37°C,--.
Claim 19, column 238, line 20, delete "37° C.," and insert --37°C,--.
Claim 19, column 238, line 22, delete "49° C" and insert --49°C--.

Signed and Sealed this

Twenty-second Day of May, 2001

*Attest:*

NICHOLAS P. GODICI

*Attesting Officer*     *Acting Director of the United States Patent and Trademark Office*